(12) United States Patent
Katoh et al.

(10) Patent No.: US 6,562,828 B1
(45) Date of Patent: May 13, 2003

(54) AMIDINE COMPOUNDS

(75) Inventors: Susumu Katoh, Takatsuki (JP);
Katsuyuki Yokota, Takatsuki (JP);
Mikio Hayashi, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/647,847
(22) PCT Filed: Apr. 9, 1999
(86) PCT No.: PCT/JP99/01900
§ 371 (c)(1),
(2), (4) Date: Oct. 6, 2000
(87) PCT Pub. No.: WO99/52895
PCT Pub. Date: Oct. 21, 1999

(30) Foreign Application Priority Data

Apr. 10, 1998 (JP) .......................................... 10-116233
Aug. 25, 1998 (JP) .......................................... 10-237869

(51) Int. Cl.$^7$ .................. A61K 31/506; A61K 31/4725;
C07D 401/12; C07D 401/14
(52) U.S. Cl. ...................... 514/256; 514/307; 514/322;
514/394; 514/318; 514/367; 514/213.01;
546/145; 546/194; 546/199; 544/328; 544/333;
540/593; 548/159; 548/306.1
(58) Field of Search ................................ 546/141, 189,
546/145; 514/307, 309, 310, 318, 330,
331, 256; 544/328, 333

(56) References Cited

U.S. PATENT DOCUMENTS

| | | | |
|---|---|---|---|
| 3,725,388 A | 4/1973 | Grell et al. ................. 260/239 |
| 4,324,794 A | 4/1982 | Tidwell et al. | |
| 4,634,783 A | 1/1987 | Fujii et al. .................. 549/475 |
| 5,455,348 A | 10/1995 | Austel et al. | |
| 5,541,343 A | 7/1996 | Himmelsbach et al. | |
| 5,693,515 A | 12/1997 | Clark et al. | |
| 5,866,122 A | 2/1999 | Turecek et al. | |

FOREIGN PATENT DOCUMENTS

| | | |
|---|---|---|
| EP | 0 540 051 | 5/1993 |
| EP | 798295 | * 10/1997 |
| EP | 0 798 295 | 10/1997 |
| JP | 46-24009 | 7/1971 |
| JP | 5-78344 | 3/1993 |
| JP | 5 208946 A | 8/1993 |
| JP | 6 227971 A | 8/1994 |
| JP | 6-327488 | 11/1994 |
| JP | 7-179407 | 7/1995 |
| JP | 8-20532 | 1/1996 |
| JP | 9-2977 | 1/1997 |
| JP | 10 17549 A | 1/1998 |
| JP | 10 17549 | 1/1998 |
| WO | WO 92/20642 A1 | 11/1992 |
| WO | WO 95/08540 A1 | 3/1995 |
| WO | WO 95/15758 A1 | 6/1995 |
| WO | WO 95/19772 A1 | 7/1995 |
| WO | 96/16940 | 6/1996 |
| WO | WO 96/38421 A1 | 12/1996 |
| WO | WO 96/39145 A2 | 12/1996 |
| WO | 97/08165 | * 3/1997 |
| WO | WO 97/09311 A1 | 3/1997 |
| WO | WO 97/45424 A1 | 12/1997 |
| WO | WO 97/46576 A1 | 12/1997 |
| WO | WO 99/10339 A1 | 3/1999 |
| WO | WO 99/11627 A1 | 3/1999 |
| WO | WO 01/30333 A2 | 5/2001 |
| WO | WO 02/14311 A1 | 2/2002 |

OTHER PUBLICATIONS

Zhu et al. in Annual Reports in Medicinal Chemistry, vol. 35, pp. 83–102 (2000).*
Sibirtsev et al., "Mechanisms of interactions of some phenylbenzoimidaxole and phenylindole dyes with DNA," *Bioorganicheskaya Khimiya* (1994), vol. 20, No. 6, pp. 650–668. (English Abstract).

(List continued on next page.)

Primary Examiner—Emily Bernhardt
(74) Attorney, Agent, or Firm—Foley & Lardner

(57) ABSTRACT

A compound of the formula [I]

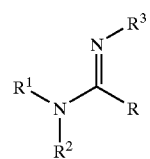

wherein $R^1$, $R^2$ and $R^3$ are the same or different and each is hydrogen atom,

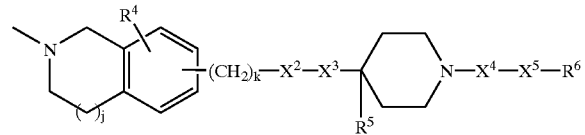

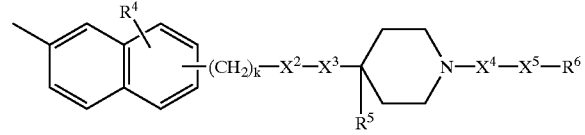

or

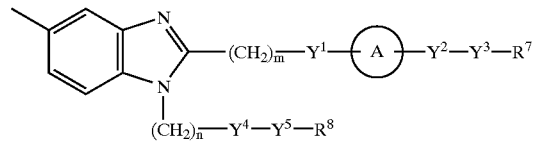

wherein each symbol is as defined in the specification, a salt thereof or a prodrug thereof. The compound of the present invention, a salt thereof and a prodrug thereof are useful as factor Xa inhibitor and blood coagulation inhibitor, and are useful for the prophylaxis and/or treatment of diseases caused by blood coagulation or thrombus.

15 Claims, No Drawings

OTHER PUBLICATIONS

Kehr et al., "A Short Synthesis of the Factor–Xa Inhibitor DX–9065a Using Palladium–Catalyzed Key Steps," *Helvetica Chimica Acta* (1997), vol. 80, pp. 892–895.

Kim et al., "In vivo Evaluation of DX–9065a, a Synthetic Factor Xa Inhibitor, in Experimental Vein Graft," *Journal of Atherosclerosis and Thrombosis* (1996), vol. 2, No. 2, pp. 110–116.

Hara et al., "DX–9065a, a New Synthetic, Potent Anticoagulant and Selective Inhibitor for Factor Xa," *Thrombosis and Haemostasis* (1994), vol. 71, No. 3, pp. 314–319.

Herbert et al., "DX 9065A, a Novel, Synthetic, Selective and Orally Active Inhibitor of Factor Xa: In Vitro and in Vivo Studies," *The Journal of Pharmacology and Experimental Therapeutics* (1996), vol. 276, No. 3, pp. 1030–1038.

Yokoyama et al., "Antithromboitc Effects of Orally Active Synthetic Antagonist of Activated Factor X in Nonhuman Primates," *Circulation* (Aug. 1, 1995), vol. 92, No. 3, pp. 485–491.

Hara et al., "Species Differences in Anticoagulant and Anti–Xa Activity of DX–9065a, A Highly Selective Factor Xa Inhibitor," *Thrombosis Research* (1995), vol. 80, No. 1, pp. 99–104.

Hara et al., "DX–9065a, an Orally Active, Specific Inhibitor of Factor Xa, Inhibits Thrombosis without Affecting Bleeding Time in Rats," *Thrombosis and Haemostasis* (1995), vol. 74, No. 2, pp. 635–639.

Wong et al., "Antithrombotic Actions of Selective Inhibitors of Blood Coagulation Factor Xa in Rat Models of Thrombosis," *Thrombosis Research* (1996), vol. 83, No. 2, pp. 117–126, Elsevier Science Ltd.

Yamashita et al., "The Antithrombotic Effect of Synthetic Low Molecular Weight Human Factor Xa Inhibitor, DX–9065a, on He–Ne Laser–Induced Thrombosis in Rat Mesenteric Microvessels," *Thrombosis Research* (1997), vol. 85, No. 1, pp. 45–51, Elsevier Science Ltd.

Nagahara et al., "Design, Synthesis and Biological Activities of Orally Active coagulation Factor Xa Inhibitors," *Eur. J. Med. Chem.* (1995), vol. 30, Suppl., pp. 139s–143s.

Yamazaki et al., "Effects of DX–9065a, an Orally Active, Newly Synthesized and Specific Inhibitor of Factor Xa, against Experimental Disseminated Intravascular Coagulation in Rats," *Thrombosis and Haemostasis* (1994), vol. 72, No. 3, pp. 393–396.

Geratz et al., Thromb. Haemostasis, vol. 39, No. 2, "Specific inhibition of platelet agglutination and aggrigation by aromatic amidino compounds," pp. 411–425 (1978).

Fairfield et al., Biochim. Biophys. Acta., vol. 824, No. 1, "Studies on mitochndrial type I topoisomerase and on its function," pp. 45–57 (1985).

Zhang et al., Yiyao–Gongye, vol. 16, No. 9, "Synthesis and antimalarial activity of some indole and benzimidazole amidine derivatives," pp. 394–399 (1985) Only Abstract.

Tidwall et al., J. Med. Chem., vol. 21, No. 7, "Diarylamidine derivatives with one or both of the aryl moieties consisting of an indole or indole–like ring. Inhibitors of arginine–specific esteroproteases," pp. 613–623 (1978).

Czarny et al., J. Heterocycl. Chem., vol. 33, No. 4, "Synthesis of mono–cationic and dicationic of Hoechst 33258," pp. 1393–1397 (1996).

Anne et al., Antimicrob. Agents Chemother., vol. 18, No. 2, "Antifungal and antibacterial activites of diarylamidine derivatives," pp. 231–239 (1980).

Czarny et al., J. Am. Chem. Soc., vol. 117, No. 16, "Analysis of van der Waals and electrostatic contributions in the interactions of minor groove binding benziidazoles with DNA," pp. 4716–4717 (1995).

Chandra et al., Cell. Mol. Biol., vol. 25, No. 6, Molecular mechanism of action of diamidinephenylindole (DAPI). III. Physicochemical binding of DAPI and its derivatives to DNA and polydeoxynucleotides, and its consequences on the template activity of nucleic acids, pp. 429–433 (1979).

Balzarini et al., Invest. New Drugs, vol. 1, No. 2, "Inhibitory activity of diarylamidine derivatives on murine leukemia L1210 cell growth," pp. 103–115 (1983).

Portoghese P. et al. "Tetrahydro–Isoquinoline–Based factor Xa Inhibitors", J. of Med. Chem. 41(22–27) pp. 4983–4994, (1998) American Chemical Society, Publications Division.

Harker L. et al., "Antithrombotic Benefits and Hemorrhagic Risks of Direct Thrombin Antagonists", Thromb. Haemostatis, (1995) 74(1) pp. 464–472, Div. Of Hematology and Oncology, Emory Univ. School of Medicine.

Guendouz F. et al., "Polymer Bound 4–Dialkylamino Pyridines: Synthesis, Characterization and Catalytic Efficiency", Tetrahedron, 44(23), pp. 7095–7108, (1988), Pergamon Press.

Singh B. et al., "A Convenient large Scale Synthesis of 2,6–Dimethyl–4–(trimethylstanny)Pyridine", J. Heterocycl. Chem. (1990), vol. 27, pp. 1841–1842, Sterling Research Group.

Drake B., "A Convenient Preparation of Monosubstituted N,N'–di(Boc)–Protected Guanidines", Synthesis (1994), pp. 579–582, Selectide Corporation.

Marsais F., "Directed Lithiation of 4–Halopyridines: Chemoselectivity, Regioselectivity and Application to Synthesis", (1988), J. Heterocycl., (25), pp. 81–87, Institut National des Sciences Appliquees.

Blank B. et al., "Inhibitors of Phenylethanolamine N–Methyltransferase and Epinephrine Biosynthesis. 2. 1,2,3, 4–Tetrahydroisoquinoline–7–sulfonanilides[1]", J. Med. Chem. (1980) 23(8), pp. 837–840, Amer. Chem. Soc.

Ye Fengchun et al., Pharmaceutical Industry, "Application of Mold Inhibitor BCM in Screening the Soil Actinomyces," vol. 16, No. 9, (1985) in Japanese.

Geratz, et al., "Streptococcal Cell Wall–induced Systemic Disease: Beneficial Effects of trans–Bis (5–amidino–2–benzimidazolyl) ethene, a Novel, Macrophage–directed Anti–inflammatory Agents," *American Journal of Pathology*, vol. 139, No. 4 (Oct. 1991), American Associated of Pathologists, United States.

Geratz, et al., "Suppression of Local and Systemic Responses in Streptococcal Cell Wall–Induced Acute Inflammation of the Air Pouch by Cyclosporine A, Comparison with Effects of Two Anti–Inflammatory Bix–Benzimidazoles," *American Journal of Pathology*, vol. 142, No. 4 (Apr. 1993), American Association for Investigative Pathology, United States.

Tidwell, et al., "Activity of Cationically Substituted Bis-Benzimidazoles against Experimental Pneumocystis carinii Pneumonia," *Antimicrobial Agents and Chomotherapy*, vol. 37, No. 8, pp. 1713–1716 (Aug. 1993), American Society for Microbiology, United States.

Katakura, et al., "Molecular model of an interaction between factor Xa and DX–9065a, a novel Xa inhibitor: contribution of the accetmidoylpyrrolidine moiety of the inhibitor to potency and selectivity for serine proteases," *Eur J Med Chem* 30, pp. 387–394 (1995), Elsevier, Japan.

Stubbs, et al., "Crystal structures of factor Xa specific inhibitors in complex with trypsin: structural grounds for inhibition of factor Xa and selectivity against thrombin," *FEBS Letters* 375, pp. 103–107 (1995), Federation of European Biochemical Societies, Germany.

Tidwell, et al., "Aromatic Amidines: Comparison of Their Ability to Block Respiratory Syncytial Virus Induced Cell Fusion and to Inhibit Plasmin, Urokinase, Thrombin, and Trypsin," *J. Med. Chem.* vol. 26, pp. 294–298 (1983), American Chemical Society, United States.

Fairley, et al., "Structure, DNA Minor Groove Binding, and Base Pair Specificity of Alkyl– and Aryl–Linked Bis (amidinobenzimidazoles) and Bis(amidinoindoles)," *J. Med. Chem.,* vol. 36, pp. 1746–1753 (1993), American Chemical Society, United States.

Nagahara, et al., Dibasic (Amidinoaryl) propanoic Acid Derivatives as Novel Blood Coagulation Factor Xa Inhibitors, *J. Med. Chem.,* vol. 37, pp. 1200–1207 (1994), American Chemical Society, Japan.

Murayama, et al., Radioimmunoassay method for DX–9065a, an anticoagulant agent. Development, evaluation and application to human plasma, *Journal of Pharmaceutical and Biomedical Analysis,* vol. 14, pp. 1435–1445 (1996), Elsevier Science B.V., Japan.

Caughey, et al., "Bis(5–Amidino–2–Benzimidazolyl)Methane and Related Amidines Are Potent, Reversible Inhibitors of Mast Cell Tryptases," *The Journal of Pharmacology and Experimental Therapeutics,* vol. 264, No. 2 (1993), The American Society for Pharmacolgy and Experimental Therapeutics, United States.

Dann, et al., "Trypanocide Diamidine mit vier Ringen in einem oder zwei Ringsystemen," *Justus Liebigs Ann. Chem.,* vol. 7, pp. 1112–1140 (1973), database CA [Online], STN International, American Chemical Society, Germany.

Engh, et al., "Enzyme flexibility, solvent and 'weak' interactions characterize thrombin–ligand interactions: implications for drug design," *Structure,* vol. 4, No. 11, pp. 1353–1362 (Nov. 15, 1996), Current Biology Ltd ISSN, Germany.

Tidwell, et al., "Strategies for Anticoagulation with Synthetic Protease Inhibitors. Xa Inhibitors Versus Thrombin Inhibitors," *Thrombosis Research,* vol. 19, pp. 339–349 (1980), Pergamon Press Ltd, United States.

* cited by examiner

AMIDINE COMPOUNDS

FIELD OF THE INVENTION

The present invention relates to a novel amidine compound having a blood coagulation factor Xa inhibitory activity. The present invention also relates to a pharmaceutical composition, a factor Xa inhibitor and a therapeutic agent for the diseases caused by blood coagulation or thrombus, which comprises this compound.

BACKGROUND OF THE INVENTION

One of the etiologies of thrombosis, such as unstable angina, deep vein thrombosis and disseminated intravascular coagulation (DIC), is promotion of blood coagulation. For the prophylaxis and treatment of thrombus, heparin and warfarin have been conventionally used. Heparin acts on antithrombin III (ATIII) to indirectly inhibit the coagulation system and, therefore, may show a weak action on arterial thrombus. Heparin is associated with generation of an antibody against platelet factor (PF4), which promotes coagulation in some patients, and a propensity toward hemorrhage as a side effect. Warfarin requires longer time for the expression of the drug effect and is not necessarily an easy and safe drug. Under the circumstances, a new anticoagulant is desired to overcome these problems.

The factor X is a glycoprotein having a molecular weight of 58,000, and in an intrinsic pathway, the factor X is activated on a phospholipid membrane in the presence of a factor IXa/factor VIIIa/$Ca^{2+}$ complex and becomes factor Xa. In the coagulation system called extrinsic pathway, factor X is activated by factor VIIa in the presence of a tissue factor and becomes factor Xa. The factor Xa generated in the both pathways activates prothrombin to give thrombin. The generated thrombin further activates the upstream of this cascade to produce a large amount of thrombin. Consequently, fibrinogen becomes fibrin and coagulation of blood occurs.

Inasmuch as the blood coagulation system is an amplification reaction, inhibition of generation of thrombin in the early stage is considered to be more efficient than direct inhibition of the activity of the generated thrombin. In addition, since factor Xa is the confluence of intrinsic and extrinsic coagulation pathways, inhibition of factor Xa is considered to be extremely effective. Some reports have documented that low molecular weight heparin showed a lower tendency of bleeding than heparin in clinical applications, and in a test using baboon (Thrombosis and Haemostas, 74, 464 (1995)), it was found that inhibition of factor Xa rather than thrombin showed less tendency of bleeding. Therefore, a factor Xa inhibitor has a potential of showing antithrombus effect without influencing the bleeding time observed in the use of conventional anticoagulants.

As a factor Xa inhibitor, WO97/08165 discloses a compound of the formula

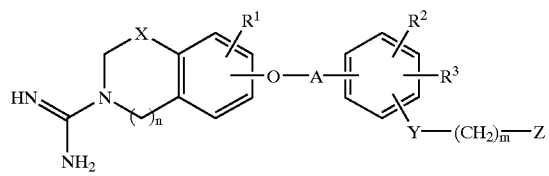

wherein $R^1$, $R^2$ and $R^3$ are each hydrogen atom, hydroxy, halogen atom, hydroxyalkyl, alkyl, alkenyl, alkynyl, alkoxy, aralkyloxy, alkenyloxy, alkynyloxy, carboxy, alkoxycarbonyl, alkenyloxycarbonyl, alkynyloxycarbonyl, carboxyalkyl, alkoxycarbonylalkyl, alkenyloxycarbonylalkyl or alkynyloxycarbonylalkyl, A is alkylene optionally substituted by hydroxy, carboxy, alkoxycarbonyl or halogen atom, X is a bond, alkylene or alkyleneoxy, Y is a single bond, chalcogen atom or CO, Z is a saturated or unsaturated optionally substituted hetero ring or carbon ring, optionally substituted amino, hydroxy, carboxy, alkoxycarbonyl or alkyl, n is an integer of 1 or 2, and m is an integer of 0 to 4. In addition, Japanese Patent Unexamined Publication No. 5-208946 (U.S. Pat. No. 5,620,991, EP No. 540051) discloses a compound of the formula

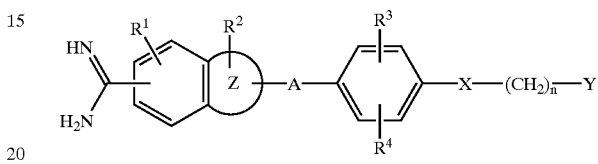

wherein $R^1$ is hydrogen atom or lower alkoxy, $R^2$ is hydrogen atom, lower alkyl, lower alkoxy, carboxy, alkoxycarbonyl, carboxyalkyl or alkoxycarbonylalkyl, $R^3$ is hydrogen atom, carboxy, alkoxycarbonyl, carboxyalkyl, alkoxycarbonylalkyl, carboxyalkoxy or alkoxycarbonylalkoxy, $R^4$ is hydrogen atom, hydroxy, lower alkyl or lower alkoxy, n is an integer of 0 or 1, A is $C_1$–$C_4$ alkylene optionally substituted by 1 or 2 substituents from hydroxyalkyl, carboxyl, alkoxycarbonyl, carboxyalkyl and alkoxycarbonylalkyl, X is a single bond, oxygen atom, sulfur atom or carbonyl, Y is optionally substituted saturated or unsaturated 5 or 6-membered heterocyclic group or cyclic hydrocarbon group, optionally substituted amino or optionally substituted aminoalkyl, and a group of the formula

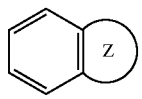

is selected from indolyl, benzofuranyl, benzothienyl, benzimidazolyl, benzoxazolyl, benzothiazolyl, naphthyl, tetrahydronaphthyl and indanyl. Furthermore, WO96/16940 discloses a compound of the formula

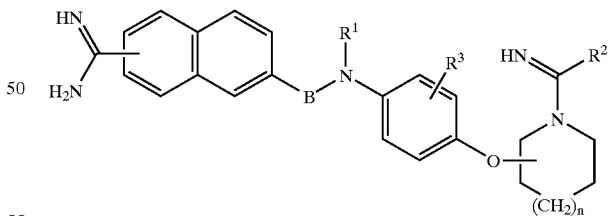

wherein $R^1$ is hydrogen atom or a group of the formula —A—W—$R^4$ wherein A is a group of the formula

or —$SO_2$— wherein $X^2$ is oxygen atom or sulfur atom, and W is a single bond or —$NR^5$—, $R^4$ is hydroxy, lower alkoxy, optionally substituted lower alkyl, optionally substituted cycloalkyl, optionally substituted aryl, or optionally substituted heteroaryl, with the proviso that when W is a group of the formula —NR⁵—, R⁴ may be hydrogen atom but is not hydroxy or lower alkoxy; wherein R⁵ is hydrogen atom, carbamoyl, lower alkoxycarbonyl, mono- or di(lower) alkylaminocarbonyl, lower alkylsulfonyl, mono- or di(lower)alkylaminothiocarbonyl, optionally substituted lower alkyl or optionally substituted lower alkanoyl; R² is lower alkyl; R³ is hydrogen atom, halogen atom, carboxy, amino, cyano, nitro, hydroxy, lower alkoxy, lower alkyl or lower alkoxycarbonyl; B is lower alkylene or carbonyl; and n is an integer of 0 or 1.

DISCLOSURE OF THE INVENTION

The present invention aims at providing a novel compound useful as a factor Xa inhibitor. The present invention also aims at providing a novel factor Xa inhibitor.

In view of the above situation, the present inventors conducted intensive studies in an attempt to find a compound useful as a factor Xa inhibitor and found the amidine compound of the following formula [I]. They have further found that the compound can be a superior factor Xa inhibitor and completed the present invention.

The compound of the present invention specifically inhibits blood coagulation factor Xa and shows strong anticoagulation action. Therefore, the compound is useful as an agent for the prophylaxis and/or treatment of various diseases caused by blood coagulation or thrombus, namely, cerebrovascular diseases such as cerebral infarction, cerebral thrombosis, cerebral embolism, transient ischemia attack (TIA), subarachnoid hemorrhage and the like; ischemic heart diseases such as acute or chronic myocardial infarction, unstable angina, coronary thrombosis and the like; pulmonary vascular diseases such as pulmonary infarction, pulmonary embolism and the like; and diseases caused by various vascular disorders such as peripheral arterial embolism, deep vein thrombosis, disseminated intravascular coagulation, thrombosis after surgery of artificial blood vessels or replacement of artificial valve, reocclusion or restenosis after coronary bypass, reocclusion or restenosis after recanalization such as percutaneous transluminal coronary angioplasty (PTCA), percutaneous transluminal coronary recanalization (PTCR) and the like, thrombosis due to extracorporeal circulation and the like, glomerulonephritis, nephrotic syndrome, diabetic retinopathy, arteriosclerotic obliteration, Buerger disease, tumor thrombosis, thrombus by atrial fibrillation, and the like.

As is evident from Experimental Example 2 to be mentioned later, since the compound of the present invention does not have inhibitory activity against thrombin, namely, factor IIa (FIIa), hemorrhage as a side effect is considered to be noticeably less. Experimental Examples 6 and 7 to be mentioned later reveal striking factor Xa inhibitory effect by oral administration.

There is also a finding that factor Xa is involved in the growth of influenza virus (Japanese Patent Unexamined Publication No.6-227971). Thus, the compound of the present invention is expected to be useful for the prophylaxis and/or treatment of influenza.

The present invention relates to a compound of the following formula [I], which is useful as a factor Xa inhibitor. In addition, the present invention relates to a factor Xa inhibitory agent containing a compound of the following formula [I] or a salt thereof or a prodrug thereof as an active ingredient. More particularly, the present invention provides the following (1)–(23).

(1) An amidine compound of the formula [I]

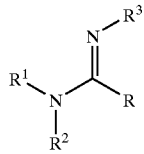

wherein

R is a group of the formula

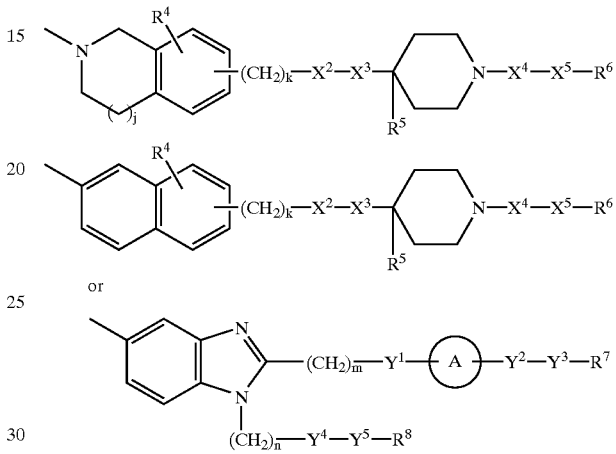

or wherein

R⁴ is hydrogen atom, hydroxy group, lower alkyl group, lower alkoxy group or halogen atom, R⁵ is hydrogen atom, cyano group, carboxy group or lower alkoxycarbonyl group, R⁶ is hydrogen atom, cycloalkyl group, hydroxy group, carboxy group, lower alkoxycarbonyl group, aralkyloxycarbonyl group wherein said aralkyloxycarbonyl group is optionally substituted by halogen atom, nitro group, alkyl group, alkoxy group or trifluoromethyl group, nitro group, amino group, lower alkylamino group, di(lower)alkylamino group, aryl group, heteroaryl group wherein said aryl group or heteroaryl group is optionally substituted by 1 to 3 substituents selected from lower alkyl group, hydroxy group, lower alkoxy group, carboxy group, lower alkoxycarbonyl group, aralkyloxycarbonyl group, nitro group, amino group, acylamino group, amidino group and hydroxyamidino group, 5- to 7-membered saturated heterocycle having at least one nitrogen atom wherein said saturated heterocycle is optionally substituted by lower alkyl group, acyl group, di(lower)alkylamino(power)alkanoyl group or imidoyl group or

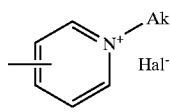

wherein Ak is lower alkyl group and Hal is halogen atom, $X^2$ is oxygen atom, sulfur atom, —$SO_2$—, —$SO_2NH$— or a single bond, $X^3$ is —$(CH_2)_m$— wherein m is 0 or an integer of 1 to 3, $X^4$ is —CO—, —C(=NH)—, —$SO_2$—, —CONH—, —CSNH—, —$SO_2NH$—, —$(CH_2)_r$CONH—, —$(CH_2)_r$CH(OH)—,

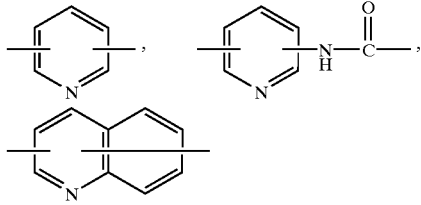

wherein r is 0 or an integer of 1 to 3, or a single bond, $X^5$ is alkylene group having 1 to 6 carbon atoms, alkenylene group having 2 to 6 carbon atoms, or a single bond, $R^7$ is hydrogen atom, lower alkyl group or

wherein $R^9$ is oxygen atom, sulfur atom, NH, $NR^{11}$ wherein $R^{11}$ is lower alkyl group, aralkyl group wherein said aralkyl group is optionally substituted by 1 to 3 substituents selected from halogen atom, lower alkyl group, hydroxy group, lower alkoxy group, haloalkyl group, cyano group, nitro group, amino group and acyloxy group, or hydroxy group, and $R^{10}$ is lower alkyl group, lower alkoxy group, amino group, lower alkylamino group or di(lower)alkylamino group, $R^8$ is hydrogen atom, lower alkyl group, cycloalkyl group wherein said cycloalkyl group is optionally substituted by lower alkyl group or carboxy group, carboxy group, lower alkoxycarbonyl group, aryl group, heteroaryl group wherein said aryl group or heteroaryl group is optionally substituted by 1 to 3 substituents selected from halogen atom, lower alkyl group wherein said lower alkyl group is optionally substituted by halogen atom, hydroxy group, lower alkoxy group, carboxy group and lower alkoxycarbonyl group, aralkyl group wherein said aralkyl group is optionally substituted by 1 to 3 substituents selected from halogen atom, lower alkyl group, hydroxy group, lower alkoxy group, haloalkyl group, cyano group, nitro group, amino group and acyloxy group, or 5 to 7-membered saturated heterocycle having at least one nitrogen atom, $Y^1$ is oxygen atom, —NH—, —CONH—, —$NR^{12}$— wherein $R^{12}$ is lower alkyl group or —$Y^6$—$R^{13}$ wherein $R^{13}$ is hydrogen atom, lower alkyl group or aryl group wherein said lower alkyl group or aryl group is optionally substituted by carboxy group, lower alkoxycarbonyl group or aralkyloxycarbonyl group, $Y^6$ is —CO—, —$CO_2$—, —$COCO_2$—, —$SO_2$—, —$SO_2(CH_2)_r$— or —$(CH_2)_r$— wherein r is 0 or an integer of 1 to 3, or a single bond, $Y^2$ is oxygen atom, sulfur atom or a single bond, $Y^3$ is

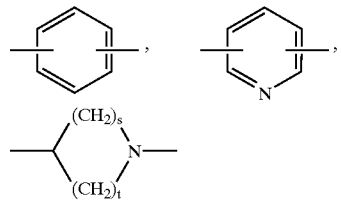

wherein s and t are the same or different and each is an integer of 1 to 3, or a single bond, $Y^4$ is oxygen atom, —CO—, —$CO_2$—, —$SO_2$—, —CONH—, —CH=CH— or a single bond, $Y^5$ is —$(CH_2)_p$—, —$(CH_2)_{p'}$—CHAk—$(CH_2)_{p''}$—, —$(CH_2)_{p'}$—CAkAk'—$(CH_2)_{p''}$—,

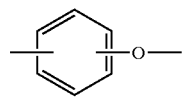

wherein Ak, Ak' are the same or different and each is lower alkyl group, p is 0 or an integer of 1 to 3, p' and p" are the same or different and each is 0 or an integer of 1 or 2, or a single bond, ring A is

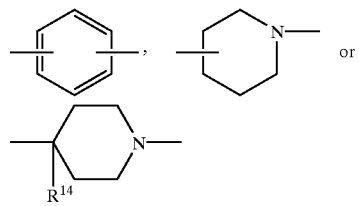

wherein $R^{14}$ is carboxy group, lower alkoxycarbonyl group or aralkyloxycarbonyl group wherein said aralkyloxycarbonyl group is optionally substituted by halogen atom, nitro group, alkyl group, alkoxy group or trifluoromethyl group, j is 1 or 2, k is 0 or 1, and m and n are the same or different and each is 0 or an integer of 1 to 3; and $R^1$, $R^2$ and $R^3$ are the same or different and each is hydrogen atom, hydroxy group, lower alkyl group or aryl group, or a salt thereof or a prodrug thereof.

(2) The amidine compound of the formula [I] described in (1) above, wherein R is a group of the formula

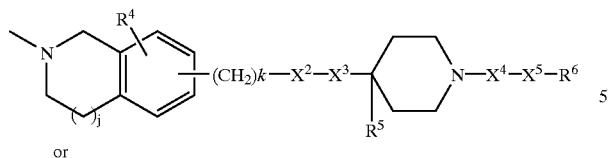

or

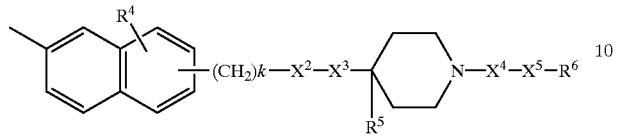

wherein R⁴, R⁵, R⁶, X², X³, X⁴, X⁵, j and k are as defined above,
or a salt thereof or a prodrug thereof.

(3) The amidine compound of the formula [I] described in (2) above, wherein R is a group of the formula

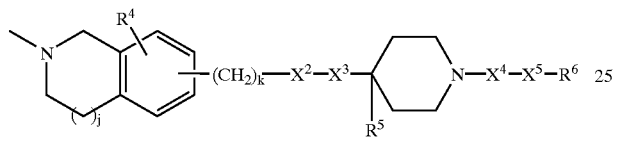

wherein R⁴, R⁵, R⁶, X², X³, X⁴, X⁵, j and k are as defined above,
or a salt thereof or a prodrug thereof.

(4) The amidine compound of the formula [I] described in (3) above, wherein R is a group of the formula

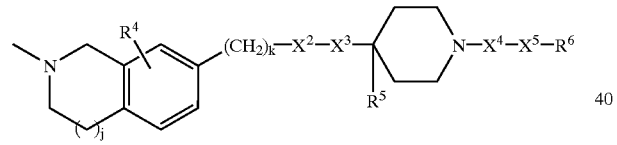

wherein R⁴, R⁵, R⁶, X², X³, X⁴, X⁵, j and k are as defined above,
or a salt thereof or a prodrug thereof.

(5) The amidine compound of the formula [I] described in (4) above, wherein X³ is —(CH₂)$_m$— wherein m is as defined above and X⁴ is a group of the formula

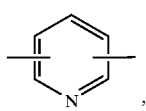, and j is 1,
or a salt thereof or a prodrug thereof.

(6) The amidine compound of the formula [I] described in (5) above, wherein R⁶ is hydrogen atom, X² is oxygen atom, and X₅ is a single bond,
or a salt thereof or a prodrug thereof.

(7) The amidine compound of the formula [I] described in (1) above, wherein R is a group of the formula

wherein R⁷, R⁸, Y¹, Y², Y³, Y⁴, Y⁵, ring A, m and n are as defined above,
or a salt thereof or a prodrug thereof.

(8) The amidine compound of the formula [I] described in (7) above, wherein ring A is a group of the formula or a salt thereof or a prodrug thereof.

(9) The amidine compound of (1) above, which is selected from the group consisting of 7-[1-(pyridin-4-yl)piperidin-4-ylmethoxy]-1,2,3,4-tetrahydroisoquinoline-2-carboxamidine, 7-[1-(quinolin-4-yl)piperidin-4-ylmethoxy]-1,2,3,4-tetrahydroisoquinoline-2-carboxamidine, N-methyl-7-[1-(pyridin-4-yl)piperidin-4-ylmethoxy]-1,2,3,4-tetrahydroisoquinoline-2-carboxamidine, 7-[1-(pyridin-4-yl)piperidin-4-ylmethoxy]-1,2,3,4-tetrahydroisoquinoline-2-carboxamidine oxime, N-phenyl-7-[1-(pyridin-4-yl)piperidin-4-ylmethoxy]-1,2,3,4-tetrahydroisoquinoline-2-carboxamidine, 4-(2-amidino-1,2,3,4-tetrahydroisoquinolin-7-yloxymethyl)-1-(pyridin-4-yl)piperidine-4-carboxylic acid ethyl ester, 4-(2-amidino-1,2,3,4-tetrahydroisoquinolin-7-yloxymethyl)-1-(pyridin-4-yl)piperidine-4-carboxylic acid, 4-(2-amidino-1,2,3,4-tetrahydroisoquinolin-7-yloxymethyl)-1-(2,6-dimethylpyridin-4-yl)piperidine-4-carboxylic acid ethyl ester, 4-(2-amidino-1,2,3,4-tetrahydroisoquinolin-7-yloxymethyl)-1-(2,6-dimethylpyridin-4-yl)piperidine-4-carboxylic acid, 4-(2-amidino-1,2,3,4-tetrahydroisoquinolin-7-yloxymethyl)-1-(2-methylpyridin-4-yl)piperidine-4-carboxylic acid methyl ester, 4-(2-amidino-1,2,3,4-tetrahydroisoquinolin-7-yloxymethyl)-1-(2-methylpyridin-4-yl)piperidine-4-carboxylic acid, 4-(2-amidino-1,2,3,4-tetrahydroisoquinolin-7-yloxymethyl)-1-(pyrimidin-4-yl)piperidine-4-carboxylic acid, 4-[2-(2-amidino-1,2,3,4-tetrahydroisoquinolin-7-yloxy)ethyl]-1-(pyridin-4-yl)piperidine-4-carboxylic acid ethyl ester, 4-[2-(2-amidino-1,2,3,4-tetrahydroisoquinolin-7-yloxy)ethyl]-1-(pyridin-4-yl)piperidine-4-carboxylic acid, 4-[N-[5-amidino-1-(1-phenylethylcarbamoylmethyl)benzimidazol-2-ylmethyl]-N-[4-(1-acetimidoylpiperidin-4-yloxy)phenyl]carbamoyl]benzoic acid, 4-[N-[5-amidino-1-(4-benzyloxyphenylcarbamoylmethyl)benzimidazol-2- ylmethyl]-N-[4-(1-acetimidoylpiperidin-4-yloxy) phenyl]carbamoyl]benzoic acid,

2-[4-(pyrrolidin-3-yloxy)phenoxymethyl]-1-(2-methoxyethyl)benzimidazole-5-carboxamidine, 2-[4-(1-acetimidoylpyrrolidin-3-yloxy)phenoxymethyl]-1-(2-methoxyethyl)-benzimidazole-5-carboxamidine, 7-[1-(2-hydroxyethyl)piperidin-4-ylmethoxy]-1,2,3,4-tetrahydroisoquinoline-2-carboxamidine, 7-[1-(pyridin-4-ylmethyl)piperidin-4-ylmethoxy]-1,2,3,4-tetrahydroisoquinoline-2-carboxamidine, 7-[1-(2-hydroxy-2-phenylethyl)piperidin-4-ylmethoxy]-1,2,3,4-tetrahydroisoquinoline-2-carboxamidine, 4-(2-amidino-1,2,3,4-tetrahydroisoquinolin-7-yloxymethyl)piperidin-1-ylacetylglycine ethyl ester, 4-(2-amidino-1,2,3,4-tetrahydroisoquinolin-7-yloxymethyl)piperidine-1-acetic acid N-methylamide, 7-(1-acetylpiperidin-4-ylmethoxy)-1,2,3,4-tetrahydroisoquinoline-2-carboxamidine, 7-(1-benzylsulfonylpiperidin-4-ylmethoxy)-1,2,3,4-tetrahydroisoquinoline-2-carboxamidine, 7-[1-(2-naphthylsulfonyl)piperidin-4-ylmethoxy]-1,2,3,4-tetrahydroisoquinoline-2-carboxamidine, 7-(1-acetimidoylpiperidin-4-ylmethoxy)-1,2,3,4-tetrahydroisoquinoline-2-carboxamidine, 7-(1-phenylacetimidoylpiperidin-4-ylmethoxy)-1,2,3,4-tetrahydroisoquinoline-2-carboxamidine, N-[2-[4-(2-amidino-1,2,3,4-tetrahydroisoquinolin-7-yloxymethyl)piperidin-1-yl]pyridin-5-yl]acetamide, N-[2-[4-(2-amidino-1,2,3,4-tetrahydroisoquinolin-7-yloxymethyl)piperidin-1-yl]pyridin-5-yl]benzamide, 3-[4-[4-(2-amidino-1,2,3,4-tetrahydroisoquinolin-7-yloxymethyl)piperidin-1-yl]pyridin-3-yl]-2-propenoic acid ethyl ester, 4-[4-(2-amidino-1,2,3,4-tetrahydroisoquinolin-7-yloxymethyl)piperidin-1-yl]pyridine-3-carboxylic acid methyl ester, 4-[4-(2-amidino-1,2,3,4-tetrahydroisoquinolin-7-yloxymethyl)piperidin-1-yl]pyridine-3-carboxylic acid, 6-[1-(pyridin-4-yl)piperidin-4-ylmethoxy]-1,2,3,4-tetrahydroisoquinoline-2-carboxamidine, 7-[2-[4-cyano-1-(pyridin-4-yl)piperidin-4-yl]ethoxy]-1,2,3,4-tetrahydroisoquinoline-2-carboxamidine, 4-(2-amidino-2,3,4,5-tetrahydro-1H-benzo[c]azepin-8-yloxymethyl)-1-(pyridin-4-yl)piperidine-4-carboxylic acid ethyl ester, 4-(2-amidino-2,3,4,5-tetrahydro-1H-benzo[c]azepin-8-yloxymethyl)-1-(pyridin-4-yl)piperidine-4-carboxylic acid, 4-(2-amidino-1,2,3,4-tetrahydroisoquinolin-7-ylthiomethyl)-1-(pyridin-4-yl)piperidine-4-carboxylic acid, 4-[2-(2-amidino-1,2,3,4-tetrahydroisoquinolin-7-ylthio)ethyl]-1-(pyridin-4-yl)piperidine-4-carboxylic acid, 4-(2-amidino-1,2,3,4-tetrahydroisoquinolin-7-ylsulfonylmethyl)-1-(pyridin-4-yl)piperidine-4-carboxylic acid, 4-[2-(2-amidino-1,2,3,4-tetrahydroisoquinolin-7-ylsulfonyl)ethyl]-1-(pyridin-4-yl)piperidine-4-carboxylic acid, 4-(2-amidino-1,2,3,4-tetrahydroisoquinolin-7-ylsulfonylamino)-1-(pyridin-4-yl)piperidine-4-carboxylic acid methyl ester, 4-(2-amidino-1,2,3,4-tetrahydroisoquinolin-7-ylsulfonylamino)-1-(pyridin-4-yl)piperidine-4-carboxylic acid, 4-(2-amidino-1,2,3,4-tetrahydroisoquinolin-7-ylsulfonylaminomethyl)-1-(pyridin-4-yl)piperidine-4-carboxylic acid ethyl ester, 4-(2-amidino-1,2,3,4-tetrahydroisoquinolin-7-ylsulfonylaminomethyl)-1-(pyridin-4-yl)piperidine-4-carboxylic acid, 1-[2-(benzothiazol-2-yl)-2-oxyethyl]-2-phenoxymethylbenzimidazole-5-carboxamidine, trans-4-[2-[4-(1-acetimidoylpiperidin-4-yloxy)phenoxymethyl]-5-amidinobenzimidazol-1-ylacetylaminomethyl]cyclohexanecarboxylic acid, trans-4-[2-[4-(1-acetimidoylpiperidin-4-yloxy)phenoxymethyl]-5-(N-methylamidino)benzimidazol-1-ylacetylaminomethyl]cyclohexanecarboxylic acid, trans-4-[2-[4-(1-acetimidoylpiperidin-4-yloxy)phenoxymethyl]-5-[amino-(hydroxyimino)methyl]benzimidazol-1-ylacetylaminomethyl]cyclohexanecarboxylic acid, 2-[4-(piperidin-4-yloxy)phenoxymethyl]-1-phenacylbenzimidazole-5-carboxamidine, 2-[4-(1-acetimidoylpiperidin-4-yloxy)phenoxymethyl]-1-phenacylbenzimidazole-5-carboxamidine, 2-[2-[4-ethoxycarbonyl-1-(pyridin-4-yl)piperidin-4-yl]ethyl]-1-(cyclohexylcarbamoylmethyl)benzimidazole-5-carboxamidine, 4-[2-[5-amidino-1-(cyclohexylcarbamoylmethyl)benzimidazol-2-yl]ethyl]-1-(pyridin-4-yl)piperidine-4-carboxylic acid, 1-(cyclohexylcarbamoylmethyl)-2-[N-[1-(pyridin-4-yl)piperidin-4-yl]-N-ethoxalylaminomethyl]benzimidazole-5-carboxamidine, N-[5-amidino-1-(cyclohexylcarbamoylmethyl)benzimidazol-2-ylmethyl]-N-[1-(pyridin-4-yl)piperidin-4-yl]aminooxalic acid, 2-[N-[4-(1-acetimidoylpiperidin-4-yloxy)phenyl]-N-ethoxycarbonylmethyl-aminomethyl]-1-(cyclohexylcarbamoylmethyl)benzimidazole-5-carboxamidine, N-[5-amidino-1-(cyclohexylcarbamoylmethyl)benzimidazol-2-ylmethyl]-N-[4-(1-acetimidoylpiperidin-4-yloxy)phenyl]carbamoylbenzoic acid, 2-[N-[4-(1-amidinopiperidin-4-yloxy)phenyl]-N-(4-methoxycarbonylbenzoyl)-aminomethyl]-1-(cyclohexylcarbamoylmethyl)benzimidazole-5-carboxamidine, N-[5-amidino-1-(cyclohexylcarbamoylmethyl)benzimidazol-2-ylmethyl]-N-[4-(1-amidinopiperidin-4-yloxy)phenyl]carbamoylbenzoic acid, N-[5-amidino-1-(cyclohexylcarbamoylmethyl)benzimidazol-2-ylmethyl]-N-[4-(1-acetimidoylpiperidin-4-yloxy)phenyl]sulfamoylacetic acid, 7-[1-(pyridin-4-ylacetyl)piperidin-4-ylmethoxy]-1,2,3,4-tetrahydroisoquinoline-2-carboxamidine, 7-[1-(3-aminobenzyl)piperidin-4-ylmethoxy]-1,2,3,4-tetrahydroisoquinoline-2-carboxamidine, 7-[1-(2-hydroxybenzyl)piperidin-4-ylmethoxy]-1,2,3,4-tetrahydroisoquinoline-2-carboxamidine, 7-[1-(pyridin-2-ylmethyl)piperidin-4-ylmethoxy]-1,2,3,4-tetrahydroisoquinoline-2-carboxamidine, 2-[4-(2-amidino-1,2,3,4-tetrahydroisoquinolin-7-yloxymethyl)piperidin-1-ylmethyl]indole-1-carboxylic acid methyl ester, 4-(2-amidino-1,2,3,4-tetrahydroisoquinolin-7-yloxymethyl)piperidine-1-acetic acid benzyl ester, N-benzyl-4-(2-amidino-1,2,3,4-tetrahydroisoquinolin-7-yloxymethyl)piperidine-1-carboxamide, 7-[1-(indol-2-ylmethyl)piperidin-4-ylmethoxy]-1,2,3,4-tetrahydroisoquinoline-2-carboxamidine, 4-(2-amidino-1,2,3,4-tetrahydroisoquinolin-7-yloxymethyl)piperidine-1-acetic acid, N-benzyl-4-(2-amidino-1,2,3,4-tetrahydroisoquinolin-7-yloxymethyl)piperidine-1-acetamide, 4-(2-amidino-1,2,3,4-tetrahydroisoquinolin-7-yloxymethyl)piperidin-1-ylacetylaminoacetic acid, 7-[1-(5-nitropyridin-2-yl)piperidin-4-ylmethoxy]-1,2,3,4-tetrahydroisoquinoline-2-carboxamidine, 7-[1-(2-nitrobenzyl)piperidin-4-ylmethoxy]-1,2,3,4-tetrahydroisoquinoline-2-carboxamidine, 7-[1-(2-aminobenzyl)piperidin-4-ylmethoxy]-1,2,3,4-tetrahydroisoquinoline-2-carboxamidine, 7-(1-hexaneimidoylpiperidin-4-ylmethoxy)-1,2,3,4-tetrahydroisoquinoline-2-carboxamidine, N-benzyl-4-(2-amidino-1,2,3,4-tetrahydroisoquinolin-7-yloxymethyl)piperidine-1-sulfonamide, N-butyl-4-(2-amidino-1,2,3,4-tetrahydroisoquinolin-7-yloxymethyl)piperidine-1-sulfonamide, N-cyclohexyl-4-(2-amidino-1,2,3,4-tetrahydroisoquinolin-7-yloxymethyl)-piperidine-1-sulfonamide, N-(2-nitrophenyl)-4-(2-amidino-1,2,3,4-tetrahydroisoquinolin-7-yloxymethyl)-piperidine-1-carbothioamide, 7-[1-(benzimidazol-2-yl)piperidin-4-ylmethoxy]-1,2,3,4-tetrahydroisoquinoline-2-carboxamidine, 3-[4-[4-(2-amidino-1,2,3,4-tetrahydroisoquinolin-7-yloxymethyl)piperidin-1-yl]pyridin-3-yl]propionic acid ethyl ester, 3-[4-[4-(2-amidino-1,2,3,4-tetrahydroisoquinolin-7-yloxymethyl)piperidin-1-yl]pyridin-3-yl]propionic acid, 4-(2-amidino-1,2,3,4-tetrahydroisoquinolin-7-yloxyymethyl)-1-(2-aminopyridin-5-ylcarbonyl)piperidine-4-carboxylic acid, 4-(2-amidino-1,2,3,4-tetrahydroisoquinolin-7-yloxymethyl)-1-(3-aminopropionyl)-piperidine-4-carboxylic acid, 4-(2-amidino-1,2,3,4-tetrahydroisoquinolin-7-yloxymethyl)-1-(imidazol-4-ylacetyl)piperidine-4-carboxylic acid, 4-(2-amidino-1,2,3,4-tetrahydroisoquinolin-7-yloxymethyl)-1-(piperidin-4-ylsulfamoyl)piperidine-4-carboxylic acid, 4-(2-amidino-1,2,3,4-tetrahydroisoquinolin-7-yloxymethyl)-1-dimethylaminoacetylpiperidine-4-carboxylic acid, 4-(2-amidino-1,2,3,4-tetrahydroisoquinolin-7-yloxymethyl)-1-(pyridin-3-ylcarbamoyl)piperidine-4-carboxylic acid ethyl ester, 4-(2-amidino-1,2,3,4-tetrahydroisoquinolin-7-yloxymethyl)-1-(1-dimethylaminoacetylpiperidin-2-ylcarbonyl)piperidine-4-carboxylic acid ethyl ester, 4-[4-(2-amidino-1,2,3,4-tetrahydroisoquinolin-7-yloxymethyl)-4-carboxypiperidin-1-yl]-1-methylpyridinium chloride, 4-(2-amidino-1,2,3,4-tetrahydroisoquinolin-7-yloxymethyl)-1-(4-amidinophenyl)-piperidine-4-carboxylic acid ethyl ester, 4-(2-amidino-1,2,3,4-tetrahydroisoquinolin-7-yloxymethyl)-1-(2,6-dimethylpyridin-4-yl)piperidine-4-carboxylic acid ethyl ester, 4-(2-amidino-1,2,3,4-tetrahydroisoquinolin-7-yloxymethyl)-1-(2-methylpyridin-4-yl)piperidine-4-carboxylic acid ethyl ester, 4-(2-amidino-1,2,3,4-tetrahydroisoquinolin-7-yloxymethyl)-1-(1-ethylpiperidin-4-yl)piperidine-4-carboxylic acid ethyl ester, 4-(2-amidino-1,2,3,4-tetrahydroisoquinolin-7-yloxymethyl)-1-(1-ethylpiperidin-4-yl)piperidine-4-carboxylic acid, 7-[2-(4-cyanopiperidin-4-yl)ethoxy]-1,2,3,4-tetrahydroisoquinoline-2-carboxamidine, 4-[2-(2-amidino-1,2,3,4-tetrahydroisoquinolin-7-yloxy)ethyl]-1-(pyridin-4-yl)piperidine-4-carboxylic acid ethyl ester, 4-(2-amidino-6-methoxy-1,2,3,4-tetrahydroisoquinolin-7-yloxymethyl)-1-(pyridin-4-yl)piperidine-4-carboxylic acid, and 4-(2-amidino-6-methyl-1,2,3,4-tetrahydroisoquinolin-7-yloxymethyl)-1-(pyridin-4-yl)piperidine-4-carboxylic acid, or a salt thereof or a prodrug thereof.

(10) The amidine compound of (3) above, which is selected from the group consisting of 7-[1-(pyridin-4-yl)piperidin-4-ylmethoxy]-1,2,3,4-tetrahydroisoquinoline-2-carboxamidine, 7-[1-(quinolin-4-yl)piperidin-4-ylnethoxy]-1,2,3,4-tetrahydroisoquinoline-2-carboxamidine, N-methyl-7-[1-(pyridin-4-yl)piperidin-4-ylmethoxy]-1,2,3,4-tetrahydroisoquinoline-2-carboxamidine, 7-[1-(pyridin-4-yl)piperidin-4-ylmethoxy]-1,2,3,4-tetrahydroisoquinoline-2-carboxamide oxime, N-phenyl-7-[1-(pyridin-4-yl)piperidin-4-ylmethoxy]-1,2,3,4-tetrahydroisoquinoline-2-carboxamidine, 4-(2-amidino-1,2,3,4-tetrahydroisoquinolin-7-yloxymethyl)-1-(pyridin-4-yl)piperidine-4-carboxylic acid ethyl ester, 4-(2-amidino-1,2,3,4-tetrahydroisoquinolin-7-yloxymethyl)-1-(pyridin-4-yl)piperidine-4-carboxylic acid, 4-(2-amidino-1,2,3,4-tetrahydroisoquinolin-7-yloxymethyl)-1-(2,6-dimethylpyridin-4-yl)piperidine-4-carboxylic acid ethyl ester, 4-(2-amidino-1,2,3,4-tetrahydroisoquinolin-7-yloxymethyl)-1-(2,6-dimethylpyridin-4-yl)piperidine-4-carboxylic acid, 4-(2-amidino-1,2,3,4-tetrahydroisoquinolin-7-yloxymethyl)-1-(2-methylpyridin-4-yl)piperidine-4-carboxylic acid methyl ester, 4-(2-amidino-1,2,3,4-tetrahydroisoquinolin-7-yloxymethyl)-1-(2-methylpyridin-4-yl)piperidine-4-carboxyhc acid, 4-(2-amidino-1,2,3,4-tetrahydroisoquinolin-7-yloxymethyl)-1-(pyrmidin-4-yl)piperidine-4-carboxylic acid, 4-[2-(2-amidino-1,2,3,4-tetrahydroisoquinolin-7-yloxy)ethyl]-1-(pyridin-4-yl)piperidine-4-carboxylic acid ethyl ester, 4-[2-(2-amidino-1,2,3,4-tetrahydroisoquinolin-7-yloxy)ethyl]-1-(pyridin-4-yl)piperidine-4-carboxylic acid, 7-[1-(2-hydroxyethyl)piperidin-4-ylmethoxy]-1,2,3,4-tetrahydroisoquinoline-2-carboxamidine, 7-[1-(pyridin-4-ylmethyl)piperidin-4-ylmethoxy]-1,2,3,4-tetrahydroisoquinoline-2-carboxamidine, 7-[1-(2-hydroxy-2-phenylethyl)piperidin-4-ylmethoxy]-1,2,3,4-tetrahydroisoquinoline-2-carboxamidine, 4-(2-amidino-1,2,3,4-tetrahydroisoquinolin-7-yloxymethyl)piperidin-1-ylacetylglycine ethyl ester, 4-(2-amidino-1,2,3,4-tetrahydroisoquinolin-7-yloxymethyl)piperidine-1-acetic acid N-methylamide, 7-(1-acetylpiperidin-4-ylmethoxy)-1,2,3,4-tetrahydroisoquinoline-2-carboxamidine, 7-(1-benzylsulfonylpiperidin-4-ylmethoxy)-1,2,3,4-tetrahydroisoquinoline-2-carboxamidine, 7-[1-(2-naphthylsulfonyl)piperidin-4-ylmethoxy]-1,2,3,4-tetrahydroisoquinoline-2-carboxamidine, 7-(1-acetimidoylpiperidin-4-ylmethoxy)-1,2,3,4-tetrahydroisoquinoline-2-carboxamidine, 7-(1-phenylacetimidoylpiperidin-4-ylmethoxy)-1,2,3,4-tetrahydroisoquinoline-2-carboxamidine, N-[2-[4-(2-amidino-1,2,3,4-tetrahydroisoquinolin-7-yloxymethyl)piperidin-1-yl]pyridin-5-yl]acetamide, N-[2-[4-(2-amidino-1,2,3,4-tetrahydroisoquinolin-7-yloxymethyl)piperidin-1-yl]pyridin-5-yl]benzamide, 3-[4-[4-(2-amidino-1,2,3,4-tetrahydroisoquinolin-7-yloxymethyl)piperidin-1-yl]pyridin-3-yl]-2-propenoic acid ethyl ester, 4-[4-(2-amidino-1,2,3,4-tetrahydroisoquinolin-7-yloxymethyl)piperidin-1-yl]pyridine-3-carboxylic acid methyl ester, 4-[4-(2-amidino-1,2,3,4-tetrahydroisoquinolin-7-yloxymethyl)piperidin-1-yl]pyridine-3-carboxylic acid, 6-[1-(pyrdin-4-yl)piperidin-4-ylmethoxy]-1,2,3,4-tetrahydroisoquinoline-2-carboxamidine, 7-[2-[4-cyano-1-(pyridin-4-yl)piperidin-4-yl]ethoxy]-1,2,3,4-tetrahydroisoquinoline-2-carboxamidine, 4-(2-amidino-2,3,4,5-tetrahydro-1H-benzo[c]azepin-8-yloxymethyl)-1-(pyridin-4-yl)piperidine-4-carboxylic acid ethyl ester, 4-(2-amidino-2,3,4,5-tetrahydro-1H-benzo[c]azepin-8-yloxymethyl)-1-(pyridin-4-yl)piperidine-4-carboxylic acid, 4-(2-amidino-1,2,3,4-tetrahydroisoquinolin-7-ylthiomethyl)-1-(pyridin-4-yl)piperidine-4-carboxylic acid, 4-[2-(2-amidino-1,2,3,4-tetrahydroisoquinolin-7-ylthio)ethyl]-1-(pyridin-4-yl)piperidine-4-carboxylic acid, 4-(2-amidino-1,2,3,4-tetrahydroisoquinolin-7-ylsulfonylmethyl)-1-(pyridin-4-yl)piperidine-4-carboxylic acid, 4-[2-(2-amidino-1,2,3,4-tetrahydroisoquinolin-7-ylsulfonyl)ethyl]-1-(pyridin-4-yl)piperidine-4-carboxylic acid, 4-(2-amidino-1,2,3,4-tetrahydroisoquinolin-7-ylsulfonylamino)-1-(pyridin-4-yl)piperidine-4-carboxylic acid methyl ester, 4-(2-amidino-1,2,3,4-tetrahydroisoquinolin-7-ylsulfonylamino)-1-(pyridin-4-yl)piperidine-4-carboxylic acid, 4-(2-amidino-1,2,3,4-tetrahydroisoquinolin-7-ylsulfonylaminomethyl)-1-(pyridin-4-yl)piperidine-4-carboxylic acid ethyl ester, 4-(2-amidino-1,2,3,4-tetrahydroisoquinolin-7-ylsulfonylaminomethyl)-1-(pyridin-4-yl)piperidine-4-carboxylic acid, 7-[1-(pyridin-4-ylacetyl)piperidin-4-ylmethoxy]-1,2,3,4-tetrahydroisoquinoline-2-carboxamidine, 7-[1-(3-aminobenzyl)piperidin-4-ylmethoxy-1,2,3,4-tetrahydroisoquinoline-2-carboxamidine, 7-[1-(2-hydroxybenzyl)piperidin-4-ylmethoxy]-1,2,3,4-tetrahydroisoquinoline-2-carboxamidine, 7-[1-(pyridin-2-ylmethyl)piperidin-4-ylmethoxy]-1,2,3,4-tetrahydroisoquinoline-2-carboxamidine, 2-[4-(2-amidino-1,2,3,4-tetrahydroisoquinolin-7-yloxymethyl)piperidin-1-ylmethyl]indole-1-carboxylic acid methyl ester, 4-(2-amidino-1,2,3,4-tetrahydroisoquinolin-7-yloxymethyl)piperidine-1-acetic acid benzyl ester, N-benzyl-4-(2-amidino-1,2,3,4-tetrahydroisoquinolin-7-yloxymethyl)piperidine-1-carboxamide, 7-[1-(indol-2-ylmethyl)piperidin-4-ylmethoxy]-1,2,3,4-tetrahydroisoquinoline-2-carboxamidine, 4-(2-amidino-1,2,3,4-tetrahydroisoquinolin-7-yloxymethyl)piperidine-1-acetic acid, N-benzyl-4-(2-amidino-1,2,3,4-tetrahydroisoquinolin-7-yloxymethyl)piperidine-1-acetamide, 4-(2-amidino-1,2,3,4-tetrahydroisoquinolin-7-yloxymethyl)piperidin-1-ylacetylaminoacetic acid, 7-[1-(5-nitropyridin-2-yl)piperidin-4-ylmethoxy]-1,2,3,4-tetrahydroisoquinoline-2-carboxamidine, 7-[1-(2-nitrobenzyl)piperidin-4-ylmethoxy]-1,2,3,4-tetrahydroisoquinoline-2-carboxamidine, 7-[1-(2-aminobenzyl)piperidin-4-ylmethoxy]-1,2,3,4-tetrahydroisoquinoline-2-carboxamidine, 7-(1-hexaneidoylpiperidin-4-ylmethoxy)-1,2,3,4-tetrahydroisoquinoline-2-carboxamidine, N-benzyl-4-(2-amidino-1,2,3,4-tetrahydroisoquinolin-7-yloxymethyl)piperidine-1-sulfonamide, N-butyl-4-(2-amidino-1,2,3,4-tetrahydroisoquinolin-7-yloxymethyl)piperidine-1-sulfonamide, N-cyclohexyl-4-(2-amidino-1,2,3,4-tetrahydroisoquinolin-7-yloxymethyl)-piperidine-1-sulfonamide, N-(2-nitrophenyl)-4-(2-amidino-1,2,3,4-tetrahydroisoquinolin-7-yloxymethyl)piperidine-1-carbothioamide, 7-[1-(benzimidazol-2-yl)piperidin-4-ylmethoxy]-1,2,3,4-tetrahydroisoquinoline-2-carboxamidine, 3-[4-[4-(2-amidino-1,2,3,4-tetrahydroisoquinolin-7-yloxymethyl)piperidin-1-yl]pyridin-3-yl]propionic acid ethyl ester, 3-[4-[4-(2-amidino-1,2,3,4-tetrahydroisoquinolin-7-yloxymethyl)piperidin-1-yl]pyridin-3-yl]propionic acid, 4-(2-amidino-1,2,3,4-tetrahydroisoquinolin-7-yloxymethyl)-1-(2-aminopyridin-5-ylcarbonyl)piperidine-4-carboxylic acid, 4-(2-amidino-1,2,3,4-tetrahydroisoquinolin-7-yloxymethyl)-1-(3-aminopropionyl)-piperidine-4-carboxylic acid, 4-(2-amidino-1,2,3,4-tetrahydroisoquinolin-7-yloxymethyl)-1-(imidazol4-ylacetyl)piperidine-4-carboxylic acid, 4-(2-amidino-1,2,3,4-tetrahydroisoquinolin-7-yloxymethyl)-1-(piperidin-4-ylsulfamoyl)piperidine-4-carboxylic acid, 4-(2-amidino-1,2,3,4-tetrahydroisoquinolin-7-yloxymethyl)-1-dimethylaminoacetylpiperidine-4-carboxylic acid, 4-(2-amidino-1,2,3,4-tetrahydroisoquinolin-7-yloxymethyl)-1-(pyridin-3-ylcarbamoyl)piperidine-4-carboxylic acid ethyl ester, 4-(2-amidino-1,2,3,4-tetrahydroisoquinolin-7-yloxymethyl)-1-(1-dimethylaminoacetylpiperidin-2-ylcarbonyl)piperidine-4-carboxylic acid ethyl ester, 4-[4-(2-amidino-1,2,3,4-tetrahydroisoquinolin-7-yloxymethyl)-4-carboxypiperidin-1-yl]--methylpyridinium chloride, 4-(2-amidino-1,2,3,4-tetrahydroisoquinolin-7-yloxymethyl)-1-(4-amidinophenyl)-piperidine-4-carboxylic acid ethyl ester, 4-(2-amidino-1,2,3,4-tetrahydroisoquinolin-7-yloxymethyl)-1-(2,6-dimethylpyridin-4-yl)piperidine-4-carboxylic acid ethyl ester, 4-(2-amidino-1,2,3,4-tetrahydroisoquinolin-7-yloxymethyl)-1-(2-methylpyridin-4-yl)piperidine-4-carboxylic acid ethyl ester, 4-(2-amidino-1,2,3,4-tetrahydroisoquinolin-7-yloxymethyl)-1-(1-ethylpiperidin-4-yl)piperidine-4-carboxylic acid ethyl ester, 4-(2-amidino-1,2,3,4-tetrahydroisoquinolin-7-yloxymethyl)-1-(1-ethylpiperidin-4-yl)piperidine-4-carboxylic acid, 7-[2-(4-cyanopiperidin-4-yl)ethoxy]-1,2,3,4-tetrahydroisoquinoline-2-carboxamidine, 4-[2-(2-amidino-1,2,3,4-tetrahydroisoquinolin-7-yloxy)ethyl]-1-(pyridin-4-yl)piperidine-4-carboxylic acid ethyl ester, 4-(2-amidino-6-methoxy-1,2,3,4-tetrahydroisoquinolin-7-yloxymethyl)-1-(pyridin-4-yl)piperidine-4-carboxylic acid, and 4-(2-amidino-6-methyl-1,2,3,4-tetrahydroisoquinolin-7-yloxymethyl)-1-(pyridin-4-yl)piperidine-4-carboxylic acid, or a salt thereof or a prodrug thereof.

(11) A pharmaceutical composition comprising an amidine compound of any of the above (1) to (10) or a salt thereof or a prodrug thereof, and a pharmaceutically acceptable additive.

(12) A blood coagulation inhibitor comprising an amidine compound of any of the above (1) to (10) or a salt thereof or a prodrug thereof as an active ingredient.

(13) A factor Xa inhibitor comprising an amidine compound of any of the above (1) to (10) or a salt thereof or a prodrug thereof as an active ingredient.

(14) An agent for the prophylaxis or treatment of diseases caused by blood coagulation or thrombus, which comprises an amidine compound of any of the above (1) to (10) or a salt thereof or a prodrug thereof as an active ingredient.

(15) A method for inhibiting coagulation of blood, which comprises administering the amidine compound of any of the above (1) to (10) or a salt thereof or a prodrug thereof.

(16) A method for inhibiting factor Xa, which comprises administering the amidine compound of any of the above (1) to (10) or a salt thereof or a prodrug thereof.

(17) A method for the prophylaxis or treatment of diseases caused by blood coagulation or thrombus, which comprises administering the amidine compound of any of the above (1) to (10) or a salt thereof or a prodrug thereof.

(18) Use of the amidine compound of any of the above (1) to (10) or a salt thereof or a prodrug thereof for the production of a blood coagulation inhibitor.

(19) Use of the amidine compound of any of the above (1) to (10) or a salt thereof or a prodrug thereof for the production of a factor Xa inhibitor.

(20) Use of the amidine compound of any of the above (1) to (10) or a salt thereof or a prodrug thereof for the production of an agent for the prophylaxis or treatment of diseases caused by blood coagulation or thrombus.

(21) A commercial package comprising the blood coagulation inhibitor of the above (12) and a written matter associated therewith, the written matter stating that the inhibitor can or should be used for inhibiting coagulation of blood.

(22) A commercial package comprising the factor Xa inhibitor of the above (13) and a written matter associated therewith, the written matter stating that the inhibitor can or should be used for inhibiting factor Xa.

(23) A commercial package comprising the agent for the prophylaxis or treatment of the above (14) and a written matter associated therewith, the written matter stating that the agent can or should be used for the prophylaxis or treatment of diseases caused by blood coagulation or thrombus.

DETAILED DESCRIPTION OF THE INVENTION

The terms used in the present specification to explain the inventive compound are defined as follows.

"Lower alkyl group" is linear or branched alkyl group having 1 to 6 carbon atoms, which is exemplified by methyl group, ethyl group, propyl group, isopropyl group, butyl group, isobutyl group, tert-butyl group, pentyl group, tert-pentyl group, hexyl group and the like, with preference given to methyl group, ethyl group, propyl group, isopropyl group, butyl group, isobutyl group, tert-butyl group and the like having 1 to 4 carbon atoms. Lower alkyl group at $R^{13}$ is optionally be substituted by carboxy group, lower alkoxycarbonyl group or aralkyloxycarbonyl group.

"Cycloalkyl group" is alkyl having cyclic alkyl moiety having 3 to 10 carbon atoms. Examples thereof include cyclopropyl group, 2,3-dimethylcyclopropyl group, cyclobutyl group, 3-methylcyclobutyl group, cyclopentyl group 3,4-dimethylcyclopentyl group, cyclohexyl group, 4-methylcyclohexyl group, cycloheptyl group, cyclooctyl group, norbornyl group, adamantyl group, bicyclo[3.3.0]octan-1-yl group or bicyclo[3.3.1]nonan-9-yl group and the like. Preferred are cycloalkyl having 3 to 7 carbon atoms, such as cyclopropyl group, cyclobutyl group, cyclopentyl group, cyclohexyl group and the like. Cycloalkyl group at $R^8$ is optionally substituted by lower alkyl group or carboxy group.

"Alkylene group having 1 to 6 carbon atoms" is linear or branched alkylene group having 1 to 6 carbon atoms, such as methylene group, ethylene group, propylene group, butylene group, pentylene group, hexylene group and the like, which is preferably methylene group, ethylene group, propylene group, butylene group and the like having 1 to 4 carbon atoms.

"Alkenylene group having 2 to 6 carbon atoms" is linear or branched alkenylene group having 2 to 6 carbon atoms, such as ethylene group, 1-propenylene group, 1-butenylene group, 2-butenylene group, 3-butenylene group, 1-pentenylene group, 2-pentenylene group, 3-pentenylene group, 1-hexenylene group, 2-hexenylene group, 3-hexenylene group, 4-hexenylene group, 5-hexenylene group and the like. Preferred are ethylene group, 1-propenylene group, 1-butenylene group, 2-butenylene group, 3-butenylene group and the like having 2 to 4 carbon atoms.

"Aryl group" is phenyl group, naphthyl group or biphenyl group having 6 to 12 carbon atoms, with preference given to phenyl group. Aryl group at $R^6$ is optionally substituted by 1 to 3 substituents selected from lower alkyl group, hydroxy group, lower alkoxy group, carboxy group, lower alkoxycarbonyl group, aralkyloxycarbonyl group, nitro group, amino group, acylamino group, amidino group and hydroxyamidino group. Aryl group at $R^8$ is optionally substituted by 1 to 3 substituents selected from halogen atom, lower alkyl group (said lower alkyl group is optionally substituted by halogen atom), hydroxy group, lower alkoxy group, carboxy group and lower alkoxycarbonyl group. Aryl group at $R^{13}$ is optionally substituted by carboxy group, lower alkoxycarbonyl group or aralkyloxycarbonyl group.

"Heteroaryl group" is 5 or 6-membered aromatic ring having 1 to 3 hetero atoms selected from nitrogen atom, oxygen atom and sulfur atom, and may form a condensed ring with other ring that may be partially saturated. Examples thereof include imidazolyl group, pyridyl group, pyridine-1-oxide group, pyrimidyl group, thienyl group, thiazolyl group, isoxazolyl group, oxadiazolyl group, triazolyl group, indolyl group, quinolyl group, furyl group, benzofuryl group, 1H-benzimidazolyl group, 2-benzothiazolyl group and the like. Preferred are pyridyl group, pyridine-1-oxide group, thienyl group, thiazolyl group, isoxazolyl group, indolyl group and the like. Heteroaryl group at $R^6$ is optionally substituted by 1 to 3 substituents selected from lower alkyl group, hydroxy group, lower alkoxy group, carboxy group, lower alkoxycarbonyl group, aralkyloxycarbonyl group, nitro group, amino group, acylamino group, amidino group and hydroxyamidino group. Heteroaryl group at $R^8$ is optionally substituted by 1 to 3 substituents selected from halogen atom, lower alkyl group (said lower alkyl group is optionally substituted by halogen atom), hydroxy group, lower alkoxy group, carboxy group and lower alkoxycarbonyl group. The binding site of these heteroaryl groups is not limited as long as the site is chemically acceptable.

"Aralkyl group" is arylalkyl group wherein aryl moiety is as exemplified for the above-mentioned "aryl group" and alkyl moiety is as exemplified for the above-mentioned "lower alkyl group", and is exemplified by benzyl group, phenethyl group, phenylpropyl group, phenylbutyl group, phenylhexyl group and the like. Aralkyl group may have, on the aryl group, 1 to 3 substituents selected from halogen atom, lower alkyl group, hydroxy group, lower alkoxy group, haloalkyl group, cyano group, nitro group, amino group, acyloxy group and the like. It may be substituted simultaneously with two or more substituents, but preferably mono-substituted. The position of substitution is not particularly limited as long as it is chemically acceptable.

"Lower alkoxy group" is linear or branched alkoxy group having 1 to 6 carbon atoms and is exemplified by methoxy group, ethoxy group, propoxy group, isopropoxy group, butoxy group, tert-butoxy group, pentyloxy group, tert-pentyloxy group, hexyloxy group and the like. Preferred are methoxy group, ethoxy group, propoxy group, isopropoxy group, butoxy group, tert-butoxy group and the like having 1 to 4 carbon atoms.

"Lower alkoxycarbonyl group" is that wherein the lower alkoxy moiety is those exemplified for the above-mentioned "lower alkoxy group". Examples thereof include methoxycarbonyl group, ethoxycarbonyl group, propoxycarbonyl group, isopropoxycarbonyl group, butoxycarbonyl group, isobutoxycarbonyl group, tert-butoxycarbonyl group and the like, with preference given to methoxycarbonyl group, ethoxycarbonyl group, propoxycarbonyl group and the like.

"Aralkyloxycarbonyl group" is that wherein the aralkyl moiety is those exemplified for the above-mentioned "aralkyl group". Examples thereof include benzyloxycarbonyl group, 2-phenylethoxycarbonyl group, 3-phenylpropoxycarbonyl group and the like, which may be substituted by halogen atom, nitro group, alkyl group, alkoxy group, trifluoromethyl group and the like. Preferred is benzyloxycarbonyl group.

"Acyl group" is formyl group; alkanoyl group having 2 to 6 carbon atoms such as acetyl group, propionyl group, butyryl group, pivaloyl group and the like; or aroyl group such as benzoyl group and the like wherein aryl group may have 1 to 3 substituents. Preferred are formyl group, acetyl group, pivaloyl group, benzoyl group and the like.

"Imidoyl group" is formimidoyl group, acetimidoyl group, propanimidoyl group, butanimidoyl group, pentanimidoyl group or hexanimidoyl group and the like having 1 to 6 carbon atoms. Preferred are acetimidoyl group, propanimidoyl group and the like.

"Lower alkylamino group" is amino group monosubstituted by those exemplified to the above-mentioned "lower alkyl group". Examples thereof include methylamino group, ethylamino group, propylamino group or butylamino group and the like, with preference given to methylamino group, ethylamino group, propylamino group and the like.

"Di(lower)alkylamino group" is amino group disubstituted by those exemplified for the above-mentioned "lower alkyl group", and is exemplified by dimethylamino group, diethylamino group, dipropylamino group, methylethylamino group, methylpropylamino group and the like. Preferred are dimethylamino group, diethylamino group and the like.

"Di(lower)alkylamino(lower)alkanoyl group" is alkanoyl group substituted by those exemplified for the above-mentioned "di(lower)alkylamino group". Examples thereof include dimethylaminoacetyl group, dimethylaminoacetyl group, dipropylaminoacetyl group, methylethylaminoacetyl group, methylpropylaminoacetyl group, dimethylaminopropanoyl group, diethylaminopropanoyl group, dipropylaminopropanoyl group and the like. Preferred are dimethylaminoacetyl group, diethylaminoacetyl group and the like.

"Acylamino group" is amino group substituted by those exemplified for the above-mentioned "acyl group". Examples thereof include formylamino group; alkanoylamino group having 2 to 6 carbon atoms such as acetylamino group, propionylamino group, butyrylamino group, pivaloylamino group and the like; and aroylamino group such as benzoylamino group and the like, wherein aryl group may be substituted by 1 to 3 substituents. Preferred are formylamino group, acetylamino group, pivaloylamino group, benzoylamino group and the like.

"Halogen atom" is chlorine, bromine, fluorine or iodine, with preference given to chlorine or bromine.

"Saturated 5- to 7-membered heterocycle having at least one nitrogen atom" is exemplified by pyrrolidine, piperidine, hexahydroazepine, and oxazolidine, thiazolidine, imidazolidine, morpholine, thiomorpholine, piperazine, tetrahydrooxazepine, tetrahydrothiazepine, hexahydrodiazepine and the like having, as hetero atom, oxygen, sulfur and/or nitrogen atom. Saturated 5- to 7-membered heterocycle having at least one nitrogen atom at $R^6$ may be substituted by lower alkyl group, acyl group, di(lower)alkylamino(lower)alkanoyl group or imidoyl group.

"The salt" of the compound includes, but not limited to, inorganic acid addition salt such as hydrochloride, hydrobromide, sulfate, phosphate, nitrate and the like;

organic acid addition salt such as acetate, propionate, succinate, glycolate, lactate, malate, oxalate, tartrate, citrate, maleate, fumarate, methanesulfonate, benzenesulfonate, p-toluenesulfonate, ascorbate and the like; addition salt with amino acid such as aspartate, glutamate and the like; salt with inorganic base such as sodium, potassium, calcium, magnesium and the like; salt with organic base such as methylamine, dimethylamine, ethylamine, diethylamine, triethylamine, triethanolamine, trishydroxymethylaminomethane, dicyclohexylamine, ethylenedimane, quinine, guanidine and the like; and base salt with amino acid such as asparagine, glutamine, arginine, histidine, lysine and the like. The salt may be water containing compound or hydrate.

"The prodrug" of a compound is a derivative of the compound of the present invention, which has a chemically or metabolically degradable group and which shows pharmaceutical activity upon hydrolysis, solvolysis, or decomposition under physiolocial conditions.

"Various diseases caused by blood coagulation or thrombus" include cerebrovascular deseases such as cerebral infarction, cerebral thrombosis, cerebral embolism, transient ischemia attack (TIA), subarachnoid hemorrhage and the like; ischemic heart diseases such as acute or chronic myocardial infarction, unstable angina, coronary thrombosis and the like; pulmonary vascular diseases such as pulmonary infarction, pulmonary embolism and the like; and diseases associated with various vascular disorders such as peripheral arterial embolism, deep vein thrombosis, disseminated intravascular coagulation, thrombosis after surgery of artificial blood vessels or replacement of artificial valve, reocclusion or restenosis after coronary bypass, reocclusion or restenosis after percutaneous transluminal coronary angioplasty (PICA) or percutaneous transluminal coronary recanalization (PIFCR), thrombosis due to extracorporeal circulation, and the like.

The compound of the present invention is explained in detail in the following.

Of the inventive compounds of the formula [I], R is a group of the formula

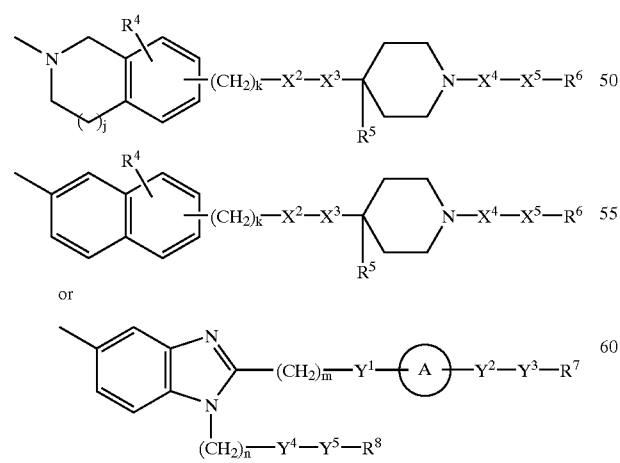

and preferably a group of the formula

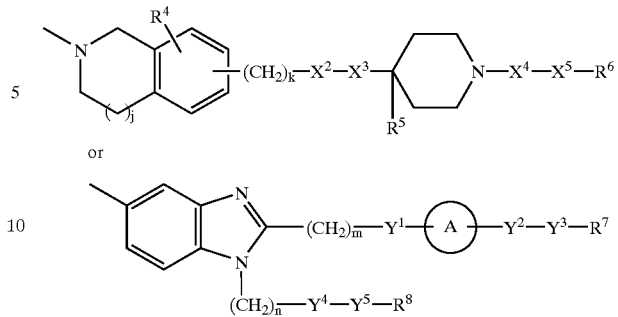

and particularly preferably a group of the formula

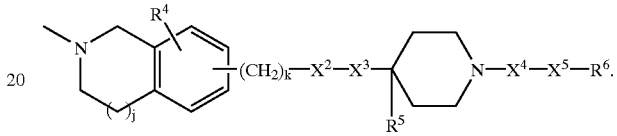

$R^1$, $R^2$ and $R^3$ are preferably hydrogen atom.
The mode of connection of

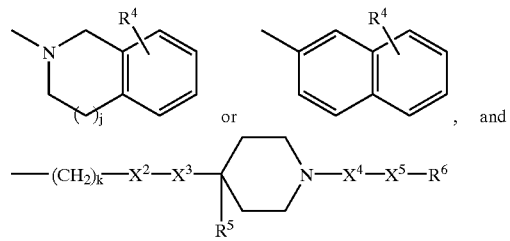

is preferably as shown by the formula

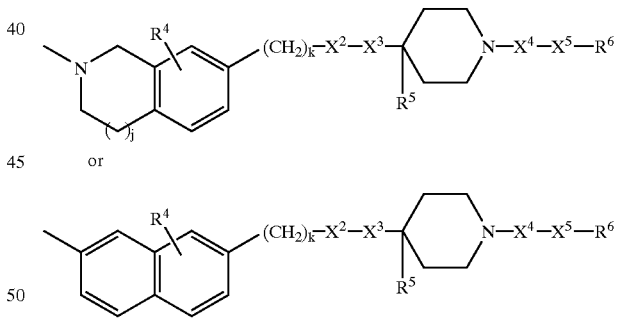

Preferable $R^4$ is hydrogen atom, lower alkoxy group or halogen atom, which is particularly preferably hydrogen atom. Preferable $R^5$ is hydrogen atom, carboxy group or lower alkoxycarbonyl group, particularly preferably carboxy group. Preferable $R^6$ is hydrogen atom, carboxy group, lower alkoxycarbonyl group, aryl group or heteroaryl group wherein aryl group or heteroaryl group is optionally substituted by 1 to 3 substituents selected from lower alkyl group, hydroxy group, lower alkoxy group, carboxy group, lower alkoxycarbonyl group, aralkyloxycarbonyl group, nitro group, amino group, acylamino group, amidino group and hydroxyamidino group, which is particularly preferably pyridyl group.

Preferable $X^2$ is oxygen atom or sulfur atom, which is particularly preferably oxygen atom. $X^3$ is preferably —$(CH_2)_m$—, particularly preferably —$(CH_2)_0$—. $X^4$ is preferably

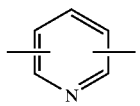

or a single bond, particularly preferably a single bond. $X^5$ is preferably alkenylene group having 2 to 6 carbon atoms or a single bond, which is particularly preferably a single bond. Preferred j is 1, and k is preferably 0.

$R^7$ is preferably

wherein $R^9$ is preferably oxygen atom or NH, and particularly preferably NH. $R^{10}$ is preferably lower alkyl group, lower alkoxy group or amino group, and particularly preferably lower alkyl group or amino group. $R^8$ is preferably hydrogen atom, aryl group, heteroaryl group wherein aryl group or heteroaryl group is optionally substituted by 1 to 3 substituents selected from halogen atom, lower alkyl group (said lower alkyl group is optionally substituted by halogen atom), hydroxy group, lower alkoxy group, carboxy group and lower alkoxycarbonyl group, particularly preferably phenyl group.

$Y^1$ is preferably oxygen atom or —$NR^{12}$— wherein $R^{12}$ is preferably —$Y^6$—$R^{13}$ wherein $R^{13}$ is preferably phenyl group optionally substituted by carboxy group or lower alkoxycarbonyl group, $Y^6$ is preferably —CO—, particularly preferably —N—$Y^6$—$R^{13}$. $Y^2$ is preferably oxygen atom. $Y^3$ is preferably

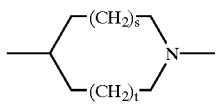

wherein s and t are each preferably 2. $Y^4$ is preferably —CONH—. $Y^5$ is preferably —$(CH_2)_p$—, —$(CH_2)_p{}'$—CHAk—$(CH_2)_p{}''$—, —$(CH_2)_p{}'$—CAk Ak'—$(CH_2)_p{}''$— wherein p is preferably 1 or 2, p' is preferably 1 and p" is preferably 0, which is particularly preferably —$(CH_2)_p{}'$—CHAk—$(CH_2)_p{}''$—. The ring A is preferably a group of the formula

The compound of the formula [I] of the present invention includes tautomer, stereoisomer, optical isomer and geometrical isomer. The present invention encompasses all of them.

The production method of the compound of the present invention is explained in the following, to which the production method of the inventive compound is not limited.

Production Method 1

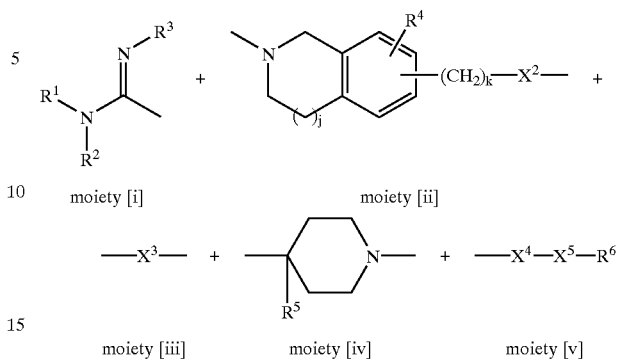

moiety [i]   moiety [ii]

moiety [iii]   moiety [iv]   moiety [v]

The production method shown here is suitable for producing, of the compounds of the formula [I], compound of the formula [I']

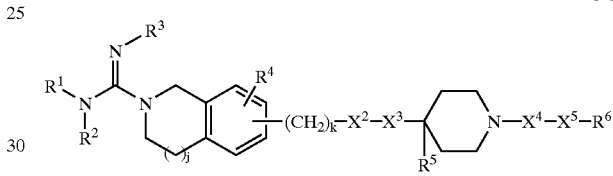

[I']

In this case, connection between moieties [i], [ii], [iii], [iv] and [v] can be started from any position. Construction or conversion of each moiety may be carried out independently or may be done after connecting some moieties. When reactive functional group is present, a protecting group may be introduced or removed as appropriate.

[1] Connection of moiety [i] and moiety [ii]

A compound at the moiety [ii] of the formula (2)

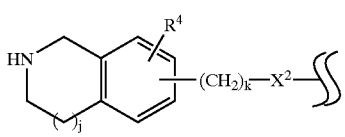

(2)

wherein

means connection with other moiety or binding of a convertible group such as hydrogen atom, protecting group or leaving group and the like (hereinafter the same in the following formulas), and $R^4$, $X^2$, j and k are each as defined above, is reacted with the compound of the moiety [i] of the formula (3)

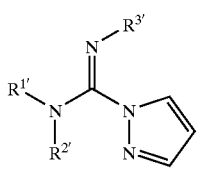

(3)

wherein $R^{1'}$, $R^{2'}$ and $R^{3'}$ are the same or different and each is hydrogen atom, hydroxy group, lower alkyl group, aryl group or a protecting group of nitrogen atom, or a salt thereof, in the presence of a base such as triethylamine, N,N-diisopropylethylamine, N-methylmorpholine and the like to give a compound of the formula (4)

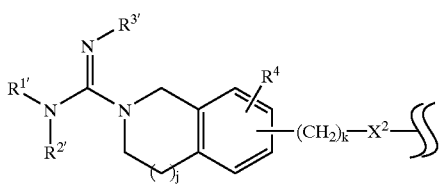

(4)

wherein $R^{1'}$, $R^{2'}$, $R^{3'}$, $R^4$, $X^2$, j and k are each as defined above. When any of $R^{1'}$, $R^{2'}$ and $R^{3'}$ is a protecting group, this protecting group can be removed by a conventional method.

Alternatively, ammonium thiocyanate and benzoyl chloride are reacted in advance under heating and a compound of the formula (2) is reacted to give a thioamide compound. Then, after treating with an acid such as hydrogen chloride, hydrogen bromide and the like, the compound is reacted with methyl iodide under heating, preferably at 50° C.–70° C. The compound may be reacted with amine having the desired substituent.

Alternatively, the compound of the formula (2) and the compound of the formula (5)

$R^1$—NCS (5)

wherein $R^1$ is as defined above, are reacted and then with methyl iodide to give thiomethyl compound, followed by reaction with ammonium acetate or amine having the desired substituent.

When a compound of moiety [ii] wherein j is 2 is desired, a compound of the formula (6)

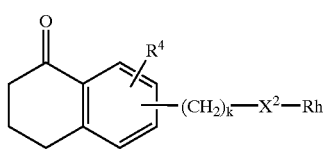

(6)

wherein Rh is a protecting group such as methyl group and the like, and $R^4$, $X^2$ and k are as defined above, is reacted with sodium azide and subjected to rearrangement reaction to give an azepinone compound. This compound is reduced with lithium aluminum hydride to give a compound of the formula (7)

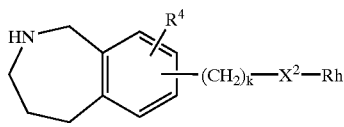

(7)

wherein $R^4$, $X^2$, Rh and k are as defined above.

[2] Connection or construction of moiety [ii] and moiety [iii]
A compound at the moiety [ii] of the formula (8)

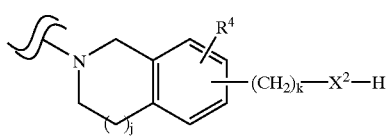

(8)

wherein $R^4$, $X^2$, j and k are as defined above, and a compound at the moiety [iii] of the formula (9)

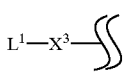

(9)

wherein $L^1$ is leaving group such as halogen atom and the like or hydroxy and $X^3$ is as defined above, are reacted to give a compound of the formula (10)

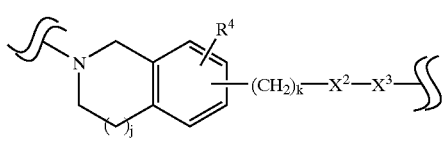

(10)

wherein $R^4$, $X^2$, $X^3$, j and k are as defied above. When $L^1$ is a leaving group, it is subjected to alkylation using a base such as sodium hydride, sodium hydroxide, potassium hydroxide, sodium carbonate, potassium carbonate, triethylamine, N,N-diisopropylethylamine and the like, and when $L^1$ is hydroxy, it is subjected to Mitsunobu reaction using triphenylphosphine and diisopropyl azodicarboxylate.

When a compound wherein $X^2$ is —$SO_2$— is desired, a compound of the formula (10) wherein $X^2$ is sulfur atom is oxidized using a peracid such as m-chloroperbenzoic acid or peracetic acid and the like to give a compound of the formula (11)

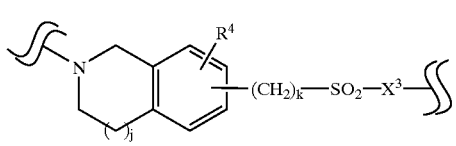

(11)

wherein $R^4$, $X^3$, j and k are as defined above.

When a compound wherein $X^2$ is —$SO_2NH$— is desired, a compound of the formula (12)

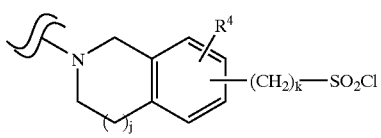
(12)

wherein R⁴, j and k are as defined above, and a compound of the formula (13)

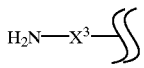
(13)

wherein X³ is as defined above, are subjected to typical amnidation under basic conditions to give a compound of the formula (14)

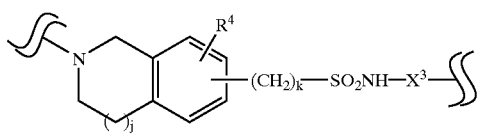
(14)

wherein R⁴, X³, j and k are as defined above.

When a compound wherein k is 1 and X² is oxygen atom is desired, a compound of the formula (15)

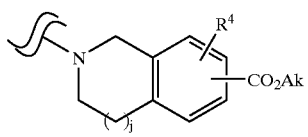
(15)

wherein R⁴, Ak and j are as defined above is reduced using a reducing reagent such as sodium borohydride, lithium borohydride, lithium aluminum hydride, sodium cyanoborohydride and the like to give a compound of the formula (16)

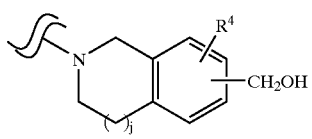
(16)

wherein R⁴ and j are as defined above. The resultant compound is condensed with a compound of the formula (9) by the method shown in the production method of a compound of the formula (10) to give a compound of the formula (17)

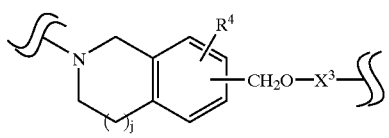
(17)

wherein R⁴, X³ and j are as defined above.

[3] Connection or construction of moiety [iii] and moiety [iv]

When a compound wherein R⁵ is hydrogen atom and X³ is —CH₂—, —(CH₂)₂— or —(CH₂)₃— is desired, the formula (18)

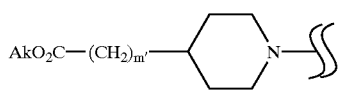
(18)

wherein m' is 0 or an integer of 1 or 2 and Ak is as defined above, is reduced using a reducing reagent such as lithium aluminum hydride, sodium borohydride, lithium borohydride, sodium cyanoborohydride and the like to give a compound of the formula (19)

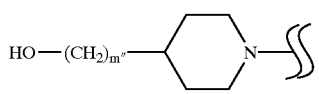
(19)

wherein m" is an integer of 1 to 3.

Alternatively, a compound of the formula (20)

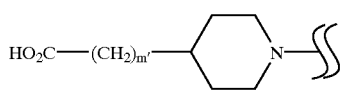
(20)

wherein m' is as defined above, is reduced using a reducing reagent such as borane and the like to give a compound of the formula (19). This compound corresponds to a compound of the formula (9) wherein X³ is —(CH₂)$_{m''}$— and L¹ is hydroxy group.

When a compound wherein R⁵ is cyano group, lower alkoxycarbonyl group or carboxy group and X³ is —CH₂—, —(CH₂)₂— or —(CH₂)₃— is desired, a compound of the formula (21)

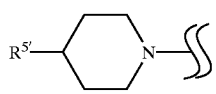
(21)

wherein R⁵' is cyano group, lower alkoxycarbonyl group or carboxy group, is reacted with a compound of the formula (22)

(22)

wherein L² is a leaving group such as halogen atom and the like and m' is as defined above, in the presence of a base such as lithium diisopropylamide and the like at −80° C. to 0° C. to give a compound of the formula (23)

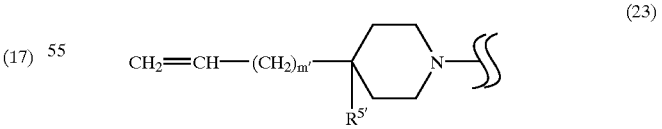
(23)

wherein R⁵' and m' are as defined above. The obtained compound is reacted with an oxidizing reagent such as osmium tetroxide and the like to give a diol compound wherein the double bond was oxidized. This diol compound is subjected to periodate oxidation to allow adjacent diol to be oxidatively cleaved to give an aldehyde compound. This is reduced using a reducing reagent such as sodium borohydride, lithium borohydride, sodium cyanoborohydride and the like to give a compound of the formula (24)

$$HO-(CH_2)_{m''}-\underset{R^{5'}}{\underset{|}{C}}\overset{}{\underset{}{\diagdown}}N-\xi \quad (24)$$

wherein $R^{5'}$ and m" are as defined above. This compound corresponds to a compound of the formula (9) wherein $X^3$ is —$(CH_2)_{m''}$— and $L^1$ is hydroxy group.

Alternatively, a compound of the formula (23) is subjected to periodate oxidation to give a carboxylic acid, which is reduced with a reducing reagent such as borane and the like to give a compound of the formula (24).

Alternatively, a compound of the formula (21) and a compound of the formula (25)

$$\xi-(CH_2)_{\overline{m}}-L^2 \quad (25)$$

wherein $L^2$ and m are as defined above, may be reacted in the presence of a base such as lithium diisopropylamide and the like at −80° C. to 0° C.

When a compound wherein $R^5$ is cyano group is desired, a compound of the formula (26)

$$HO_2C-\diagup\overset{}{\diagdown}N-\xi \quad (26)$$

is amidated and reacted using a dehydrating reagent such as triphenylphosphine and the like to give a compound of the formula (27)

$$NC-\diagup\overset{}{\diagdown}N-\xi \quad (27)$$

Then, this compound may be bonded with a compound of moiety [iii] by a method similar to the production method of a compound of the formula (23) or a known method.

The leaving group $L^2$ can be introduced into a compound of the formula (25) by, for example, a compound of the formula (28)

$$\xi-(CH_2)_{\overline{m}}-SMe \quad (28)$$

wherein m is as defined above is reacted with a halogenation reagent such as sulfuryl chloride and the like to give a compound of the formula (25). The compound of the formula (25) may be converted to a compound with a leaving group having higher reactivity by the use of alkai metal halide.

When a compound wherein $X^2$ is —$SO_2NH$— and $X^3$ is —$(CH_2)_m$— is desired, a compound of the formula (29)

$$HO_2C-(CH_2)_m-\underset{R^5}{\underset{|}{C}}\overset{}{\diagdown}N-\xi \quad (29)$$

wherein $R^5$ and m are as defined above, is subjected to Curtius rearrangement, Hofmann rearrangement and the like to give a carbamate compound, which is subjected to typical removing reaction of amino group to give a compound of the formula (30)

$$H_2N-(CH_2)_m-\underset{R^5}{\underset{|}{C}}\overset{}{\diagdown}N-\xi \quad (30)$$

wherein $R^5$ and m are as defined above. This compound corresponds to a compound of the formula (13) wherein $X^3$ is —$(CH_2)_m$—.

Alternatively, a compound of the formula (31)

$$O=\diagup\overset{}{\diagdown}N-\xi \quad (31)$$

is subjected to Strecker reaction by reacting hydrogen cyanide in the presence of ammonia to give a compound of the formula (32)

$$H_2N-\underset{CN}{\underset{|}{C}}\overset{}{\diagdown}N-\xi \quad (32)$$

This compound corresponds to a compound of the formula (30) wherein $R^5$ is cyano group and m is 0. Subsequent alcoholysis gives a compound of the formula (33) wherein $R^5$ of the formula (30) is lower alkoxycarbonyl $$H_2N-\underset{CO_2Ak}{\underset{|}{C}}\overset{}{\diagdown}N-\xi \quad (33)$$

wherein Ak is as defined above, and hydrolysis of the resultant compound gives a compound of the formula (34) wherein $R^5$ of the formula (30) is carboxy group $$H_2N-\underset{CO_2H}{\underset{|}{C}}\overset{}{\diagdown}N-\xi \quad (34)$$

[4] Connection or construction of moiety [iv] and moiety [v]

A compound at the moiety [iv] of the formula (35)

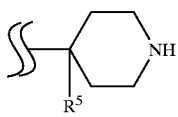
(35)

wherein $R^5$ is as defined above, is reacted with a compound at the moiety [v] of the formula (36)

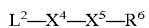
(36)

wherein $R^6$, $X^4$, $X^5$ and $L^2$ are as defined above, in the presence of a base such as sodium hydride, potassium hydride, sodium hydroxide, potassium hydroxide, lithium hydroxide, sodium carbonate, potassium carbonate, sodium hydrogencarbonate, potassium hydrogencarbonate, triethylamine, N,N-diisopropylethylamine, pyridine and the like or reacted using a base such as triethylamine, N,N-diisopropylethylamine and the like at 120–160° C. to give a compound of the formula (37)

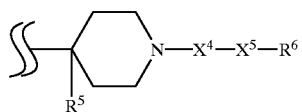
(37)

wherein $R^5$, $R^6$, $X^4$ and $X^5$ are as defined above.

When a compound wherein $R^6$ is aryl group or heteroaryl group and the aryl group or heteroaryl group is substituted by amino group or acylamino group is desired, a compound having nitro group as a substituent at aryl group or heteroaryl group is reduced to give a compound having amino as a substituent. Further, an acylation reagent such as acyl halide, acid anhydride and the like is reacted to give a compound having of acylamino group as a substituent.

When a compound wherein $X^5$ is —CH=CH— is desired, a compound of the formula (38)

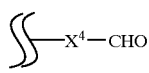
(38)

wherein $X^4$ is as defined above, is reacted with a compound of the formula (39)

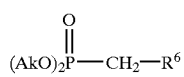
(39)

wherein $R^6$ and Ak are as defined above, in the presence of a base such as sodium hydride, potassium hydride and the like, to give a compound of the formula (40)

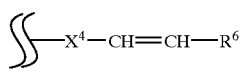
(40)

wherein $R^6$ and $X^4$ are as defined above.

Production Method 2

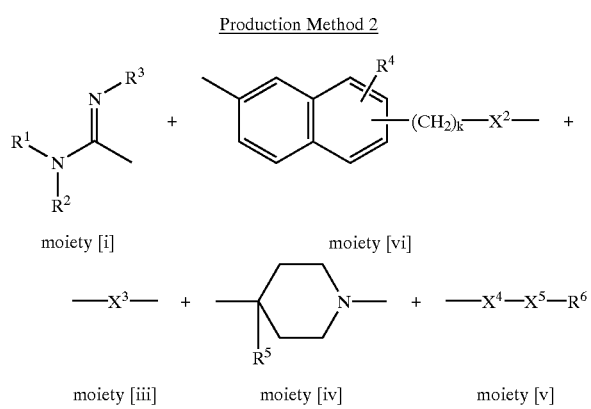

The production method shown here is suitable for producing, of the compounds of the formula [I], a compound of the formula [I"]

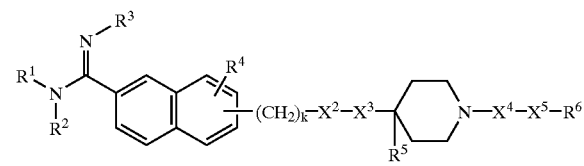
[I"]

In this case, connection between moieties [i], [iii], [iv], [v] and [vi] can be started from any position. Construction or conversion of each moiety may be carried out independently or may be done after connecting some moieties. When reactive functional group is present, a protecting group may be introduced or removed as appropriate.

[5] Connection and construction of moiety [i] and moiety [vi]

A compound at the moiety [vi] of the formula (41)

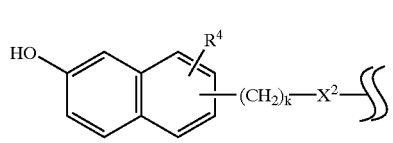
(41)

wherein $R^4$, $X^2$ and k are as defined above, is reacted with a sulfonylation reagent such as trifluoromethanesulfonic anhydride and the like to convert hydroxy group thereof to a leaving group and reacted with cyanation reagent such as zinc cyanide and the like in the presence of a catalyst such as tetrakis-(triphenylphosphine)palladium and the like to give a cyano compound. The resultant compound is reacted with hydrogen sulfide under basic conditions to give a thioamide compound, which is further S-alkylated with methyl iodide and the like and reacted with ammonium acetate or amine having a desired substituent to give a compound of the formula (42)

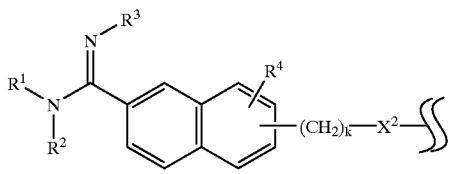
(42)

wherein $R^1$, $R^2$, $R^3$, $R^4$, $X^2$ and k are as defined above.

When a compound of the formula (43) having halogen atom at the 8-position at $R^4$

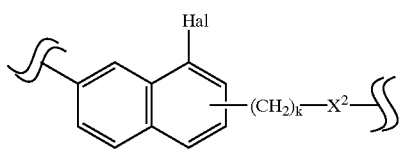
(43)

wherein Hal is halogen atom, and $X^2$ and k are as defined above, is desired, a compound of the formula (44)

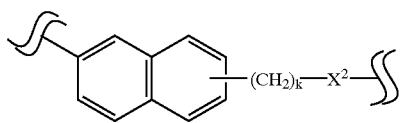
(44)

wherein $X^2$ and k are as defined above is halogenized with a halogenizing reagent such as tert-butyl hypochlorite and the like.

Connection of moiety [vi] and moiety [iii], and moiety [iii]-moiety [v] can be carried out in the same manner as in the connection of moiety [ii]-moiety [v] shown in Production Method 1.

The production method shown here is suitable for producing, of the compounds of the formula [I], a compound of the formula [I''']

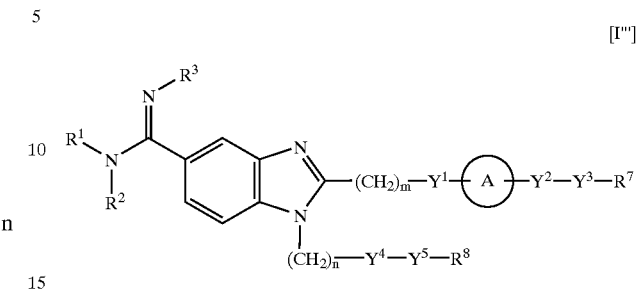
[I''']

In this case, connection between moieties [i], [vii], [viii], [ix], [x] and [xi] can be started from any position. Construction or conversion of each moiety may be carried out independently or may be done after connecting some moieties. When reactive functional group is present, a protecting group may be introduced or removed as appropriate.

[6] Connection and construction of moiety [i] and moiety [vii]

Using a compound of the formula (45)

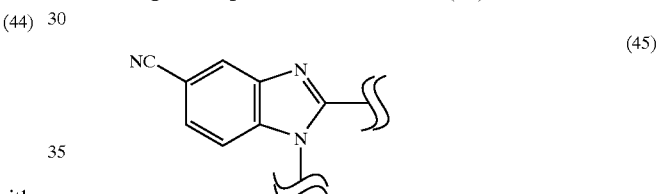
(45)

and connection or construction of moiety [i] and moiety [vi] as shown in Production Method 2 is carried out to give a compound of the formula (46)

Production Method 3

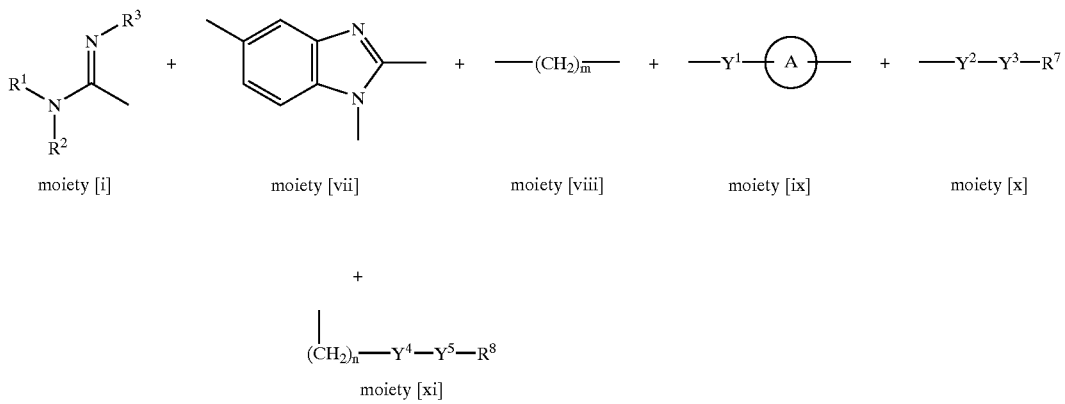

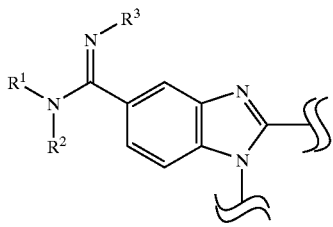
(46)

wherein $R^1$, $R^2$, $R^3$ are each as defined above.

[7] Connection and construction of moiety [vii] and moiety [viii], moiety [xi]

A compound of the formula (47)

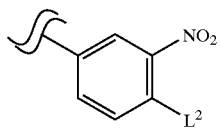
(47)

wherein $L^2$ is as defined above, is reacted with a compound at the moiety [xi] of the formula (48)

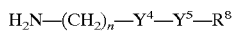
(48)

wherein $R^8$, $Y^4$, $Y^5$ and n are each as defined above, or a salt thereof, in the presence of a base such as triethylamine, N,N-diisoropylethylamine, sodium hydrogencarbonate, potassium hydrogencarbonate, sodium carbonate, potassium carbonate and the like to give a compound of the formula (49)

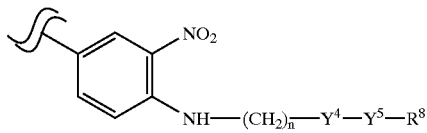
(49)

wherein $R^8$, $Y^4$, $Y^5$ and n are as defined above. The compound of the formula (48) itself may be used as a base.

The nitro group of a compound of the formula (49) is reduced by a known method to give a compound of the formula (50)

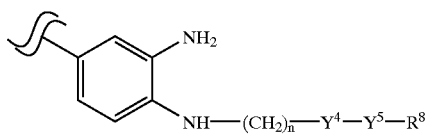
(50)

wherein $R^8$, $Y^4$, $Y^5$ and n are each as defined above, and reacted with a compound of moiety [viii] of the formula (51)

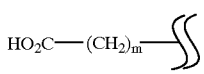
(51)

wherein m is as defined above, to give a compound of the formula (52)

(52)

wherein $R^8$, $Y^4$, $Y^5$, m and n are as defined above.

Alternatively, a compound of the formula (53)

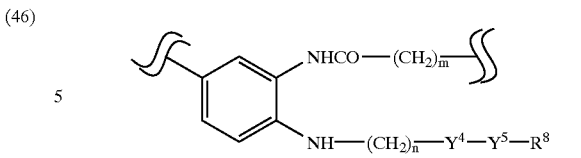
(53)

and a compound of the formula (51) are reacted to give a compound of the formula (54)

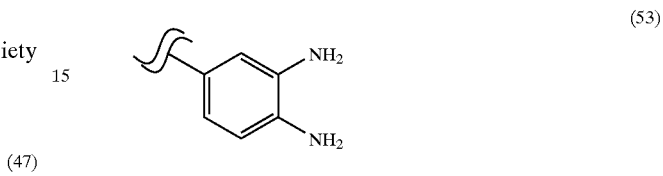
(54)

wherein m is as defined above. This reaction can be a typical amidation reaction. For example, a condensing reagent such as dicyclohexylcarbodiimide (DCC), diisopropylcarbodiimide, 1-ethyl-3-(3-dimethylaminopropyl)carbodiimide hydrochloride (EDC·HCl), diphenylphosphorylazide or 2-ethoxy-1-ethoxycarbonyl-1,2-dihydroquinoline (EEDQ) and the like is used, or mixed acid anhydride method using alkylhalocarbonate and the like, or after conversion of carboxylic acid to acid halide using thionyl chloride, oxalyl chloride and the like, reaction under basic conditions, or other method may be used.

A compound of the formula (55)

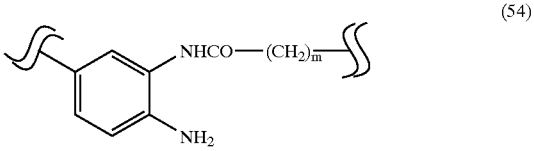
(55)

wherein Rh' is a protecting group such as methyl group, ethyl group and the like and m is as defined above, is deprotected by a conventional method to give a compound of the formula (51). Alternatively, a compound of the formula (56)

(56)

wherein m is as defined above, is oxidized by a typical method to give a compound of the formula (51).

A compound of the formula (52) and a compound of the formula (54) are subjected to ring-closing reaction under acidic conditions using acetic acid, methanesulfonic acid, p-toluenesulfonic acid and the like to give a compound of the formula (57)

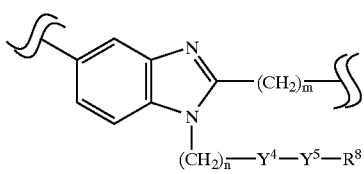
(57)

wherein $R^8$, $Y^4$, $Y^5$, m and n are as defined above, or a compound of the formula (58)

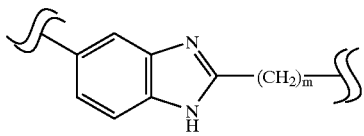
(58)

wherein m is as defined above, respectively.

Alternatively, a compound of the formula (59)

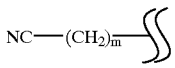
(59)

is converted to imidate using an alkoxide, such as sodium methoxide, sodium ethoxide, potassium tert-butoxide and the like, and reacted with a compound of the formula (50) or a compound of the formula (53) under acidic conditions to give a compound of the formula (57) or a compound of the formula (58), respectively.

When a compound wherein $Y^4$ is CONH— is desired, a compound of the formula (60)

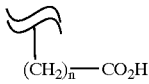
(60)

wherein n is as defined above, and a compound of the formula (61)

$H_2N-Y^5-R^8$ (61)

wherein $R^8$ and $Y^5$ are as defined above, are reacted in the same manner as shown in the production method of a compound of the formula (52) or a compound of the formula (54), to give a compound of the formula (62)

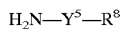
(62)

wherein $R^8$, $Y^5$ and n are as defined above.

When a compound wherein $Y^4$ is oxygen atom, $Y^5$ is a single bond and $R^8$ is lower alkyl group is desired, a compound of the formula (63)

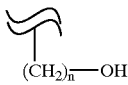
(63)

wherein n is as defined above, and a compound of the formula (64)

$L^1-R^{8'}$ (64)

wherein $R^{8'}$ is lower alkyl group and $L^1$ is as defined above, are reacted in the same manner as shown in the production method of a compound of the formula (37) to give a compound of the formula (65)

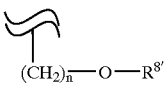
(65)

wherein $R^{8'}$ and n are as defined above.

When a compound wherein $Y^4$ is —CO—, $Y^5$ is a single bond and $R^8$ is heteroaryl group is desired, a compound of the formula (60) is reacted with N,O-dimethylhydroxylamine in the same manner as shown in the production method of a compound of the formula (52) or a compound of the formula (54) to give a compound of the formula (66)

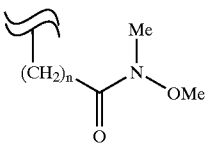
(66)

wherein n is as defined above. Separately, a compound of the formula (67)

$H-R^{8''}$ (67)

wherein $R^{8''}$ is heteroaryl group is activated with a base such as butyl lithium and the like and reacted with the above-mentioned compound (66) to give a compound of the formula (68)

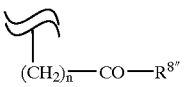
(68)

wherein $R^{8''}$ and n are as defined above.

[8] Connection and construction of moiety [viii] and moiety [ix]

A compound at the moiety [viii] of the formula (69)

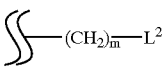
(69)

wherein $L^2$ and m are as defined above, is reacted with a compound of the formula (70)

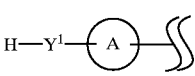
(70)

wherein $Y^1$ and ring A are as defined above, in the presence of a base such as sodium hydride, potassium hydride, sodium hydroxide, potassium hydroxide, lithium hydroxide, sodium carbonate, potassium carbonate, sodium hydrogencarbonate, potassium hydrogencarbonate, triethylamine, N,N-diisopropylethylamine, pyridine and the like to give a compound of the formula (71)

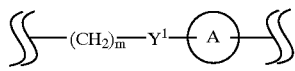 (71)

wherein $Y^1$, ring A and m are each as defined above.

When a compound wherein $Y^1$ is NH is desired, the compound is protected with a protecting group such as benzyloxycarbonyl, tert-butoxycarbonyl and the like and subjected to the reaction and deprotected to give a compound of the formula (72)

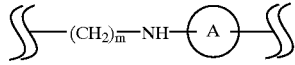 (72)

wherein ring A and m are as defined above. In addition, when a compound wherein $Y^1$ is —$NR^{12}$— is desired, a compound of the formula (72) is reacted with a compound of the formula (73)

 (73)

wherein $R^{12}$ and $L^2$ are as defined above, in the same manner as in the production method of a compound of the formula (49) to give a compound of the formula (74)

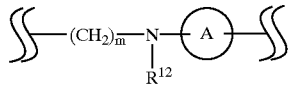 (74)

wherein $R^{12}$ and m are as defined above.

When a compound wherein $R^{12}$ is —$Y^{6}$—$R^{13}$, $Y^6$ is —CO—, —$CO_2$—, —$COCO_2$— or —$SO_2$— is desired, a compound of the formula (72) is reacted with a compound of the formula (75)

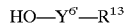 (75)

wherein $Y^{6'}$ is —CO—, —$CO_2$—, —$COCO_2$— or —$SO_2$— and $R^{13}$ is as defined above, in the same manner as in the production method of a compound of the formula (52) or the formula (54) to give a compound of the formula (76)

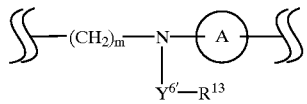 (76)

wherein $R^{13}$, $Y^{6'}$, ring A and m are as defined above.

When a compound wherein $Y^1$ is a single bond and the ring A is a group of the formula

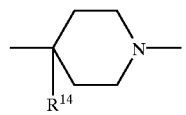

is desired, a compound of the formula (77)

 (77)

wherein $R^{14}$ is as defined above, and a compound of the formula (69) are reacted in the same manner as in the production method of a compound of the formula (23) to give a compound of the formula (78)

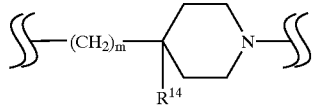 (78)

wherein $R^{14}$ and m are as defined above.

When a compound wherein $Y^1$ is oxygen atom is desired, a compound of the formula (79)

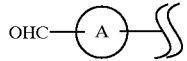 (79)

wherein ring A is as defined above, is oxidized with peracid such as m-chloroperbenzoic acid, peracetic acid and the like to give a compound of the formula (80)

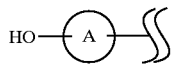 (80)

wherein ring A is as defined above. This compound corresponds to a compound of the formula (70) wherein $Y^1$ is oxygen atom.

[9] Connection and construction of moiety [ix] and moiety [x]

A compound at the moiety [ix] of the formula (81)

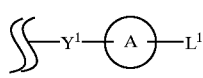 (81)

wherein $Y^1$, $L^1$ and ring A are as defined above, is reacted with a compound of the formula (82)

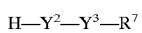 (82)

wherein $R^7$, $Y^2$ and $Y^3$ are as defined above, in the same manner as in the production method of a compound of the formula (10) to give a compound of the formula (83)

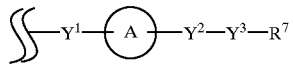 (83)

wherein $R^7$, $Y^1$, $Y^2$, $Y^3$ and ring A are as defined above.

When a compound wherein ring A has the following formula

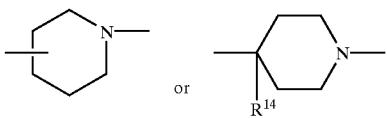

and $Y^2$ is a single bond, is desired, a compound of the formula (84)

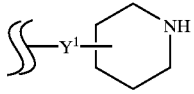
(84)

wherein $Y^1$ is as defined above, or a compound of the formula (85)

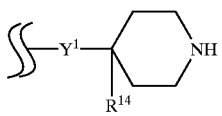
(85)

wherein $R^{14}$ and $Y^1$ are as defined above, is reacted with a compound of the formula (86)

$$L^2\text{—}Y^3\text{—}R^7 \tag{86}$$

wherein $R^7$, $Y^3$ and $L^2$ are as defined above, in the same manner as in the production method of a compound of the formula (37) to give a compound of the formula (87)

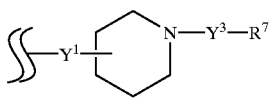
(87)

wherein $R^7$, $Y^1$ and $Y^3$ are as defined above, or a compound of the formula (88)

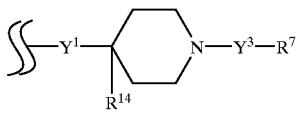
(88)

wherein $R^7$, $R^{14}$, $Y^1$ and $Y^3$ are as defined above.

When a compound wherein $Y^3$ is a group of the formula

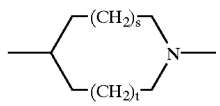

and $R^7$ is lower alkyl group or

is desired, a compound of the formula (89)

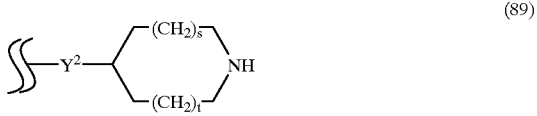
(89)

wherein $Y^2$, s and t are as defined above, is reacted with a compound of the formula (90)

$$L^3\text{—}R^{7'} \tag{90}$$

wherein $L^3$ is a leaving group such as ethoxy group, 1-pyrazolyl group, halogen atom and the like and $R^{7'}$ is lower alkyl group or a group of the formula

wherein $R^9$ and $R^{10}$ are as defined above, in the presence of a base such as triethylamine, N,N-diisopropylethylamine, sodium hydrogencarbonate, potassium hydrogencarbonate, sodium carbonate, potassium carbonate, sodium hydroxide, potassium hydroxide, lithium hydroxide, sodium hydride, potassium hydride and the like to give a compound of the formula (91)

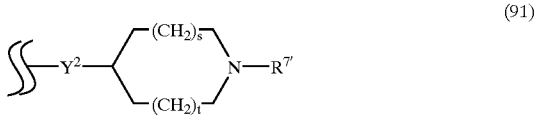
(91)

wherein $R^7$, $Y^2$, s and t are as defined above.

The compound of the formula [I] of the present invention thus obtained has a factor Xa inhibitory action. When the inventive compound is used as a factor Xa inhibitor or anti-blood coagulation agent, it is generally administered orally or parenterally and systemically or locally.

While the dose varies depending on the age, body weight, symptom, therapeutic effect, administration route, treatment time and the like, it is generally from 0.01 mg to 1 g for an adult, which is orally or parenterally administered once to several doses per day.

When the compound of the present invention is formulated into solid compositions for oral administration, it can be prepared into a dosage form such as tablet, pill, powder, granule and the like. In such solid compositions, one or more active substances are admixed with at least one inert diluent, dispersing agent or absorbent, such as lactose, mannitol, glucose, hydroxypropylcellulose, microcrystralline cellulose, starch, polyvinylpyrrolidone, magnesium aluminometasilicate and anhydrous silicate powder. Moreover, the composition may comprise additives other than the diluent according to a conventional method.

When the compound is formulated into tablet or pill, gastric coating or enteric coating of, for example, sucrose, gelatin, hydroxypropylcellulose or hydroxymethylcellulose phthalate may be applied, or two more layers may be formed. Moreover, a capsule made from a substance such as gelatin and ethylcellulose may be used.

When a liquid composition for oral administration is desired, the compound can be formulated into a dosage form such as pharmaceutically acceptable emulsion, solution, suspension, syrup, elixir and the like. Examples of diluent to be used include purified water, ethanol, vegetable oil and emulsifier. This composition may also comprise, besides the diluent, auxiliary agents such as wetting agent, suspending agent, sweetener, flavor, aromatic and preservative.

When the compound is prepared into an injection for parenteral administration, a sterile aqueous or nonaqueous solution, solubilizer, suspending agent or emulsifier is used. Examples of the aqueous solution, solubilizer and suspending agent include distilled water for injection, physiological saline, cyclodextrin and its derivatives, organic amines such as triethanolamine, diethanolamine, monoethanolamine, triethylamine, and inorganic alkaline solution.

When the compound is prepared into an aqueous solution, propylene glycol, polyethylene glycol, vegetable oils such as olive oil, alcohols such as ethanol and the like may be used. As the solubilizer, for example, polyoxyethylene hydrogenated castor oil, surfactants such as sucrose fatty acid ester (forming mixed micelle), lecithin and hydrogenated lecithin (forming liposome) may be used. In addition, an emulsion preparation comprising a nonaqueous solvent such as vegetable oil, and lecithin, polyoxyethylene hydrogenated castor oil, or polyoxyethylene polyoxypropylene glycol may be produced.

As other composition for parenteral administration, an external liquid, liniment such as ointment, suppository or pessary comprising one or more active ingredients, which can be formulated by a method known in this field of the art, may be employed.

EXAMPLES

The compound of the formula [I] of the present invention and production method thereof are explained in detail by way of the Examples below. It is needless to say that the present invention is not to be limited to these Examples.

Example 1

Synthesis of 7-[1-(Pyridin-4-yl)piperidin-4-ylmethoxy]-1,2,3,4-tetrahydroisoquinoline-2-carboxamidine Dihydrochloride Step 1
7-Hydroxy-1,2,3,4-tetrahydroisoquinoline-2-carboxylic Acid Tert-butyl Ester

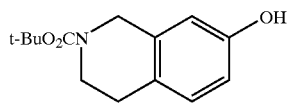

7-Hydroxy-1,2,3,4-tetrahydroisoquinoline hydrobromide (370 mg) was dissolved in 1N aqueous sodium hydroxide solution (4 ml) and 1,4-dioxane (8 ml) and di-tert-butyl dicarbonate (386 mg) was added, which was followed by stirring at room temperature overnight. The reaction mixture was extracted with ethyl acetate and the organic layer was washed with saturated brine. The organic layer was dried over anhydrous sodium sulfate and the solvent was evaporated under reduced pressure to give the title compound (385 mg).

Step 2
4-Hydroxymethyl-1-(pyridin-4-yl)piperidine

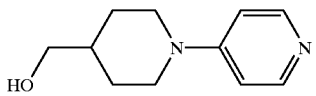

Under an argon atmosphere, to a solution of 1-(pyridin-4-yl)piperidine-4-carboxylic acid (*Tetrahedron*, vol. 44, No. 23, page 7095 (1988)) (500 mg) in tetrahydrofuran (5 ml) was added 1M borane-tetrahydrofuran solution (14.5 ml) with ice-cooling, and the mixture was stirred at room temperature for 12 hours. After completion of the reaction, the reaction mixture was poured into ice water and extracted with ethyl acetate. The organic layer was washed successively with water and saturated brine, and dried over anhydrous sodium sulfate. The solvent was evaporated under reduced pressure and the obtained residue was dissolved in 12% hydrochloric acid and stirred at 50° C. for 1 hour. The reaction mixture was neutralized with aqueous sodium hydrogencarbonate and 4N aqueous sodium hydroxide solution, and extracted with ethyl acetate. The organic layer was washed with saturated brine and dried over anhydrous sodium sulfate. The solvent was evaporated under reduced pressure and dried under reduced pressure to give the title compound (400 mg).

$^1$H-NMR (δ ppm, CDCl$_3$) 1.24–1.38 (m, 2H), 1.70–1.90 (m, 3H), 2.86 (m, 2H), 3.53 (d, 2H), 3.92 (m, 2H), 6.66 (d, J=5.1 Hz, 2H), 8.22 (d, J=5.1 Hz, 2H).

Step 3
7-[1-(Pyridin-4-yl)piperidin-4-ylmethoxy]-1,2,3,4-tetrahydroisoquinoline-2-carboxylic Acid tert-Butyl Ester

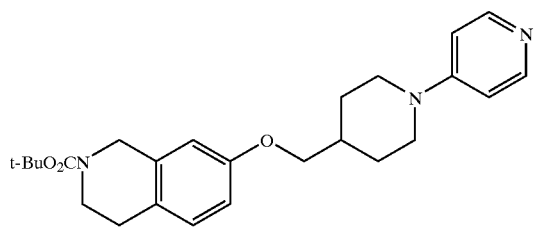

To a mixture of 7-hydroxy-1,2,3,4-tetrahydroisoquinoline-2-carboxylic acid tert-butyl ester (389 mg) and 4-hydroxymethyl-1-(pyridin-4-yl)piperidine (300 mg) in tetrahydrofuran (15 ml) and methylene chloride (5 ml) were added triphenylphosphine (450 mg) and diisopropyl azodicarboxylate (0.34 ml) and the mixture was stirred at room temperature for 24 hours. After completion of the reaction, the reaction mixture was concentrated under reduced pressure and the obtained residue was purified by silica gel column chromatography (hexane:acetone=3:2–1:1, 1% triethylamine) and dried under reduced pressure to give the title compound (500 mg).

$^1$H-NMR (δ ppm, CDCl$_3$) 1.36–1.50 (m, 11H), 1.92–2.15 (m, 3H), 2.76 (brtr, 2H), 2.90 (brtr, 2H), 3.62 (brtr, 2H), 3.80 (d,2H), 3.90–3.96 (m, 2H), 4.53 (s, 2H), 6.62–6.74 (m, 4H), 7.04 (1H), 8.25 (2H).

Step 4
7-[1-(Pyridin-4-yl)piperidin-4-ylmethoxy]-1,2,3,4-tetrahydroisoquinoline

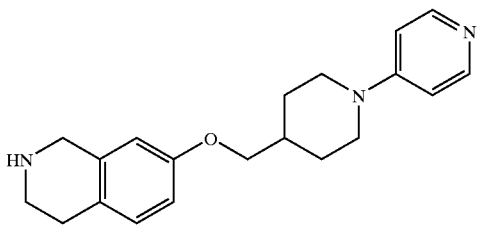

To a solution of 7-[1-(pyridin-4-yl)piperidin-4-ylmethoxy]-1,2,3,4-tetrahydroisoquioline-2-carboxylic acid tert-butyl ester (500 mg) in chloroform (5 ml) was added trifluoroacetic acid (2.5 ml) and the mixture was stirred at room temperature for 1 hour. After completion of the reaction, the reaction mixture was concentrated under reduced pressure. Aqueous sodium hydrogencarbonate solution was added and the mixture was extracted with ethyl acetate. The organic layer was washed successively with water and saturated brine and dried over anhydrous sodium sulfate. The solvent was evaporated and dried under reduced pressure to give the title compound (350 mg).

$^1$H-NMR (δ ppm, CDCl$_3$) 1.30–1.49 (m, 2H), 1.91–2.15 (m, 3H), 2.72 (tr, J=6.0Hz, 2H), 2.90 (m, 2H), 3.11 (tr, J=6.0 Hz, 2H), 3.79 (d, 2H), 3.90–3.98 (m, 4H), 6.54 (1H), 6.66–6.72 (m, 3H), 6.99 (1H), 8.25 (2H).

Step 5
7-[1-(Pyridin-4-yl)piperidin-4-ylmethoxy]-1,2,3,4-tetrahydroisoquinoline-2-carboxamidine Dihydrochloride

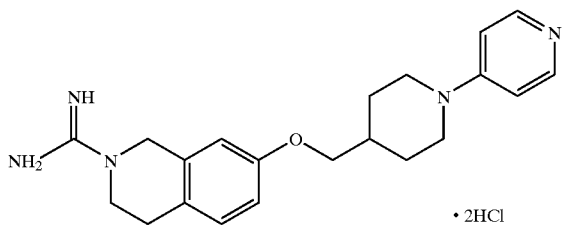

To a solution of 7-[1-(pyridin-4-yl)piperidin-4-ylmethoxy]-1,2,3,4-tetrahydroisoquinoline (50 mg) in dimethylformamide (0.5 ml) were added diisopropylethylamine (0.027 ml) and 1H-pyrazole-1-carboxamidine hydrochloride (23 mg), and the mixture was stirred at room temperature for 12 hours. After completion of the reaction, diethyl ether was added and insoluble material was collected by filtration. The obtained solid was washed with diethyl ether. A part (45 mg) of the obtained solid was treated with hydrogen chloride-methanol and dried under reduced pressure to give the title compound (44 mg).

$^1$H-NMR (δ ppm, DMSO-d$_6$) 1.20–1.45 (m, 2H), 1.88–1.93 (m, 2H), 2.17 (m, 1H), 2.81 (tr, J=6.0 Hz, 2H), 3.20 (m, 2H), 3.57 (tr, J=6.0Hz, 2H), 3.85 (m, 2H), 4.23–4.28 (m, 2H), 4.54 (s, 2H), 6.70 (d, J=2.7 Hz, 1H), 6.82 (dd, J=2.7, 8.4 Hz, 1H), 7.13 (d, J=8.4 Hz, 1H), 7.19 (d, J=7.8 Hz, 2H), 7.64 (brs, 4H), 8.19 (d, J=7.8 Hz, 2H), 13.68 (brs, 1H).

Example 2

Synthesis of 7-[1-(Quinolin-4-yl)piperidin-4-ylmethoxy]-1,2,3,4-tetrahydroisoquinoline-2-carboxamidine Dihydrochloride Step 1
1-(Quinolin-4-yl)piperidine-4-carboxylic Acid Ethyl Ester

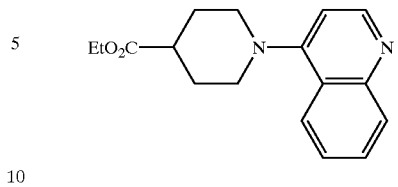

A solution of 4-chloroquinoline (2 g), isonipecotinic acid ethyl ester (2.8 ml) and triethylamine (3.4 ml) in ethanol (7.5 ml) was stirred in a sealed tube at 150° C. for 5 days. After completion of the reaction, water was added and the mixture was extracted with ethyl acetate. The organic layer was washed successively with water and saturated brine, and dried over anhydrous sodium sulfate. The solvent was evaporated and the obtained residue was purified by silica gel column chromatography (hexane:acetone=3:1) and dried under reduced pressure to give the title compound (3.2 g).

Step 2
4-Hydroxymethyl-1-(quinolin-4-yl)piperidine

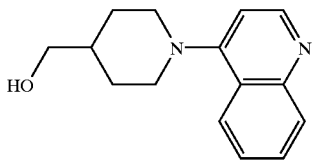

To a solution of lithium aluminum hydride (267 mg) in tetrahydrofuran (10 ml) was added dropwise 1-(quinolin4-yl)piperidine-4-carboxylic acid ethyl ester (1 g) in tetrahydrofuran (10 ml) under nitrogen atmosphere and with ice-cooling, and the mixture was stirred at the same temperature for 2 hours. After completion of the reaction, aqueous sodium sulfate was added with ice-cooling and the mixture was filtered through celite. The solvent was evaporated and the obtained solid was washed with diisopropyl ether and dried under reduced pressure to give the title compound (750 mg).

$^1$H-NMR (δ ppm, CDCl$_3$) 1.57–1.90 (m, 3H), 1.93–2.05 (m, 2H), 2.85 (m, 2H), 3.64–3.68 (m, 4H), 6.84 (d, J=4.8 Hz, 1H), 7.47 (m, 1H), 7.65 (m, 1H), 8.01 (m, 2H), 8.67 (d, J=4.8 Hz, 1H).

Step 3
7-[1-(Quinolin-4-yl)piperidin-4-ylmethoxy]-1,2,3,4-tetrahydroisoquinoline-2-carboxylic Acid tert-Butyl Ester

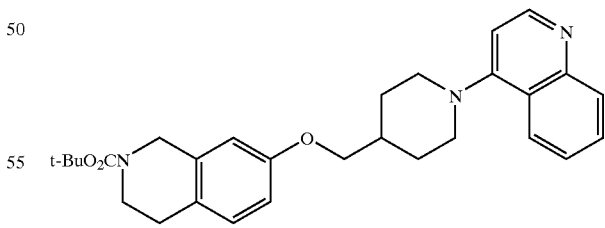

In the same manner as in Example 1, Step 3, the title compound (280 mg) was obtained from 7-hydroxy-1,2,3,4-tetrahydroisoquinoline-2-carboxylic acid tert-butyl ester (206 mg), 4-hydroxymethyl-1-(quinolin-4-yl)pipenidine (200 mg), triphenylphosphine (238 mg) and diisopropyl azodicarboxylate (0.18 ml).

Step 4
7-[1-(Quinolin-4-yl)piperidin-4-ylmethoxy]-1,2,3,4-tetrahydroisoquinoline

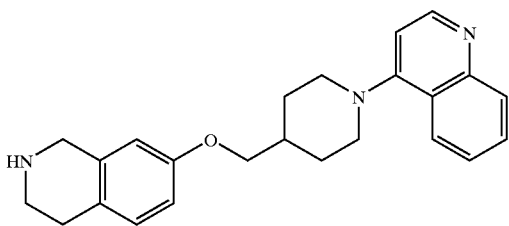

In the same manner as in Example 1, Step 4, the title compound (200 mg) was obtained from 7-[1-(quinolin-4-yl)piperidin-4-ylmethoxy]-1,2,3,4-tetrahydroisoquinoline-2-carboxylic acid tert-butyl ester (275 mg).

Step 5
7-[1-(Quinolin-4-yl)piperidin-4-ylmethoxy]-1,2,3,4-tetrahydroisoquinoline-2-carboxamidine Dihydrochloride

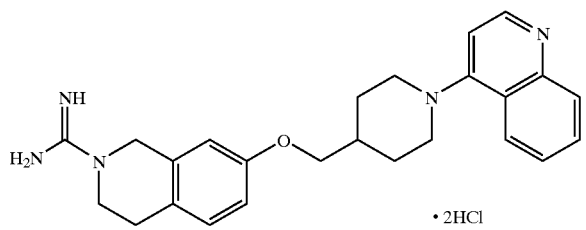

In the same manner as in Example 1, Step 5, the title compound (75 mg) was obtained from 7-[1-(quinolin-4-yl)piperidin-4-ylmethoxy]-1,2,3,4-tetrahydroisoquinoline (70 mg), diisopropylethylamine (0.033 ml) and 1H-pyrazole-1-carboxamidine hydrochloride (28 mg).

$^1$H-NMR (δ ppm, DMSO-$d_6$) 1.55–1.66 (m, 2H), 1.96–2.02 (m, 2H), 2.22 (m, 1H), 2.82 (tr, J=6.0 Hz, 2H), 3.49 (m, 2H), 3.58 (tr, J=6.0 Hz, 2H), 3.92 (m, 2H), 4.17–4.23 (m, 2H), 4.56 (s, 2H), 6.73 (d, J=2.4 Hz, 1H), 6.85 (dd, J=2.4, 8.1 Hz, 1H), 7.15 (d, J=8.4 Hz, 1H), 7.20 (1H), 7.64 (brs, 4H), 7.69 (1H), 7.96 (1H), 8.12 (m, 2H), 8.63 (1H).

Example 3

Synthesis of N-methyl-7-[1-(pyridin-4-yl)piperidin-4-ylmethoxy]-1,2,3,4-tetrahydroisoquinoline-2-carboxamidine Dihydrochloride Step 1
7-[1-(Pyridin-4-yl)piperidin-4-ylmethoxy]-1,2,3,4-tetrahydroisoquinoline-2-carbothioamide

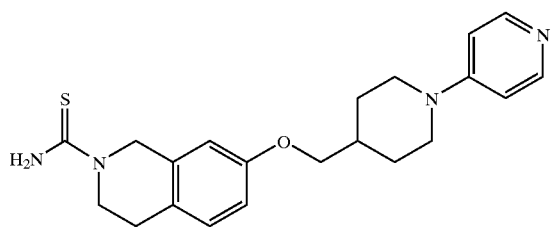

To a solution of ammonium isothiocyanate (220 mg) in acetone (4.5 ml) was dropwise added benzoyl chloride (0.32 ml) at room temperature, and the mixture was stirred at 75° C. for 10 min. Then, a mixture of 7-[1-(pyridin-4-yl)piperidin-4-ylmethoxy]-1,2,3,4-tetrahydroisoquinoline (850 mg) in acetone (4.5 ml) and methylene chloride (4.5 ml) was added dropwise, and the mixture was stirred at the same temperature for 1 hour. After completion of the reaction, the solvent was evaporated and water was added. The mixture was extracted with chloroform. The organic layer was washed successively with water and saturated brine and dried over anhydrous sodium sulfate, and the solvent was evaporated. To the obtained residue was added conc. hydrochloric acid (10 ml), and the mixture was stirred under reflux for 1 hour. After completion of the reaction, water was added and the mixture was washed successively with ethyl acetate and chloroform. The aqueous layer was concentrated and the resultant residue was dissolved in water and ethanol, and neutralized with ion-exchange resin (IRA-410). This was filtrated and the filtrate was concentrated. The obtained residue was purified by silica gel column chromatography (chloroform:methanol=100:1–20:1) and dried under reduced pressure to give the title compound (450 mg).

$^1$H-NMR (δ ppm, DMSO-$d_6$) 1.22–1.35 (m, 2H), 1.76–1.88 (m, 2H), 2.01 (m, 1H), 2.74 (m, 2H), 2.84 (m, 2H), 3.81–4.00 (m, 6H), 4.85 (s, 2H), 6.70–6.82 (m, 4H), 7.08 (1H), 7.44 (brs, 2H), 8.11 (2H).

Step 2
7-[1-(Pyridin-4-yl)piperidin-4-ylmethoxy]-1,2,3,4-tetrahydroisoquinoline-2-carbothioimidic Acid Methyl Ester

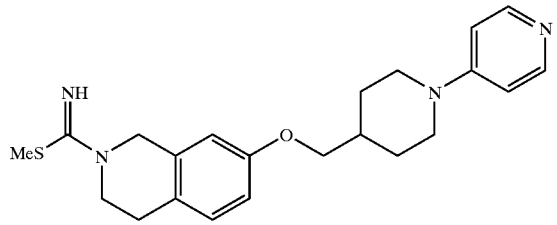

7-[1-(Pyridin-4-yl)piperidin-4-ylmethoxy]-1,2,3,4-tetrahydroisoquinoline-2-carbothioamide (200 mg) was treated with hydrogen chloride—ethanol solution. To a suspension of the obtained residue in methanol (6 ml) was added methyl iodide (0.1 ml), and the mixture was stirred at 60° C. for 2 hours. After completion of the reaction, the solvent was evaporated and the obtained residue was dissolved in water and ethanol and neutralized with ion-exchange resin (IRA-410). This was filtrated and the filtrate was concentrated and dried under reduced pressure to give the title compound (200 mg).

$^1$H-NMR (δ ppm, DMSO-$d_6$) 1.20–1.40 (m, 2H), 1.80–1.90 (m, 2H), 2.03 (m, 1H), 2.47 (s, 3H), 2.79 (tr, J=6.0 Hz, 2H), 2.89 (m, 2H), 3.72 (tr, J=6.0 Hz, 2H), 3.82 (d, 2H), 3.96–4.02 (m, 2H), 4.67 (s, 2H), 6.77–6.86 (m, 4H), 7.08 (1H), 8.12 (2H).

Step 3
N-Methyl-7-[1-(Pyridin-4-yl)piperidin-4-ylmethoxy]-1,2,3,4-tetrahydroisoquinoline-2-carboxamidine Dihydrochloride

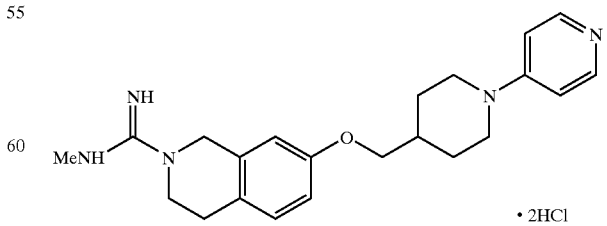

To an ethanol solution (2 ml) of 7-[1-(pyridin-4-yl)piperidin-4-ylmethoxy]-1,2,3,4-tetrahydroisoquinoline-2-carbothioimidic acid methyl ester (100 mg) were added methylamine hydrochloride (20 mg) and sodium acetate (25 mg), and the mixture was stirred at 80° C. for 3 hours. After completion of the reaction, water was added and the mixture was washed with chloroform. Thereto was added aqueous sodium hydrogencarbonate solution and the mixture was washed with chloroform. To the aqueous layer was added 4N aqueous sodium hydroxide solution and the mixture was extracted with chloroform. The extract was washed successively with water and saturated brine. The organic layer was dried over anhydrous sodium sulfate and the solvent was evaporated and the obtained residue was treated with hydrogen chloride—ethanol solution and dried under reduced pressure to give the title compound (80 mg).

$^1$H-NMR (δ ppm, DMSO-d$_6$) 1.19–1.38 (m, 2H), 1.87–1.94 (m, 2H), 2.17 (m, 1H), 2.80 (m, 5H), 3.20 (m, 2H), 3.59 (m, 2H), 3.84 (m, 2H), 4.20–4.29 (m, 2H), 4.56 (s, 2H), 6.70 (1H), 6.81 (1H), 7.12 (1H), 7.19 (2H), 7.75 (2H), 8.03 (1H), 8.20 (2H), 13.74 (1H).

Example 4

Synthesis of 7-[1-(Pyridin-4-yl)piperidin-4-ylmethoxy]-1,2,3,4-tetrahydroisoquinoline-2-carboxamide Oxime Dihydrochloride

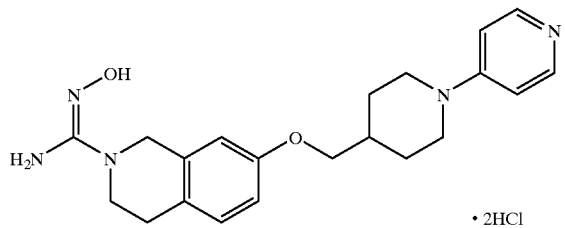

To a solution of 7-[1-(pyridin-4-yl)piperidin-4-ylmethoxy]-1,2,3,4-tetrahydroisoquinoline-2-carbothioimidic acid methyl ester (135 mg) in ethanol (3 ml) were added hydroxyamine hydrochloride (47 mg) and sodium acetate (56 mg), and the mixture was stirred at 40° C. for 2 hours. After completion of the reaction, water was added and the mixture was washed with chloroform. Thereto was added 4N aqueous sodium hydroxide solution, and the mixture was extracted with chloroform. The organic layer was washed successively with water and saturated brine and dried over anhydrous sodium sulfate. The solvent was evaporated and the obtained solid was treated with hydrogen chloride—ethanol solution and dried under reduced pressure to give the title compound (82 mg).

$^1$H-NMR (δ ppm, DMSO-d$_6$) 1.25–1.38 (m, 2H), 1.88–1.95 (m, 2H), 2.17 (m, 1H), 2.81 (tr, J=5.7 Hz, 2H), 3.05–3.25 (m, 2H), 3.56 (tr, J=5.7 Hz, 2H), 3.84 (m, 2H), 4.22–4.29 (m, 2H), 4.52 (s, 2H), 6.70 (d, J=2.4 Hz, 1H), 6.82 (dd, J=2.4, 8.0 Hz, 1H), 7.12 (d, J=8.0 Hz, 1H), 7.19 (d, J=7.5 Hz, 2H), 8.08 (brs, 2H), 8.19 (d, J=7.5 Hz, 2H), 10.06 (s, 1H), 10.86 (brs, 1H), 13.71 (brs, 1H).

Example 5

Synthesis of N-Phenyl-7-[1-(pyridin-4-yl)piperidin-4-ylmethoxy]-1,2,3,4-tetrahydroisoquinoline-2-carboxamidine Dihydrochloride Step 1
N-Phenyl-7-[1-(pyridin-4-yl)piperidin-4-ylmethoxy]-1,2,3,4-tetrahydroisoquinoline-2-carbothioamide

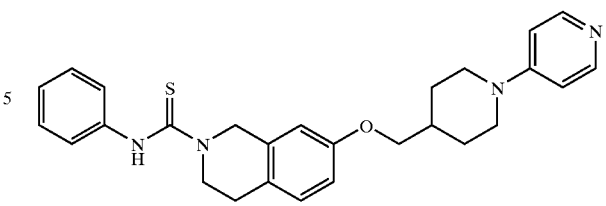

To a solution of 7-[1-(pyridin-4-yl)piperidin-4-ylmethoxy]-1,2,3,4-tetrahydroisoquinoline (30 mg) in methylene chloride (0.5 ml) was added phenyl isothiocyanate (0.012 ml), and the mixture was stirred at room temperature for 1 hour. After completion of the reaction, the solvent was evaporated and the obtained residue was purified by silica gel column chromatography (chloroform:methanol=100:1, 1% triethylamine) and dried under reduced pressure to give the title compound (40 mg).

$^1$H-NMR (δ ppm, CDCl$_3$) 1.36–1.49 (m, 2H), 1.90–2.15 (m, 3H), 2.85–2.95 (m, 4H), 3.79 (d, 2H), 3.84–4.00 (m, 4H), 4.92 (s, 2H), 6.66–6.68 (m, 3H), 6.76 (1H), 7.09–7.38 (m, 6H), 8.24 (2H).

Step 2
N-Phenyl-7-[1-(pyridin-4-yl)piperidin-4-ylmethoxy]-1,2,3,4-tetrahydroisoquinoline-2-carboxamidine Dihydrochloride

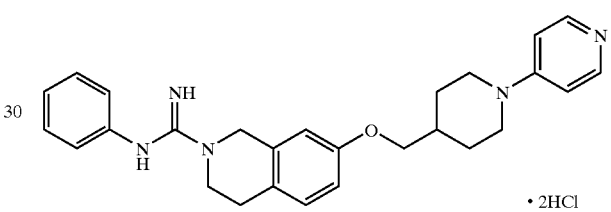

N-Phenyl-7-[1-(pyridin-4-yl)piperidin-4-ylmethoxy]-1,2,3,4-tetrahydroisoquinoline-2-carbothioamide (35 mg) was treated with hydrogen chloride—ethanol solution. To a suspension of the obtained residue in methanol (1 ml) was added methyl iodide (0.014 ml), and the mixture was stirred at 60° C. for 1.5 hours. After completion of the reaction, the solvent was evaporated and the obtained residue was dissolved in water and ethanol and neutralized with ion-exchange resin (IRA-410). This was filtrated and the filtrate was concentrated. To the obtained residue were added ethanol (1 ml) and ammonium acetate (24 mg), and the mixture was stirred under reflux for 12 hours. After completion of the reaction, water was added and the mixture was washed with chloroform. Thereto was added aqueous sodium hydrogencarbonate solution and the mixture was extracted with chloroform. The organic layer was washed successively with water and saturated brine and dried over anhydrous sodium sulfate. The solvent was evaporated and the obtained residue was purified by reverse phase preparative TLC (50% acetonitrile-water, 1.5% trifluoroacetic acid). The obtained residue was treated with hydrogen chloride—ethanol solution and dried under reduced pressure to give the title compound (12 mg).

$^1$H-NMR (δ ppm, DMSO-d$_6$) 1.21–1.37 (m, 2H), 1.88–1.93 (m, 2H), 2.17 (m, 1H), 2.89 (m, 2H), 3.69 (m, 2H), 3.85 (m, 2H), 4.23–4.28 (m, 2H), 4.64 (s, 2H), 6.74 (1H), 6.84 (1H), 7.15–7.28 (m, 6H), 7.43 (2H), 7.96 (2H), 8.20 (2H), 9.66 (brs, 1H), 13.38 (brs, 1H).

Example 6

Synthesis of 4-(2-Amidino-1,2,3,4-tetrahydroisoquinolin-7-yloxymethyl)-1-(pyridin-4-yl)piperidine-4-carboxylic Acid Ethyl Ester Dihydrochloride Step 1
7-Methylthiomethoxy-1,2,3,4-tetrahydroisoquinoline-2-carboxylic Acid tert-Butyl Ester

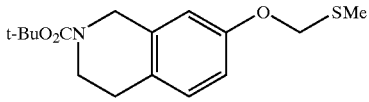

To a solution of 7-hydroxy-1,2,3,4-tetrahydroisoquinoline-2-carboxylic acid tert-butyl ester (13 g) in dimethylformamide (100 ml) was added 60% sodium hydride (2.5 g) under an argon atmosphere, and the mixture was stirred at room temperature for 30 minutes. Then, chloromethyl methyl sulfide (5.2 ml) was dropwise added with ice-cooling, and the mixture was stirred at room temperature overnight. After completion of the reaction, the reaction mixture was poured into water, extracted with ethyl acetate and washed successively with water and saturated brine. The organic layer was dried over anhydrous sodium sulfate and the solvent was evaporated and the obtained residue was purified by silica gel column chromatography (hexane:acetone=20:1–10:1) and dried under reduced pressure to give the title compound (9.6 g).

$^1$H-NMR (δ ppm, CDCl$_3$) 1.49 (s, 9H), 2.25 (s, 3H), 2.77 (tr, J=5.7 Hz, 2H), 3.62 (tr, J=5.7 Hz, 2H), 4.54 (s, 2H), 5.13 (s, 2H), 6.70 (1H), 6.78 (1H), 7.06 (1H).

Step 2
7-Chloromethoxy-1,2,3,4-tetrahydroisoquinoline-2-carboxylic Acid tert-Butyl Ester

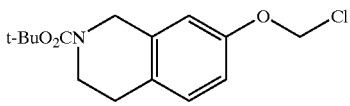

To a solution of 7-methylthiomethoxy-1,2,3,4-tetrahydroisoquinoline-2-carboxylic acid tert-butyl ester (9.6 g) in methylene chloride (100 ml) was added a solution of sulfuryl chloride (2.75 ml) in methylene chloride (30 ml) under an argon atmosphere and with ice-cooling, and the mixture was stirred at the same temperature for 1 hour. The solvent was evaporated and toluene was added to the obtained residue to filter off insoluble material. The solvent was evaporated and dried under reduced pressure to give the title compound (7.4 g).

$^1$H-NMR (δ ppm, CDCl$_3$) 1.49 (s, 9H), 2.79 (tr, J=6.3 Hz, 2H), 3.64 (tr, J=6.3 Hz, 2H), 4.57 (s, 2H), 5.88 (s, 2H), 6.85 (1H), 6.91 (1H), 7.11 (1H).

Step 3
7-[4-Ethoxycarbonyl-1-(pyridin-4-yl)piperidin-4-ylmethoxy]-1,2,3,4-tetrahydroisoquinoline-2-carboxylic Acid tert-Butyl Ester

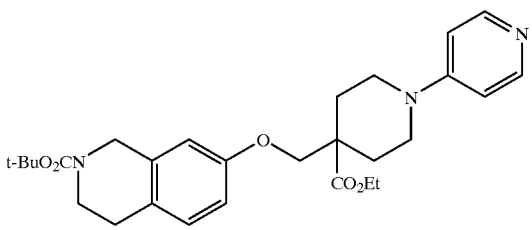

To a solution of 1-(pyridin-4-yl)piperidine-4-carboxylic acid ethyl ester (*Tetrahedron*, vol. 44, No. 23, p. 7095 (1988)) (13.4 g) in tetrahydrofuran (300 ml) was dropwise added a 2M-lithium diisopropylamide-tetrahydrofuran solution (31 ml) at −70° C. under an argon atmosphere, and the mixture was stirred at the same temperature for 45 min. To this solution was dropwise added a solution of 7-chloromethoxy-1,2,3,4-tetrahydroisoquinoline-2-carboxylic acid tert-butyl ester (7.4 g) in tetrahydrofuran (80 ml) at the same temperature, and the mixture was allowed to warm to room temperature in 5.5 hours in stirring. After completion of the reaction, aqueous ammonium chloride solution (50 ml) and water (50 ml) were added, and the mixture was extracted with ethyl acetate. The organic layer was dried over anhydrous sodium sulfate and the solvent was evaporated and the obtained residue was dissolved in methanol (150 ml). Thereto was dropwise added 1N aqueous sodium hydroxide solution (50 ml) with ice-cooling, and the mixture was stirred at room temperature for 1 hour. The solvent was evaporated and the obtained residue was extracted with ethyl acetate and dried over anhydrous sodium sulfate. The solvent was evaporated and the obtained residue was purified by silica gel column chromatography (chloroform:methanol=20:1–10:1) and dried under reduced pressure to give the title compound (10.87 g).

$^1$H-NMR (δ ppm, CDCl$_3$) 1.26 (tr, J=7 Hz, 3H), 1.49 (s, 9H), 1.68–1.80 (m, 2H), 2.30–2.40 (m, 2H), 2.75 (m, 2H), 3.10–3.20 (m, 2H), 3.61 (brtr, 2H), 3.68–3.76 (m, 2H), 3.97 (s, 2H), 4.22 (q, J=7 Hz, 2H), 4.52 (s, 2H), 6.61 (1H), 6.65–6.71 (m, 3H), 7.02 (1H), 8.25 (2H).

Step 4
1-(Pyridin-4-yl)-4-(1,2,3,4-tetrahydroisoquinolin-7-yloxymethyl)piperidine-4-carboxylic Acid Ethyl Ester

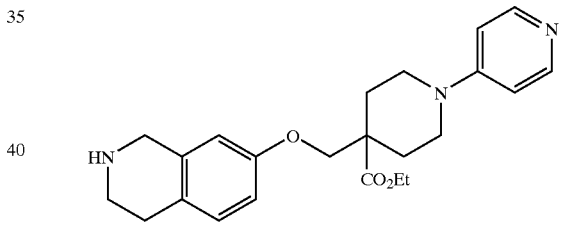

To a solution of 7-[4-ethoxycarbonyl-1-(pyridin-4-yl)piperidin-4-ylmethoxy]-1,2,3,4-tetrahydroisoquinoline-2-carboxylic acid tert-butyl ester (10.87 g) in chloroform (50 ml) was dropwise added trifluoroacetic acid (30 ml) with ice-cooling, and the mixture was stirred at room temperature for 30 min. The solvent was evaporated and to the obtained residue was added aqueous sodium hydrogencarbonate solution, and the mixture was extracted with ethyl acetate. The organic layer was dried over anhydrous sodium sulfate and the solvent was evaporated. The residue was dried under reduced pressure to give the title compound (8.29 g).

$^1$H-NMR (δ ppm, CDCl$_3$) 1.25 (tr, J=7 Hz, 3H), 1.65–1.95 (m, 2H), 2.30–2.36 (m, 2H), 2.72 (brtr, 2H), 3.05–3.18 (m, 4H), 3.69–3.76 (m, 2H), 3.96 (s, 4H), 4.21 (q, J=7 Hz, 2H), 6.52 (1H), 6.65–6.67 (m, 3H), 6.98 (1H), 8.25 (2H).

Step 5
4-(2-Amidino-1,2,3,4-tetrahydroisoquinolin-7-yloxymethyl)-1-(pyridin-4-yl)piperidine-4-carboxylic Acid Ethyl Ester Dihydrochloride

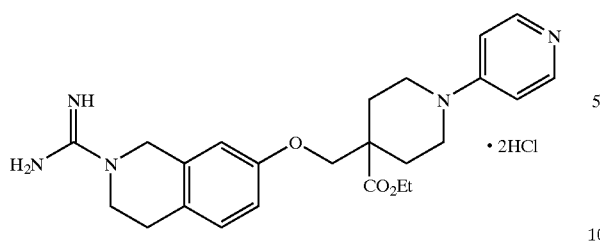

To a solution of 1-(pyridin-4-yl)-4-(1,2,3,4-tetrahydroisoquinolin-7-yloxymethyl)piperidine-4-carboxylic acid ethyl ester (8.29 g) in dimethylformamide (50 ml) were added diisopropylethylamine (4.4 ml) and 1H-pyrazole-1-carboxamidine hydrochloride (3.69 g), and the mixture was stirred at room temperature for 12 hours. The solvent was evaporated and to the obtained residue was added diethyl ether (350 ml) and the supernatant was removed. The obtained oil was dissolved in methanol (20 ml) and thereto was dropwise added diethyl ether (700 ml) with stirring. The supernatant was removed and dried under reduced pressure. Fifty (50) mg from the obtained 4-(2-amidino-1,2,3,4-tetrahydroisoquinolin-7-yloxymethyl)-1-(pyridin-4-yl)piperidine-4-carboxylic acid ethyl ester (10.0 g) was dissolved in ethanol and dil. hydrochloric acid was added. The mixture was concentrated and dried under reduced pressure to give the title compound (55 mg).

$^1$H-NMR (δ ppm, DMSO-$d_6$) 1.15 (tr, 3H), 1.65–1.80 (m, 2H), 2.15–2.22 (m, 2H), 2.81 (tr, J=6.0 Hz, 2H), 3.30–3.50 (m, 2H), 3.56 (tr, J=6.0 Hz, 2H), 3.95–4.18 (m, 6H), 4.53 (s, 2H), 6.68 (d, J=2.1 Hz, 1H), 6.81 (dd, J=2.1, 8.4 Hz, 1H), 7.14 (d, J=8.4 Hz, 1H), 7.19 (d, J=7.5 Hz, 2H), 7.58 (brs, 4H), 8.22 (d, J=7.5 Hz, 2H).

Example 7

Synthesis of 4-(2-Amidino-1,2,3,4-tetrahydroisoquinolin-7-yloxymethyl)-1-(pyridin-4-yl)piperidine-4-carboxylic Acid Dihydrochloride

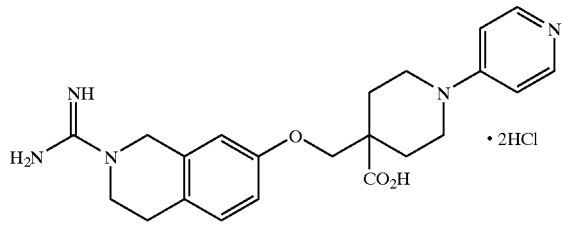

4-(2-Amidino-1,2,3,4-tetrahydroisoquinolin-7-yloxymethyl)-1-(pyridin-4-yl)piperidine-4-carboxylic acid ethyl ester dihydrochloride (9 g) was dissolved in conc. hydrochloric acid (50 ml), and the mixture was stirred under reflux for 3 hours. After completion of the reaction, insoluble material was filtered off and the solvent was evaporated. The residue was dried under reduced pressure to give the title compound (9.0 g).

$^1$H-NMR (δ ppm, DMSO-$d_6$) 1.65–1.75 (m, 2H), 2.14–2.20 (m, 2H), 2.81 (tr, J=5.7 Hz, 2H), 3.57 (tr, J=5.7 Hz, 2H), 4.00–4.15 (m, 4H), 4.54 (s, 2H), 6.70 (1H), 6.81 (1H), 7.15 (m, 3H), 7.63 (brs, 4H), 8.22 (2H), 13.71 (brs, 1H).

Example 8

Synthesis of 4-(2-Amidino-1,2,3,4-tetrahydroisoquinolin-7-yloxymethyl)-1-(pyridin-4-yl)piperidine-4-carboxylic Acid

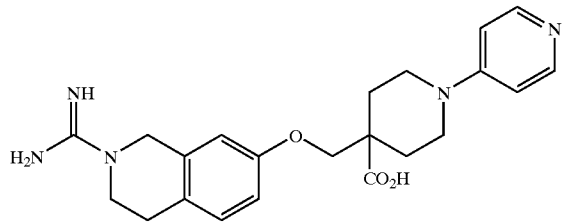

4-(2-Amidino-1,2,3,4-tetrahydroisoquinolin-7-yloxymethyl)-1-(pyridin-4-yl)piperidine-4-carboxylic acid dihydrochloride (11 g) was dissolved in water (100 ml) and filtrated. 4N Aqueous sodium hydroxide solution (20 ml) was added dropwise at 50° C., and the mixture was stirred at the same temperature for 30 min. After completion of the reaction, the resultant solid was collected by filtration, washed successively with water and ethanol, and dried under reduced pressure to give the title compound (7.7 g).

$^1$H-NMR (δ ppm, DMSO-$d_6$) 1.66–1.73 (m, 2H), 2.18–2.23 (m, 2H), 2.84 (m, 2H), 3.39 (m, 2H), 3.56 (m, 2H), 3.92–3.97 (m, 2H), 4.50 (s, 2H), 6.78 (s, 1H), 6.83 (d, J=8.3 Hz, 1H), 7.09 (d, J=7.2 Hz, 2H), 7.17 (d, J=8.3 Hz, 1H), 8.13 (d, J=7.2 Hz, 2H).

Example 9

Synthesis of 4-(2-Amidino-1,2,3,4-tetrahydroisoquinolin-7-yloxymethyl)-1-(pyridin-4-yl)piperidine-4-carboxylic Acid Hydrochloride

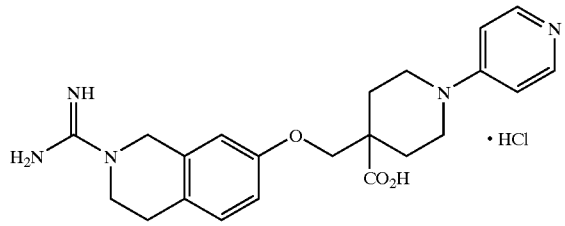

4-(2-Amidino-1,2,3,4-tetrahydroisoquinolin-7-yloxymethyl)-1-(pyridin-4-yl)piperidine-4-carboxylic acid (7.55 g) was suspended in water (135 ml) and 1N hydrochloric acid (20 ml) was added. The mixture was heated to 60° C. and thereto was successively added dropwise 1N aqueous sodium hydroxide solution (2.9 ml) and 1N hydrochloric acid (1 ml). The mixture was stood at room temperature for 12 hours and the resultant crystals were collected by filtration, washed with water and dried to give the title compound (4.7 g).

$^1$H-NMR (δ ppm, DMSO-$d_6$) 1.59–1.70 (m, 2H), 2.05–2.16 (m, 2H), 2.82 (tr, J=5.7 Hz, 2H), 3.15 (m, 2H), 3.57 (tr, J=5.7 Hz, 2H), 3.65–3.80 (m, 2H), 4.03 (m, 2H), 4.52 (s, 2H), 6.70 (1H), 6.79–6.86 (m, 3H), 7.13 (1H), 7.61 (brs, 4H), 8.14 (2H).

Example 10

Synthesis of 4-(2-Amidino-1,2,3,4-tetrahydroisoquinolin-7-yloxymethyl)-1-(2,6-dimethylpyridin-4-yl)piperidine-4-carboxylic Acid Ethyl Ester Dihydrochloride Step 1
7-Hydroxy-1,2,3,4-tetrahydroisoquinoline-2-carboxylic Acid Benzyl Ester

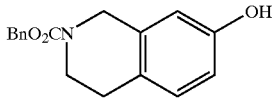

7-Hydroxy-1,2,3,4-tetrahydroisoquinoline hydrobromide (3 g) was dissolved in 1N aqueous sodium hydroxide solution (46 ml) and tetrahydrofuran (10 ml) and benzyl chlorocarbonate (2.45 g) was added. The mixture was stirred at room temperature for 30 min. The reaction mixture was extracted with chloroform and the organic layer was washed with saturated brine. The organic layer was dried over anhydrous sodium sulfate, and the solvent was evaporated. The residue was dried under reduced pressure to give the title compound (3.3 g).

Step 2
7-Methylthiomethoxy-1,2,3,4-tetrahydroisoquinoline-2-carboxylic Acid Benzyl Ester

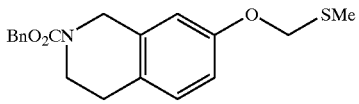

To a solution of 7-hydroxy-1,2,3,4-tetrahydroisoquinoline-2-carboxylic acid benzyl ester (2.5 g) in dimethylformamide (25 ml) was added 60% sodium hydride (390 mg) with ice-cooling and under an argon atmosphere, and the mixture was stirred at the same temperature for 30 min. Then, chloromethyl methyl sulfide (0.96 ml) was added, and the mixture was stirred at room temperature for 12 hours. After completion of the reaction, water was added and the mixture was extracted with ethyl acetate and washed with water. The organic layer was dried over anhydrous sodium sulfate and the solvent was evaporated. The obtained oil was purified by silica gel column chromatography (hexane:ethyl acetate=8:1) and dried under reduced pressure to give the title compound (2.7 g).

$^1$H-NMR (δ ppm, CDCl$_3$) 2.24 (s, 3H), 2.79 (brs, 2H), 3.71 (brtr, 2H), 4.62 (s, 2H), 5.11 (s, 2H), 5.18 (s, 2H), 6.69 (1H), 6.79 (1H), 7.06 (1H), 7.26–7.38 (m, 5H).

Step 3
7-Chloromethoxy-1,2,3,4-tetrahydroisoquinoline-2-carboxylic Acid Benzyl Ester

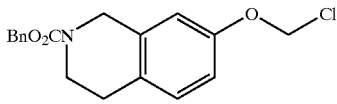

To a solution of 7-methylthiomethoxy-1,2,3,4-tetrahydroisoquinoline-2-carboxylic acid benzyl ester (200 mg) in methylene chloride (4 ml) was dropwise added sulfuryl chloride (0.052 ml) with ice-cooling and under an argon atmosphere, and the mixture was stirred at the same temperature for 1 hour. The solvent was evaporated azeotropically with toluene and the residue was dried under reduced pressure to give the title compound (213 mg).

$^1$H-NMR (δ ppm, CDCl$_3$) 2.82 (brtr, 2H), 3.72 (brtr, 2H), 4.65 (s, 2H), 5.18 (s, 2H), 5.87 (s, 2H), 6.84 (1H), 6.91 (1H), 7.11 (1H), 7.26–7.39 (m, 5H).

Step 4
1-tert-Butoxycarbonylpiperidine-4-carboxylic Acid Ethyl Ester

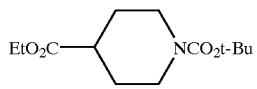

In the same manner as in Example 1, Step 1, the title compound (41.4 g) was obtained from ethyl isonipecotinate (25.5 g) and di-tert-butyl dicarbonate (36.5 g).

Step 5
7-(1-tert-Butoxycarbonyl-4-ethoxycarbonylpiperidin-4-ylmethoxy)-1,2,3,4-tetrahydroisoquinoline-2-carboxylic Acid Benzyl Ester

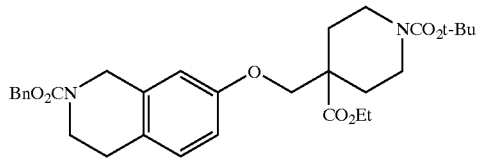

To a solution of 1-tert-butoxycarbonylpiperidine-4-carboxylic acid ethyl ester (300 mg) in tetrahydrofuran (3 ml) was dropwise added a 1.5M lithium diisopropylamide-tetrahydrofuran solution (0.97 ml) at −70° C., and the mixture was stirred at the same temperature for 50 min. Then, a solution of 7-chloromethoxy-1,2,3,4-tetrahydroisoquinoline-2-carboxylic acid benzyl ester (213 mg) in tetrahydrofuran (3 ml) was dropwise added at the same temperature, and the mixture was allowed to warm to room temperature in 2 hours in stirring. After completion of the reaction, aqueous ammonium chloride solution and water were added with ice-cooling. The mixture was extracted with ethyl acetate and the extract was washed successively with water and saturated brine. The organic layer was dried over anhydrous sodium sulfate and the solvent was evaporated and the obtained residue was purified by silica gel column chromatography (hexane:acetone=7:1) and dried under reduced pressure to give the title compound (170 mg).

$^1$H-NMR (δ ppm, CDCl$_3$) 1.23 (tr, J=7.2 Hz, 3H), 1.46 (s, 9H), 1.52–1.62 (m, 2H), 2.16–2.21 (m, 2H), 2.77 (m, 2H), 3.04 (m, 2H), 3.69 (m, 2H), 3.80–4.00 (m, 4H), 4.19 (q, J=7.2 Hz, 2H), 4.60 (s, 2H), 5.17 (s, 2H), 6.60 (1H), 6.69 (1H), 7.02 (1H), 7.32–7.38 (m, 5H).

Step 6
7-(4-Ethoxycarbonylpiperidin-4-ylmethoxy)-1,2,3,4-tetrahydroisoquinoline-2-carboxylic Acid Benzyl Ester

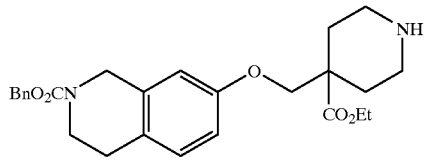

To a solution of 7-(1-tert-butoxycarbonyl-4-ethoxycarbonylpiperidin-4-ylmethoxy)-1,2,3,4-tetrahydroisoquinoline-2-carboxylic acid benzyl ester (165 mg) in chloroform (1.5 ml) was added dropwise trifluoroacetic acid (0.5 ml), and the mixture was stirred at room temperature for 1 hour. The solvent was evaporated and aqueous sodium hydrogencarbonate solution was added to the obtained residue. The mixture was extracted with ethyl acetate and the organic layer was dried over anhydrous sodium sulfate. The solvent was evaporated and the residue was dried under reduced pressure to give the title compound (135 mg).

¹H-NMR (δ ppm, CDCl₃) 1.23 (tr, J=7.5 Hz, 3H), 1.50–1.65 (m, 2H), 2.15–2.25 (m, 2H), 2.65–2.90 (m, 4H), 2.95–3.05 (m, 2H), 3.69 (m, 2H), 3.93 (s, 2H), 4.19 (q, J=7.5 Hz, 2H), 4.60 (s, 2H), 5.17 (s, 2H), 6.60 (1H), 6.69 (1H), 7.02 (1H), 7.26–7.38 (m, 5H)

Step 7

7-[1-(2,6-Dimethylpyridin-4-yl)-4-ethoxycarbonylpiperidin-4-ylmethoxy]-1,2,3,4-tetrahydroisoquinoline-2-carboxylic Acid Benzyl Ester

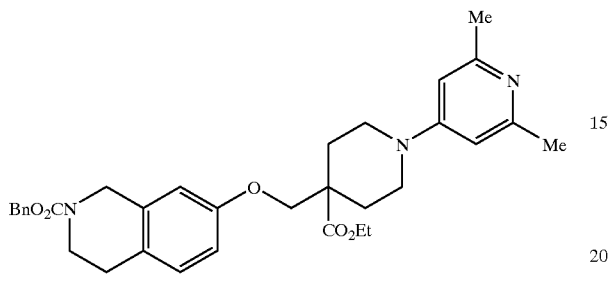

To a solution of 7-(4-ethoxycarbonylpiperidin-4-ylmethoxy)-1,2,3,4-tetrahydroisoquinoline-2-carboxylic acid benzyl ester (140 mg) in ethanol (3 ml) were added triethylamine (0.05 ml) and 4-chloro-2,6-dimethylpyridine (*Journal of Heterocyclic Chemistry*, vol. 27, p. 1841 (1990)) (45 mg) and the mixture was stirred at 150° C. for 25 hours in a sealed tube. After completion of the reaction, the solvent was evaporated and the obtained residue was purified by silica gel column chromatography (chloroform:methanol= 4:1) and dried under reduced pressure to give the title compound (160 mg).

¹H-NMR (δ ppm, CDCl₃) 1.26 (tr, J=6.6 Hz, 3H), 1.70–1.85 (m, 2H), 2.35–2.45 (m, 2H), 2.66 (s, 6H), 2.78 (m, 2H), 3.28–3.37 (m, 2H), 3.70 (m, 2H), 3.80–3.90 (m, 2H), 3.97 (s, 2H), 4.24 (q, J=6.6 Hz, 2H), 4.60 (s, 2H), 5.17 (s, 2H), 6.41 (s, 2H), 6.60 (1H), 6.69 (1H), 7.04 (1H), 7.34–7.38 (m, 5H).

Step 8

4-(2-Amidino-1,2,3,4-tetrahydroisoquinolin-7-yloxymethyl)-1-(2,6-dimethylpyridin-4-yl)piperidine-4-carboxylic Acid Ethyl Ester Dihydrochloride

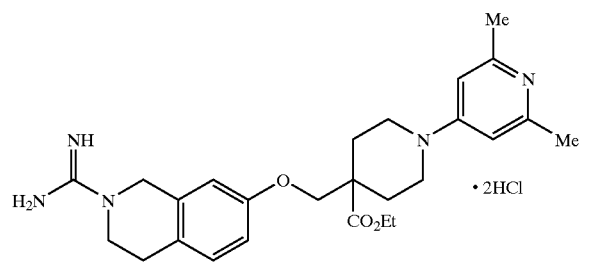

To 7-[1-(2,6-dimethylpyridin-4-yl)-4-ethoxycarbonylpiperidin-4-ylmethoxy]-1,2,3,4-tetrahydroisoquinoline-2-carboxylic acid benzyl ester (155 mg) was added 25% hydrogen bromide-acetic acid solution (3 ml), and the mixture was stirred for 10 min. After completion of the reaction, diisopropyl ether was added and the resultant solid was collected by filtration. To the obtained solid were added dimethylformamide (1 ml), diisopropylethylamine (0.25 ml) and 1H-pyrazole-1-carboxamidine hydrochloride (80 mg), and the mixture was stirred at room temperature for 12 hours. The solvent was evaporated and the obtained residue was washed with tetrahydrofuran and separated by HPLC (0.05% aqueous trifluoroacetic acid:methanol=4:1–2:3). The obtained residue was treated with dil. hydrochloric acid and dried under reduced pressure to give the title compound (120 mg).

Example 11

Synthesis of 4-(2-Amidino-1,2,3,4-tetrahydroisoquinolin-7-yloxymethyl)-1-(2,6-dimethylpyridin-4-yl)piperidine-4-carboxylic Acid Dihydrochloride

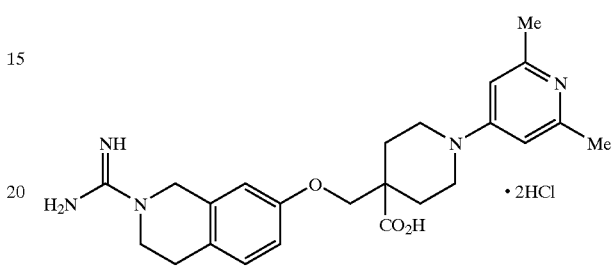

To 4-(2-amidino-1,2,3,4-tetrahydroisoquinolin-7-yloxymethyl)-1-(2,6-dimethylpyridin-4-yl)piperidine-4-carboxylic acid ethyl ester dihydrochloride (85 mg) was added 6N hydrochloric acid, and the mixture was stirred under reflux for 3 hours. After completion of the reaction, insoluble material was removed and the solvent was evaporated. The obtained residue was washed with diethyl ether and dried under reduced pressure to give the title compound (76 mg).

¹H-NMR (δ ppm, DMSO-d₆) 1.60–1.75 (m, 2H), 2.05–2.20 (m, 2H), 2.46 (s, 6H), 2.83 (m, 2H), 3.59 (m, 2H), 3.80–4.15 (m, 4H), 4.57 (s, 2H), 6.72 (1H), 6.82 (1H), 6.99 (s, 2H), 7.15 (1H), 7.72 (brs, 4H), 13.69 (brs, 1H).

Example 12

Synthesis of 4-(2-Amidino-1,2,3,4-tetrahydroisoquinolin-7-yloxymethyl)-1-(2-methylpyridin-4-yl)piperidine-4-carboxylic Acid Methyl Ester Dihydrochloride Step 1

4-Chloro-2-methylpyridine Hydrochloride

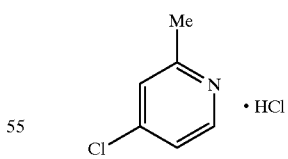

According to the method of *Journal of Heterocyclic Chemistry*, vol. 27; p. 1841 (1990), the title compound (743 mg) was obtained from 2-methylpyridine N-oxide (5.1 g).

¹H-NMR (δ ppm, CDCl₃) 2.99 (s, 3H), 7.70 (s, 1H), 7.77 (d, J=6.3 Hz, 1H), 8.01 (d, J=6.3 Hz, 1H).

Step 2

7-[4-Ethoxycarbonyl-1-(2-methylpyridin-4-yl)piperidin-4-ylmethoxy]-1,2,3,4-tetrahydroisoquinoline-2-carboxylic Acid Benzyl Ester

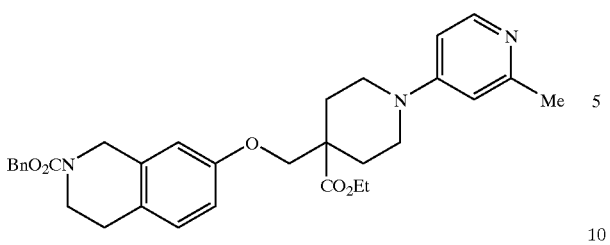

In the same manner as in Example 10, Step 7, the title compound (105 mg) was obtained from 7-(4-ethoxycarbonylpiperidin-4-ylmethoxy)-1,2,3,4-tetrahydroisoquinoline-2-carboxylic acid benzyl ester (100 mg), 4-chloro-2-methylpyridine hydrochloride (40 mg) and triethylamine (0.07 ml).

Step 3
4-(2-Amidino-1,2,3,4-tetrahydroisoquinolin-7-yloxymethyl)-1-(2-methylpyridin-4-yl)piperidine-4-carboxylic Acid Ethyl Ester Dihydrochloride

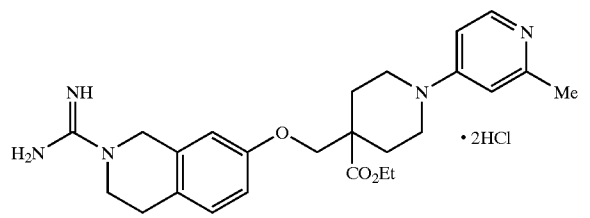

In the same manner as in Example 10, Step 8, the title compound (83 mg) was obtained from 7-[4-ethoxycarbonyl-1-(2-methylpyridin-4-yl)piperidin-4-ylmethoxy]-1,2,3,4-tetrahydroisoquinoline-2-carboxylic acid benzyl ester (100 mg), 25% hydrogen bromide-acetic acid solution (2 ml), diisopropylethylamine (0.16 ml) and 1H-pyrazole-1-carboxamidine hydrochloride (55 mg).

Example 13

Synthesis of 4-(2-Amidino-1,2,3,4-tetrahydroisoquinolin-7-yloxymethyl)-1-(2-methylpyridin-4-yl)piperidine-4-carboxylic Acid Dihydrochloride

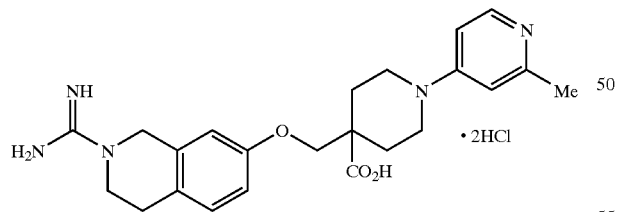

In the same manner as in Example 11, the title compound (53 mg) was obtained from 4-(2-amidino-1,2,3,4-tetrahydroisoquinolin-7-yloxymethyl)-1-(2-methylpyridin-4-yl)piperidine-4-carboxylic acid ethyl ester dihydrochloride (63 mg).

$^1$H-NMR (δ ppm, DMSO-$d_6$) 1.63–1.75 (m, 2H), 2.05–2.25 (m, 2H), 2.47 (s, 3H), 2.83 (m, 2H), 3.30–3.70 (m, 4H), 3.95–4.10 (m, 4H), 4.55 (s, 2H), 6.71 (1H), 6.83 (1H), 7.07–7.16 (m, 3H), 7.63 (brs, 4H), 8.12 (1H), 13.74 (brs, 1H).

Example 14

Synthesis of 4-(2-Amidino-1,2,3,4-tetrahydroisoquinolin-7-yloxymethyl)-1-(pyrimidin-4-yl)piperidine-4-carboxylic Acid Dihydrochloride Step 1
7-[1-(2-Chloropyrimdin-4-yl)-4-ethoxycarbonylpiperidin-4-ylmethoxy]-1,2,3,4-tetrahydroisoquinoline-2-carboxylic Acid Benzyl Ester

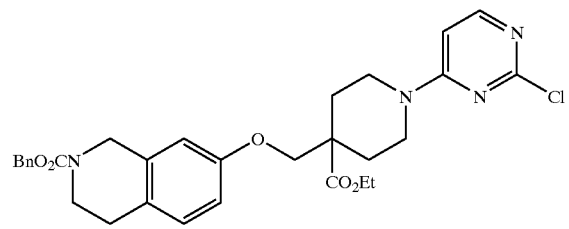

To a solution of 7-(4-ethoxycarbonylpiperidin-4-ylmethoxy)-1,2,3,4-tetrahydroisoquinoline-2-carboxylic acid benzyl ester (295 mg) in ethanol (5 ml) were added triethylamine (0.15 ml) and 2,4-dichloropyrimidine (150 mg), and the mixture was stirred under reflux for 1 hour. After completion of the reaction, water was added and the mixture was extracted with ethyl acetate. The extract was dried over anhydrous sodium sulfate. The solvent was evaporated and the obtained residue was purified by silica gel column chromatography (hexane:ethyl acetate=1:2) and dried under reduced pressure to give the title compound (263 mg).

$^1$H-NMR (δ ppm, CDCl$_3$) 1.25 (tr, J=6.9 Hz, 3H), 1.50–1.70 (m, 2H), 2.25–2.40 (m, 2H), 2.78 (m, 2H), 3.18–3.30 (m, 2H), 3.70 (m, 2H), 3.95 (s, 2H), 4.09–4.26 (m, 4H), 4.60 (s, 2H), 5.17 (s, 2H), 6.40 (d, J=6.1 Hz, 1H), 6.60 (1H), 6.69 (1H), 7.03 (1H), 7.26–7.38 (m, 5H), 8.03 (d, J=6.1 Hz, 1H).

Step 2
1-(Pyrimidin-4-yl)-4-(1,2,3,4-tetrahydroisoquinolin-7-yloxymethyl)piperidine-4-carboxylic Acid Ethyl Ester

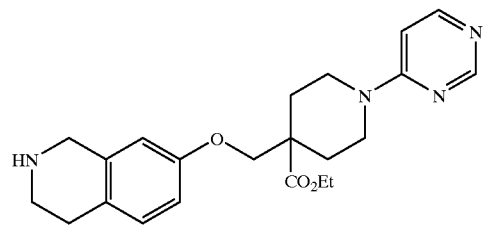

To a solution of 7-[1-(2-chloropyrimidin-4-yl)-4-ethoxycarbonylpiperidin-4-ylmethoxy]-1,2,3,4-tetrahydroisoquinoline-2-carboxylic acid benzyl ester (263 mg) in ethanol(5 ml) were added 7.5% palladium carbon (120 mg) and ammonium formate (200 mg) with ice-cooling, and the mixture was stirred under reflux for 30 min. After completion of the reaction, the solvent was evaporated and water was added to the obtained residue. The mixture was extracted with chloroform and the organic layer was washed with aqueous sodium hydrogencarbonate solution and dried over anhydrous sodium sulfate. The solvent was evaporated and the residue was dried under reduced pressure to give the title compound (270 mg).

Step 3
4-(2-Amidino-1,2,3,4-tetrahydroisoquinolin-7-yloxymethyl)-1-(pyrimidin-4-yl)piperidine-4-carboxylic Acid Dihydrochloride

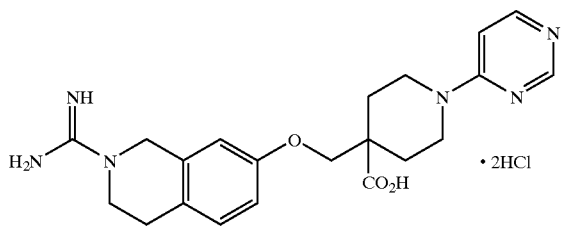

To a solution of 1-(pyrimidin-4-yl)-4-(1,2,3,4-tetrahydroisoquinolin-7-yloxymethyl)piperidine-4-carboxylic acid ethyl ester (260 mg) in dimethylformamide (1 ml) were added diisopropylethylamine (0.24 ml) and 1H-pyrazole-1-carboxamidine hydrochloride (200 mg), and the mixture was stirred at room temperature for 2 hours. After completion of the reaction, the solvent was evaporated and the obtained residue was separated by HPLC (0.05% aqueous trifluoroacetic acid:methanol=6:4–2:8). The obtained residue was refluxed with conc. hydrochloric acid for 2 hours. After completion of the reaction, the solvent was evaporated and the obtained residue was washed with diethyl ether and dried under reduced pressure to give the title compound (51 mg).

$^1$H-NMR (δ ppm, DMSO-$d_6$) 1.60–1.80 (m, 2H), 2.10–2.25 (m, 2H), 2.81 (m, 2H), 3.40–3.60 (m, 4H), 4.05 (s, 2H), 4.05–4.80 (2H), 4.54 (s, 2H), 6.69 (d, J=2.4 Hz, 1H), 6.81 (dd, J=2.4, 8.4 Hz, 1H), 7.13 (d, J=8.4 Hz, 1H), 7.23 (d, J=7.8 Hz, 1H), 7.66 (brs, 4H), 8.32 (d, J=7.8 Hz, 1H), 8.81 (s, 1H).

Example 15

Synthesis of 4-[2-(2-Amidino-1,2,3,4-tetrahydroisoquinolin-7-yloxy)ethyl]-1-(pyridin-4-yl)piperidine-4-carboxylic Acid Ethyl Ester Dihydrochloride Step 1
7-(2-Iodoethoxy)-1,2,3,4-tetrahydroisoquinoline-2-carboxylic Acid Benzyl Ester

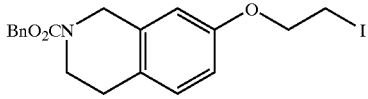

To a solution of 7-hydroxy-1,2,3,4-tetrahydroisoquinoline-2-carboxylic acid benzyl ester (1.21 g), 2-bromoethanol (5.46 ml) and triphenylphosphine (20.11 g) in tetrahydrofuran (30 ml) was added 400% diethyl azodicarboxylate-toluene solution (33.6 ml), and the mixture was stirred at room temperature for 1 hour. After completion of the reaction, the solvent was evaporated and to the obtained residue were added dimethylformamide (30 ml) and sodium iodide (9.6 g). The mixture was stirred at 90° C. for 15 hours. After completion of the reaction, the solvent was evaporated and the obtained residue was purified by silica gel column chromatography (hexane:ethyl acetate=4:1) and dried under reduced pressure to give the title compound (1.19 g).

$^1$H-NMR (δ ppm, CDCl$_3$) 2.79 (m, 2H), 3.40 (tr, J=6.9 Hz, 2H), 3.70 (m, 2H), 4.21 (tr, J=6.9 Hz, 2H), 4.61 (s, 2H), 5.18 (s, 2H), 6.63 (1H), 6.74 (1H), 7.05 (1H), 7.26–7.38 (m, 5H).

Step 2
7-[2-(1-tert-Butoxycarbonyl-4-ethoxycarbonylpiperidin-4-yl)ethoxy]-1,2,3,4-tetrahydroisoquinoline-2-carboxylic Acid Benzyl Ester

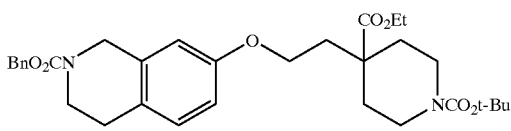

In the same manner as in Example 10, Step 5, the title compound (935 mg) was obtained from 7-(2-iodoethoxy)-1,2,3,4-tetrahydroisoquinoline-2-carboxylic acid benzyl ester (1.4 g), 1-tert-butoxycarbonylpiperidine-4-carboxylic acid ethyl ester (1.81 g) and 2M-lithium diisopropylamide-tetrahydrofuran solution (0.82 ml).

$^1$H-NMR (δ ppm, CDCl$_3$) 1.25 (tr, J=6.9 Hz, 3H), 1.60–1.65 (m, 2H), 2.01–2.04 (m, 2H), 2.13–2.19 (m, 2H), 2.77 (m, 2H), 2.94 (m, 2H), 3.70 (m, 2H), 3.80–4.00 (m, 4H), 4.18 (q, J=6.9 Hz, 2H), 4.60 (s, 2H), 5.18 (s, 2H), 6.56 (1H), 6.67 (1H), 7.01 (1H), 7.31–7.38 (m, 5H).

Step 3
7-[2-[4-Ethoxycarbonyl-1-(pyridin-4-yl)piperidin-4-yl]ethoxy]-1,2,3,4-tetrahydroisoquinoline-2-carboxylic Acid Benzyl Ester

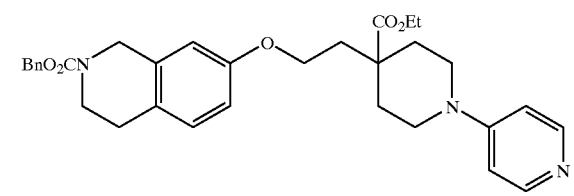

In the same manner as in Example 10,

Step 6, 7-[2-(4-ethoxycarbonylpiperidin-4-yl)ethoxy]-1,2,3,4-tetrahydroisoquinoline-2-carboxylic acid benzyl ester was obtained from 7-[2-(1-tert-butoxycarbonyl-4-ethoxycarbonylpiperidin-4-yl)ethoxy]-1,2,3,4-tetrahydroisoquinoline-2-carboxylic acid benzyl ester (935 mg) and trifluoroacetic acid (5 ml). In the same manner as in Example 10, Step 7, the title compound (680 mg) was obtained from this compound, 4-chloropyridine hydrochloride (248 mg) and triethylamine (1.38 ml). The reaction was carried out for 2 days.

Step 4
4-[2-(2-Amidino-1,2,3,4-tetrahydroisoquinolin-7-yloxy)ethyl]-1-(pyridin-4-yl)piperidine-4-carboxylic Acid Ethyl Ester Dihydrochloride

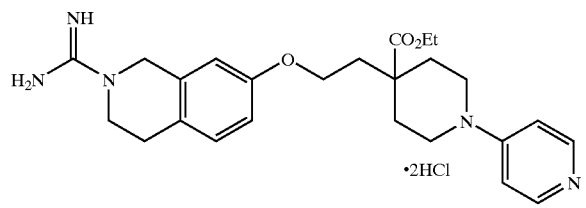

In the same manner as in Example 10, Step 8, the title compound (208 mg) was obtained from 7-[2-4-ethoxycarbonyl-1-(pyridin-4-yl)piperidin-4-yl]ethoxy]-1,2,3,4-tetrahydroisoquinoline-2-carboxylic acid benzyl ester (397 mg), 25% hydrogen bromide-acetic acid solution (3 ml), diisopropylethylamine (0.64 ml) and 1H-pyrazole-1-carboxamidine hydrochloride (214 mg).

Example 16

Synthesis of 4-[2-(2-Amidino-1,2,3,4-tetrahydroisoquinolin-7-yloxy)ethyl]-1-(pyridin-4-yl)piperidine-4-carboxylic Acid Dihydrochloride

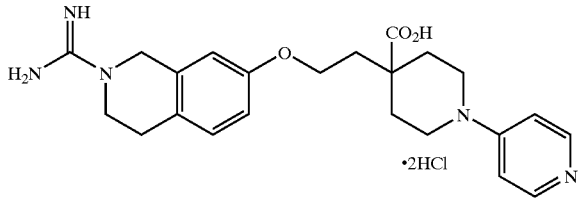

In the same manner as in Example 11, 4-[2-(2-amidino-1,2,3,4-tetrahydroisoquinolin-7-yloxy)ethyl]-1-(pyridin-4-yl)piperidine-4-carboxylic acid ethyl ester dihydrochloride (200 mg) was reacted. The obtained residue was separated by HPLC (0.05% aqueous trifluoroacetic acid:methanol= 1:1) and the obtained residue was treated with dil. hydrochloric acid to give the title compound (29 mg).

$^1$H-NMR ($\delta$ ppm, DMSO-d$_6$) 1.54–1.68 (m, 2H), 1.95–2.22 (m, 4H), 2.82 (m, 2H), 3.58 (m, 2H), 3.92–4.12 (m, 4H), 4.55 (s, 2H), 6.67 (1H), 6.78 (1H), 7.14 (1H), 7.19 (d, J=7.4 Hz, 2H), 7.61 (brs, 4H), 8.21 (d, J=7.4 Hz, 2H).

Example 17

Synthesis of (S)-4-[N-[5-Amidino-1-(1-phenylethylcarbamoylmethyl)benzimidazol-2-ylmethyl]-N-[4-(1-acefimidoylpiperidin-4-yloxy)phenyl]carbamoyl]benzoic Acid Dihydrochloride Step 1
4-(4-Nitrophenoxy)piperidine-1-carboxylic Acid tert-Butyl Ester

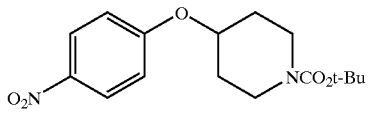

To a solution of 4-hydroxypiperidine-1-carboxylic acid tert-butyl ester (38.28 g) and 4-fluoronitrobenzene (26.84 g) in dimethyl sulfoxide (326 ml) was added 60% sodium hydride (7.99 g) under nitrogen atmosphere and with ice-cooling, and the mixture was stirred at room temperature for 1 hour. After completion of the reaction, water was added and the mixture was extracted with ethyl acetate and washed with water. The organic layer was dried over anhydrous sodium sulfate and the solvent was evaporated. The obtained residue was purified by silica gel column chromatography (hexane:ethyl acetate=10:1) to give the title compound (52.384 g).

$^1$H-NMR ($\delta$ ppm, CDCl$_3$) 1.48 (s, 9H), 1.80 (m, 2H), 1.96 (m, 2H), 3.39 (m, 2H), 3.70 (m, 2H), 4.61 (m, 1H), 6.96 (d, J=9.3 Hz, 2H), 8.20 (d, J=9.3 Hz, 2H).

Step 2
4-(4-Aminophenoxy)piperidine-1-carboxylic Acid tert-Butyl Ester

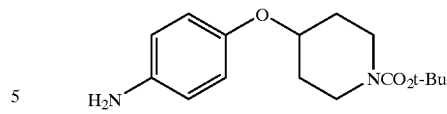

4-(4-Nitrophenoxy)piperidine-1-carboxylic acid tert-butyl ester (53.687 g) was hydrogenated using 7.5% palladium carbon (8.05 g) in a mixture of tetrahydrofuran (215 ml) and ethanol (215 ml) at 3 atm over 3 hours. After completion of the reaction, the reaction mixture was filtered through celite and the solvent was evaporated. Hexane was added to the obtained residue, and the obtained solid was collected by filtration and dried under reduced pressure to give the title compound (42.157 g).

$^1$H-NMR ($\delta$ ppm, CDCl$_3$) 1.46 (s, 9H), 1.71 (m, 2H), 1.86 (m, 2H), 3.27 (m, 2H), 3.71 (m, 2H), 4.26 (m, 1H), 6.63 (d, J=8.7 Hz, 2H), 6.76 (d, J=8.7 Hz, 2H).

Step 3
4-(4-Benzyloxycarbonylaminophenoxy)piperidine-1-carboxylic Acid tert-Butyl ester

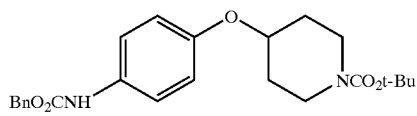

To a solution of 4-(4-aminophenoxy)piperidine-1-carboxylic acid tert-butyl ester (6.63 g) and sodium hydrogencarbonate (2.1 g) in a mixture of tetrahydrofuran (100 ml)-water (100 ml) was dropwise added benzyl chlorocarbonate (3.24 ml), and the mixture was stirred at room temperature for 1 hour. After completion of the reaction, the mixture was extracted with ethyl acetate and washed with saturated brine. The organic layer was dried over anhydrous magnesium sulfate and the solvent was evaporated. The obtained residue was washed with diisopropyl ether, collected by filtration, and dried under reduced pressure to give the title compound (7.189 g).

$^1$H-NMR ($\delta$ ppm, CDCl$_3$) 1.47 (s, 9H), 1.74 (m, 2H), 1.88 (m, 2H), 3.31 (m, 2H), 3.69 (m, 2H), 4.39 (m, 1H), 5.19 (s, 2H), 6.54 (brs, 1H), 6.86 (2H), 7.26–7.42 (m, 7H).

Step 4
4-[4-(N-Benzyloxycarbonyl-N-ethoxycarbonylmethylalino)phenoxy]piperidine-1-carboxylic Acid tert-Butyl Ester

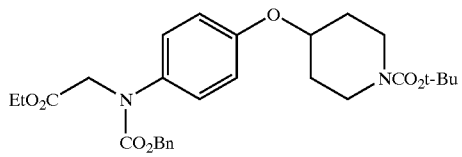

To a solution of 4-(4-aminophenoxy)piperidine-1-carboxylic acid tert-butyl ester (42.28 g) in dimethylformamide (254 ml) was added 60% sodium hydride (3.97 g), and the mixture was stirred at room temperature for 20 min. Then, ethyl bromoacetate (12.1 ml) was added with ice-cooling, and the mixture was stirred at room temperature for 15 hours. Thereto were added 60% sodium hydride (3.97 g) and ethyl bromoacetate (12.1 ml), and the mixture was stirred at room temperature for 4 hours. Further, 60% sodium hydride (1.19 g) and ethyl bromoacetate (3.3 ml) were added, and the mixture was stirred at room temperature for 2 hours. After completion of the reaction, water was added and the mixture was extracted with ethyl acetate and washed with water. The organic layer was dried over anhydrous sodium sulfate and the solvent was evaporated. The obtained residue was purified by silica gel column chromatography (hexane:ethyl acetate=7:3) to give the title compound (49.916 g).

$^1$H-NMR (δ ppm, CDCl$_3$) 1.28 (3H), 1.47 (s, 9H), 1.75 (m, 2H), 1.89 (m, 2H), 3.34 (m, 2H), 3.68 (m, 2H), 4.19 (2H), 4.30 (brs, 2H), 4.43 (m, 1H), 5.19, 5.17 (2H), 6.86 (2H), 7.13–7.35 (m, 7H).

Step 5

N-[4-(1-tert-Butoxycarbonylpiperidin-4-yloxy)phenyl]-N-benzyloxycarbonyl-aminoacetic Acid

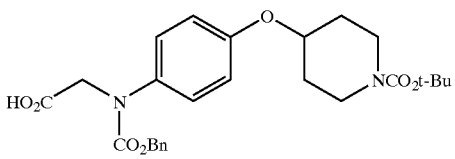

To a solution of 4-[4-(N-benzyloxycarbonyl-N-ethoxycarbonyl-methylamino)phenoxy]piperidine-1-carboxylic acid tert-butyl ester (49.916 g) in ethanol (102 ml) were added 1N aqueous sodium hydroxide solution (102 ml) and tetrahydrofuran (102 ml), and the mixture was stirred at room temperature for 10 min and at 50° C. for 1 hour. After completion of the reaction, the solvent was evaporated. The obtained residue was extracted with ethyl acetate and washed with 10% aqueous citric acid solution and saturated brine. The organic layer was dried over anhydrous sodium sulfate. The solvent was evaporated and dried under reduced pressure to give the title compound (47.18 g).

$^1$H-NMR (δ ppm, CDCl$_3$) 1.47 (s, 9H), 1.76 (m, 2H), 1.89 (m, 2H), 3.34 (m, 2H), 3.68 (m, 2H), 4.35 (s, 2H), 4.44 (m, 1H), 5.16 (brs, 2H), 6.86 (2H), 7.15–7.45 (m, 7H).

Step 6

N-(4-Cyano-2-nitrophenyl)glycine tert-Butyl Ester

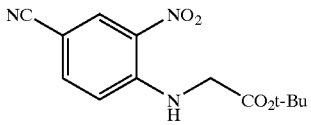

To a solution of 4-chloro-3-nitrobenzonitrile (33.87 g) and glycine tert-butyl ester hydrochloride (55.98 g) in ethanol (400 ml) was added triethylamine (77.6 ml), and the mixture was stirred at room temperature for 15 hours and then at 50° C. for 3 hours. After completion of the reaction, the solvent was evaporated and the obtained residue was extracted with ethyl acetate. The extract was washed with 10% aqueous citric acid solution and saturated brine. The organic layer was dried over anhydrous magnesium sulfate and the solvent was evaporated. The obtained residue was washed with diisopropyl ether and collected by filtration to give the title compound (38.419 g).

$^1$H-NMR (δ ppm, CDCl$_3$) 1.53 (s, 9H), 4.03 (d, J=5.0 Hz, 2H), 6.75 (d, J=8.9 Hz, 1H), 7.64 (dd, J=2.0, 8.9 Hz, 1H), 8.55 (d, J=2.0 Hz, 1H), 8.81 (brs, 1H).

Step 7

N-(2-Amino-4-cyanophenyl)glycine tert-Butyl Ester

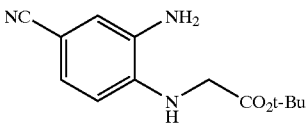

N-(4-Cyano-2-nitrophenyl)glycine tert-butyl ester (17.337 g) was hydrogenated using 7.5% palladium carbon (1.73 g) in tetrahydrofuran (173 ml) at atmospheric pressure for 2 hours and by adding 7.5% palladium carbon (3.84 g) for one more hour. After completion of the reaction, the reaction mixture was filtered through celite and the solvent was evaporated. The obtained residue was washed with diisopropyl ether, collected by filtration and dried under reduced pressure to give the title compound (8.324 g).

$^1$H-NMR (δ ppm, CDCl$_3$) 1.51 (s, 9H), 3.84 (s, 2H), 6.45 (1H), 6.95 (1H), 7.15 (1H).

Step 8

4-[4-[N-Benzyloxycarbonyl-N-(2-tert-butoxycarbonylmethylamino-5-cyanophenyl)carbamoylmethylamino]phenoxy]piperidine-1-carboxylic Acid tert-Butyl Ester

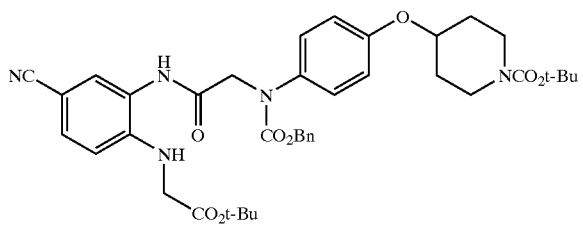

To a solution of N-(2-amino-4-cyanophenyl)glycine tert-butyl ester (21.53 g) and N-[4-(1-tert-butoxycarbonylpiperidin-4-yloxy)phenyl]-N-benzyloxycarbonyl-aminoacetic acid (42.18 g) in chloroform (300 ml) was added 1-ethoxycarbonyl-2-ethoxy-1,2-dihydroquinoline (23.68 g), and the mixture was stirred at room temperature for 3 hours. After completion of the reaction, the solvent was evaporated and the obtained residue was purified by silica gel column chromatography (hexane:ethyl acetate=2:3) to give the title compound (44.479 g).

$^1$H-NMR (δ ppm, CDCl$_3$) 1.47 (s, 9H), 1.76 (m, 2H), 1.90 (m, 2H), 3.34 (m, 2H), 3.67 (m, 2H), 3.78 (brd, 2H), 4.36 (s, 2H), 4.45 (m, 1H), 5.10–5.25 (m, 1H), 5.20 (s, 2H), 6.53 (1H), 6.89 (2H), 7.20–7.31 (m, 7H), 7.40 (2H), 7.96 (brs, 1H).

Step 9

2-[N-Benzyloxycarbonyl-N-[4-(1-tert-butoxycarbonylpiperidin-4-yloxy)phenyl]-aminomethyl]-5-cyanobenzimidazole-1-acetic Acid

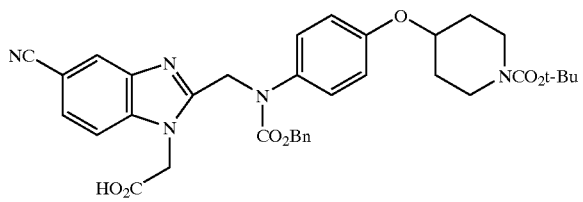

A solution of 4-[4-[N-benzyloxycarbonyl-N-(2-tert-butoxycarbonyl-methylamino-5-cyanophenyl)carbamoylmethylamino]phenoxy]piperidine-1-carboxylic acid tert-butyl ester (44.479 g) in acetic acid (600 ml) was stirred at 90° C. for 4 days. After completion of the reaction, the solvent was evaporated and the obtained residue (51 g) was reacted with sodium carbonate (19.8 g) and di-tert-butyl dicarbonate (13.6 g) by a conventional method. The obtained residue was purified by silica gel column chromatography (chloroform:methanol=9:1) and dried under reduced pressure to give the title compound (23.545 g).

$^1$H-NMR (δ ppm, CDCl$_3$) 1.46 (s, 9H), 1.67 (m, 2H), 1.81 (m, 2H), 3.27 (m, 2H), 3.63 (m, 2H), 4.35 (m, 1H), 5.05 (brs, 6H), 6.75 (2H), 7.02–7.27 (m, 7H), 7.30 (d, J=8.4 Hz, 1H), 7.50 (dd, J=1.1, 8.4 Hz, 1H), 7.99 (d, J=1.1 Hz, 1H).

Step 10

(S)-2-[N-Benzyloxycarbonyl-N-[4-(1-tert-butoxycarbonylpiperidin-4-yloxy)phenyl]-aminomethyl]-5-cyano-1-(1-phenylethylcarbamoyl-methyl)benzmidazole

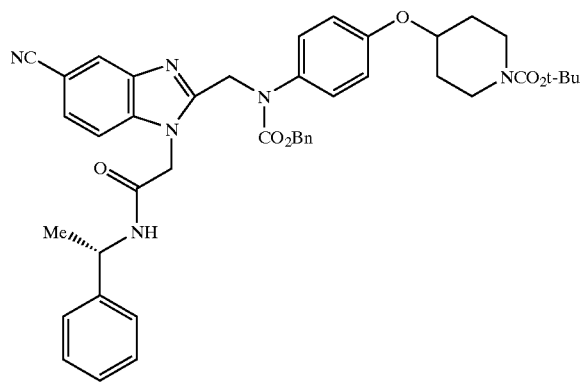

To a solution of 2-[N-benzyloxycarbonyl-N-[4-(1-tert-butoxycarbonylpiperidin-4-yloxy)phenyl]aminomethyl]-5-cyanobernimidazole-1-acetic acid (583 mg) and 1-hydroxybenzotriazole hydrate (135 mg) in dimethylformamide (5 ml) were added (S)-phenethylamine (0.118 ml) and 1-(3-dimethylaminopropyl)-3-ethylcarbodiimide hydrochloride (193 mg), and the mixture was stirred at room temperature for 15 hours. After completion of the reaction, the mixture was extracted with ethyl acetate and washed successively with water, aqueous sodium hydrogencarbonate solution, 10% aqueous citric acid solution and saturated brine. The organic layer was dried over anhydrous magnesium sulfate and the solvent was evaporated. To the obtained residue was added diisopropyl ether and the resultant solid was collected by filtration to give the title compound (623 mg).

$^1$H-NMR (δ ppm, CDCl$_3$) 1.46–1.48 (s, 12H), 1.70 (m, 2H), 1.86 (m, 2H), 3.30 (m, 2H), 3.65 (m, 2H), 4.38 (m, 1H), 4.95–5.05 (m, 3H), 5.14 (s, 2H), 5.21 (s, 2H), 6.81 (2H), 7.10–7.30 (m, 12H), 7.48 (d, J=8.0 Hz, 1H), 7.63 (d, J=8.0 Hz, 1H), 8.06 (s, 1H).

Step 11

(S)-2-[N-[4-(1-tert-Butoxycarbonylpiperidin-4-yloxy) phenyl]-N-(4-methoxycarbonylbenzoyl)aminomethyl]-5-cyano-1-(1-phenylethylcarbamoyl-methyl)benzimidazole

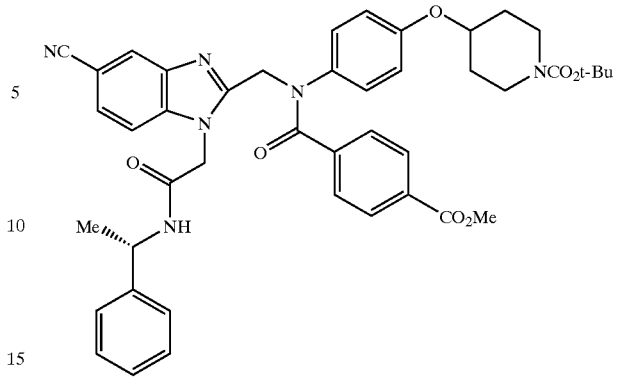

(S)-2-[N-Benzyloxycarbonyl-N-[4-(1-tert-butoxycarbonylpiperidin-4-yloxy)phenyl]aminomethyl]-5-cyano-1-(1-phenylethylcarbamoylmethyl)-benzimidazole (623 mg) was hydrogenated in tetrahydrofuran (6 ml) using 7.5% palladium carbon (310 mg) at 3 atm for 7 hours. After completion of the reaction, the reaction mixture was filtered through celite and the solvent was evaporated. The obtained residue was dissolved in chloroform (6 ml) and thereto were added triethylamine (0.176 ml), methyl 4-chloroformyl benzoate (167 mg) and 4-dimethylaminopyridine (10 mg), and the mixture was stirred at room temperature for 18 hours. After completion of the reaction, the solvent was evaporated and the obtained residue was purified by silica gel column chromatography (hexane:ethyl acetate=3:7) and dried under reduced pressure to give the title compound (284 mg).

$^1$H-NMR (δ ppm, CDCl$_3$) 1.36 (d, 3H), 1.46 (s, 9H), 1.70 (m, 2H), 1.86 (m, 2H), 3.30 (m, 2H), 3.69 (m, 2H), 3.87 (s, 3H), 4.36 (m, 1H), 5.02–5.09 (m, 3H), 5.15–5.28 (s, 2H), 5.21 (m, 2H), 6.73 (d, J=9 Hz, 2H), 7.11 (d, J=9 Hz, 2H), 7.15–7.23 (m, 6H), 7.30 (d, J=8.4 Hz, 2H), 7.40 (1H), 7.51 (1H), 7.82 (d, J=8.4 Hz, 2H), 8.04 (1H).

Step 12

(S)-2-[N-[4-(1-tert-Butoxycarbonylpiperidin-4-yloxy) phenyl]-N-(4-methoxycarbonylbenzoyl)aminomethyl]-1-(1-phenylethylcarbamoylmethyl)-benzimidazole-5-carboxamidine

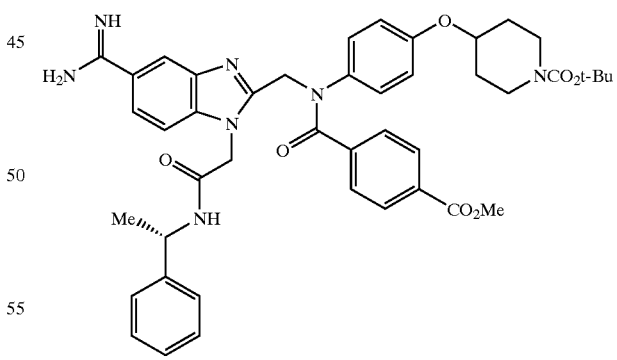

Hydrogen sulfide was blown into a solution of (S)-2-[N-[4-(1-tert-butoxycarbonylpiperidin-4-yloxy)phenyl]-N-(4-methoxycarbonylbenzoyl)-aminomethyl]-5-cyano-1-(1-phenylethylcarbamoylmethyl)benzimidazole (284 mg) in a mixture of pyridin-triethylamine (5:1) (10 ml) with ice-cooling, and the mixture was stirred at room temperature for 12 hours. After completion of the reaction, the solvent was evaporated and the residue was treated with hydrogen chloride-ethanol. Thereto were added acetone (6 ml), methanol (6 ml) and methyl iodide (0.229 ml), and the mixture was stirred under reflux for 2 hours. After completion of the reaction, the solvent was evaporated and the obtained residue was dissolved in ethanol (12 ml). Ammonium acetate (43 mg) was added, and the mixture was stirred at 75° C. for 2 hours. After completion of the reaction, the solvent was evaporated and the obtained residue was purified by silica gel column chromatography (chloroform:methanol= 95:5–90:10) and dried under reduced pressure to give the title compound (113 mg).

$^1$H-NMR (δ ppm, DMSO-$d_6$) 1.30–1.45 (m, 14H), 1.76 (m, 2H), 3.07 (m, 2H), 3.57 (m, 2H), 3.80 (s, 3H), 4.40 (m, 1H), 4.92 (m, 1H), 5.21–5.38 (m, 4H), 6.75 (d, J=9.0 Hz, 2H), 7.14 (d, J=9.0 Hz, 2H), 7.21–7.33 (m, 7H), 7.63–7.70 (m, 2H), 7.75 (2H), 8.14 (s, 1H), 8.96 (brs, 1H).

Step 13
(S)-4-[N-[5-Amidino-1-(1-phenylethylcarbamoylmethyl) benzimidazole-2-ylmethyl]-N-[4-(1-acetimidoylpiperidin-4-yloxy)phenyl]carbamoyl]benzoic Acid Dihydrochloride

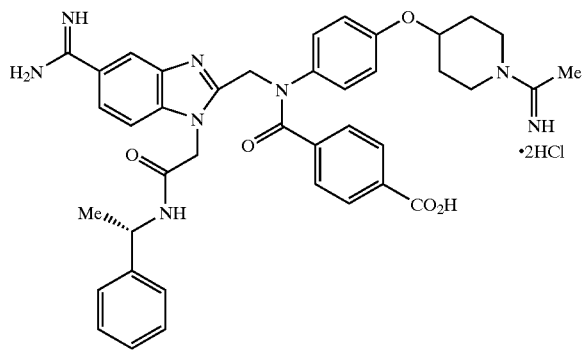

To a solution of (S)-2-[N-[4-(1-tert-butoxycarbonylpiperidin-4-yloxy)phenyl]-N-(4-methoxycarbonylbenzoyl)aminomethyl]-1-(1-phenylethylcarbamoylmethyl)benzimidazole-5-carboxamidine (113 mg) in chloroform (2 ml) was added trifluoroacetic acid (1 ml), and the mixture was stirred for 5 min. The solvent was evaporated and to the obtained residue was added 4N aqueous sodium hydroxide solution (1.1 ml), and the mixture was stirred for 5 hours. After completion of the reaction, dil. hydrochloric acid was added and the solvent was evaporated. The residue was dried under reduced pressure to give a residue. The obtained residue was dissolved in methanol (2 ml), and triethylamine (0.2 ml) and ethyl acetoimidate hydrochloride (89 mg) were added. The mixture was stirred at room temperature for 18 hours. After completion of the reaction, insoluble material was removed and the solvent was evaporated. The obtained residue was separated by HPLC (50% methanol-water, 0.05% trifluoroacetic acid). To the obtained residue was added dil. hydrochloric acid, and the solvent was evaporated and dried under reduced pressure to give the title compound (78 mg).

$^1$H-NMR (δ ppm, DMSO-$d_6$) 1.37 (d, J=7.2 Hz, 3H), 1.63 (m, 2H), 1.94 (m, 2H), 2.25 (s, 3H), 3.43 (m, 2H), 3.72 (m, 2H), 4.56 (m, 1H), 4.91 (quint, J=7.2 Hz, 1H), 5.23–5.39 (m, 4H), 6.80 (2H), 7.16–7.37 (m, 9H), 7.72–7.74 (m, 4H), 8.17 (s, 1H), 8.73 (brs, 1H), 9.09 (brs, 2H), 9.20 (d, J=7.2 Hz, 1H), 9.31 (brs, 3H).

Example 18
Synthesis of 4-[N-[5-Amidino-1-(4-benzyloxyphenylcarbamoylmethyl)-benzinidazol-2-ylmethyl]-N-[4-(1-acetimidoylpiperidin-4-yloxy) phenyl]carbamoyl]-benzoic Acid Dihydrochloride Step 1
2-[N-[4-(1-tert-Butoxycarbonylpiperidin-4-yloxy)phenyl] aminomethyl]-5-cyanobenzinidazole-1-acetic Acid

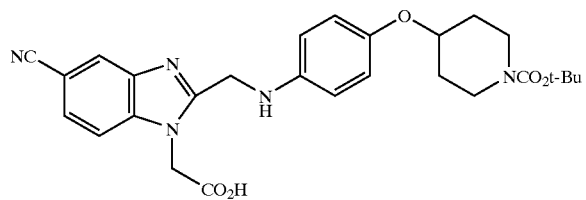

2-[N-Benzyloxycarbonyl-N-[4-(1-tert-butoxycarbonylpiperidin-4-yloxy)phenyl]aminomethyl]-5-cyanobenzimidazole-1-acetic acid (7.037 g) was hydrogenated using 7.5% palladium carbon (3.52 g) in ethanol (70 ml) at 3 atm over 3 hours. After completion of the reaction, the reaction mixture was filtered through celite and the solvent was evaporated. The obtained residue was washed with diisopropyl ether, filtrated and dried under reduced pressure to give the title compound (4.189 g).

$^1$H-NMR (δ ppm, $CD_3OD$) 1.44 (s, 9H), 1.58 (m, 2H), 1.84 (m, 2H), 3.25 (m, 2H), 3.66 (m, 2H), 4.29 (m, 1H), 4.60 (s, 2H), 5.23 (s, 2H), 6.67 (d, J=6.6 Hz, 2H), 6.77 (d, J=6.6 Hz, 2H), 7.59 (d, J=6.6 Hz, 1H), 7.63 (d, J=6.6 Hz, 1H), 8.02 (s, 1H).

Step 2
2-[N-[4-(1-tert-Butoxycarbonylpiperidin-4-yloxy)phenyl]-N-(4-methoxycarbonylbenzoyl)aminomethyl]-5-cyanobenzimidazole-1-acetic Acid

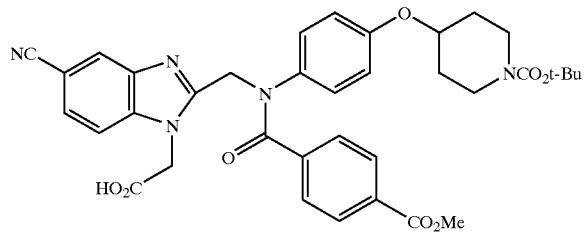

To a solution of 2-[N-[4-(1-tert-butoxycarbonylpiperidin-4-yloxy)phenyl]aminomethyl]-5-cyanobenzimidazole-1-acetic acid (3.36 g) and sodium hydrogencarbonate (1.67 g) in a mixture of water (34 ml) and tetrahydrofuran (34 ml) was added methyl 4-chloroformyl benzoate (1.32 g), and the mixture was stirred at room temperature for 30 min. After completion of the reaction, the mixture was extracted with ethyl acetate and washed successively with water, 10% aqueous citric acid solution and saturated brine. The organic layer was dried over anhydrous magnesium sulfate and the solvent was evaporated. The obtained residue was purified by silica gel column chromatography (ethyl acetate) to give the title compound (2.907 g).

$^1$H-NMR (δ ppm, $CDCl_3$) 1.45 (s, 9H), 1.63 (m, 2H), 1.80 (m, 2H), 3.25 (m, 2H), 3.63 (m, 2H), 3.83 (s, 3H), 4.31 (m, 1H), 5.28 (s, 2H), 5.32 (s, 2H), 6.65 (d, J=9.0 Hz, 2H), 6.90 (d, J=9.0 Hz, 2H), 7.23 (d, J=8.4 Hz, 2H), 7.37 (1H), 7.55 (1H), 7.64 (d, J=8.4 Hz, 2H), 7.99 (1H).

Step 3
2-[N-[4-(1-tert-Butoxycarbonylpiperidin-4-yloxy)phenyl]-N-(4-methoxycarbonyl-benzoyl)aminomethyl]-5-cyano-1-(4-benzyloxyphenylcarbamoylmethyl)-benzimidazole

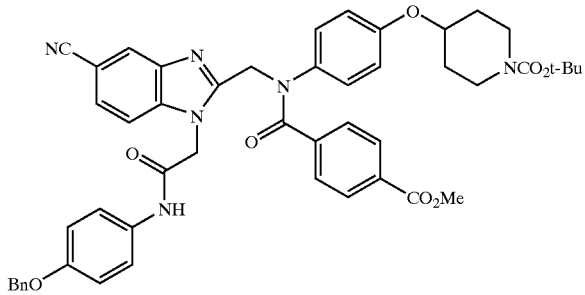

2-[N-[4-(1-tert-Butoxycarbonylpiperidin-4-yloxy) phenyl]-N-(4-methoxycarbonylbenzoyl)aminomethyl]-5-cyanobenzimidazole-1-acetic acid (632 mg), 1-hydroxybenzotriazole hydrate (128 mg), 4-benzyloxyaniline hydrochloride (223 mg), 1-(3-dimethylaminopropyl)-3-ethylcarbodiimide hydrochloride (182 mg) and N-methylmorpholine (0.104 ml) were treated in the same manner as in Example 17, Step 10. The solvent was evaporated and the obtained residue was purified by silica gel column chromatography (hexane:ethyl acetate= 3:7–2:8) to give the title compound (605 mg).

$^1$H-NMR (δ ppm, CDCl$_3$) 1.46 (s, 9H), 1.85 (m, 2H), 3.29 (m, 2H), 3.66 (m, 2H), 3.84 (s, 3H), 4.35 (m, 1H), 4.98 (s, 2H), 5.23 (s, 2H), 5.31 (s, 2H), 6.72 (d, J=9.0 Hz, 2H), 6.80 (d, 2H), 7.07 (d, J=9.0 Hz, 2H), 7.27 (d, J=8.4 Hz, 2H), 7.30–7.41 (m, 7H), 7.56 (s, 2H), 7.73 (d, J=8.4 Hz, 2H), 8.06 (s, 1H), 8.72 (brs, 1H).

Step 4
2-[N-[4-(1-tert-Butoxycarbonylpiperidin-4-yloxy)phenyl]-N-(4-methoxycarbonyl-benzoyl)aminomethyl]-1-(4-benzyloxyphenylcarbamoylmethyl)benzmidazole-5-carboxamidine

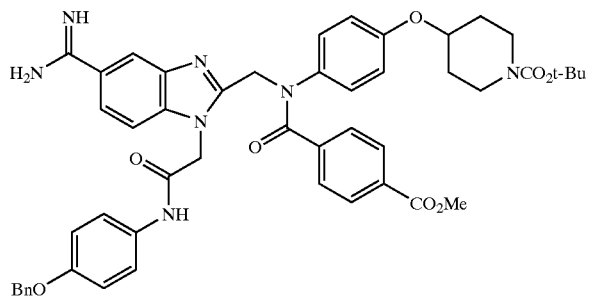

Hydrogen sulfide was blown into a solution of 2-[N-[4-(1-tert-butoxycarbonylpiperidin-4-yloxy)phenyl]-N-(4-methoxycarbonylbenzoyl)-aminomethyl]-5-cyano-1-(4-benzyloxyphenylcarbamoylmethyl)benzimidazole (605 mg) in a mixed solution (15 ml) of pyridin-triethylamine (5:1) with ice-cooling, and the mixture was stirred at room temperature for 15 hours. After completion of the reaction, the solvent was evaporated and the obtained residue was collected by filtration and washed with toluene. To the obtained solid were added acetone (15 ml) and methyl iodide (0.443 ml), and the mixture was stirred under reflux for 1 hour. After completion of the reaction, the solvent was evaporated and dried under reduced pressure to give a crude product (804 mg). From the obtained crude product, 434 mg was dissolved in ethanol (10 ml) and thereto was added ammonium acetate (44 mg) at room temperature. The mixture was stirred at 75° C. for 3.5 hours. After completion of the reaction, the solvent was evaporated and the obtained residue was purified by silica gel column chromatography (chloroform:methanol=95:5–90:10) and dried under reduced pressure to give the title compound (141 mg).

$^1$H-NMR (δ ppm, DMSO-d$_6$) 1.38 (s, 9H), 1.75 (m, 2H), 3.05 (m, 2H), 3.60 (m, 2H), 3.79 (s, 3H), 4.40 (m, 1H), 5.06 (s, 2H), 5.35 (brs, 4H), 6.77 (2H), 6.97 (2H), 7.25–7.50 (10H), 7.65–7.76 (4H), 8.13 (1H).

Step 5
4-[N-[5-Amidino-1-(4-benzyloxyphenylcarbamoylmethyl) benzimidazol-2-ylmethyl]-N-[4-(1-acetimidoylpiperidin-4-yloxy)phenyl]carbamoyl]benzoic Acid Dihydrochloride

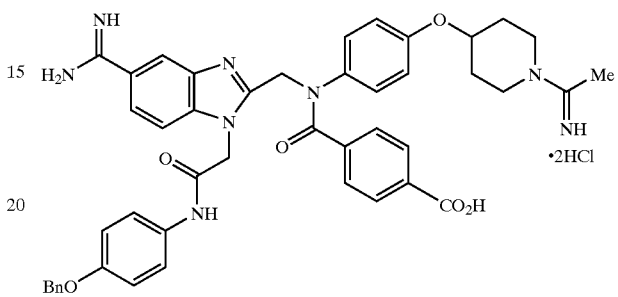

In the same manner as in Example 17, Step 13, the title compound (59 mg) was obtained from 2-[N-[4-(1-tert-butoxycarbonylpiperidin-4-yloxy)phenyl]-N-(4-methoxycarbonylbenzoyl)aminomethyl]-1-(4-benzyloxyphenylcarbamoyl-methyl)benzimidazole-5-carboxamidine (141 mg), trifluoroacetic acid (1 ml), 4N aqueous sodium hydroxide solution (0.973 ml), triethylamine (0.226 ml) and ethyl acetoimidate hydrochloride (100 mg).

$^1$H-NMR (δ ppm, DMSO-d$_6$) 1.63 (m, 2H), 1.95 (m, 2H), 2.27 (s, 3H), 3.45 (m, 2H), 4.57 (m, 1H), 5.06 (s, 2H), 5.39 (brs, 2H), 5.45 (brs, 2H), 6.82 (d, 2H), 6.97 (d, 2H), 7.18 (d, 2H), 7.27–7.45 (m, 8H), 7.53 (d, 2H), 7.65 (d, 2H), 7.75 (d, J=8.4 Hz, 1H), 7.88 (d, J=8.4 Hz, 1H), 8.19 (s, 1H), 8.74 (brs, 1H), 9.09 (brs, 2H), 9.30–9.33 (m, 3H).

Example 19

Synthesis of 2-[4-(pyrrolidin-3-yloxy) phenoxymethyl]-1-(2-methoxyethyl)-benzimidazole-5-carboxamidine Dihydrochloride Step 1
4-(1-tert-Butoxycarbonylpyrrolidin-3-yloxy)benzaldehyde

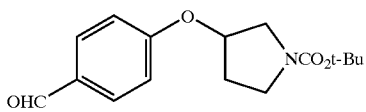

To a solution of 3-hydroxypyrrolidine-1-carboxylic acid tert-butyl ester (3.07 g), 4-hydroxybenzaldehyde (2 g) and triphenylphosphine (4.51 g) in tetrahydrofuran (50 ml) was added diethyl azodicarboxylate (2.7 ml), and the mixture was stirred at room temperature for 2 hours. After completion of the reaction, the solvent was evaporated and the obtained residue was purified by silica gel column chromatography (hexane:acetone=5:1) and dried under reduced pressure to give the title compound (3.2 g).

$^1$H-NMR (δ ppm, CDCl$_3$) 1.47 (s, 9H), 2.19 (m, 2H), 3.59 (m, 4H), 4.99 (m, 1H), 6.98 (d, J=9.0 Hz, 2H), 7.85 (d, J=9.0 Hz, 2H), 9.89 (s, 1H).

Step 2
4-(1-tert-Butoxycarbonylpyrrolidin-3-yloxy)phenol

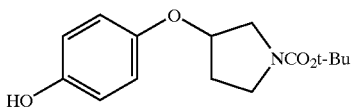

To a solution of 4-(1-tert-butoxycarbonylpyrrolidin-3-yloxy)benzaldehyde (500 mg) in methylene chloride (10 ml) was added 70% 3-chloroperbenzoic acid (712 mg) with ice-cooling, and the mixture was stirred at room temperature for 4.5 hours. After completion of the reaction, aqueous sodium hydrogencarbonate solution and aqueous sodium thiosulfate solution were added, and the mixture was extracted with methylene chloride and washed successively with water and saturated brine. The organic layer was dried over anhydrous sodium sulfate and the solvent was evaporated. The obtained residue was dissolved in methanol (3.4 ml) and thereto was added 1N aqueous sodium hydroxide solution (1.7 ml), and the mixture was stirred at room temperature for 1 hour. After completion of the reaction, 10% aqueous citric acid solution was added, and the mixture was extracted with chloroform and washed successively with water and saturated brine. The organic layer was dried over anhydrous sodium sulfate and the solvent was evaporated. The obtained solid was washed with diethyl ether and dried under reduced pressure to give the title compound (350 mg).

$^1$H-NMR (δ ppm, CDCl$_3$) 1.47 (s, 9H), 2.09(m, 2H), 3.54 (m, 4H), 4.75 (m, 1H), 6.71–6.79 (m, 4H).

Step 3
4-(1-tert-Butoxycarbonylpyrrolidin-3-yloxy)phenoxyacetic Acid Ethyl Ester

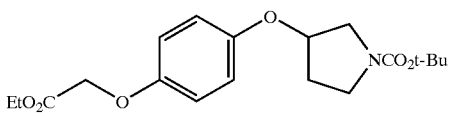

To a solution of 4-(1-tert-butoxycarbonylpyrrolidin-3-yloxy)phenol (2.14 g) in tetrahydrofuran (43 l) were added ethyl bromoacetate (1.1 ml) and 60% sodium hydride (368 mg) with ice-cooling, and the mixture was stirred at room temperature for 1 hour. After completion of the reaction, ice water was added and the mixture was extracted with ethyl acetate and washed with 10% aqueous citric acid solution. The organic layer was dried over anhydrous magnesium sulfate and the solvent was evaporated. The obtained residue was purified by silica gel column chromatography (hexane:ethyl acetate=7:3) and dried under reduced pressure to give the title compound (2.605 g).

$^1$H-NMR (δ ppm, CDCl$_3$) 1.30 (tr, J=7.2 Hz, 3H), 1.46 (s, 9H), 2.13 (m, 2H), 3.54 (m, 4H), 4.27 (q, J=7.2 Hz, 2H), 4.57 (s, 2H), 4.79 (brs, 1H), 6.78–6.87 (m, 4H).

Step 4
4-(1-tert-Butoxycarbonylpyrrolidin-3-yloxy)phenoxyacetic Acid

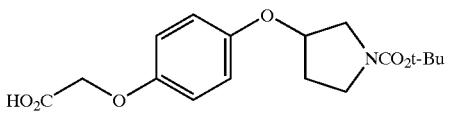

To a solution of 4-(1-tert-butoxycarbonylpyrrolidin-3-yloxy)phenoxyacetic acid ethyl ester (2.5 g) in a mixture of tetrahydrofuran (5 ml) and ethanol (5 ml) was added 1N aqueous lithium hydroxide solution (7.5 ml) with ice-cooling, and the mixture was stirred at room temperature for 30 min. After completion of the reaction, the solvent was evaporated and to the obtained residue were added ice water and 10% aqueous citric acid solution, and the mixture was extracted with ethyl acetate. The organic layer was washed successively with water and saturated brine and dried over anhydrous magnesium sulfate. The solvent was evaporated and the residue was dried under reduced pressure to give the title compound(2.30 g).

$^1$H-NMR (δ ppm, CDCl$_3$) 1.47 (s, 9H), 2.14 (m, 2H), 3.54 (m, 4H), 4.61 (brs, 2H), 4.79 (m, 1H), 6.80–6.89 (m, 4H).

Step 5
4-(2-Hydroxyethylamino)-3-nitrobenzonitrile

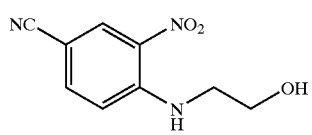

A solution of 4-chloro-3-nitrobenzonitrile (10.13 g) and ethanolamine (3.52 ml) in a mixture of ethanol (150 ml) and tetrahydrofuran (50 ml) was stirred at room temperature for 2 hours. Ethanolamine (3.35 ml) was added and the mixture was stirred at 50° C. for 1 hour. Then, ethanolamine (3.35 ml) was added, and the mixture was stirred at the same temperature for 1 hour. After completion of the reaction, the solvent was evaporated and the obtained solid was washed with isopropanoyl, collected by filtration, and dried under reduced pressure to give the title compound (7.25 g).

$^1$H-NMR (δ ppm, DMSO-d$_6$) 3.48 (m, 2H), 3.63 (m, 2H), 5.00 (brs, 1H), 7.22 (d, J=9.0 Hz, 1H), 7.81 (dd, J=1.8, 9.0 Hz, 1H), 8.50 (d, J=1.8 Hz, H), 8.62 (brtr, 1H).

Step 6
3-Amino-4-(2-hydroxyethylamino)benzonitrile

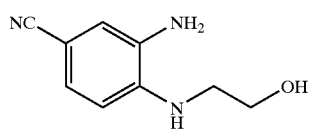

A solution of 4-(2-hydroxyethylamino)-3-nitrobenzonitrile (3.11 g) and tin chloride dihydrate (16.94 g) in ethanol (50 ml) was stirred at 70° C. for 1 hour. After completion of the reaction, the solvent was evaporated and to the obtained residue were added tetrahydrofuran and 15% aqueous sodium hydroxide solution. The mixture was stirred and insoluble material and the aqueous layer were removed. The obtained organic layer was dried over anhydrous magnesium sulfate and the solvent was evaporated. The obtained solid was washed with chloroform, filtrated and dried under reduced pressure to give the title compound (2.08 g).

$^1$H-NMR (δ ppm, DMSO-d$_6$) 3.17 (q, J=5.6 Hz, 2H), 3.58 (q, J=5.6 Hz, 2H), 4.74 (tr, J=5.6 Hz, 1H), 4.93 (brs, 2H), 5.34 (tr, J=5.6 Hz, 2H), 6.49 (1H), 6.77 (1H), 6.91 (1H).

Step 7
3-[4-[5-Cyano-2-(2-hydroxyethylamino) phenylcarbamoylmethoxy]-phenoxy]pyrrolidine-1-carboxylic Acid tert-Butyl Ester

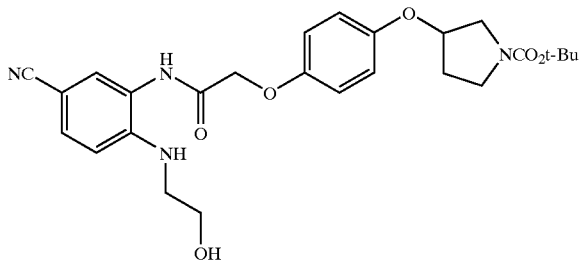

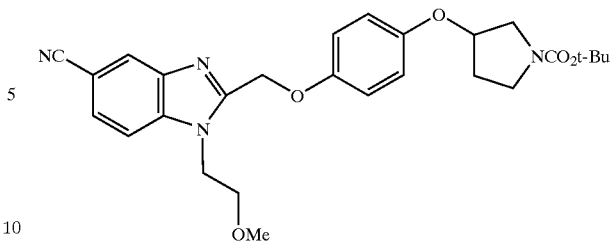

To a solution of 3-amino-4-(2-hydroxyethylamino) benzonitrile (1.21 g) and 4-(1-tert-butoxycarbonylpyrrolidin-3-yloxy)phenoxyacetic acid (2.30 g) in chloroform (50 ml) was added 1-ethoxycarbonyl-2-ethoxy-1,2-dihydroxyquinoline (2.19 g), and the mixture was stirred at room temperature for 15 hours. After completion of the reaction, the solvent was evaporated and the obtained residue was purified by silica gel column chromatography (hexane:ethyl acetate=1:4) to give the title compound (2.56 g).

$^1$H-NMR (δ ppm, CDCl$_3$) 1.46 (s, 9H), 2.13 (m, 2H), 3.31 (m, 2H), 3.55 (m, 4H), 3.73 (m, 2H), 4.64 (s, 2H), 4.82 (m, 1H), 6.73 (1H), 6.85–6.94 (m, 4H), 7.41–7.50 (2H), 7.99 (1H), 8.10 (1H).

Step 8

2-[4-(1-tert-Butoxycarbonylpyrrolidin-3-yloxy) phenoxymethyl]-5-cyano-1-(2-hydroxyethyl)benzimidazole

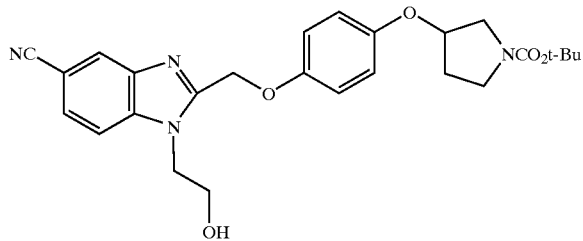

A solution of 3-[4-[5-cyano-2-(2-hydroxyethylamino) phenyl-carbamoylmethoxy]phenoxy]pyrrolidine-1-carboxylic acid tert-butyl ester (2.56 g) in acetic acid (15.4 ml) was stirred at 65° C. for 4 hours. After completion of the reaction, the solvent was evaporated and the obtained residue was extracted with ethyl acetate and washed with aqueous sodium hydrogencarbonate solution. The organic layer was dried over anhydrous magnesium sulfate and the solvent was evaporated. The obtained residue was purified by silica gel column chromatography (hexane:ethyl acetate= 1:4—ethyl acetate) to give the title compound (1.356 g).

$^1$H-NMR (δ ppm, CDCl$_3$) 1.44 (s, 9H), 2.11 (m, 2H), 3.44–3.54 (m, 4H), 3.75 (brs, 1H), 4.06 (m, 2H), 4.46 (m, 2H), 4.77 (m, 1H), 5.32 (s, 2H), 6.77 (2H), 6.93 (2H), 7.49 (2H), 7.79 (1H).

Step 9

2-[4-(1-tert-Butoxycarbonylpyrrolidin-3-yloxy) phenoxymethyl]-5-cyano-1-(2-methoxyethyl) benzimidazole To a solution of 2-[4-(1-tert-butoxycarbonylpyrrolidin-3-yloxy)-phenoxymethyl]-5-cyano-1-(2-hydroxyethyl) benzimidazole (270 mg) in tetrahydrofuran (5 ml) was added 60% sodium hydride (271 mg) at room temperature, and the mixture was stirred for 30 min. Thereto was added methyl iodide (0.105 ml), and the mixture was stirred for 24 hours. After completion of the reaction, 10% aqueous citric acid solution was added and the mixture was extracted with ethyl acetate and washed with saturated brine. The organic layer was dried over anhydrous magnesium sulfate and the solvent was evaporated. The obtained residue was purified by silica gel column chromatography (hexane:acetone=4:1) and dried under reduced pressure to give the title compound (199 mg).

$^1$H-NMR (δ ppm, CDCl$_3$) 1.46 (s, 9H), 2.10 (m, 2H), 3.27 (s, 3H), 3.55 (m, 4H), 3.72 (tr, 2H), 4.52 (tr, 2H), 4.79 (m, 1H), 5.39 (s, 2H), 6.79 (2H), 6.90 (2H), 7.50 (1H), 7.55 (1H), 8.10 (1H).

Step 10

2-[4-(1-tert-Butoxycarbonylpyrrolidin-3-yloxy) phenoxymethyl]-1-(2-methoxyethyl)benzimidazole-5-carboxamidine

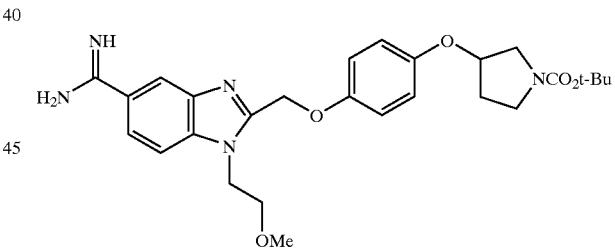

In the same manner as in Example 18, Step 4, the title compound (119 mg) was obtained from 2-[4-(1-tert-butoxycarbonylpyrrolidin-3-yloxy)-phenoxymethyl]-5-cyano-1-(2-methoxyethyl)benzimidazole (195 mg), methyl iodide (1 ml) and ammonium acetate (37 mg).

$^1$H-NMR (δ ppm, CDCl$_3$) 1.45 (s, 9H), 2.10 (m, 2H), 3.24 (s, 3H), 3.54 (m, 4H), 3.69 (brtr, 2H), 4.47 (brtr, 2H), 4.76 (m, 1H), 5.32 (s, 2H), 6.79 (2H), 6.94 (2H), 7.48 (1H), 7.66 (1H), 8.08 (1H).

Step 11

2-[4-(Pyrrolidin-3-yloxy)phenoxymethyl]-1-(2-methoxyethyl)benzimidazole-5-carboxamidine Dihydrochloride

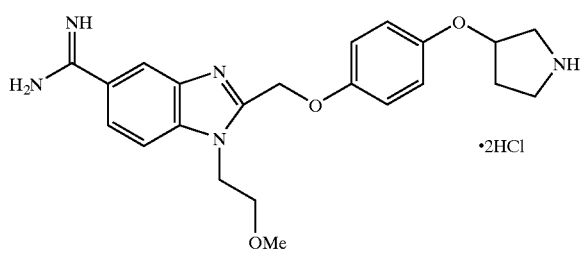

·2HCl

To a solution of 2-[4-(1-tert-butoxycarbonylpyrrolidin-3-yloxy)-phenoxymethyl]-1-(2-methoxyethyl)benzimidazole-5-carboxamidine (115 mg) in chloroform (3 ml) was added trifluoroacetic acid (3 ml), and the mixture was stirred at 5 min. The solvent was evaporated and to the obtained residue was added 1N hydrogen chloride-diethyl ether (2 ml). The solvent was evaporated and the obtained residue was washed with tetrahydrofuran and dried under reduced pressure to give the title compound (97 mg).

$^1$H-NMR (δ ppm, DMSO-$d_6$) 2.10 (m, 2H), 3.18 (s, 3H), 3.28–3.42 (m, 4H), 3.69 (brtr, 2H), 4.59 (brtr, 2H), 5.02 (m, 1H), 5.43 (s, 2H), 6.94 (d, J=9.0 Hz, 2H), 7.07 (d, J=9.0 Hz, 2H), 7.60 (d, J=9.0 Hz, 1H), 7.87 (d, J=9.0 Hz, 1H), 8.23 (s, 1H), 9.08 (brs, 2H), 9.34 (brs, 2H).

Example 20

Synthesis of 2-[4-(1-Acetimidoylpyrrolidin-3-yloxy)phenoxymethyl]-1-(2-methoxyethyl)benzimidazole-5-carboxamidine Dihydrochloride

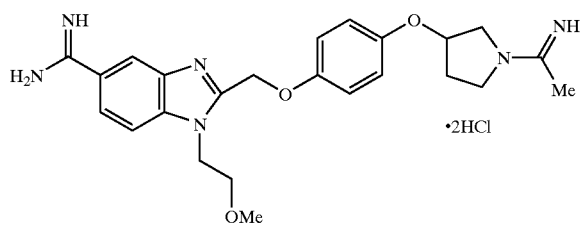

·2HCl

To a solution of 2-[4-(pyrrolidin-3-yloxy)phenoxymethyl]-1-(2-methoxyethyl)benzimidazole-5-carboxamidine dihydrochloride (44 mg) in a mixture of tetrahydrofuran (2 ml) and water (0.6 ml) were added sodium hydrogencarbonate (38 mg), and ethyl acetoimidate hydrochloride (33 mg), and the mixture was stirred at room temperature for 16 hours. After completion of the reaction, insoluble material was removed and the solvent was evaporated. The obtained residue was separated by HPLC (50% methanol-water, 0.05% trifluoroacetic acid). To the obtained residue was added dil. hydrochloric acid and the solvent was evaporated and dried under reduced pressure to give the title compound (40 mg).

$^1$H-NMR (δ ppm, DMSO-$d_6$) 2.12–2.28 (m, 5H), 3.18 (s, 3H), 3.35–3.95 (m, 6H), 4.59 (brs, 2H), 5.06–5.13 (m, 1H), 5.43 (s, 2H), 6.94 (dd, J=2.9, 9.0 Hz, 2H), 7.07 (dd, J=2.9, 9.0 Hz, 2H), 7.77 (1H), 7.88 (1H), 8.24 (1H), 8.47, 8.54 (1H), 9.13 (2H), 9.27, 9.31 (1H), 9.36 (2H).

Example 21

Synthesis of 7-[1-(2-Hydroxyethyl)piperidin-4-ylmethoxy]-1,2,3,4-tetrahydroisoquinoline-2-carboxamidine Dihydrochloride Step 1

N,N'-di-tert-Butoxycarbonyl-7-hydroxy-1,2,3,4-tetrahydroisoquinoline-2-carboxamidine

To a suspension of 7-hydroxy-1,2,3,4-tetrahydroisoquinoline hydrobromide (500 mg) in acetonitrile (5 ml) was added triethylamine (0.3 ml) with ice-cooling, and the mixture was stirred at room temperature for 1 hour. The precipitated solid was collected by filtration. The obtained solid was dissolved in dimethylformamide (5 ml) and thereto was added 1H-pyrazole-1-(N,N'-bis-tert-butoxycarbonyl)carboxamidine (Synthesis, p. 579 (1994)) (742 mg), and the mixture was stirred at room temperature for 2 hours. After completion of the reaction, water was added and the mixture was extracted with ethyl acetate and washed with saturated brine. The organic layer was dried over anhydrous sodium sulfate and the solvent was evaporated. The obtained residue was purified by silica gel column chromatography (hexane:ethyl acetate=3:1) and dried under reduced pressure to give the title compound (700 mg).

$^1$H-NMR (δ ppm, CDCl$_3$) 1.50 (s, 18H), 2.87 (m, 2H), 3.73 (m, 2H), 4.62 (brs, 2H), 6.53 (d, J=2.5 Hz, 1H), 6.66 (dd, J=2.5, 8.2 Hz, 1H), 6.97 (d, J=8.2 Hz, 1H).

Step 2

4-Hydroxymethylpiperidine-1-carboxylic Acid Benzyl Ester

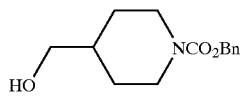

In the same manner as in Example 10, Step 1,1-benzyloxycarbonylpiperidine-4-carboxylic acid (10 g) was obtained from isonipecotic acid (15.5 g). To a solution of this obtained compound in tetrahydrofuran (100 ml) were added dropwise at −15° C. triethylarnine (5.56 ml) and isobutyl chlorocarbonate (5.2 ml) under an argon atmosphere, and the mixture was stirred at the same temperature for 20 min. After completion of the reaction, the reaction mixture was filtrated, and the filtrate was dropwise added to aqueous sodium borohydride (4.3 g) solution with ice-cooling. The mixture was stirred at the same temperature for 15 min and then at room temperature for 2 hours. After completion of the reaction, water was added and insoluble material was removed. The solvent was partially evaporated and the mixture was extracted with ethyl acetate. The organic layer was washed successively with 1N aqueous sodium hydroxide, water and saturated brine and dried over anhydrous sodium sulfate. The solvent was evaporated and the residue was dried under reduced pressure to give the title compound (7.2 g).

$^1$H-NMR (δ ppm, CDCl$_3$) 1.05–1.30 (m, 2H), 1.55–1.80 (m, 3H), 2.70–2.85 (m, 2H), 3.50 (d, 2H), 4.10–4.30 (m, 2H), 5.13 (s, 2H), 7.26–7.40 (m, 5H).

Step 3
4-Bromomethylpiperidine-1-carboxylic Acid Benzyl Ester

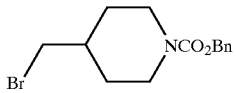

To a solution of 4-hydroxymethylpiperidine-1-carboxylic acid benzyl ester (1.11 g), carbon tetrabromide (1.77 g) in methylene chloride (11 ml) was added triphenylphosphine (1.4 g) with ice-cooling, and the mixture was stirred at room temperature for 5 hours. After completion of the reaction, the solvent was evaporated and the obtained residue was purified by silica gel column chromatography (hexane:acetone=10:1) and dried under reduced pressure to give the title compound (1.25 g).
$^1$H-NMR (δ ppm, CDCl$_3$) 1.05–1.30 (m, 2H), 1.70–1.90 (m, 3H), 2.78 (m, 2H), 3.29 (d, 2H), 4.10–4.30 (m, 2H), 5.13 (s, 2H), 7.26–7.38 (m, 5H).

Step 4
4-[2-(N,N'-Di-tert-Butoxycarbonylamidino)-1,2,3,4-tetrahydroisoquinolin-7-yloxymethyl]piperidine-1-carboxylic Acid Benzyl Ester

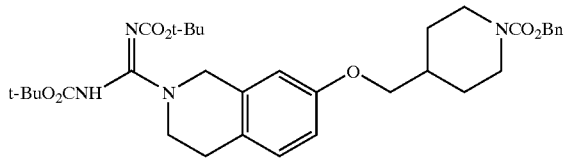

To a solution of N,N'-di-tert-butoxycarbonyl-7-hydroxy-1,2,3,4-tetrahydroisoquinoline-2-carboxamidine (50 mg) and 4-bromomethylpiperidine-1-carboxylic acid benzyl ester (120 mg) in dimethyl sulfoxide (1 ml) was added 4N aqueous sodium hydroxide solution (0.13 ml), and the mixture was stirred at room temperature for 17 hours. After completion of the reaction, water was added, and the mixture was extracted with ethyl acetate and washed successively with water and saturated brine. The organic layer was dried over anhydrous sodium sulfate, and the solvent was evaporated. The obtained residue was purified by silica gel column chromatography (hexane:acetone=5:1) and dried under reduced pressure to give the title compound (55 mg).
$^1$H-NMR (δ ppm, CDCl$_3$) 1.20–1.35 (m, 2H), 1.51 (s, 18H), 1.75–2.05 (m, 3H), 2.70–2.95 (m, 4H), 3.65–3.80 (m, 4H), 4.15–4.35 (m, 2H), 4.67 (brs, 2H), 5.14 (s, 2H), 6.61 (1H), 6.71 (1H), 7.03 (1H), 7.30–7.40 (5H).

Step 5
N,N'-Di-tert-Butoxycarbonyl-7-(piperidin-4-ylmethoxy)-1,2,3,4-tetrahydroisoquinoline-2-carboxamidine

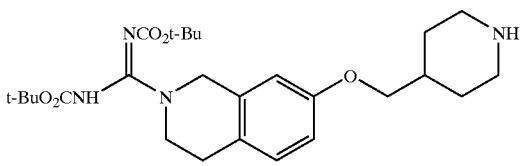

4-[2-(N,N'-Di-tert-butoxycarbonylamidino)-1,2,3,4-tetrahydroisoquinolin-7-yloxymethyl]piperidine-1-carboxylic acid benzyl ester (500 mg) was hydrogenated using 7.5% palladium carbon (150 mg) in a mixture of tetrahydrofuran (5 ml) and ethanol (100 ml) at 3 atm over 3 hours. After completion of the reaction, the reaction mixture was filtered through celite, and the solvent was evaporated. The residue was dried under reduced pressure to give the title compound (815 mg).

$^1$H-NMR (δ ppm, CDCl$_3$) 1.20–1.40 (m, 2H), 1.56 (s, 18H), 1.75–2.00 (m, 3H), 2.67 (brtr, 2H), 2.89 (brtr, 2H), 3.10–3.20 (m, 2H), 3.65–3.85 (m, 4H), 4.67 (s, 2H), 6.62 (1H), 6.72 (1H), 7.03 (1H).

Step 6
4-[2-(N,N'-Di-tert-Butoxycarbonylamidino)-1,2,3,4-tetrahydroisoquinolin-7-yloxymethyl]piperidine-1-acetic Acid Ethyl Ester

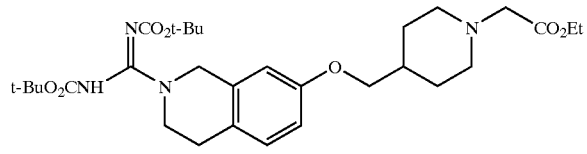

To a solution of N,N'-di-tert-butoxycarbonyl-7-(piperidin-4-ylmethoxy)-1,2,3,4-tetrahydroisoquinoline-2-carboxamidine (100 mg) in a mixture of tetrahydrofuran (1 ml) and dimethylformamide (1 ml) were added 9.1N aqueous sodium hydroxide solution (0.027 ml) and ethyl bromoacetate (0.027 ml), and the mixture was stirred at room temperature for 1 hour. After completion of the reaction, water was added and the mixture was extracted with ethyl acetate and washed successively with water and saturated brine. The organic layer was dried over anhydrous sodium sulfate and the solvent was evaporated. The obtained residue was purified by silica gel column chromatography (hexane:acetone=4:1) and dried under reduced pressure to give the title compound (100 mg).
$^1$H-NMR (δ ppm, CDCl$_3$) 1.28 (tr, J=5.2 Hz, 3H), 1.51 (s, 18H), 1.60–1.85 (m, 5H), 2.17–2.23 (m, 2H), 2.85–3.05 (m, 4H), 3.22 (s, 2H), 3.55–3.95 (m, 4H), 4.19 (q, J=5.2 Hz, 2H), 4.86 (brs, 2H), 6.61 (1H), 6.71 (1H), 7.03 (1H), 10.22 (brs, 1H).

Step 7
N,N'-Di-tert-Butoxycarbonyl-7-[1-(2-hydroxyethyl)piperidin-4-ylmethoxy]-1,2,3,4-tetrahydroisoquinoline-2-carboxamidine

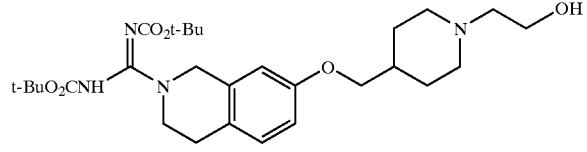

To a solution of 4-[2-(N,N'-di-tert-butoxycarbonylamidino)-1,2,3,4-tetrahydroisoquinolin-7-yloxymethyl]piperidine-1-acetic acid ethyl ester (155 mg) in a mixture of tetrahydrofuran (2 ml) and methanol (0.008 ml) was added lithium borohydride (11 mg), and the mixture was stirred at room temperature for 3 hours. After completion of the reaction, water was added and the mixture was extracted with ethyl acetate and washed successively with water and saturated brine. The organic layer was dried over anhydrous sodium sulfate and the solvent was evaporated. The obtained residue was purified by silica gel column chromatography (hexane:acetone=3:1) and dried under reduced pressure to give the title compound (65 mg).
$^1$H-NMR (δ ppm, CDCl$_3$) 1.30–1.55 (m, 20H), 1.70–1.90 (m, 3H), 2.11 (brtr, 2H), 2.54 (tr, J=5.4 Hz, 2H), 2.85–3.00 (m, 4H), 3.61 (tr, J=5.4 Hz, 2H), 3.65–3.85 (m, 4H), 4.67 (s, 2H), 6.63 (1H), 6.72 (1H), 7.03 (1H), 10.21 (brs, 1H).

Step 8
7-[1-(2-Hydroxyethyl)piperidin-4-ylmethoxy]-1,2,3,4-tetrahydroisoquinoline-2-carboxamidine Dihydrochloride

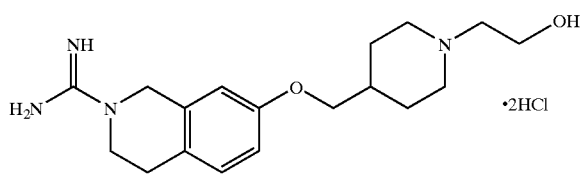

To a solution of N,N'-di-tert-butoxycarbonyl-7-[1-(2-hydroxyethyl)-piperidin-4-ylmethoxy]-1,2,3,4-tetrahydroisoquinoline-2-carboxamidine (60 mg) in chloroform (0.6 ml) solution was added trifluoroacetic acid (0.3 ml), and the mixture was stirred at room temperature for 5 hours. After completion of the reaction, the solvent was evaporated and to the obtained residue was added a hydrogen chloride—ethanol solution and insoluble material was removed. The resultant mixture was concentrated and dried under reduced pressure to give the title compound (40 mg).

$^1$H-NMR (δ ppm, DMSO-$d_6$) 1.58–1.80 (m, 2H), 1.85–2.10 (m, 3H), 2.82 (m, 2H), 2.90–3.15 (m, 5H), 3.55–3.60 (m, 2H), 3.75–3.83 (m, 6H), 4.54 (s, 2H), 6.71 (1H), 6.83 (1H), 7.14 (1H), 7.59 (4H), 10.08 (1H).

Example 22

Synthesis of 7-[1-(Pyridin-4-ylmethyl)piperidin-4-ylmethoxy-1,2,3,4-tetrahydroisoquinoline-2-carboxamidine Trihydrochloride Step 1
N,N'-Di-tert-Butoxycarbonyl-7-[1-(pyridin-4-ylmethyl)piperidin-4-ylmethoxy]-1,2,3,4-tetrahydroisoquinoline-2-carboxamidine

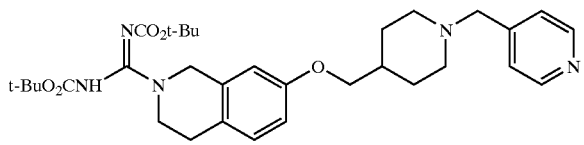

To a solution of N,N'-di-tert-butoxycarbonyl-7-(piperidin-4-ylmethoxy)-1,2,3,4-tetrahydroisoquinoline-2-carboxamidine (100 mg) in a mixture of tetrahydrofuran (1 ml) and dimethylformamide (1 ml) were added 9.1N sodium hydroxide (0.068 ml) and 4-picolyl chloride hydrochloride (51 mg), and the mixture was stirred at 50° C. for 5 hours. After completion of the reaction, water was added and the mixture was extracted with ethyl acetate and was washed successively with water and saturated brine. The organic layer was dried over anhydrous sodium sulfate, and the solvent was evaporated. The obtained residue was purified by preparative thin layer chromatography (chloroform:methanol=20:1) and dried under reduced pressure to give the title compound (93 mg).

Step 2
7-[-(Pyridin-4-ylmethyl)piperidin-4-ylmethoxy]-1,2,3,4-tetrahydroisoquinoline-2-carboxamidine Trihydrochloride

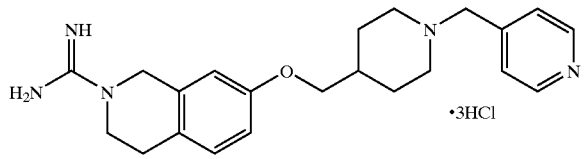

In the same manner as in Example 21, Step 8, the title compound (65 mg) was obtained from N,N'-di-tert-butoxycarbonyl-7-[1-(pyridin-4-ylmethyl)-piperidin-4-ylmethoxy]-1,2,3,4-tetrahydroisoquinoline-2-carboxamidine (88 mg) and trifluoroacetic acid (0.45 ml).

$^1$H-NMR (δ ppm, DMSO-$d_6$) 1.70–2.00 (m, 5H), 2.81 (m, 2H), 3.00 (m, 2H), 3.38 (m, 2H), 3.57 (m, 2H), 3.81 (m, 2H), 4.48–4.54 (m, 4H), 6.71 (1H), 6.82 (1H), 7.13 (1H), 7.60 (4H), 8.19 (d, J=6.0 Hz, 2H), 8.88 (d, J=6.0 Hz, 2H), 11.63 (1H).

Example 23

Synthesis of 7-[1-(2-Hydroxy-2-phenylethyl) piperidin-4-ylmethoxy]-1,2,3,4-tetrahydroisoquinoline-2-carboxamidine Dihydrochloride Step 1
N,N'-Di-tert-Butoxycarbonyl-7-(1-phenacylpiperidin-4-ylmethoxy)-1,2,3,4-tetrahydroisoquinoline-2-carboxamidine

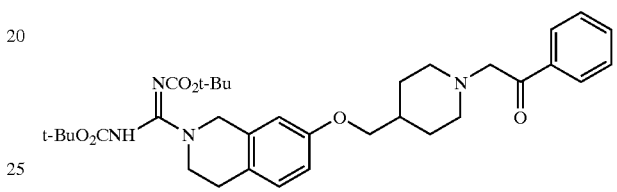

In the same manner as in Example 21, Step 6, the title compound (125 mg) was obtained from N,N'-di-tert-butoxycarbonyl-7-(piperidin-4-ylmethoxy)-1,2,3,4-tetrahydroisoquinoline-2-carboxamidine (200 mg), phenacyl bromide (90 mg) and 9.1N sodium hydroxide (0.054 ml).

Step 2
N,N'-Di-tert-butoxycarbonyl-7-[1-(2-hydroxy-2-phenylethyl)piperidin-4-ylmethoxy]-1,2,3,4-tetrahydroisoquinoline-2-carboxamidine

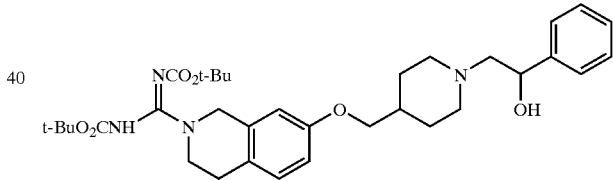

To a solution of N,N'-di-tert-butoxycarbonyl-7-(1-phenacylpiperidin-4-ylmethoxy)-1,2,3,4-tetrahydroisoquinoline-2-carboxamidine (120 mg) in a mixture of tetrahydrofuran (1 ml) and methanol (0.2 ml) was added sodium borohydride (11 mg), and the mixture was stirred at room temperature for 2 hours. After completion of the reaction, water was added and the mixture was extracted with ethyl acetate and washed successively with water and saturated brine. The organic layer was dried over anhydrous sodium sulfate and the solvent was evaporated. The obtained residue was purified by silica gel column chromatography (hexane:acetone=5:1, 1% triethylamine) and dried under reduced pressure to give the title compound (90 mg).

$^1$H-NMR (δ ppm, CDCl$_3$) 1.39–1.55 (m, 20H), 1.75–1.95 (m, 3H), 2.08 (m, 1H), 2.36 (m, 1H), 2.46–2.56 (m, 2H), 2.85–2.95 (m, 3H), 3.15–3.25 (m, 1H), 3.65–3.85 (m, 4H), 4.60–4.77 (m, 3H), 6.64 (1H), 6.73 (1H), 7.04 (1H), 7.26–7.40 (m, 5H).

Step 3
7-1-(2-Hydroxy-2-phenylethyl)piperidin-4-ylmethoxy]-1,2,3,4-tetrahydroisoquinoline-2-carboxamidine Dihydrochloride

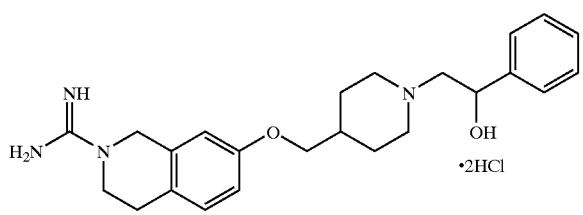

In the same manner as in Example 2 1, Step 8, the title compound (55 mg) was obtained from N,N'-di-tert-butoxycarbonyl-7-[1-(2-hydroxy-2-phenylethyl)piperidin-4-ylmethoxy]-1,2,3,4-tetrahydroisoquinoline-2-carboxamidine (85 mg).

$^1$H-NMR (δ ppm, DMSO-$d_6$) 1.60–2.10 (m, 5H), 2.82 (m, 2H), 2.95–3.25 (m, 3H), 3.58 (m, 2H), 3.84 (d, 2H), 4.55 (s, 2H), 5.17 (m, 1H), 6.73 (1H), 6.84 (1H), 7.15 (1H), 7.25–7.50 (m, 5H), 7.60 (brs, 4H), 9.98 (brs, 1H).

Example 24

Synthesis of 4-(2-Amidino-1,2,3,4-tetrahydroisoquinolin-7-yloxymethyl)piperidin-1-ylacetylglycine Ethyl Ester Dihydrochloride Step 1
4-[2-(N,N'-Di-tert-Butoxycarbonylamidino)-1,2,3,4-tetrahydroisoquinolin-7-yloxymethyl]piperidine-1-acetic Acid Benzyl Ester

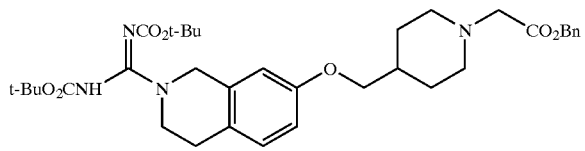

In the same manner as in Example 21, Step 6, the title compound (810 mg) was obtained from N,N'-di-tert-butoxycarbonyl-7-(piperidin-4-ylmethoxy)-1,2,3,4-tetrahydroisoquinoline-2-carboxamidine (1 g), benzyl chloroacetate (0.34 ml) and 9.1N sodium hydroxide (0.025 ml).

Step 2
4-[2-(N,N'-Di-tert-butoxycarbonylamidino)-1,2,3,4-tetrahydroisoquinolin-7-yloxymethyl]piperidine-1-acetic Acid

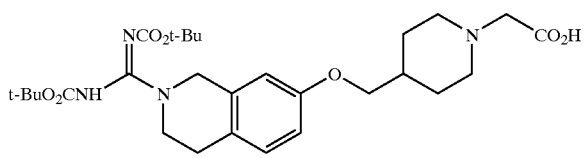

4-[2-(N,N'-Di-tert-butoxycarbonylamidino)-1,2,3,4-tetrahydroisoquinolin-7-yloxymethyl]piperidine-1-acetic acid benzyl ester (735 mg) was hydrogenated using 7.5% palladium carbon (220 mg) in a mixture of tetrahydrofuran (7 ml) and methanol (14 ml) at atmospheric pressure over 3 hours. After completion of the reaction, the reaction mixture was filtered through celite and the solvent was evaporated. The residue was dried under reduced pressure to give the title compound (600 mg).

$^1$H-NMR (δ ppm, CDCl$_3$) 1.34–1.56 (m, 20H), 1.80–2.10 (m, 5H), 2.77 (brtr, 2H), 2.89 (brtr, 2H), 3.49 (s, 2H), 3.55–3.90 (m, 4H), 4.66 (s, 2H), 6.60 (1H), 6.70 (1H), 7.03 (1H).

Step 3
4-[2-(N,N'-Di-tert-Butoxycarbonylarnidino)-1,2,3,4-tetrahydroisoquinohin-7-yloxymethyl]piperidin-1-ylacetylglycine Ethyl Ester

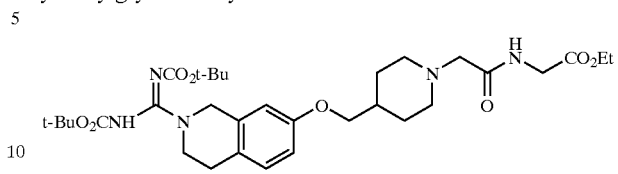

To a solution of 4-[2-(N,N'-di-tert-butoxycarbonylamidino)-1,2,3,4-tetrahydroisoquinolin-7-yloxymethyl]piperidine-1-acetic acid (120 mg) and glycine ethyl ester hydrochloride in methylene chloride (1.5 ml) were added triethylamine (0.031 ml), 4-dimethylarninopyridine (27 mg) and 1-(3-dimethylaminopropyl)-3-ethylcarbod mide hydrochloride (42 mg), and the mixture was stirred at room temperature for 12 hours. After completion of the reaction, water was added and the mixture was extracted with ethyl acetate and washed successively with water and saturated brine. The organic layer was dried over anhydrous sodium sulfate and the solvent was evaporated. The obtained residue was purified by silica gel column chromatography (hexane:acetone=5:2) and dried under reduced pressure to give the title compound (100 mg).

$^1$H-NMR (δ ppm, CDCl$_3$) 1.29 (tr, J=7.2 Hz, 3H), 1.45–1.65 (m, 2H), 1.70–1.90 (m, 3H), 2.21 (brtr, 2H), 2.87–3.00 (m, 4H), 3.05 (s, 2H), 3.70–3.85 (m, 4H), 4.07 (d, 2H), 4.22 (q, J=7.2 Hz, 2H), 4.67 (brs, 2H), 6.63 (1H), 6.73 (1H), 7.04 (1H), 7.70 (brtr, 1H), 10.20 (brs, 1H).

Step 4
4-(2-Amidino-1,2,3,4-tetrahydroisoquinolin-7-yloxymethyl)piperidin-1-ylacetylglycine Ethyl Ester Dihydrochloride

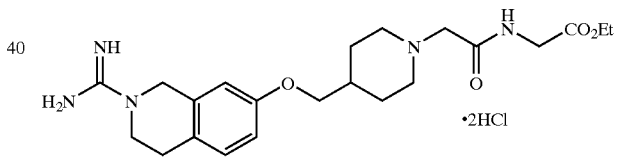

In the same manner as in Example 21, Step 8, the title compound (75 mg) was obtained from 4-[2-(N,N'-di-tert-butoxycarbonylamidino)-1,2,3,4-tetrahydroisoquinolin-7-yloxymethyl]piperidin-1-ylacetylglycine ethyl ester (100 mg).

$^1$H-NMR (δ ppm, DMSO-$d_6$) 1.20 (tr, J=7.0 Hz, 3H), 1.58–2.1 (m, 5H), 2.82 (m, 2H), 3.00–3.20 (m, 2H), 3.5 1 (m, 2H), 3.82 (m, 2H), 3.9.–3.98 (m, 4H), 4.11 (q, J=7.0 Hz), 4.56 (s, 2H), 6.72 (d, J=2.1 Hz, 1H), 6.83 (dd, J=2.1, 8.3 Hz, 1H), 7.15 (d, J=8.3 Hz, 1H), 7.68 (brs, 4H), 9.24 (brtr, 1H), 10.07 (brs, 1H).

Example 25

Synthesis of 4-(2-Amidino-1,2,3,4-tetrahydroisoquinolin-7-yloxymethyl)-piperidine-1-acetic Acid N-Methylamide Dihydrochloride Step 1
4-[2-(N',N"-Di-tert-Butoxycarbonylamidino)-1,2,3,4-tetrahydroisoquinolin-7-yloxymethyl]piperidine-1-acetic Acid N-Methylamide

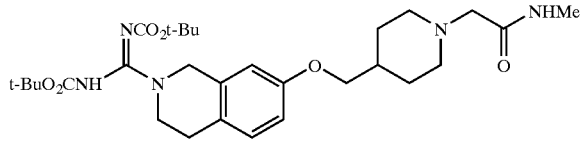

In the same manner as in Example 24, Step 3, the title compound (25 mg) was obtained from 4-[2-(N,N'-di-tert-butoxycarbonylamidino)-1,2,3,4-tetrahydroisoquinolin-7-yloxymethyl]piperidine-1-acetic acid (120 mg), methylamine hydrochloride (148 mg), triethylamine (0.6 ml), 4-dimethylaminopyridine (27 mg), 1-(3-dimethylaminopropyl)-3-ethylcarbodiimide hydrochloride (42 mg) and N-methylmorpholine (0.24 ml).

Step 2
4-(2-Amidino-1,2,3,4-tetrahydroisoquinolin-7-yloxymethyl)piperidine-1-acetic Acid N-methylamide Dihydrochloride

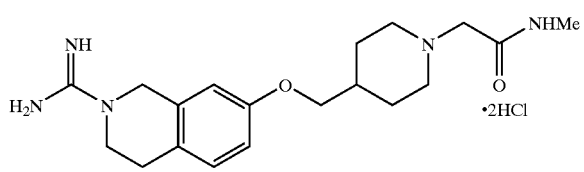

In the same manner as in Example 21, Step 8, the title compound (15 mg) was obtained from 4-[2-(N',N''-di-tert-butoxycarbonylamidino)-1,2,3,4-tetrahydroisoquinolin-7-yloxymethyl]piperidine-1-acetic acid N-methylamide (20 mg).

$^1$H-NMR (δ ppm, DMSO-$d_6$) 1.60–1.78 (m, 2H), 1.88–2.08 (m, 2H), 2.67 (s, 3H), 2.83 (tr, J=4.4 Hz, 2H), 3.00–3.15 (m, 2H), 3.45–3.55 (m, 2H), 3.58 (tr, J=4.4 Hz, 2H), 3.82–3.92 (m, 4H), 4.62 (s, 2H), 6.72 (1H), 6.85 (1H), 7.15 (1H), 7.63 (brs, 4H), 8.67 (brs, 1H), 9.93 (brs, 1H).

Example 26

Synthesis of 7-(1-Acetylpiperidin-4-ylmethoxy)-1,2,3,4-tetrahydroisoquinoline-2-carboxamidine Hydrochloride Step 1
N,N'-Di-tert-Butoxycarbonyl-7-(1-acetylpiperidin-4-ylmethoxy)-1,2,3,4-tetrahydroisoquinoline-2-carboxamidine

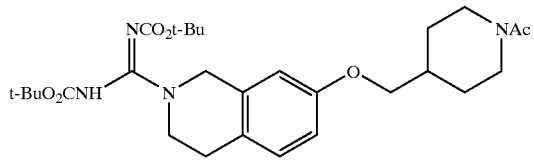

To a solution of N,N'-ditert-butoxycarbonyl-7-(piperidin-4-ylmethoxy)-1,2,3,4-tetrahydroisoquinoline-2-carboxamidine (100 mg) in tetrahydrofuran (1.5 ml) were added acetic anhydride (0.021 ml) and pyridine (0.025 ml), and the mixture was stirred at room temperature for 2 hours. After completion of the reaction, the mixture was extracted with ethyl acetate and washed successively with water and saturated brine. The organic layer was dried over anhydrous sodium sulfate and the solvent was evaporated. The residue was dried under reduced pressure to give the title compound (100 mg).

$^1$H-NMR (δ ppm, CDCl$_3$) 1.20–1.40 (m, 2H), 1.45–1.65 (m, 20H), 1.80–2.10 (m, 6H), 2.59 (m, 1H), 2.90 (brtr, 2H), 3.08 (m, 2H), 3.85–3.90 (m, 4H), 4.67 (brs, 2H), 6.62 (1H), 6.72 (1H), 7.04 (1H).

Step 2
7-(1-Acetylpiperidin-4-ylmethoxy)-1,2,3,4-tetrahydroisoquinoline-2-carboxamidine Hydrochloride

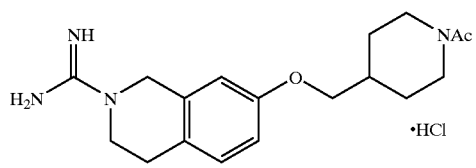

In the same manner as in Example 21, Step 8, the title compound (60 mg) was obtained from N,N'-di-tert-butoxycarbonyl-7-(1-acetylpiperidin-4-ylmethoxy)-1,2,3,4-tetrahydroisoquinoline-2-carboxamidine (94 mg).

$^1$H-NMR (δ ppm, DMSO-$d_6$) 1.00–1.30 (m, 2H), 1.70–1.85 (m, 2H), 1.98 (m, 4H), 2.52 (m, 1H), 2.81 (tr, J=6.0 Hz, 2H), 3.02 (m, 1H), 3.57 (tr, J=6.0 Hz, 2H), 3.75–3.90 (m, 3H), 4.53 (s, 2H), 6.69 (d, J=2.4 Hz, 1H), 6.82 (dd, J=2.4, 8.4 Hz, 1H), 7.13 (d, J=8.4 Hz, 1H), 7.57 (brs, 4H).

Example 27

Synthesis of 7-(1-Benzylsulfonylpiperidin-4-ylmethoxy)-1,2,3,4-tetrahydroisoquinoline-2-carboxamidine Hydrochloride Step 1
N,N'-Di-tert-Butoxycarbonyl-7-(1-benzylsulfonylpiperidin-4-ylmethoxy)-1,2,3,4-tetrahydroisoquinoline-2-carboxamidine

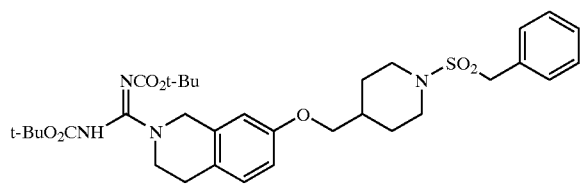

To a solution of N,N'-di-tert-butoxycarbonyl-7-(piperidin-4-ylmethoxy)-1,2,3,4-tetrahydroisoquinoline-2-carboxamidine (100 mg) in tetrahydrofuran (1.5 ml) were added pyridine (0.02 ml), 4-dimethylaminopyridine (12 mg) and α-toluenesulfonyl chloride (43 mg), and the mixture was stirred at room temperature for 12 hours and then at 50° C. for 6 hours. After completion of the reaction, the mixture was extracted with ethyl acetate and washed successively with water and saturated brine. The organic layer was dried over anhydrous sodium sulfate, and the solvent was evaporated. The obtained residue was purified by silica gel column chromatography (hexane:acetone=3:1) and dried under reduced pressure to give the title compound (48 mg).

$^1$H-NMR (δ ppm, CDCl$_3$) 1.20–1.40 (m, 2H), 1.45–1.60 (m, 20H), 1.70–1.90 (m, 3H), 2.60 (m, 2H), 2.89 (m, 2H), 3.65–3.80 (m, 4H), 4.22 (s, 2H), 4.66 (brs, 2H), 6.59 (1H), 6.68 (1H), 7.03 (1H), 7.36–7.40 (5H).

Step 2
7-(1-Benzylsulfonylpiperidin-4-ylmethoxy)-1,2,3,4-tetrahydroisoquinoline-2-carboxarmidine Hydrochloride

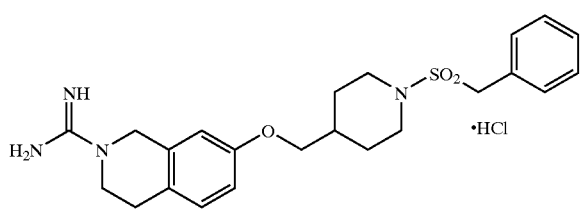

In the same manner as in Example 21, Step 8, the title compound (30 mg) was obtained from N,N'-di-tert-butoxycarbonyl-7-(1-benzylsulfonylpiperidin-4-ylmethoxy)-1,2,3,4-tetrahydroisoquinoline-2-carboxamidine (43 mg).

$^1$H-NMR (δ ppm, DMSO-d$_6$) 1.14–1.30 (m, 2H), 1.70–1.88 (m, 3H), 2.68–2.83 (m, 4H), 3.56 (m, 4H), 3.80 (m, 2H), 4.38 (s, 2H), 4.52 (s, 2H), 6.69 (d, J=2.7 Hz, 1H), 6.82 (dd, J=2.7, 8.3 Hz, 1H), 7.13 (d, J=8.3 Hz, 1H), 7.35–7.40 (m, 5H), 7.53 (s, 4H).

Example 28

Synthesis of 7-[1 1-(2-Naphthylsulfonyl)piperidin-4-ylmethoxy]-1,2,3,4-tetrahydroisoquinoline-2-carboxamidine Hydrochloride Step 1
N,N'-Di-tert-Butoxycarbonyl-7-[1-(2-naphthylsulfonyl)piperidin-4-ylmethoxy]-1,2,3,4-tetrahydroisoquinoline-2-carboxamidine

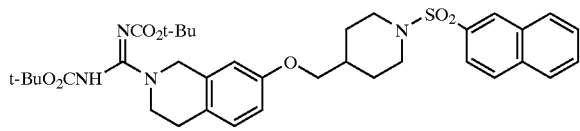

In the same manner as in Example 27, Step 1, the title compound (75 mg) was obtained from N,N'-di-tert-butoxycarbonyl-7-(piperidin-4-ylmethoxy)-1,2,3,4-tetrahydroisoquinoline-2-carboxamidine (100 mg), 2-naphthalenesulfonyl chloride (51 mg) and pyridine (0.02 ml).

Step 2
7-[1-(2-Naphthylsulfonyl)piperidin-4-ylmethoxy]-1,2,3,4-tetrahydroisoquinoline-2-carboxamidine Hydrochloride

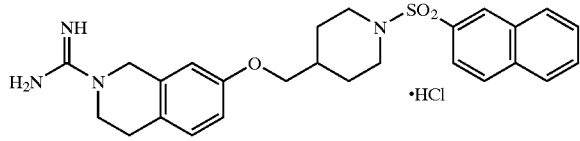

In the same manner as in Example 21, Step 8, the title compound (55 mg) was obtained from N,N'-di-tert-butoxycarbonyl-7-[1-(2-naphthylsulfonyl)-piperidin-4-ylmethoxy]-1,2,3,4-tetrahydroisoquinoline-2-carboxamidine (70 mg).

$^1$H-NMR (δ ppm, DMSO-d$_6$) 1.22–1.40 (m, 2H), 1.60–1.84 (m, 3H), 2.32 (m, 2H), 2.78 (tr, J=5.7 Hz, 2H), 3.54 (tr, J=5.7 Hz, 2H), 3.72–3.80 (m, 4H), 4.49 (s, 2H), 6.62 (d, J=2.3 Hz, 1H), 6.74 (dd, J=2.3, 8.4 Hz, 1H), 7.08 (d, J=8.4 Hz, 1H), 7.50 (brs, 4H), 7.66–7.77 (m, 3H), 8.07–8.20 (m, 3H), 8.43 (s, 1H).

Example 29

Synthesis of 7-(1-Acetimidoylpiperidin-4-ylmethoxy)-1,2,3,4-tetrahydroisoquinoline-2-carboxamidine Dihydrochloride Step 1
N,N'-Di-tert-Butoxycarbonyl-7-(1-acetimidoylpiperidin-4-ylmethoxy)-1,2,3,4-tetrahydroisoquinoline-2-carboxamidine

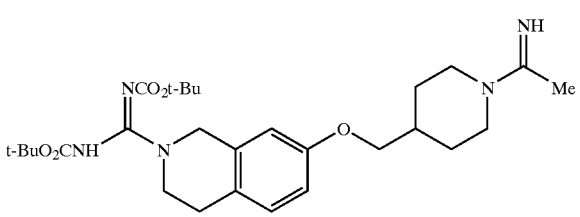

To a solution of N,N'-di-tert-butoxycarbonyl-7-(piperidin-4-ylmethoxy)-1,2,3,4-tetrahydroisoquinoline-2-carboxamidine (100 mg) in a mixture of tetrahydrofuran (1.5 ml) and ethanol (1.5 ml) were added triethylamine (0.086 ml) and ethylacetoimidate hydrochloride (38 mg), and the mixture was stirred at room temperature for 18 hours. After completion of the reaction, ethyl acetate and diethyl ether were added and insoluble material was removed. The solvent was evaporated and the residue was dried under reduced pressure to give the title compound (120 mg).

$^1$H-NMR (δ ppm, CDCl$_3$) 1.43–1.54 (m, 20H), 2.00–2.20 (m, 3H), 2.46 (s, 3H), 2.90 (m, 2H), 3.05–3.15 (m, 2H), 3.70–3.95 (m, 5H), 4.67 (brs, 2H), 4.80–4.90 (m, 1H), 6.60 (1H), 6.70 (1H), 7.04 (1H).

Step 2
7-(1-Acetimidoylpiperidin-4-ylmethoxy)-1,2,3,4-tetrahydroisoquinoline-2-carboxamidine Dihydrochloride

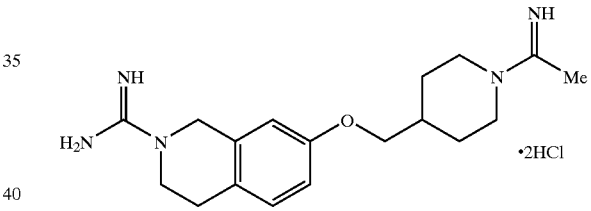

In the same manner as in Example 21, Step 8, the title compound (80 mg) was obtained from N,N'-di-tert-butoxycarbonyl-7-(1-acetimidoylpiperidin-4-ylmethoxy)-1,2,3,4-tetrahydroisoquinoline-2-carboxamidine (120 mg).

$^1$H-NMR (δ ppm, DMSO-d$_6$) 1.28–1.48 (m, 2H), 1.86–1.90 (m, 2H), 2.12 (m, 1H), 2.29 (s, 3H), 2.83 (tr, J=4.4 Hz, 2H), 3.00–3.29 (m, 2H), 3.59 (tr, J=4.4 Hz, 2H), 3.85 (m, 2H), 3.92–4.20 (m, 2H), 4.56 (s, 2H), 6.72 (d, J=1.7 Hz, 1H), 6.84 (dd, J=1.7, 6.3 Hz, 1H), 7.15 (d, J=6.3 Hz, 1H), 7.65 (brs, 4H), 8.77 (brs, 1H), 9.33 (brs, 1H).

Example 30

Synthesis of 7-(1-Phenylacetimidoylpiperidin-4-ylmethoxy)-1,2,3,4-tetrahydroisoquinoline-2-carboxamidine Dihydrochloride Step 1
Ethyl Phenylacetoimidate Hydrochloride Hydrogen chloride was blown into a solution of benzyl cyanide (5.8 ml) in diethyl ether (10 ml) with ice-cooling, and the mixture was stood at room temperature for 12 hours. After completion of the reaction, the solvent was evaporated. The obtained solid was washed with diethyl ether, collected by filtration and dried under reduced pressure to give the title compound (9.43 g).

Step 2
N,N'-Di-tert-Butoxycarbonyl-7-(1-phenylacetimidoylpiperidin-4-ylmethoxy)-1,2,3,4-tetrahydroisoquinoline-2-carboxamidine

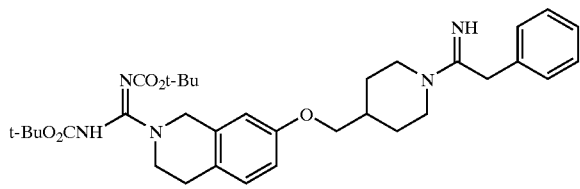

In the same manner as in Example 29, Step 1, the title compound (105 mg) was obtained from N,N'-di-tert-butoxycarbonyl-7-(piperidin-4-ylmethoxy)-1,2,3,4-tetrahydroisoquinoline-2-carboxamidine (105 mg) and ethyl phenyl acetoimidate hydrochloride (64 mg).

Step 3
7-(1-Phenylacetimidoylpiperidin-4-ylmethoxy)-1,2,3,4-tetrahydroisoquinoline-2-carboxamidine Dihydrochloride

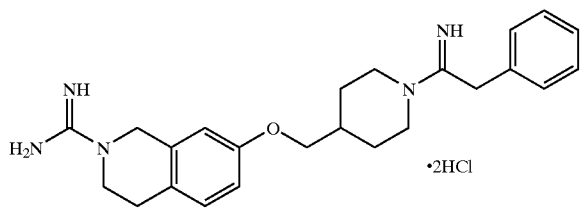

In the same manner as in Example 21, Step 8, the title compound (70 mg) was obtained from N,N'-di-tert-butoxycarbonyl-7-(1-phenylacetnimdoylpiperidin-4-ylmethoxy)-1,2,3,4-tetrahydroisoquinoline-2-carboxamidine (100 mg).

$^1$H-NMR (δ ppm, DMSO-d$_6$) 0.80–1.00 (m, 1H), 1.20–1.40 (m, 1H), 1.60–1.65 (m, 1H), 1.80–1.95 (m, 1H), 2.05 (m, 1H), 2.80 (m, 2H), 3.05–3.25 (m, 2H), 3.56 (m, 2H), 3.74 (m, 2H), 3.93–4.26 (m, 2H), 4.07 (s, 2H), 4.53 (s, 2H), 6.66 (1H), 6.77 (1H), 7.12 (1H), 7.25–7.42 (m, 5H), 7.62 (brs, 4H), 9.13 (brs, 1H), 9.75 (brs, 1H).

Example 31

Synthesis of N-[2-[4-(2-Amidino-1,2,3,4-tetrahydroisoquinolin-7-yloxymethyl)-piperidin-1-yl]pyridin-5-yl]acetamide Dihydrochloride Step 1
N,N'-Di-tert-Butoxycarbonyl-7-[1-(5-nitropyridin-2-yl)piperidin-4-ylmethoxy]-1,2,3,4-tetrahydroisoquinoline-2-carboxamidine

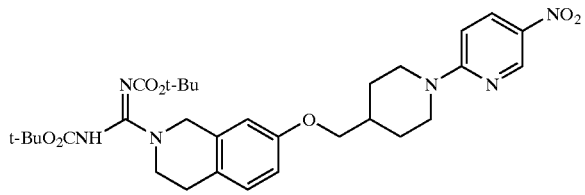

To a solution of N,N'-di-tert-butoxycarbonyl-7-(piperidin-4-ylmethoxy)-1,2,3,4-tetrahydroisoquinoline-2-carboxamidine (120 mg) in a mixture of tetrahydrofuran (1.2 ml) and dimethylformamide (1.2 ml) were added triethylamine (0.068 ml) and 2-chloro-5-nitropyridine (58 mg), and the mixture was stirred at room temperature for 2 hours. After completion of the reaction, the mixture was extracted with ethyl acetate and washed successively with water and saturated brine. The organic layer was dried over anhydrous sodium sulfate and the solvent was evaporated. The obtained residue was purified by silica gel column chromatography (hexane:acetone=4:1) and dried under reduced pressure to give the title compound (120 mg).

$^1$H-NMR (δ ppm, CDCl$_3$) 1.30–1.50 (m, 20H), 1.90–2.20 (m, 3H), 2.90 (brtr, 2H), 3.06 (m, 2H), 3.65–3.82 (m, 4H), 4.50–4.70 (m, 4H), 6.57–6.63 (2H), 6.72 (1H), 7.04 (1H), 8.19 (1H), 9.03 (1H), 10.19 (brs, 1H).

Step 2
N,N'-Di-tert-Butoxycarbonyl-7-[1-(5-aminopyridin-2-yl)piperidin-4-ylmethoxy]-1,2,3,4-tetrahydroisoquinolne-2-carboxamidine

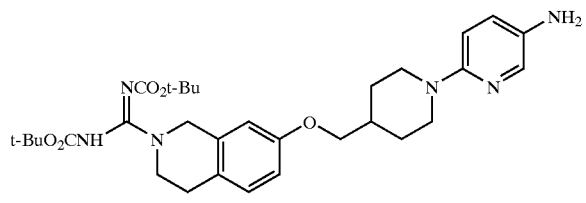

N,N'-Di-tert-butoxycarbonyl-7-[1-(5-nitropyridin-2-yl)piperidin-4-ylmethoxy]-1,2,3,4-tetrahydroisoquinoline-2-carboxamidine (100 mg) was hydrogenated using 7.5% palladium carbon (30 mg) in a mixture of tetrahydrofuran (1 ml) and methanol (2 ml) at 2.5 atm over 4 hours. After completion of the reaction, the reaction mixture was filtered through celite, and the solvent was evaporated. The obtained residue was purified by preparative thin layer chromatography (chloroform:methanol=10:1) and dried under reduced pressure to give the title compound (90 mg).

Step 3
N-[2-[4-[2-(N,N'-Di-tert-Butoxycarbonylamidino)-1,2,3,4-tetrahydroisoquinolin-7-yloxymethyl]piperidin-1-yl]pyridin-5-yl]acetamide

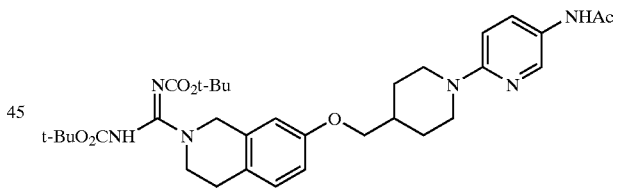

To a solution of N,N'-di-tert-butoxycarbonyl-7-[1-(5-aminopyridin-2-yl)piperidin-4-ylmethoxy]-1,2,3,4-tetrahydroisoquinoline-2-carboxamidine (100 mg) in tetrahydrofuran (1.5 ml) were added acetic anhydride (0.017 ml) and pyridine (0.017 ml), and the mixture was stirred at room temperature for 2 hours. After completion of the reaction, the mixture was extracted with ethyl acetate and washed successively with water and saturated brine. The organic layer was dried over anhydrous sodium sulfate and the solvent was evaporated. The obtained residue was purified by silica gel column chromatography (hexane:acetone=2:1). The obtained residue was dissolved in methanol and treated with active charcoal, and dried under reduced pressure to give the title compound (75 mg).

$^1$H-NMR (δ ppm, CDCl$_3$) 1.30–1.55 (m, 20H), 1.85–2.10 (m, 3H), 2.17 (s, 3H), 2.80–2.90 (m, 2H), 3.65–3.85 (m, 4H), 4.20–4.30 (m, 2H), 4.67 (s, 2H), 6.60–6.76 (m, 3H), 7.04 (1H), 7.11 (1H), 7.82 (1H), 8.09 (1H).

Step 4
N-[2-[4-(2-Amidino-1,2,3,4-tetrahydroisoquinolin-7-yloxymethyl)piperidin-1-yl]pyridin-5-yl]acetamide Dihydrochloride

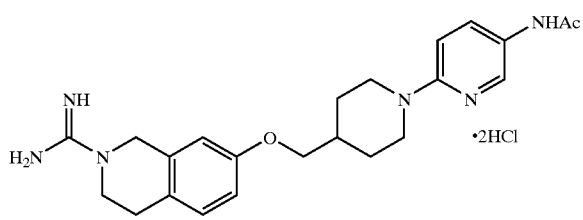

In the same manner as in Example 21, Step 8, the title compound (50 mg) was obtained from N-[2-[4-[2-(N,N'-di-tert-butoxycarbonylamidino)-1,2,3,4-tetrahydroisoquinolin-7-yloxymethyl]piperidin-1-yl]pyridin-5-yl]acetamide (70 mg).

$^1$H-NMR (δ ppm, DMSO-$d_6$) 1.25–1.45 (m, 2H), 1.88–1.95 (m, 2H), 2.00–2.20 (m, 4H), 2.81 (m, 2H), 3.16 (m, 2H), 3.57 (m, 2H), 3.85 (m, 2H), 4.24–4.30 (m, 2H), 4.53 (s, 2H), 6.71 (1H), 6.83 (1H), 7.13 (1H), 7.39 (1H), 7.57 (brs, 4H), 8.00 (1H), 8.46 (1H), 10.49 (1H).

Example 32

Synthesis of N-[2-[4-(2-Amidino-1,2,3,4-tetrahydroisoquinolin-7-yloxymethyl)-piperidin-1-yl]pyridin-5-yl]benzamide Dihydrochloride Step 1
N-[2-[4-[2-(N,N'-Di-tert-Butoxycarbonylamidino)-1,2,3,4-tetrahydroisoquinolin-7-yloxymethyl]piperidin-1-yl]pyridin-5-yl]benzamide

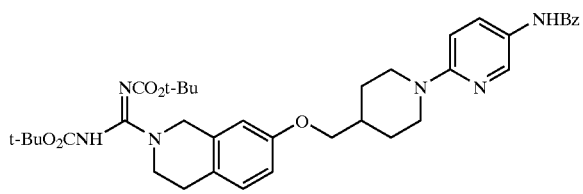

In the same manner as in Example 31, Step 3, the title compound (90 mg) was obtained from N,N'-di-tert-butoxycarbonyl-7-[1-(5-aminopyridin-2-yl)piperidin-4-ylmethoxy]-1,2,3,4-tetrahydroisoquinoline-2-carboxamidine (100 mg), benzoyl chloride (0.021 ml) and pyridine (0.017 ml).

Step 2
N-[2-[4-(2-Amidino-1,2,3,4-tetrahydroisoquinolin-7-yloxymethyl)piperidin-1-yl]pyridin-5-yl]benzamide Dihydrochloride

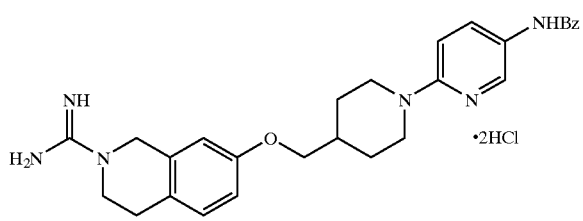

In the same manner as in Example 21, Step 8, the title compound (70 mg) was obtained from N-[2-[4-[2-(N,N'-di-tert-butoxycarbonylamidino)-1,2,3,4-tetrahydroisoquinolin-7-yloxymethyl]piperidin-1-yl]pyridin-5-yl]benzamide (84 mg).

$^1$H-NMR (δ ppm, DMSO-$d_6$) 1.30–1.48 (m, 2H), 1.87–1.93 (m, 2H), 2.12 (m, 1H), 2.82 (tr, J=5.8 Hz, 2H), 3.19 (m, 2H), 3.57 (tr, J=5.8 Hz, 2H), 3.86 (m, 2H), 4.29–4.36 (m, 2H), 4.54 (s, 2H), 6.71 (d, J=2.7 Hz, 1H), 6.84 (dd, J=2.7, 8.4 Hz, H), 7.14 (d, J=8.4 Hz, 1H), 7.43 (1H), 7.51–7.64 (7H), 8.02 (2H), 8.30 (1H), 8.63 (1H), 10.65 (1H).

Example 33

Synthesis of 3-[4-[4-(2-Amidino-1,2,3,4-tetrahydroisoquinolin-7-yloxymethyl)-piperidin-1-yl]pyridin-3-yl]-2-propenoic Acid Ethyl Ester Dihydrochloride Step 1
4-(2-tert-Butoxycarbonyl-1,2,3,4-tetrahydroisoquinolin-7-yloxymethyl)piperidine-1-carboxylic Acid Benzyl Ester

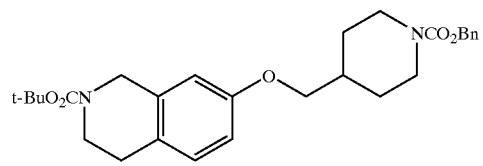

To a solution of 7-hydroxy-1,2,3,4-tetrahydroisoquinoline-2-carboxylic acid tert-butyl ester (1.2 g), 4-hydroxymethylpiperidine-1-carboxylic acid benzyl ester (2.39 g) in tetrahydrofuran (30 ml) were added triphenylphosphine (2.52 g) and diisopropyl azodicarboxylate (1.90 ml), and the mixture was stirred at room temperature for 20 hours. After completion of the reaction, the solvent was evaporated and the obtained residue was purified by silica gel column chromatography (hexane:acetone=6:1) and dried under reduced pressure to give the title compound (1.82 g).

$^1$H-NMR (δ ppm, CDCl$_3$) 1.20–1.35 (m, 2H), 1.48 (s, 9H), 1.75–2.05 (m, 3H), 2.70–2.90 (m, 4H), 3.62 (m, 2H), 3.77 (d, 2H), 4.10–4.35 (m, 2H), 4.53 (s, 2H), 5.14 (s, 2H), 6.67 (d, J=2.5 Hz, 1H), 6.71 (dd, J=2.5, 8.3 Hz, 1H), 7.29 (d, J=8.3 Hz, 1H), 7.26–15 7.38 (m, 5H).

Step 2
7-(Piperidin-4-ylmethoxy)-1,2,3,4-tetrahydroisoquinoline-2-carboxylic Acid tert-Butyl Ester

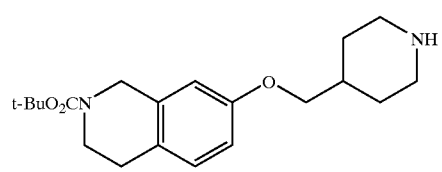

4-(2-tert-Butoxycarbonyl-1,2,3,4-tetrahydroisoquinolin-7-yloxymethyl)-piperidine-1-carboxylic acid benzyl ester (1.3 g) was hydrogenated using 7.5% palladium carbon (300 mg) in a mixture of tetrahydrofuran (10 ml) and methanol (20 ml) at 3 atm over 3 hours. After completion of the reaction, the reaction mixture was filtered through celite and the solvent was evaporated. The residue was dried under reduced pressure to give the title compound (815 mg).

$^1$H-NMR (δ ppm, CDCl$_3$) 1.20–1.35 (m, 2H), 1.49 (s, 9H), 1.75–2.00 (m, 4H), 2.62–2.76 (m, 4H), 3.10–3.20 (m, 2H), 3.62 (m, 2H), 3.76 (d, 2H), 4.53 (s, 2H), 6.63 (1H), 6.71 (1H), 7.03 (1H).

Step 3
7-[1-(3-Formylpyridin-4-yl)piperidin-4-ylmethoxy]-1,2,3,4-tetrahydroisoquinoline-2-carboxylic Acid tert-Butyl Ester

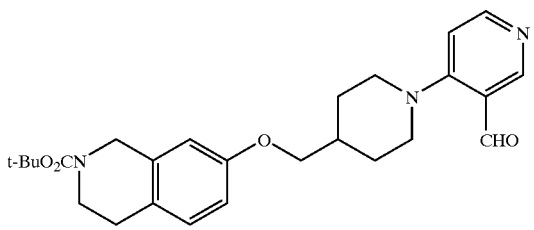

To a solution of 7-(piperidin-4-ylmethoxy)-1,2,3,4-tetrahydroisoquinoline-2-carboxylic acid tert-butyl ester (442 mg) in ethanol (3 ml) were added triethylamine (0.3 ml) and 4-chloro-3-formylpyridine (Journal of Heterocyclic Chemistry, vol. 25, p. 81 (1988)) (150 mg), and the mixture was stirred under reflux for 27 hours. After completion of the reaction, tetrahydrofuran and diethyl ether were added and insoluble material was removed. The solvent was evaporated and the obtained residue was purified by silica gel column chromatography (chloroform:methanol=100:1) and dried under reduced pressure to give the title compound (430 mg).

$^1$H-NMR (δ ppm, CDCl$_3$) 1.49 (s, 9H), 1.60–1.70 (m, 2H), 1.95–2.15 (m, 3H), 2.76 (m, 2H), 3.07 (m, 2H), 3.60–3.65 (m, 4H), 3.86 (d, 2H), 4.54 (s, 2H), 6.65 (1H), 6.73 (1H), 6.84 (d, J=6.0 Hz, 1H), 7.05 (1H), 8.42 (d, J=6.0 Hz, 1H), 8.74 (s, 1H), 10.02 (s, 1H).

Step 4

3-[4-[4-(2-tert-Butoxycarbonyl-1,2,3,4-tetrahydroisoquinolin-7-yloxymethyl)-piperidin-1-yl]pyridin-3-yl]-2-propenoic Acid Ethyl Ester

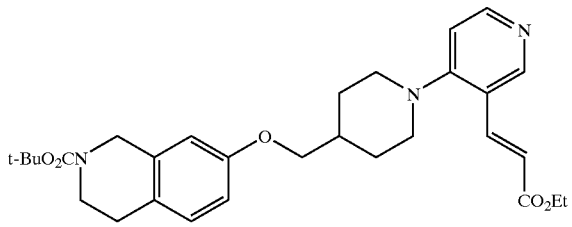

To a solution of triethyl phosphonoacetate (0.05 ml) in tetrahydrofuran(1 ml) was added sodium hydride (12 mg) with ice-cooling, and the mixture was stirred at the same temperature for 1 hour. A solution of 7-[1-(3-formylpyridin-4-yl)piperidin-4-ylmethoxy]-1,2,3,4-tetrahydroisoquinoline-2-carboxylic acid tert-butyl ester (95 mg) in tetrahydrofuran (1 ml) was added dropwise and the mixture was stirred for 2 hours. After completion of the reaction, aqueous ammonium chloride solution was added with ice-cooling, and the mixture was extracted with ethyl acetate and washed successively with water and saturated brine. The organic layer was dried over anhydrous sodium sulfate and the solvent was evaporated. The obtained residue was purified by silica gel column chromatography (chloroform:methanol=20:1–10:1) and dried under reduced pressure to give the title compound (100 mg).

$^1$H-NMR (δ ppm, CDCl$_3$) 1.35 (tr, J=6.4 Hz, 3H), 1.49 (s, 9H), 1.50–1.80 (m, 2H), 1.95–2.10 (m, 3H), 2.75–2.95 (m, 4H), 3.40–3.50 (m, 2H), 3.63 (m, 2H), 3.86 (d, 2H), 4.27 (q, J=6.4 Hz, 2H), 4.54 (s, 2H), 6.45 (d, J=15.9 Hz, 1H), 6.65 (1H), 6.74 (1H), 6.83 (d, J=6.0 Hz, 1H), 7.05 (1H), 7.76 (d, J=15.9 Hz, 1H), 8.38 (d, J=6.0 Hz, 1H), 8.55 (s, 1H).

Step 5

3-[4-[4-(1,2,3,4-Tetrahydroisoquinolin-7-yloxymethyl)piperidin-1-yl]pyridin-3-yl]-2-propenoic Acid Ethyl Ester

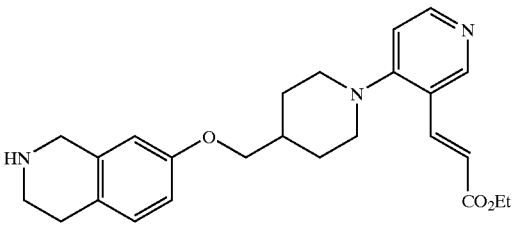

To a solution of 3-[4-[4-(2-tert-butoxycarbonyl-1,2,3,4-tetrahydroisoquinolin-7-yloxymethyl)piperidin-1-yl]pyridin-3-yl]-2-propenoic acid ethyl ester (100 mg) in chloroform (1.5 ml) was added trifluoroacetic acid (0.45 ml), and the mixture was stirred at room temperature for 1 hour. After completion of the reaction, the solvent was evaporated. To the obtained residue was added aqueous sodium hydrogencarbonate solution and the mixture was extracted with ethyl acetate and washed successively with water and saturated brine. The organic layer was dried over anhydrous sodium sulfate and the solvent was evaporated. The residue was dried under reduced pressure to give the title compound (70 mg).

$^1$H-NMR (δ ppm, CDCl$_3$) 1.35 (tr, J=7.1 Hz, 3H), 1.50–1.65 (m, 2H), 1.90–2.10 (m, 3H), 2.70–2.90 (m, 4H), 3.13 (m, 2H), 3.40–3.50 (m, 2H), 3.84 (d, 2H), 3.99 (s, 2H), 4.28 (q, J=7.1 Hz, 2H), 6.45 (d, J=16.2 Hz, 1H), 6.55 (d, J=2.3 Hz, 1H), 6.72 (dd, J=2.3, 8.2 Hz, 1H), 6.83 (d, J=6.0 Hz, 1H), 7.01 (d, J=8.2 Hz, 1H), 7.76 (d, J=16.2 Hz, 1H), 8.37 (d, J=6.0 Hz, 1H), 8.55 (s, 1H).

Step 6

3-[4-[4-(2-Amidino-1,2,3,4-tetrahydroisoquinolin-7-yloxymethyl)piperidin-1-yl]pyridin-3-yl]-2-propenoic Acid Ethyl Ester Dihydrochloride

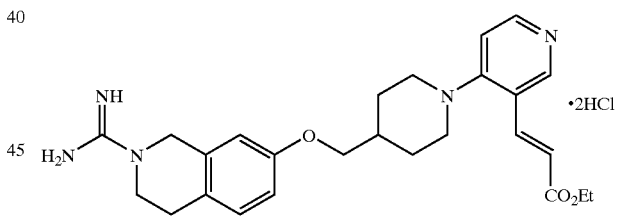

To a solution of 3-[4-[4-(1,2,3,4-tetrahydroisoquinolin-7-yloxymethyl)piperidin-1-yl]pyridin-3-yl]-2-propenoic acid ethyl ester (70 mg) in dimethylformamide (1 ml) were added diisopropylethylamine (0.032 ml) and 1H-pyrazole-1-carboxamidine hydrochloride (27 mg), and the mixture was stirred at room temperature for 12 hours. The solvent was evaporated and to the obtained residue was added diethyl ether and the supernatant was removed. This procedure was repeated twice and hydrogen chloride-ethanol solution was added to the obtained residue and insoluble material was removed. The solution was concentrated and dried under reduced pressure to give the title compound (50 mg).

$^1$H-NMR (δ ppm, DMSO-d$_6$) 1.25 (tr, J=7.3 Hz, 3H), 1.40–1.55 (m, 2H), 1.82–2.05 (m, 3H), 2.76–2.96 (m, 4H), 3.42 (m, 2H), 3.57 (m, 2H), 3.90 (m, 2H), 4.18 (q, J=7.3 Hz, 2H), 4.53 (s, 2H), 6.63 (d, J=16.1 Hz, 1H), 6.73 (1H), 6.85 (1H), 7.04 (1H), 7.14 (1H), 7.51 (brs, 4H), 7.60 (d, J=16.1 Hz, 1H), 8.35 (1H), 8.64 (s, 1H).

Example 34

Synthesis of 4-[4-(2-Amidino-1,2,3,4-tetrahydroisoquinolin-7-yloxymethyl)-piperidin-1-yl]pyridine-3-carboxylic Acid Methyl Ester Dihydrochloride Step 1
7-[1-(3-Methoxycarbonylpyridin-4-yl)piperidin-4-ylmethoxy]-1,2,3,4-tetrahydroisoquinoline-2-carboxylic Acid tert-Butyl Ester

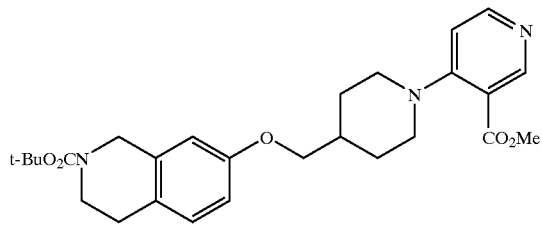

To a soution of 7-[1-(3-formylpyridin-4-yl)piperidin4-ylmethoxy]-1,2,3,4-tetrahydroisoquinoline-2-carboxylic acid tert-butyl ester (50 mg) in a mixture of chloroform (0.5 ml) and methanol (0.2 ml) were added sodium cyanide (8 mg), manganese dioxide (250 mg) and acetic acid (0.003 ml), and the mixture was stirred at room temperature for 12 hours. After completion of the reaction, the reaction mixture was filtrated and the solvent was evaporated. The obtained residue was purified by preparative thin layer chromatography (chloroform:methanol=15:1) and dried under reduced pressure to give the title compound (50 mg).

$^1$H-NMR (δ ppm, CDCl$_3$) 1.49–1.70 (m, 1H), 1.90–2.10 (m, 3H), 2.76 (m, 2H), 2.97 (m, 2H), 3.50–3.68 (m, 4H), 3.83 (d, 2H), 3.91 (s, 3H), 4.54 (s, 2H), 6.64 (1H), 6.72 (1H), 6.78 (d, J=6.0 Hz, 1H), 7.04 (1H), 8.35 (d, J=6.0 Hz, 1H), 8.73 (s, 1H).

Step 2
4-[4-(1,2,3,4-Tetrahydroisoquinolin-7-yloxymethyl)piperidin-1-yl]pyridine-3-carboxylic Acid Methyl Ester

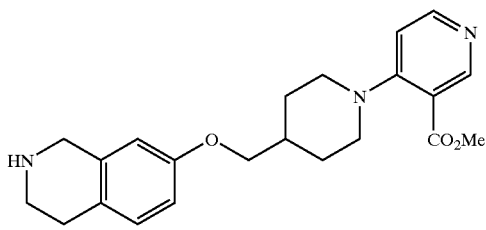

To a solution of 7-[1-(3-methoxycarbonylpyridin-4-yl)piperidin-4-ylmethoxy]-1,2,3,4-tetrahydroisoquinoline-2-carboxylic acid tert-butyl ester (37 mg) in chloroform (0.5 ml) was added trifluoroacetic acid (0.15 ml), and the mixture was stirred at room temperature for 1 hour. After completion of the reaction, the solvent was evaporated. To the obtained residue was added aqueous sodium hydrogencarbonate solution, and the mixture was extracted with ethyl acetate. The organic layer was washed successively with water and saturated brine and dried over anhydrous sodium sulfate. The solvent was evaporated and dried under reduced pressure to give the title compound (30 mg).

Step 3
4-[4-(2-Amidino-1,2,3,4-tetrahydroisoquinolin-7-yloxymethyl)piperidin-1-yl]pyridine-3-carboxylic Acid Methyl Ester Dihydrochloride

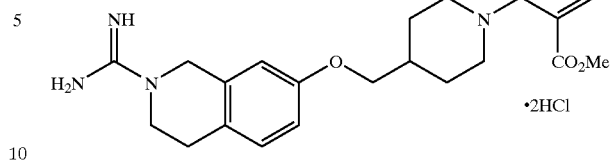

In the same manner as in Example 33, Step 6, the title compound (15 mg) was obtained from 4-[4-(1,2,3,4-tetrahydroisoquinolin-7-yloxymethyl)-piperidin-1-yl]pyridine-3-carboxylic acid methyl ester (30 mg).

$^1$H-NMR (δ ppm, DMSO-d$_6$) 1.34–1.54 (m, 2H), 1.87–1.93 (m, 2H), 2.15 (m, 1H), 2.82 (m, 2H), 3.29 (m, 2H), 3.57 (m, 2H), 3.76–3.87 (m, 7H), 4.54 (s, 2H), 6.71 (1H), 6.82 (1H), 7.14 (1H), 7.40 (d, J=7.2 Hz, 1H), 7.59 (brs, 4H), 8.30 (d, J=7.2 Hz, 1H), 8.58 (s, 1H).

Example 35

Synthesis of 4-[4-(2-Amidino-1,2,3,4-tetrahydroisoquinolin-7-yloxymethyl)-piperidin-1-yl]pyridine-3-carboxylic Acid Dihydrochloride

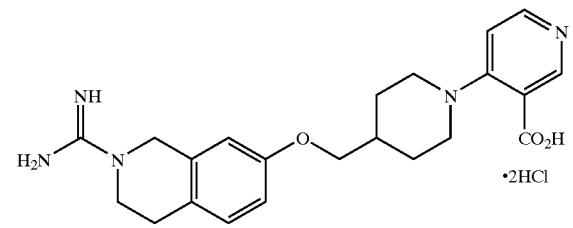

To a solution of 4-[4-(2-amidino-1,2,3,4-tetrahydroisoquinolin-7-yloxymethyl)piperidin-1-yl]pyridine-3-carboxylic acid methyl ester dihydrochloride (43 mg) in methanol (0.2 ml) was added 1N aqueous sodium hydroxide solution (0.1 ml), and the mixture was stirred under reflux for 3 hours. After completion of the reaction, the reaction mixture was neutralized with 1N-hydrochloric acid and the solvent was evaporated. The obtained residue was purified by reverse phase preparative thin layer chromatography (40% aqueous acetonitrile, 1% trifluoroacetic acid) and the obtained residue was treated with hydrogen chloride-ethanol solution and dried under reduced pressure to give the title compound (15 mg).

$^1$H-NMR (δ ppm, DMSO-d$_6$) 1.38–1.58 (m, 2H), 1.85–1.95 (m, 2H), 2.15 (m, 1H), 2.82 (m, 2H), 3.56 (m, 2H), 3.80–3.95 (m, 4H), 4.51 (s, 2H), 6.70 (1H), 6.82 (1H), 7.14 (1H), 7.34 (d, J=7.4 Hz, 1H), 7.44 (brs, 4H), 8.27 (d, J=7.4 Hz, 1H), 8.59 (s, 1H).

Example 36

Synthesis of 6-[1-(Pyridin-4-yl)piperidin-4-ylmethoxy]-1,2,3,4-tetrahydroisoquinoline-2-carboxamidine Dihydrochloride Step 1
6-Hydroxy-1,2,3,4-tetrahydroisoquinoline Hydrobromide

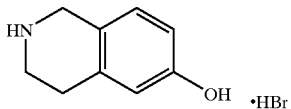

6-Methoxy-1,2,3,4-tetrahydroisoquinoline (2.89 g) was dissolved in 48% aqueous hydrogen bromide solution (70 ml) and the mixture was refluxed for 2 hours. The solvent was evaporated and to the obtained residue were added ethanol and diethyl ether. The mixture was filtrated and dried under reduced pressure to give the title compound (3.93 g).
$^1$H-NMR ($\delta$ ppm, DMSO-$d_6$) 2.90 (tr, J=6.3 Hz, 2H), 3.35 (m, 2H), 4.13 (brs, 2H), 6.59 (d, J=2.4 Hz, 1H), 6.65 (dd, J=2.4, 8.4 Hz, 1H), 7.00 (d, J=8.4 Hz, 1H), 8.91 (brs, 2H), 9.43 (brs, 1H).
Step 2
6-Hydroxy-1,2,3,4-tetrahydroisoquinoline-2-carboxylic Acid tert-Butyl Ester

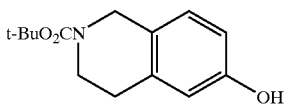

In the same manner as in Example 1, Step 1, the title compound (325 mg) was obtained from 6-hydroxy-1,2,3,4-tetrahydroisoquinoline hydrobromide (350 mg) and di-tert-butyl dicarbonate (365 mg).
$^1$H-NMR ($\delta$ ppm, CDCl$_3$) 1.49 (s, 9H), 2.76 (tr, J=6.0 Hz, 2H), 3.61 (tr, J=6.0 Hz, 2H), 4.49 (s, 2H), 5.33 (s, 1H), 6.63 (1H), 6.67 (1H), 6.95 (1H).
Step 3
6-[1-(Pyridin-4-yl)piperidin-4-ylmethoxy]-1,2,3,4-tetrahydroisoquinoline-2-carboxylic Acid tert-Butyl Ester

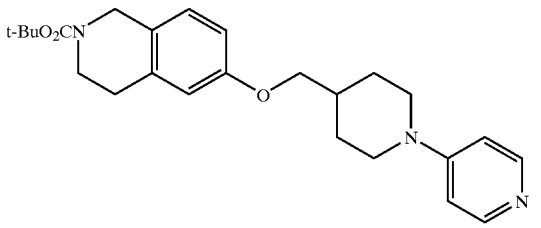

To a solution of 6-hydroxy-1,2,3,4-tetrahydroisoquinoline-2-carboxylic acid tert-Butyl Ester (320 mg) and 4-hydroxymethyl-1-(pyridin-4-yl)piperidine (247 mg) in a mixture of tetrahydrofuran (15 ml) and methylene chloride (5 ml) were successively added triphenylphosphine (370 mg) and diisopropyl azodicarboxylate (0.28 ml), and the mixture was stirred at room temperature for 12 hours. After completion of the reaction, the solvent was evaporated and the obtained residue was purified by silica gel column chromatography (hexane:acetone= 3:2–1:1, 1% triethylamine) and dried under reduced pressure to give the title compound (400 mg).
$^1$H-NMR ($\delta$ ppm, CDCl$_3$) 1.35–1.54 (m, 11H), 1.90–2.15 (m, 2H), 2.79 (tr, J=6.0 Hz, 2H), 2.90 (m, 2H), 3.62 (tr, J=6.0 Hz, 2H), 3.81 (d, 2H), 3.90–3.96 (m, 2H), 4.50 (s, 2H), 6.66–6.68 (m, 3H), 6.73 (1H), 7.01 (1H), 8.25 (2H).
Step 4
6-[1-(Pyridin-4-yl)piperidin-4-ylmethoxy]-1,2,3,4-tetrahydroisoquinoline

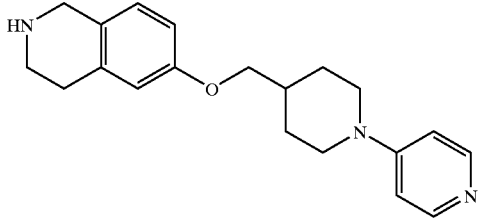

In the same manner as in Example 33, Step 5, the title compound (265 mg) was obtained from 6-[1-(pyridin-4-yl)piperidin-4-ylmethoxy]-1,2,3,4-tetrahydroisoquinoline-2-carboxylic acid tert-butyl ester (400 mg) and trifluoroacetic acid (1.5 ml).
$^1$H-NMR ($\delta$ ppm, CDCl$_3$) 1.36–1.50 (m, 2H), 1.90–2.15 (m, 3H), 2.80 (tr, J=6.0 Hz, 2H), 2.93 (m, 2H), 3.15 (tr, J=6.0 Hz, 2H), 3.80 (d, 2H), 3.92–3.99 (m, 4H), 6.62 (1H), 6.67–6.70 (m, 3H), 6.93 (1H), 8.24 (2H).
Step 5
6-[1-(Pyridin-4-yl)piperidin-4-ylmethoxy]-1,2,3,4-tetrahydroisoquinoline-2-carboxamidine Dihydrochloride

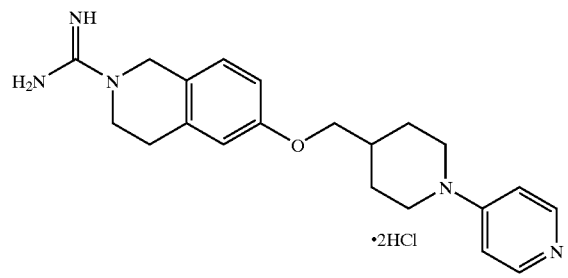

In the same manner as in Example 33, Step 6, the title compound (60 mg) was obtained from 6-[1-(pyridin-4-yl)piperidin-4-ylmethoxy]-1,2,3,4-tetrahydroisoquinoline (70 mg), diisopropylethylamine (0.042 ml), 1H-pyrazole-1-carboxamidine hydrochloride (35 mg).
$^1$H-NMR ($\delta$ ppm, DMSO-$d_6$) 1.20–1.45 (m, 2H), 1.84–2.00 (m, 2H), 2.17 (m, 1H), 2.86 (tr, J=5.8 Hz, 2H), 3.20 (m, 2H), 3.56 (tr, J=5.8 Hz, 2H), 3.85 (m, 2H), 4.23–4.28 (m, 2H), 4.48 (s, 2H), 6.80 (2H), 7.05 (1H), 7.19 (2H), 7.60 (4H), 8.19 (2H), 13.65 (1H).

Example 37

Synthesis of 7-[2-[4-Cyano-1-(pyridin-4-yl) piperidin-4-yl]ethoxy]-1,2,3,4-tetrahydroisoquinoline-2-carboxamidine Dihydrochloride Step 1
4-Carbamoylpiperidine-1-carboxylic Acid Benzyl Ester

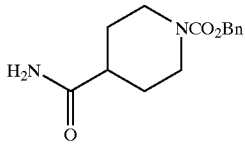

To a solution of 1-benzyloxycarbonylpiperidine-4-carboxylic acid (10.5 g) in tetrahydrofuran (100 ml) were dropwise added N-methylmorpholine (4.6 ml) and isobutyl chlorocarbonate (5.4 ml) with ice-cooling and under an argon atmosphere, and the mixture was stirred at the same temperature for 10 min. Then, 28% aqueous ammonia (100 ml) was added dropwise, and the mixture was stirred at room temperature for 1 hour. After completion of the reaction, the solvent was evaporated and water was added. The mixture was extracted with ethyl acetate and washed successively with aqueous sodium hydrogencarbonate solution, 10% aqueous citric acid solution and saturated brine. The organic layer was dried over anhydrous sodium sulfate and the solvent was evaporated and dried under reduced pressure to give the title compound (8.3 g).

$^1$H-NMR (δ ppm, CDCl$_3$) 1.58–1.75 (m, 2H), 1.80–1.95 (m, 2H), 2.25–2.40 (m, 1H), 2.75–2.95 (m, 2H), 4.05–4.30 (m, 2H), 5.13 (s, 2H), 5.30–5.90 (brd, 2H), 7.26–7.62 (m, 5H).

Step 2
4-Carbamoylpiperidine-1-carboxylic Acid tert-Butyl Ester

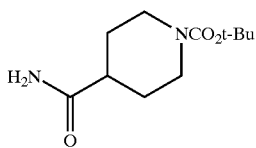

4-Carbamoylpiperidine-1-carboxylic acid benzyl ester (8.3 g) was hydrogenated using 7.5% palladium carbon (2 g) in a mixture of tetrahydrofuran (50 ml) and methanol (50 ml) at 3 atm over 2 hours. After completion of the reaction, the reaction mixture was filtered through celite, and to the obtained solution was added di-tert-butyl dicarbonate (7.6 g). The mixture was stirred at room temperature for 1 hour. After completion of the reaction, the solvent was evaporated and water was added. The mixture was extracted with ethyl acetate. The organic layer was washed with saturated brine and dried over anhydrous sodium sulfate. The solvent was evaporated and hexane was added. The mixture was filtrated and dried under reduced pressure to give the title compound (5.6 g).

$^1$H-NMR (δ ppm, CDCl$_3$) 1.46 (s, 9H), 1.57–1.70 (m, 2H), 1.78–1.90 (m, 2H), 2.26–2.38 (m, 1H), 2.65–2.88 (m, 2H), 4.00–4.25 (m, 2H), 5.30–5.80 (m, 2H).

Step 3
4-Cyanopiperidine-1-carboxylic Acid tert-Butyl Ester

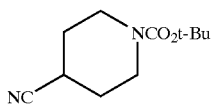

To a solution of 4-carbamoylpiperidine-1-carboxylic acid tert-butyl ester (5.6 g) in a mixture of tetrahydrofuran (110 ml) and carbon tetrachloride (90 ml) was added triphenylphosphine (24.4 g), and the mixture was stirred under reflux for 1.5 hours. After completion of the reaction, the reaction mixture was filtrated and the solvent was evaporated. The obtained residue was purified by silica gel column chromatography (hexane:ethyl acetate=3:1) and dried under reduced pressure to give the title compound (3.5 g).

$^1$H-NMR (δ ppm, CDCl$_3$) 1.46 (s, 9H), 1.70–1.95 (m, 4H), 2.75–2.85 (m, 1H), 3.30–3.38 (m, 2H), 3.62–3.70 (m, 2H).

Step 4
4-Allyl-4-cyanopiperidine-1-carboxylic Acid tert-Butyl Ester

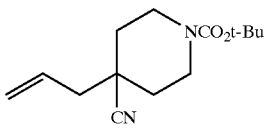

To a solution of 2M lithium diisopropylamide-tetrahydrofuran solution (9.96 ml) in tetrahydrofuran (20 ml) was dropwise added a solution of 4-cyanopiperidine-1-carboxylic acid tert-butyl ester (3.5 g) in tetrahydrofuran (15 ml) at –78° C. and under argon atmosphere, and the mixture was stirred at room temperature for 30 min. Then, allyl bromide (2.15 ml) was added at –78° C., and the mixture was stirred at the same temperature for 30 min and at room temperature for 1 hour. After completion of the reaction, 10% aqueous citric acid was added and the mixture was extracted with diethyl ether. The organic layer was washed with saturated brine and dried over anhydrous sodium sulfate. The solvent was evaporated and the obtained residue was purified by silica gel column chromatography (hexane:ethyl acetate=5:1) and dried under reduced pressure to give the title compound (3.5 g).

$^1$H-NMR (δ ppm, CDCl$_3$) 1.37–1.55 (m, 11H), 1.85–1.95 (m, 2H), 2.33 (d, 2H), 2.98–3.10 (m, 2H), 4.00–4.25 (m, 2H), 5.17–5.23 (m, 2H), 5.81–5.95 (m, 1H).

Step 5
4-Cyano-4-(2,3-dihydroxypropyl)piperidine-1-carboxylic Acid tert-Butyl Ester

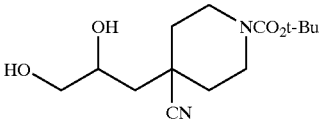

To a solution of 4-allyl-4-cyanopiperidine-1-carboxylic acid tert-butyl ester (3.5 g) in a mixture of acetone (160 ml) and water (20 ml) were added N-methylmorpholine N-oxide (2.5 g) and osmium tetroxide (5% tert-butanol solution, 8 ml), and the mixture was stirred at room temperature for 1 hour. After completion of the reaction, aqueous sodium thiosulfate was added and the mixture was filtrated. The solvent was evaporated and water was added to the obtained residue. The mixture was extracted with ethyl acetate and washed with saturated brine. The organic layer was dried over anhydrous sodium sulfate and the solvent was evaporated. The obtained residue was purified by silica gel column chromatography (ethyl acetate) and dried under reduced pressure to give the title compound (3.65 g).

$^1$H-NMR (δ ppm, CDCl$_3$) 1.40–1.81 (m, 13H), 1.90–1.96 (m, 1H), 2.00 (brs, 1H), 2.15–2.21 (m, 1H), 2.50 (brs, 1H), 2.95–3.20 (m, 2H), 3.49 (brtr, 1H), 3.65–3.72 (brd, 1H), 4.00–4.20 (m, 3H).

Step 6
4-Cyano-4-(2-hydroxyethyl)piperidine-1-carboxylic Acid tert-Butyl Ester

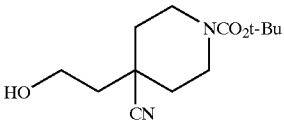

To a solution of 4-cyano-4-(2,3-dihydroxypropyl) piperidine-1-carboxylic acid tert-butyl ester (3.65 g) in tetrahydrofuran (100 ml) was added 10% aqueous sodium periodate solution (100 ml), and the mixture was stirred at room temperature for 40 min. After completion of the reaction, water was added and the mixture was extracted with ethyl acetate and washed with saturated brine. The organic layer was dried over anhydrous sodium sulfate and the solvent was evaporated. The obtained residue (3.3 g) was dissolved in tetrahydrofuran (100 ml) and sodium borohydride (360 mg) and methanol (20 ml) were added with ice-cooling, and the mixture was stirred at room temperature for 30 min. After completion of the reaction, 10% aqueous citric acid was added and the mixture was extracted with ethyl acetate and washed with saturated brine. The organic layer was dried over anhydrous sodium sulfate and the solvent was evaporated. The obtained residue was purified by silica gel column chromatography (chloroform:methanol=95:5) and dried under reduced pressure to give the title compound (3.13 g).

$^1$H-NMR (δ ppm, CDCl$_3$) 1.49–1.55 (m, 11H), 1.86 (m, 2H), 1.96–2.00 (m, 2H), 3.00–3.09 (m, 2H), 3.93 (m, 2H), 4.05–4.20 (m, 2H).

Step 7
7-[2-(1-tert-Butoxycarbonyl-4-cyanopiperidin-4-yl) ethoxy]-1,2,3,4-tetrahydroisoquinoline-2-carboxylic Acid Benzyl Ester

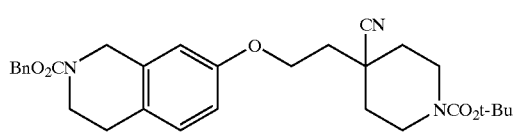

To a solution of 7-hydroxy-1,2,3,4-tetrahydroisoquinoline-2-carboxylic acid benzyl ester (1.1 g), 4-cyano-4-(2-hydroxyethyl)piperidine-1-carboxylic acid tert-butyl ester (1 g) and triphenylphosphine (1.22 g) in tetrahydrofuran (40 ml) was added diethyl azodicarboxylate (2 g) with ice-cooling, and the mixture was stirred at room temperature for 16 hours. After completion of the reaction, the solvent was evaporated. The obtained residue was purified by silica gel column chromatography (hexane:ethyl acetate=3:1) and dried under reduced pressure to give the title compound (1.6 g).

$^1$H-NMR (δ ppm, CDCl$_3$) 1.46–1.55 (m, 11H), 1.96–2.10 (m, 4H), 2.78 (m, 2H), 3.00–3.14 (m, 2H), 3.71 (m, 2H), 4.05–4.25 (m, 4H), 4.61 (s, 2H), 5.18 (s, 2H), 6.60–6.80 (m, 2H), 7.04 (1H), 7.26–7.40 (m, 5H).

Step 8
7-[2-(4-Cyanopiperidin-4-yl)ethoxy]-1,2,3,4-tetrahydroisoquinoline-2-carboxylic Acid Benzyl Ester

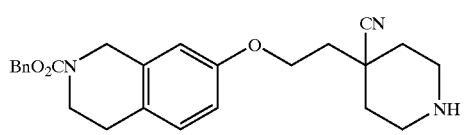

In the same manner as in Example 10, Step 6, the title compound (1 g) was obtained from 7-[2-(1-tert-butoxycarbonyl-4-cyanopiperidin-4-yl)ethoxy]-1,2,3,4-tetrahydroisoquinoline-2-carboxylic acid benzyl ester (1.2 g) and trifluoroacetic acid (10 ml).

$^1$H-NMR (δ ppm, CDCl$_3$) 1.53–1.64 (m, 2H), 1.99–2.05 (m, 2H), 2.07 (tr, J=6.3 Hz, 2H), 2.78 (brs, 2H), 2.92–3.12 (m, 4H), 3.70 (brtr, 2H), 4.18 (tr, J=6.3 Hz, 2H), 4.61 (s, 2H), 5.18 (s, 2H), 6.63–6.75 (m, 2H), 7.04 (1H), 7.26–7.38 (m, 5H).

Step 9
7-[2-[4-Cyano-1-(pyridin-4-yl)piperidin-4-yl]ethoxy]-1,2,3,4-tetrahydroisoquinoline-2-carboxylic Acid Benzyl Ester

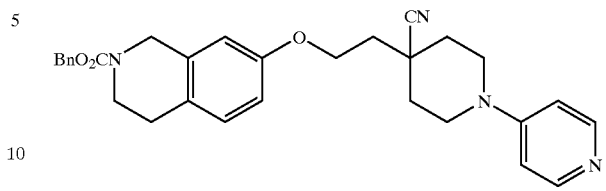

In the same manner as in Example 10, Step 7, the title compound (590 mg) was obtained from 7-[2-(4-cyanopiperidin-4-yl)ethoxy]-1,2,3,4-tetrahydroisoquinoline-2-carboxylic acid benzyl ester (850 mg), 4-chloropyridine hydrochloride (300 mg) and triethylamine (0.84 ml).

$^1$H-NMR (δ ppm, CDCl$_3$) 1.68–1.78 (m, 2H), 2.08–2.16 (m, 4H), 2.79 (brs, 2H), 3.17–3.24 (m, 2H), 3.71 (brtr, 2H), 3.84–3.91 (m, 2H), 4.21 (m, 2H), 4.62 (s, 2H), 5.18 (s, 2H), 6.63 (1H), 6.68 (dd, J=1.0, 3.9 Hz, 2H), 6.74 (1H), 7.05 (1H), 7.32–7.40 (m, 5H), 8.29 (dd, J=1.0, 3.9 Hz, 2H).

Step 10
7-[2-[4-Cyano-1-(pyridin-4-yl)piperidin-4-yl]ethoxy]-1,2,3,4-tetrahydroisoquinoline

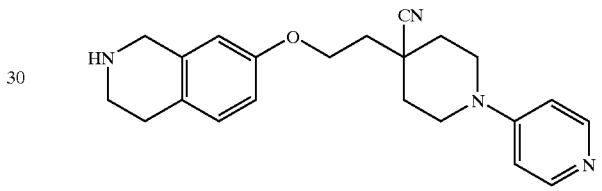

To a solution of 7-[2-[4-cyano-1-(pyridin-4-yl)piperidin-4-yl]ethoxy]-1,2,3,4-tetrahydroisoquinoline-2-carboxylic acid benzyl ester (585 mg) in ethanol (5 ml) were added 7.5% palladium carbon (220 mg) and ammonium formate (220 mg), and the mixture was stirred under reflux for 3 hours. After completion of the reaction, the reaction mixture was filtrated and the solvent was evaporated. To the obtained residue was added aqueous sodium hydrogencarbonate and the mixture was extracted with chloroform. The organic layer was washed with saturated brine and dried over anhydrous sodium sulfate. The solvent was evaporated and the residue was dried under reduced pressure to give the title compound (385 mg).

$^1$H-NMR (δ ppm, CDCl$_3$) 1.68–1.84 (m, 2H), 2.02–2.21 (m, 4H), 2.73 (m, 2H), 3.12 (m, 2H), 3.17–3.24 (m, 2H), 3.84–3.95 (m, 2H), 3.98 (s, 2H), 4.21 (m, 2H), 6.55 (1H), 6.67–6.71 (3H)), 7.00 (1H), 8.29 (2H)

Step 11
7-[2-[4-Cyano-1-(pyridin-4-yl)piperidin-4-yl]ethoxy]-1,2,3,4-tetrahydroisoquinoline-2-carboxamidine Dihydrochloride

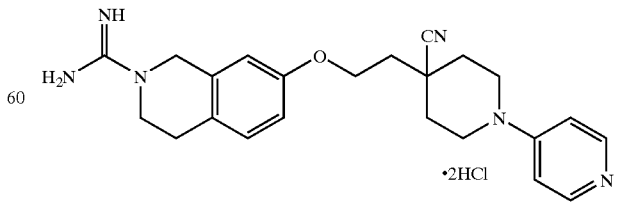

To a solution of 7-[2-[4-cyano-1-(pyridin-4-yl)piperidin-4-yl]ethoxy]-1,2,3,4-tetrahydroisoquinoline (70 mg) in dimethylformamide (5 ml)solution were added diisopropylethylamine (0.1 ml) and 1H-pyrazole-1-carboxamidine hydrochloride (85 mg), and the mixture was stirred at room temperature for 15 hours. After completion of the reaction, the solvent was evaporated and the obtained residue was purified by HPLC (0.05% aquesous trifluoroacetic acid:methanol=1:1). The obtained residue was treated with dil. hydrochloric acid and dried under reduced pressure to give the title compound (67 mg).

$^1$H-NMR ($\delta$ ppm, DMSO-$d_6$) 1.65–1.80 (m, 2H), 2.05–2.20 (m, 4H), 2.82 (tr, J=6.0 Hz, 2H), 3.29 (m, 2H), 3.58 (m, 2H), 4.17 (tr, J=6.0 Hz, 2H), 4.27–4.34 (m, 2H), 4.56 (s, 2H), 6.74 (d, J=2.4 Hz, 1H), 6.85 (dd, J=2.4, 8.4 Hz, 1H), 7.16 (d, J=8.4 Hz, 1H), 7.25 (d, J=7.5 Hz, 1H), 7.61 (brs, 4H), 8.26 (d, J=7.5 Hz, 11H), 13.80 (brs, 1H).

Example 38

Synthesis of 4-(2-Amidino-8-chloronaphthalen-7-yloxymethyl)-1-(pyridin-4-yl)piperidine-4-carboxylic Acid Ethyl Ester Dihydrochloride Step 1
7-Methoxy-2-trifluoromethanesulfonyloxynaphthalene

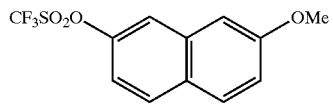

To a solution of 2-hydroxy-7-methoxynaphthalene (12.34 g) and triethylamine (9.87 ml) in chloroform (185 ml) was added trifluoromethanesulfonic anhydride (20 g) with ice-cooling, and the mixture was stirred at the same temperature for 30 min. After completion of the reaction, aqueous sodium hydrogencarbonate was added and the mixture was extracted with chloroform and washed successively with water and saturated brine. The organic layer was dried over anhydrous magnesium sulfate and the solvent was evaporated. The obtained residue was purified by silica gel column chromatography (hexane:ethyl acetate=9:1) and dried under reduced pressure to give the title compound (15.36 g).

$^1$H-NMR ($\delta$ ppm, CDCl$_3$) 3.96 (s, 3H), 7.14 (d, J=2.4 Hz, 1H), 7.21 (dd, J=2.4, 8.9 Hz, 2H), 7.64 (d, J=2.4 Hz, 1H), 7.77 (d, J=8.9 Hz, 1H), 7.83 (d, J=8.9 Hz, 1H).

Step 2
7-Methoxynaphthalene-2-carbonitrile

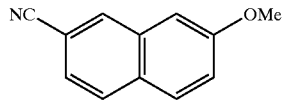

To a solution of 7-methoxy-2-trifluoromethanesulfonyloxynaphthalene (2.23 g) in dimethylformamide (8.9 ml) were added zinc cyanide (598 mg) and tetrakis(triphenylphosphine) palladium (337 mg) at room temperature, and the mixture was stirred at 80° C. for 1 hour. After completion of the reaction, water and ethyl acetate were added and insoluble material was removed. The organic layer was separated and concentrated, and the obtained residue was purified by silica gel column chromatography (hexane:ethyl acetate=19:1) and dried under reduced pressure to give the title compound (965 mg).

$^1$H-NMR ($\delta$ ppm, CDCl$_3$) 3.95 (s, 3H), 7.15 (d, J=2.5 Hz, H), 7.29 (dd, J=2.5, 9.0 Hz, 1H), 7.47 (1H), 7.78 (d, J=9.0 Hz, 1H), 7.83 (1H), 8.11 (1H).

Step 3
7-Hydroxynaphthalene-2-carbonitrile

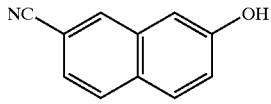

To a solution of 7-methoxynaphthalene-2-carbonitrile (6 g) in chlorobenzene (60 ml) was added aluminum chloride (15.3 g) at room temperature and the mixture was heated under refluxing for 30 min. After completion of the reaction, the reaction mixture was ice-cooled and ice, ethyl acetate and conc. hydrochloric acid were added, and the mixture was stirred. The organic layer was separated and concentrated. To the obtained residue was added hexane and the resultant solid was collected by filtration and dried under reduced pressure to give the title compound (5.21 g).

$^1$H-NMR ($\delta$ ppm, CDCl$_3$) 5.42 (1H), 7.20 (1H), 7.25–7.28 (1H), 7.46 (1H), 7.79–7.85 (2H), 8.07 (1H).

Step 4
8-Chloro-7-hydroxynaphthalene-2-carbonitrile

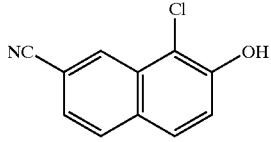

To a solution of 7-hydroxynaphthalene-2-carbonitrile (2.23 g) in chloroform (120 ml) was dropwise added tert-butyl hypochlorite (1.64 ml) with ice-cooling, and the mixture was stirred at room temperature for 15 min. After completion of the reaction, the resultant solid was collected by filtration and dried under reduced pressure to give the title compound (1.88 g).

$^1$H-NMR ($\delta$ ppm, DMSO-$d_6$) 7.49 (d, J=9.0 Hz, 1H), 7.68 (1H), 7.94 (d, J=9.0 Hz, 1H), 8.19 (1H), 8.46 (1H).

Step 5
8-Chloro-7-methylthiomethoxynaphthalene-2-carbonitrile

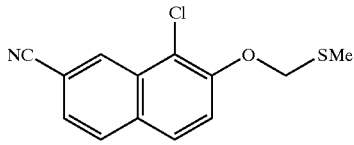

In the same manner as in Example 10, Step 2, the title compound (1.31 g) was obtained from 8-chloro-7-hydroxynaphthalene-2-carbonitrile (1.88 g).

$^1$H-NMR ($\delta$ ppm, CDCl$_3$) 2.32 (s, 3H), 5.40 (s, 2H), 7.48 (d, J=9.0 Hz, 1H), 7.57 (dd, J=1.5, 8.4 Hz, 1H), 7.82 (d, J=9.0 Hz, 1H), 7.90 (d, J=8.4 Hz, 1H), 8.63 (d, J=1.5 Hz, 1H).

Step 6
8-Chloro-7-chloromethoxynaphthalene-2-carbonitrile

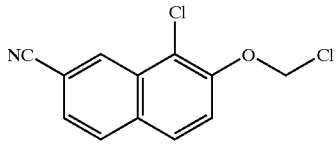

In the same manner as in Example 10, Step 3, the title compound (939 mg) was obtained from 8-chloro-7-methylthiomethoxynaphthalene-2-carbonitrile (1.28 g).

$^1$H-NMR (δ ppm, CDCl$_3$) 6.04 (s, 2H), 7.61–7.67 (2H), 7.88 (1H), 7.94 (1H), 8.65 (1H).

Step 7

4-(8-Chloro-2-cyanonaphthalen-7-yloxymethyl)-1-(pyridin-4-yl)piperidine-4-carboxylic Acid Ethyl Ester

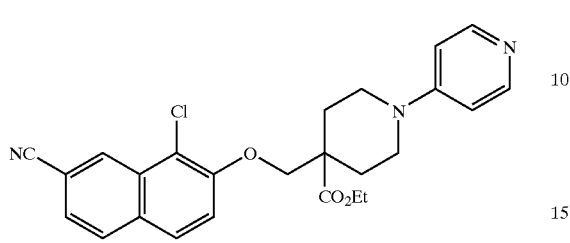

In the same manner as in Example 10, Step 5, the title compound (128 mg) was obtained from 8-chloro-7-chloromethoxynaphthalene-2-carbonitrile (295 mg) and 1-(pyridin-4-yl)piperidine-4-carboxylic acid ethyl ester (603 mg).

$^1$H-NMR (δ ppm, CDCl$_3$) 1.28 (tr, J=7.1 Hz, 3H), 1.78–1.88 (m, 2H), 2.41–2.48 (m, 2H), 3.16–3.25 (m, 2H), 3.75–3.85 (m, 2H), 4.22 (s, 2H), 4.26 (q, J=7.1 Hz, 2H), 6.69 (dd, J=1.4, 5.1 Hz, 2H), 7.38 (d, J=9.0 Hz, 1H), 7.55 (1H), 7.81 (d, J=9.0 Hz, 1H), 7.88 (1H), 8.27 (dd, J=1.4, 5.1 Hz, 2H), 8.61 (1H), Step 8

4-(2-Amidino-8-chloronaphthalen-7-yloxymethyl)-1-(pyridin-4-yl)piperidine-4-carboxylic Acid Ethyl Ester Dihydrochloride

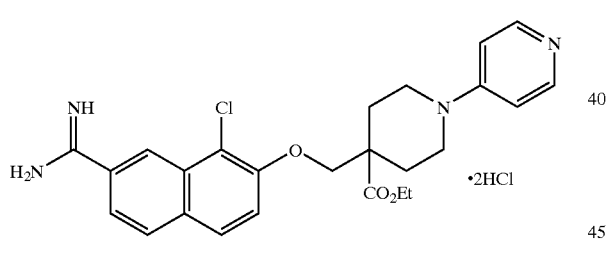

Hydrogen sulfide was blown into a solution of 4-(8-chloro-2-cyanonaphthalen-7-yloxymethyl)-1-(pyridin-4-yl) piperidine-4-carboxylic acid ethyl ester (124 mg) in a mixture of pyridine (2.5 ml) and triethylamine (0.5 ml) with ice-cooling, and the mixture was stirred at room temperature for 12 hours. After completion of the reaction, the solvent was evaporated and the residue was treated with hydrogen chloride-ethanol. To the residue were added acetone (2 ml), methanol (2 ml) and methyl iodide (0.172 ml), and the mixture was stirred under reflux for 2 hours. After completion of the reaction, the solvent was evaporated and the obtained residue was dissolved in ethanol (4 ml). Ammonium acetate (106 mg) was added, and the mixture was stirred at 75° C. for 2 hours. After completion of the reaction, the solvent was evaporated and the obtained residue was purified by silica gel column chromatography (chloroform:methanol:ammonia). The obtained residue was treated with hydrogen chloride-ethanol and dried under reduced pressure to give the title compound (92 mg).

Example 39

Synthesis of 4-(2-Amidino-8-chloronaphthalen-7-yloxymethyl)-1-(pyridin-4-yl)piperidine-4-carboxylic Acid Dihydrochloride

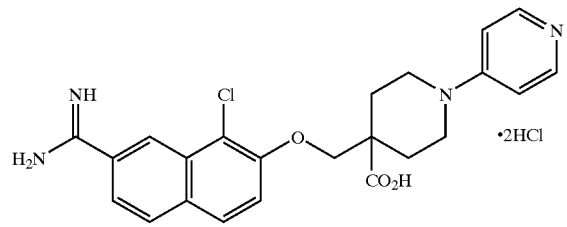

A solution of 4-(2-amidino-8-chloronaphthalen-7-yloxymethyl)-1-(pyridin-4-yl)piperidine-4-carboxylic acid ethyl ester dihydrochloride (78 mg) in conc. hydrochloric acid was stirred at 50° C.–100° C. for 3 hours. After completion of the reaction, the solvent was evaporated and the obtained residue was separated by HPLC (0.05% aqueous trifluoroacetic acid:methanol=1:1). The obtained residue was treated with hydrogen chloride-ethanol and dried under reduced pressure to give the title compound (49 mg).

$^1$H-NMR (δ ppm, DMSO-d$_6$) 1.75–1.94 (m, 2H), 2.19–2.31 (m, 2H), 3.49 (m, 2H), 4.07 (m, 2H), 4.41 (s, 2H), 7.22 (2H), 7.78 (2H), 8.12 (1H), 8.18–8.25 (m, 3H), 8.56 (s, 1H), 9.34 (brs, 2H), 9.62 (brs, 2H), 12.98 (brs, 1H), 13.65 (brs, 1H).

Example 40

Synthesis of 4-(2-Amidinonaphthalen-7-yloxymethyl)-1-(pyridin-4-yl)piperidine-4-carboxylic Acid Ethyl Ester Dihydrochloride Step 1

7-Methylthiomethoxynaphthalene-2-carbonitrile

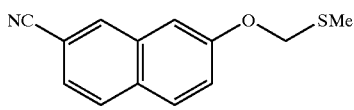

In the same manner as in Example 10, Step 2, the title compound (907 mg) was obtained from 7-hydroxynaphthalene-2-carbonitrile (1.12 g).

Step 2

7-Chloromethoxynaphthalene-2-carbonitrile

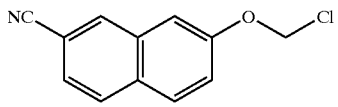

In the same manner as in Example 10, Step 3, the title compound (567 mg) was obtained from 7-methylthiomethoxynaphthalene-2-carbonitrile (647 mg).

Step 3

4-(2-Cyanonaphthalen-7-yloxymethyl)-1-(pyridin-4-yl) piperidine-4-carboxylic Acid Ethyl Ester

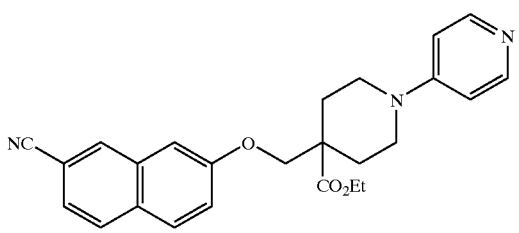

In the same manner as in Example 10, Step 5, the title compound (430 mg) was obtained from 7-chloromethoxynaphthalene-2-carbonitrile (314 mg), 1-(pyridin-4-yl)piperidine-4-carboxylic acid ethyl ester (743 mg) and a 2M-lithium diisopropylamide-tetrahydrofuran solution (1.73 ml).

Step 4
4-(2-Amidinonaphthalen-7-yloxymethyl)-1-(pyridin-4-yl) piperidine-4-carboxylic Acid Ethyl Ester Dihydrochloride

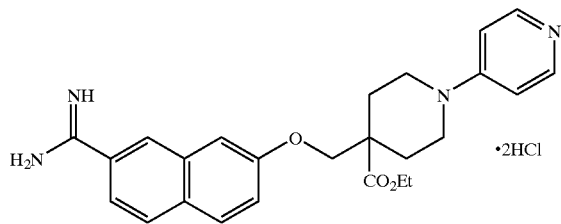

In the same manner as in Example 38, Step 8, the title compound (36 mg) was obtained from 4-(2-cyanonaphthalen-7-yloxymethyl)-1-(pyridin-4-yl) piperidine-4-carboxylic acid ethyl ester (51 mg) and methyl iodide (0.6 ml).

$^1$H-NMR (δ ppm, DMSO-$d_6$) 1.14 (tr, J=7.1 Hz, 3H), 1.75–1.88 (m, 2H), 2.19–2.31 (m, 2H), 3.44 (m, 2H), 4.00–4.20 (m, 4H), 4.27 (s, 2H), 7.21 (d, J=7.0 Hz, 2H), 7.34 (d, J=8.9 Hz, 1H), 7.48 (s, 1H), 7.66 (d, J=8.9 Hz, 1H), 7.98 (d, J=8.9 Hz, 1H), 8.07 (d, J=8.9 Hz, 1H), 8.24 (d, J=7 Hz, 2H), 8.32 (s, 1H), 9.19 (brs, 2H), 9.45 (brs, 2H), 13.53 (brs, 1H).

Example 41

Synthesis of 4-(2-Amidino-2,3,4,5-tetrahydro-1H-benz[c]azepin-8-yloxymethyl)-1-(pyridin-4-yl) piperidine-4-carboxylic Acid Ethyl Ester Dihydrochloride Step 1
8-Methoxy-2,3,4,5-tetrahydrobenz[c]azepin-1-one

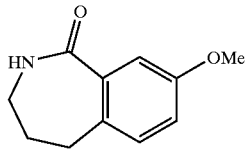

To a solution of 7-methoxy-1,2,3,4-tetrahydronaphthalen-1-one (5.21 g) in conc. hydrochloric acid (26 ml) was added sodium azide (1.98 g) by portions with ice-cooling, and the mixture was stirred at the same temperature for 2 hours, and then at room temperature for 2 hours. After completion of the reaction, the reaction mixture was poured into ice water and aqueous potassium carbonate was added. The mixture was extracted with chloroform and washed successively with water and saturated brine. The organic layer was dried over anhydrous sodium sulfate, and the solvent was evaporated. The obtained residue was purified by silica gel column chromatography (ethyl acetate) and dried under reduced pressure to give the title compound (470 mg).

$^1$H-NMR (δ ppm, CDCl$_3$) 1.98 (quint, J=6.9 Hz, 2H), 2.80 (tr, J=6.9 Hz, 2H), 3.13 (q, J=6.9 Hz, 2H), 3.83 (s, 3H), 6.96 (1H), 7.09 (1H), 7.26 (1H).

Step 2
8-Methoxy-2,3,4,5-tetrahydro-1H-benz[c]azepine

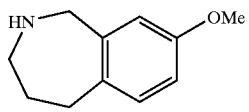

To a solution of lithium aluminum hydride (3.07 g) in tetrahydrofuran (60 ml) was dropwise added a solution of 8-methoxy-2,3,4,5-tetrahydrobenz[c]azepin-1-one (4.42 g) in 1,4-dioxane (30 ml) with ice-cooling and the mixture was refluxed for 20 hours. After completion of the reaction, 20% aqueous sodium hydroxide solution was added dropwise with ice-cooling, and the mixture was stirred at room temperature for 1 hour. After completion of the reaction, the reaction mixture was filtrated, and the solvent was evaporated and the residue was dried under reduced pressure to give the title compound (4.05 g).

$^1$H-NMR (δ ppm, CDCl$_3$) 1.68 (m, 2H), 2.82–2.90 (m, 2H), 3.10–3.25 (m, 2H), 3.77 (s, 3H), 3.88 (s, 2H), 6.60–6.70 (2H), 7.05 (1H).

Step 3
8-Hydroxy-2,3,4,5-tetrahydro-1H-benz[c]azepine Hydrobromide

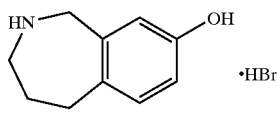

8-Methoxy-2,3,4,5-tetrahydro-1H-benz[c]azepine (3.65 g) was dissolved in 48% aqueous hydrogen bromide solution (36 ml) and the mixture was refluxed for 2 hours. The solvent was evaporated and ethanol and diethyl ether were added to the obtained residue. The mixture was filtrated and dried under reduced pressure to give the title compound (4.56 g).

$^1$H-NMR (δ ppm, DMSO-$d_6$) 1.80–1.83 (m, 2H), 2.85–2.88 (m, 2H), 3.22 (m, 2H), 4.20–4.22 (m, 2H), 6.69 (dd, J=2.5, 8.1 Hz, 1H), 6.82 (d, J=2.5 Hz, 1H), 7.05 (d, J=8.1 Hz, 1H), 8.80 (brs, 2H), 9.42 (brs, 1H).

Step 4
8-Hydroxy-2,3,4,5-tetrahydro-1H-benz[c]azepine-2-carboxylic Acid tert-Butyl Ester

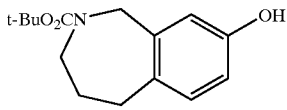

In the same manner as in Example 1, Step 1, the title compound (2.64 g) was obtained from 8-hydroxy-2,3,4,5-tetrahydro-1H-benz[c]azepine hydrobromide (3 g), 2N aqueous sodium hydroxide solution (30 ml) and di-tert-butyl dicarbonate (3.2 g).

$^1$H-NMR (δ ppm, CDCl$_3$) 1.40 (s, 9H), 1.68–1.80 (m, 2H), 2.84–2.88 (m, 2H), 3.66 (m, 2H), 4.28–4.37 (m, 2H), 5.19, 5.91 (1H), 6.63 (1H), 6.70, 6.85 (1H), 6.98 (1H).

Step 5
8-Methylthiomethoxy-2,3,4,5-tetrahydro-1H-benz[c]azepine-2-carboxylic Acid tert-Butyl Ester

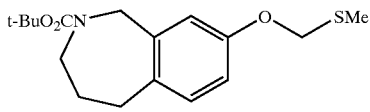

In the same manner as in Example 6, Step 1, the title compound (1.07 g) was obtained from 8-hydroxy-2,3,4,5-tetrahydro-1H-benz[c]azepine-2-carboxylic acid tert-butyl ester (1.06 g), 60% sodium hydride (195 mg) and chloromethyl methyl sulfide (0.41 ml).

$^1$H-NMR (δ ppm, CDCl$_3$) 1.40 (s, 9H), 1.75 (m, 2H), 2.24 (s, 3H), 2.87 (m, 2H), 3.68 (m, 2H), 4.30–4.45 (m, 2H), 5.13 (s, 2H), 6.74 (1H), 6.81, 6.92 (1H), 7.06 (1H).

Step 6
8-[4-Ethoxycarbonyl-1-(pyridin-4-yl)piperidin-4-ylmethoxy]-2,3,4,5-tetrahydro-1H-benz[c]azepine-2-carboxylic Acid tert-Butyl Ester

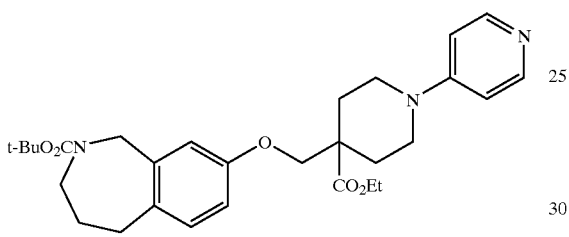

In the same manner as in Example 6, Step 2, 8-chloromethoxy-2,3,4,5-tetrahydro-1H-benz[c]azepine-2-carboxylic acid tert-butyl ester (850 mg) was obtained from 8-methylthiomethoxy-2,3,4,5-tetrahydro-1H-benz[c]azepine-2-carboxylic acid tert-butyl ester (530 mg) and sulfuryl chloride (0.145 ml) under an argon atmosphere. Then, in the same manner as in Example 6, Step 3, the title compound (755 mg) was obtained.

$^1$H-NMR (δ ppm, CDCl$_3$) 1.27 (tr, J=6.9 Hz, 3H), 1.39 (s, 9H), 1.64–1.78 (m, 4H), 2.30–2.36 (m, 2H), 2.85–2.88 (m, 2H), 3.01–3.18 (m, 2H), 3.62–3.75 (m, 4H), 3.98 (s, 2H), 4.21 (q, J=6.9 Hz, 2H), 4.30–4.38 (m, 2H), 6.62–6.67 (m, 3H), 6.72, 6.84 (1H), 7.02 (1H), 8.25 (2H).

Step 7
1-(Pyridin-4-yl)-4-(2,3,4,5-tetrahydro-1H-benz[c]azepin-8-yloxymethyl)piperidine-4-carboxylic Acid Ethyl Ester

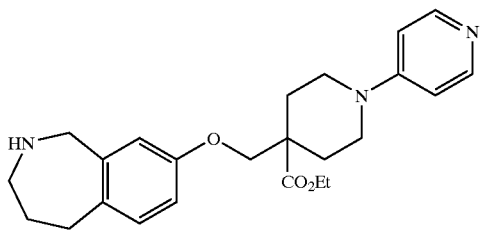

In the same manner as in Example 6, Step 4, the title compound (600 mg) was obtained from 8-[4-ethoxycarbonyl-1-(pyridin-4-yl)piperidin-4-ylmethoxy]-2,3,4,5-tetrahydro-1H-benz[c]azepine-2-carboxylic acid tert-butyl ester (750 mg) and trifluoroacetic acid (2.5 ml).

Step 8
4-(2-Amidino-2,3,4,5-tetrahydro-1H-benz[c]azepin-8-yloxymethyl)-1-pyridin-4-yl)piperidine-carboxylic Acid Ethyl Ester Dihydrochloride

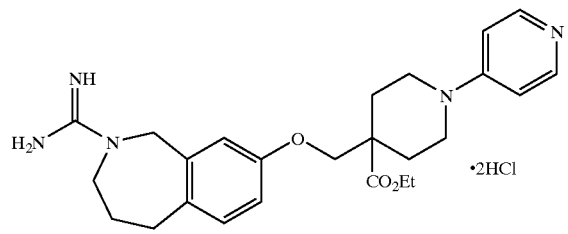

In the same manner as in Example 6, Step 5, the title compound (200 mg) was obtained from 1-(pyridin-4-yl)-4-(2,3,4,5-tetrahydro-1H-benz[c]azepin-8-yloxymethyl)piperidine-4-carboxylic acid ethyl ester (200 mg), diisopropylethylamine (0.105 ml) and 1H-pyrazole-1-carboxamidine hydrochloride (90 mg).

$^1$H-NMR (δ ppm, DMSO-d$_6$) 1.16 (tr, J=7.2 Hz, 3H), 1.75 (m, 4H), 2.20 (m, 2H), 2.89 (m, 2H), 3.41 (m, 2H), 4.04 (m, 4H), 4.16 (q, J=7.2 Hz, 2H), 4.58 (s, 2H), 4.58 (s, 2H), 6.76 (1H), 7.11–7.22 (m, 4H), 7.47 (brs, 4H), 8.24 (1H), 13.60 (brs, 1H).

Example 42

Synthesis of 4-(2-Amidino-2,3,4,5-tetrahydro-1H-benz[c]azepin-8-yloxymethyl)-1-(pyridin-4-yl)piperidine-4-carboxylic Acid Dihydrochoride

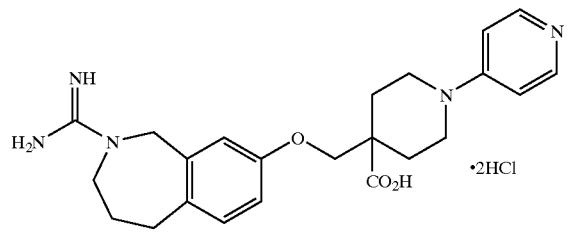

4-(2-Amidino-2,3,4,5-tetrahydro-1H-benz[c]azepin-8-yloxymethyl)-1-(pyridin-4-yl)piperidine-4-carboxylic acid ethyl ester dihydrochloride (150 mg) was dissolved in 6N-hydrochloric acid (2 ml), and the mixture was stirred under reflux for 3 hours. After completion of the reaction, insoluble material was removed and the solvent was evaporated. The residue was dried under reduced pressure to give the title compound (140 mg).

$^1$H-NMR (δ ppm, DMSO-d$_6$) 1.56–1.81 (m, 4H), 2.12–2.25 (m, 2H), 2.88–3.00 (m, 2H), 3.42 (m, 2H), 4.00–4.13 (m, 4H), 4.59 (s, 2H), 6.76 (1H), 7.12 (1H), 7.19–7.23 (m, 3H), 7.54 (brs, 4H), 8.23 (2H), 13.70 (brs, 1H).

Example 43

Synthesis of 4-(2-Amidino-1,2,3,4-tetrahydroisoquinolin-7-ylthiomethyl)-1-(pyridin-4-yl)piperidine-4-carboxylic Acid Dihydrochloride Step 1
4-Ethoxycarbonyl-4-iodomethylpiperidine-1-carboxylic Acid tert-Butyl Ester

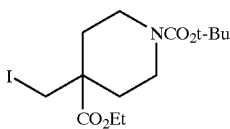

To a solution of 1-tert-butoxycarbonylisonipecotinic acid ethyl ester (7.14 g) in tetrahydrofuran (140 ml) were dropwise added a 2M-lithium diisopropylamide-tetrahydrofuran solution (16.6 ml) and diiodomethane (2.7 ml) at −78° C., and the mixture was stirred for 15 hours. After completion of the reaction, 10% aqueous citric acid solution was added, and the mixture was extracted with ethyl acetate and washed with saturated brine. The organic layer was dried over anhydrous magnesium sulfate and the solvent was evaporated. The obtained residue was purified by silica gel column chromatography (hexane:ethyl acetate=9:1) and dried under reduced pressure to give the title compound (8.68 g).

$^1$H-NMR (δ ppm, CDCl$_3$) 1.27–1.33 (m, 3H), 1.38–1.45 (m, 10H), 1.59–1.64 (m, 1H), 2.10–2.22 (m, 2H), 2.90–3.10 (m, 2H), 3.29 (s, 2H), 3.65–3.95 (m, 2H), 4.18–4.26 (m, 2H).

Step 2

4-(2-Acetyl-1,2,3,4-tetrahydroisoquinolin-7-ylthiomethyl)-4-ethoxycarbonylpiperidine-1-carboxylic Acid tert-Butyl Ester

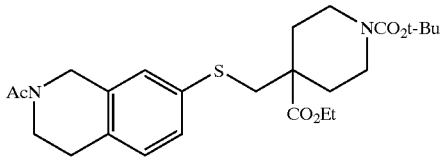

Crude crystals of 2-acetyl-1,2,3,4-tetrahydroisoquinoline-7-thiol were obtained from 2-acetyl-7-chlorosulfonyl-1,2,3,4-tetrahydroisoquinoline (U.S. Pat. No. 3,725,388)(7.68 g) and tin chloride dihydrate (25.3 g) according to the method described in Journal of Medicinal Chemistry, vol. 23, No. 8, p. 837 (1980) and the obtained crystals were dissolved in dimethylformamide (120 ml). Thereto were added potassium carbonate (4.27 g) and 4-ethoxycarbonyl-4-iodomethylpiperidine-1-carboxylic acid tert-butyl ester (3.71 g), and the mixture was stirred at 100° C. for 1 hour. After completion of the reaction, the reaction mixture was filtrated and the solvent was evaporated. The obtained residue was purified by silica gel column chromatography (hexane:ethyl acetate=2:8-ethyl acetate) and dried under reduced pressure to give the title compound (3.92 g).

$^1$H-NMR (δ ppm, CDCl$_3$) 1.18–1.24 (3H), 1.44–1.51 (11H), 2.12–2.18 (5H), 2.80–3.05 (4H), 3.12 (2H), 3.66 (1H), 3.72–3.95 (3H), 4.01–4.11 (2H), 4.57, 4.69 (2H), 7.03–7.22 (3H).

Step 3

4-(2-Acetyl-1,2,3,4-tetrahydroisoquinolin-7-ylthiomethyl)-1-(pyridin-4-yl)piperidine-4-carboxylic Acid Ethyl Ester

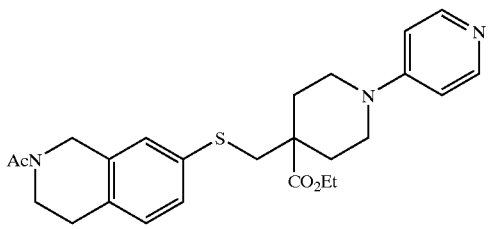

To a solution of 4-(2-acetyl-1,2,3,4-tetrahydroisoquinolin-7-ylthiomethyl)-4-ethoxycarbonylpiperidine-1-carboxylic acid tert-butyl ester (221 mg) in chloroform (0.5 ml) was added trifluoroacetic acid (1 ml), and the mixture was stirred at room temperature for 10 min. After completion of the reaction, the solvent was evaporated and to the obtained residue were added ethanol (3 ml), triethylamine (0.39 ml) and 4-chloropyridine hydrochloride (70 mg). The mixture was stirred in a sealed tube at 150° C. for 2 days. After completion of the reaction, the solvent was evaporated, and the obtained residue was purified by silica gel column chromatography (5% methanol-chloroform) and dried under reduced pressure to give the title compound (63 mg).

$^1$H-NMR (δ ppm, CDCl$_3$) 1.21–1.26 (3H), 1.58–1.70 (2H), 2.17 (3H), 2.25–2.40 (2H), 2.78–2.90 (2H), 3.05–3.22 (4H), 3.64–3.85 (4), 4.07, 4.15 (2H), 4.57–4.69 (2H), 6.69 (2H), 7.04–7.20 (3H), 8.25 (2H).

Step 4

4-(2-Amidino-1,2,3,4-tetrahydroisoquinolin-7-ylthiomethyl)-1-(pyridin-4-yl)piperidine-4-carboxylic Acid Dihydrochloride

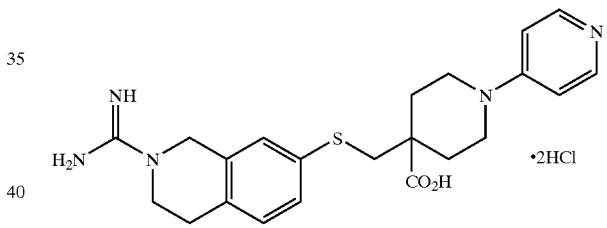

To 4-(2-acetyl-1,2,3,4-tetrahydroisoquinolin-7-ylthiomethyl)-1-(pyridin-4-yl)piperidine-4-carboxylic acid ethyl ester (63 mg) was added conc. hydrochloric acid (2 ml), and the mixture was stirred at 90° C. for 21 hours. After completion of the reaction, the solvent was evaporated and to the obtained residue were added 1N aqueous sodium hydroxide solution (0.7 ml), acetone (2 ml) and 1H-pyrazole-1-carboxamidine hydrochloride (61 mg), and the mixture was stirred for 12 hours. After completion of the reaction, dil. hydrochloric acid was added to make the solution acidic and the solvent was evaporated. To the obtained residue was added methanol and the mixture was filtrated. The solvent was evaporated and the obtained residue was separated by HPLC (25%–40% methanol-water, 0.05% trifluoroacetic acid) and treated with dil. hydrochloric acid, which was dried under reduced pressure to give the title compound (47 mg).

$^1$H-NMR (δ ppm, DMSO-d$_6$) 1.57–1.70 (m, 2H), 2.08–2.20 (m, 2H), 2.84–2.92 (m, 2H), 3.20–3.40 (m, 4H), 3.60 (m, 2H), 3.95–4.10 (m, 2H), 4.57 (s, 2H), 7.14–7.20 (m, 5H), 7.66 (brs, 4H), 8.22 (2H).

Example 44

Synthesis of 4-[2-(2-Amidino-1,2,3,4-tetrahydroisoquinolin-7-ylthio)ethyl]-1-(pyridin-4-yl)piperidine-4-carboxylic Acid Dihydrochloride Step 1
4-Allyl-4-ethoxycarbonylpiperidine-1-carboxylic Acid tert-Butyl Ester

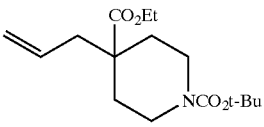

To a solution of 1-tert-butoxycarbonylisonipecotinic acid ethyl ester (6 g) in tetrahydrofuran (120 ml) were dropwise added a 2M-lithium diisopropylamide-tetrahydrofuran solution (14 ml) and alyll bromide (2.42 ml) at −78° C., and the mixture was stirred for 3 hours. After completion of the reaction, water was added and the mixture was extracted with ethyl acetate and washed with water. The organic layer was dried over anhydrous magnesium sulfate and the solvent was evaporated. The obtained residue was purified by silica gel column chromatography (hexane:ethyl acetate=4:1) and dried under reduced pressure to give the title compound (5.07 g).

Step 2
1-tert-Butoxycarbonyl-4-ethoxycarbonylpiperidin-4-ylacetic Acid

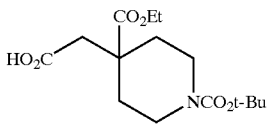

To a solution of sodium periodate (14.69 g) in a mixture of water (90 ml), carbon tetrachloride (50 ml) and acetonitrile (50 ml) was added ruthenium chloride (111 mg) and a solution of 4-allyl-4-ethoxycarbonylpiperidine-1-carboxylic acid tert-butyl ester (5.07 g) in a mixture of carbon tetrachloride (10 ml) and acetonitrile (10 ml) was added dropwise, and the mixture was stirred at room temperature for 1.5 hours. After completion of the reaction, the reaction mixture was filtrated and the residue was washed with ethyl acetate. The aqueous layer of the obtained filtrate was removed and the organic layer was dried over anhydrous magnesium sulfate. The solvent was evaporated and the obtained residue was purified by silica gel column chromatography (ethyl acetate) and dried under reduced pressure to give the title compound (4.23 g).

$^1$H-NMR (δ ppm, CDCl$_3$) 1.26 (tr, J=7.0 Hz, 3H), 1.48–1.57 (m, 11H), 2.05–2.18 (m, 2H), 2.65 (s, 2H), 3.21 (m, 2H), 3.65–3.75 (m, 2H), 4.19 (q, J=7.0 Hz, 2H).

Step 3
4-Ethoxycarbonyl-4-(2-hydroxyethyl)piperidine-1-carboxylic Acid tert-Butyl Ester

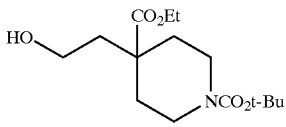

To a solution of 1-tert-butoxycarbonyl-4-ethoxycarbonyl-piperidin-4-ylacetic acid (2.34 g) in tetrahydrofuran (60 ml) was added a 1M borane tetrahydrofuran solution (7.42 ml) at −78° C., and the mixture was allowed to warm to room temperature in 15 hours in stirring. After completion of the reaction, water and potassium carbonate were added, and the mixture was stirred at room temperature for 1 hour. Water was added and the mixture was washed with hexane. The aqueous layer was extracted with ethyl acetate and washed with saturated brine. The organic layer was dried over anhydrous magnesium sulfate and the solvent was evaporated. The residue was dried under reduced pressure to give the title compound (1.92 g).

$^1$H-NMR (δ ppm, CDCl$_3$) 1.28 (tr, J=7. 1 Hz, 3H), 1.35–1.75 (m, 11H), 1.82 (tr, J=6.7 Hz, 2H), 2.10–2.20 (m, 2H), 2.91 (m, 2H), 3.68 (tr, J=6.7 Hz, 2H), 3.75–4.00 (m, 2H), 4.18 (q, J=7.1 Hz, 2H).

Step 4
4-Ethoxycarbonyl-4-(2-methanesulfonyloxyethyl)piperidine-1-carboxylic Acid tert-Butyl Ester

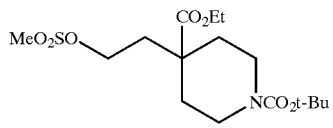

To a solution of 4-ethoxycarbonyl-4-(2-hydroxyethyl)piperidine-1-carboxylic acid tert-butyl ester (1.92 g) in a mixture of triethylamine (1.15 ml) and methylene chloride (40 ml) was added methanesulfonyl chloride (0.592 ml) at −78° C., and the mixture was stirred for 1 hour. After completion of the reaction, aqueous sodium hydrogencarbonate was added and the organic layer was separated and dried over anhydrous magnesium sulfate. The solvent was evaporated and the obtained residue was purified by silica gel column chromatography (hexane:ethyl acetate=1:1) and dried under reduced pressure to give the title compound (2.38 g).

$^1$H-NMR (δ ppm, CDCl$_3$) 1.29 (tr, 3H), 1.36–1.52 (m, 11H), 2.00 (m, 2H), 2.10–2.20 (m, 2H), 2.91 (m, 2H), 2.99 (s, 3H), 3.80–4.00 (m, 2H), 4.17–4.34 (m, 4H).

Step 5
4-Ethoxycarbonyl-4-(2-iodoethyl)piperidine-1-carboxylic Acid tert-Butyl Ester

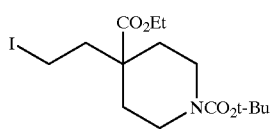

To a solution of 4-ethoxycarbonyl-4-(2-methanesulfonyloxyethyl)-piperidine-1-carboxylic acid tert-butyl ester (2.38 g) in dimethylformamide (24 ml) was added sodium iodide (4.77 g), and the mixture was stirred at 70° C. for 7 hours. After completion of the reaction, water was added and the mixture was extracted with ethyl acetate and washed with water. The organic layer was dried over anhydrous magnesium sulfate and the solvent was evaporated. The obtained residue was purified by silica gel column chromatography (hexane:ethyl acetate=1:1) and dried under reduced pressure to give the title compound (1.03 g).

$^1$H-NMR (δ ppm, CDCl$_3$) 1.28 (tr, J=7.1 Hz, 3H), 1.26–1.45 (m, 11H), 2.05–2.20 (m, 4H), 2.87 (m, 2H), 3.01–3.07 (m, 2H), 3.75–4.00 (m, 2H), 4.20 (q, J=7.1 Hz, 2H).

Step 6
4-[2-(2-Acetyl-1,2,3,4-tetrahydroisoquinolin-7-ylthio)ethyl]-4-ethoxycarbonylpiperidine-1-carboxylic Acid tert-Butyl Ester

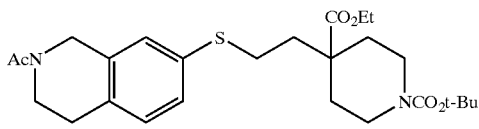

Crude crystals (1.26 g) of 2-acetyl-1,2,3,4-tetrahydroisoquinoline-7-thiol were dissolved in dimethylformamide (15 ml) and thereto were added 60% sodium hydride (243 mg) and 4-ethoxycarbonyl-4-(2-iodoethyl)piperidine-1-carboxylic acid tert-butyl ester (1 g), and the mixture was stirred at 70° C. for 1 hour. After completion of the reaction, water was added and the mixture was extracted with ethyl acetate and washed with saturated brine. The organic layer was dried over anhydrous magnesium sulfate and the solvent was evaporated. The obtained residue was purified by silica gel column chromatography (hexane:ethyl acetate=3:7) and dried under reduced pressure to give the title compound (535 mg).

$^1$H-NMR (δ ppm, CDCl$_3$) 1.26 (3H), 1.30–1.44 (11H), 1.75–1.85 (2H), 2.05–2.20 (5H), 2.75–3.00 (6H), 3.67 (1H), 3.79–3.95 (3H), 4.19 (2H), 4.57, 4.69 (2H), 7.05–7.15 (3H).

Step 7
4-[2-(2-Acetyl-1,2,3,4-tetrahydroisoquinolin-7-ylthio)ethyl]-1-(pyridin-4-yl)piperidine-4-carboxylic Acid Ethyl Ester

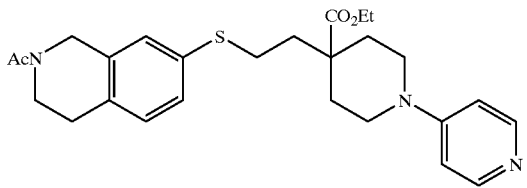

In the same manner as in Example 43, Step 3, the title compound (98 mg) was obtained from 4-[2-(2-acetyl-1,2,3,4-tetrahydroisoquinolin-7-ylthio)ethyl]-4-ethoxycarbonylpiperidine-1-carboxylic acid tert-butyl ester (233 mg), trifluoroacetic acid (1 ml), 4-chloropyridine hydrochloride (72 mg) and triethylamine (0.4 ml).

Step 8
4-[2-(2-Amidino-1,2,3,4-tetrahydroisoquinolin-7-ylthio)ethyl-1-(pyridin-4-yl)piperidine-4-carboxylic Acid Dihydrochloride

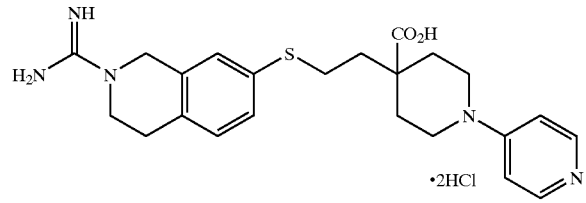

In the same manner as in Example 43, Step 4, the title compound (53 mg) was obtained from 4-[2-(2-acetyl-1,2,3,4-tetrahydroisoquinolin-7-ylthio)ethyl]-1-(pyridin-4-yl)piperidine-4-carboxylic Acid Ethyl Ester (94 mg), conc. hydrochloric acid (2 ml), 1N aqueous sodium hydroxide solution (1 ml) and 1H-pyrazole-1-carboxamidine hydrochloride (88 mg).

$^1$H-NMR (δ ppm, DMSO-d$_6$) 1.48–1.60 (m, 2H), 1.75–1.90 (m, 2H), 2.05–2.20 (m, 2H), 2.80–2.98 (m, 4H), 3.17–3.34 (m, 2H), 3.60 (m, 2H), 4.04 (m, 2H), 4.57 (s, 2H), 7.07–7.18 (m, 5H), 7.63 (brs, 4H), 8.21 (2H), 12.93 (brs, 1H), 13.62 (brs, 1H).

Example 45

Synthesis of 4-(2-Amidino-1,2,3,4-tetrahydroisoquinolin-7-ylsulfonylmethyl)-1-(pyridin-4-yl)piperidine-4-carboxylic Acid Dihydrochloride Step 1
4-(2-Acetyl-1,2,3,4-tetrahydroisoquinolin-7-ylsulfonylmethyl)-4-ethoxycarbonylpiperidine-1-carboxylic Acid tert-Butyl Ester

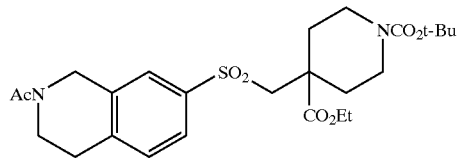

To a solution of 4-(2-acetyl-1,2,3,4-tetrahydroisoquinolin-7-ylthiomethyl)-4-ethoxycarbonylpiperidine-1-carboxylic acid tert-butyl ester (252 mg) in methylene chloride (5 ml) was added 70% 3-chloroperbenzoic acid (260 mg) at room temperature, and the mixture was stirred for 12 hours. After completion of the reaction, aqueous sodium hydrogencarbonate solution and aqueous sodium thiosulfate solution were added, and the mixture was stirred for 30 min, followed by extraction with chloroform. The organic layer was washed with saturated brine and dried over anhydrous magnesium sulfate. The solvent was evaporated and the obtained residue was purified by silica gel column chromatography (ethyl acetate) and dried under reduced pressure to give the title compound (203 mg).

$^1$H-NMR (δ ppm, CDCl$_3$) 1.32 (3H), 1.45 (9H), 1.66 (2H), 2.10–2.30 (5H), 2.88–3.04 (2H), 3.23 (2H), 3.43 (2H), 3.65–3.78 (3H), 3.85 (1H), 4.16–4.25 (2H), 4.69, 4.81 (2H), 7.32–7.75 (3H).

Step 2
4-(2-Acetyl-1,2,3,4-tetrahydroisoquinolin-7-ylsulfonylmethyl)-1-(pyridin-4-yl)piperidine-4-carboxylic Acid Ethyl Ester

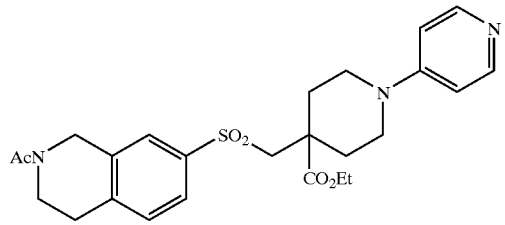

In the same manner as in Example 43, Step 3, the title compound (120 mg) was obtained from 4-(2-acetyl-1,2,3,4-tetrahydroisoquinolin-7-ylsulfonylmethyl)-4-ethoxycarbonylpiperidine-1-carboxylic acid tert-butyl ester (203 mg), trifluoroacetic acid (1 ml), 4-chloropyridine hydrochloride (72 mg) and triethylamine (0.33 ml).

Step 3
4-(2-Amidino-1,2,3,4-tetrahydroisoquinolin-7-ylsulfonylmethyl)-1-(pyridin-4-yl)piperidine-4-carboxylic Acid Dihydrochloride

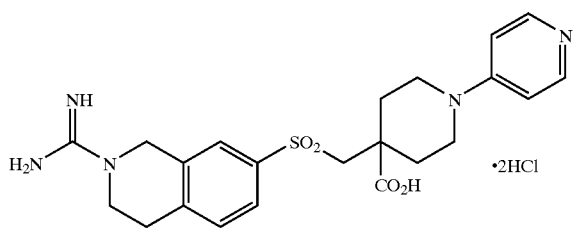

In the same manner as in Example 43, Step 4, the title compound (120 mg) was obtained from 4-(2-acetyl-1,2,3,4-tetrahydroisoquinolin-7-ylsulfonylmethyl)-1-(pyridin-4-yl)piperidine-4-carboxylic acid ethyl ester (200 mg), conc. hydrochloric acid (10 ml), 1N aqueous sodium hydroxide solution (2.06 ml) and 1H-pyrazole-1-carboxamidine hydrochloride (181 mg).

$^1$H-NMR (δ ppm, DMSO-$d_6$) 1.78–1.90 (m, 2H), 2.08–2.20 (m, 2H), 3.03 (m, 2H), 3.51 (m, 2H), 3.67 (m, 2H), 3.77 (s, 2H), 3.92 (m, 2H), 4.72 (s, 2H), 7.19 (d, J=7.5 Hz, 2H), 7.54 (1H), 7.65 (1H), 7.72–7.76 (m, 5H), 8.23 (d, J=7.5 Hz, 2H).

Example 46

Synthesis of 4-[2-(2-Amidino-1,2,3,4-tetrahydroisoquinolin-7-ylsulfonyl)ethyl]-1-(pyridin-4-yl)piperidine-4-carboxylic Acid Dihydrochloride Step 1
4-[2-(2-Acetyl-1,2,3,4-tetrahydroisoquinolin-7-ylsulfonyl)ethyl]-4-ethoxycarbonylpiperidine-1-carboxylic Acid tert-Butyl Ester

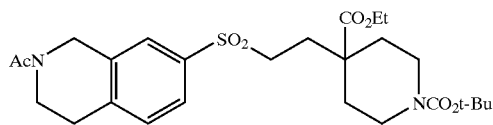

In the same manner as in Example 45, Step 1, the title compound (173 mg) was obtained from 4-[2-(2-acetyl-1,2,3,4-tetrahydroisoquinolin-7-ylthio)ethyl]-4-ethoxycarbonylpiperidine-1-carboxylic acid tert-butyl ester (295 mg) and 700% 3-chloroperbenzoic acid (297 mg).

Step 2
4-[2-(2-Acetyl-1,2,3,4-tetrahydroisoquinolin-7-ylsulfonyl)ethyl]-1-(pyridin-4-yl)piperidine-4-carboxylic Acid Ethyl Ester

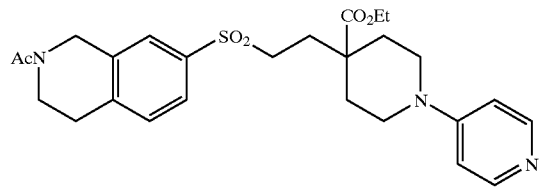

In the same manner as in Example 43, Step 3, the title compound (97 g) was obtained from 4-[2-(2-acetyl-1,2,3,4-tetrahydroisoquinolin-7-ylsulfonyl)ethyl]-4-ethoxycarbonylpiperidine-1-carboxylic acid tert-butyl ester (173 mg), trifluoroacetic acid (1 ml), 4-chloropyridine hydrochloride (60 mg) and triethylamine (0.28 ml).

Step 3
4-[2-(2-Amidino-1,2,3,4-tetrahydroisoquinolin-7-ylsulfonyl)ethyl]-1-(pyridin-4-yl)piperidine-4-carboxylic Acid Dihydrochloride

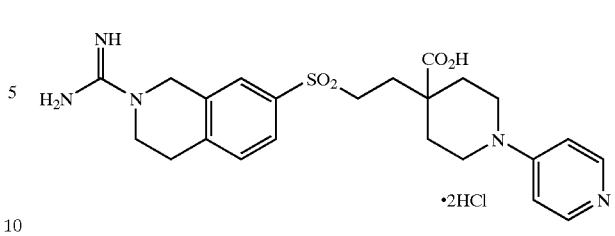

In the same manner as in Example 43, Step 4, the title compound (57 mg) was obtained from 4-[2-(2-acetyl-1,2,3,4-tetrahydroisoquinolin-7-ylsulfonyl)ethyl]-1-(pyridin-4-yl)piperidine-4-carboxylic acid ethyl ester (97 mg), conc. hydrochloric acid (2 ml), 1N aqueous sodium hydroxide solution (0.97 ml) and 1H-pyrazole-1-carboxamidine hydrochloride (86 mg).

$^1$H-NMR (δ ppm, DMSO-$d_6$) 1.42–1.56 (m, 2H), 1.78–1.90 (m, 2H), 1.96–2.12 (m, 2H), 3.03 (m, 2H), 3.17–3.30 (m, 4H), 3.66 (m, 2H), 3.95–4.10 (m, 2H), 4.71 (s, 2H), 7.17 (2H), 7.53 (1H), 7.67–7.82 (m, 6H), 8.20 (2H).

Example 47

Synthesis of 4-(2-Amidino-1,2,3,4-tetrahydroisoquinolin-7-ylsulfonylamino)-1-(pyridin-4-yl)piperidine-4-carboxylic Acid Methyl Ester Dihydrochloride Step 1
1-(Pyridin-4-yl)piperidin-4-one

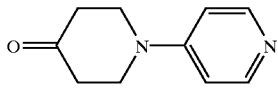

A solution of 4-chloropyridine hydrochloride (10 g), 1,4-dioxo-8-azaspiro[4,5]decane (10 g) and triethylamine (29 ml) in a mixture of ethanol (10 ml) and water (30 ml) was stirred at 150° C. for 22 hours in a sealed tube. After completion of the reaction, the solvent was evaporated and 5N aqueous sodium hydroxide solution (25 ml) was added. The mixture was extracted with a mixed solvent of chloroform-methanol (10:1). The organic layer was dried over anhydrous sodium sulfate and the solvent was evaporated. To the obtained residue was dropwise added conc. hydrochloric acid (30 ml) with ice-cooling, and the mixture was stirred at the same temperature for 10 min. After completion of the reaction, sodium hydroxide (15 g) was added. The mixture was extracted with chloroform and dried over anhydrous sodium sulfate. The solvent was evaporated and the obtained residue was purified by silica gel column chromatography (chloroform:methanol=9:1, 1% aqueous ammonia) and dried under reduced pressure to give the title compound (6.1 g).

$^1$H-NMR (δ ppm, CDCl$_3$) 2.57 (tr, J=6.2 Hz, 4H), 3.74 (tr, J=6.2 Hz, 4H), 6.71 (dd, J=1.5, 4.5 Hz, 2H), 8.33 (dd, J=1.5, 4.5 Hz, 2H).

Step 2
4-Amino-1-(pyridin-4-yl)piperidine-4-carboxylic Acid Methyl Ester

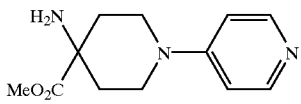

To a solution of 1-(pyridin-4-yl)piperidin-4-one (1 g) in methanol solution were added ammonium acetate (880 mg), aqueous sodium cyanide solution (560 mg/5 ml), aqeuous ammonia (5 ml) and acetic acid (2 ml), and the mixture was tirred at room temperature for 12 hours. After completion of the reaction, the solvent was evaporated and aqueous ammonia (3 ml) was added and the mixture was extracted with chloroform. The organic layer was dried over anhydrous sodium sulfate, and the solvent was evaporated to give a residue. Hydrogen chloride was blown into a solution of the residue in 10% hydrogen chloride-methanol (25 ml) with ice-cooling and the solution was stood at room temperature for 12 hours. After completion of the reaction, the solvent was evaporated and to the obtained residue was added 2N-hydrochloric acid (25 ml). After stirring for 2 hr, the mixture was neutralized with sodium hydrogencarbonate and extracted with chloroform. The organic layer was washed successively with water and saturated brine and dried over anhydrous sodium sulfate. The solvent was evaporated and the residue was dried under reduced pressure to give the title compound (760 mg).

$^1$H-NMR ($\delta$ ppm, CDCl$_3$) 1.55–1.65 (m, 2H), 2.08–2.17 (m, 2H), 3.46–3.50 (m, 4H), 3.74 (s, 3H), 6.66 (dd, J=1.5, 4.5 Hz, 2H), 8.25 (dd, J=1.5, 4.5 Hz, 2H).

Step 3

1-(Pyridin-4-yl)-4-(2-trifluoroacetyl-1,2,3,4-tetrahydroisoquinolin-7-ylsulfonylamino)piperidine-4-carboxylic Acid Methyl Ester

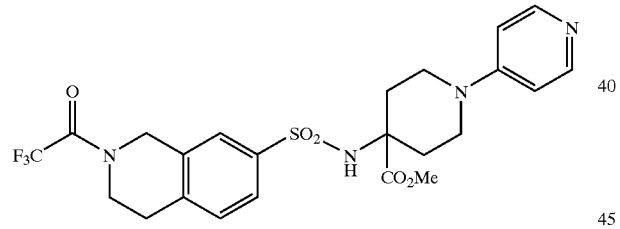

To a solution of 4-amino-1-(pyridin-4-yl)piperidine-4-carboxylic acid methyl ester (330 mg) in chloroform (5 ml) were added 7-chlorosulfonyl-2-trifluoroacetyl-1,2,3,4-tetrahydroisoquinoline (*Journal of Medicinal Chemistry*, vol. 23, No.8, p. 837 (1980)) (500 mg) and pyridine (0.23 ml), and the mixture was stirred at room temperature for 12 hours. After completion of the reaction, water was added, and the mixture was extracted with chloroform and washed successively with water and saturated brine. The organic layer was dried over anhydrous sodium sulfate, and the solvent was evaporated. The residue was dried under reduced pressure to give the title compound (627 mg).

$^1$H-NMR ($\delta$ ppm, CDCl$_3$) 2.02–2.16 (2H), 2.22–2.35 (2H), 2.94–3.08 (2H), 3.39, 3.46 (3H), 3.42–3.58 (2H), 3.62–3.76 (2H), 3.80–3.96 (2H), 4.77–4.82 (2H), 6.80 (2H), 7.16–7.32 (1H), 7.68–7.82 (1H), 8.20 (2H).

Step 4

4-(2-Amidino-1,2,3,4-tetrahydroisoquinolin-7-ylsulfonylamino)-1-(pyridin-4-yl)piperidine-4-carboxylic Acid Methyl Ester Dihydrochloride

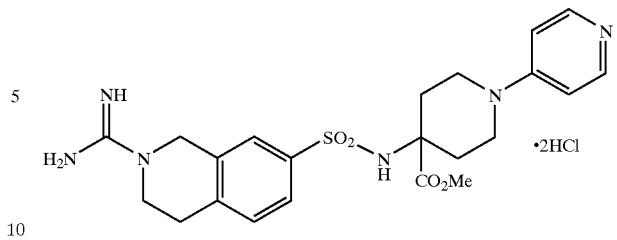

To a solution of 1-(pyridin-4-yl)-4-(2-trifluoroacetyl-1,2,3,4-tetrahydroisoquinolin-7-ylsulfonylamino)piperidine-4-carboxylic acid methy ester (627 mg) in a mixture of chloroform (5 ml) and methanol (1 ml) was added a 2N aqueous sodium hydroxide solution (1.1 ml), and the mixture was stirred at room temperature for 2 hours. After completion of the reaction, 2N-hydrochloric acid (1.1 ml) was added and the mixture was concentrated. To the obtained residue were successively added dimethylformamide (3 ml), diisopropylethylamine (0.91 ml) and 1H-pyrazole-1-carboxamidine hydrochloride (305 mg), and the mixture was stirred at room temperature for 12 hours. After completion of the reaction, the reaction mixture was filtrated, and the filtrate was dropwise added to diethyl ether. The resultant solid was separated by HPLC (0.05% aqueous trifluoroacetic acid:methanol=4:1–3:2) and treated with dil. hydrochloric acid and dried under reduced pressure to give the title compound (480 mg).

$^1$H-NMR ($\delta$ ppm, DMSO-d$_6$) 1.86–2.16 (m, 4H), 3.00 (m, 2H), 3.35–3.42 (m, 5H), 3.67 (m, 2H), 3.84 (m, 2H), 4.74 (s, 2H), 7.17 (d, J=7.1 Hz, 2H), 7.47 (1H), 7.56 (1H), 7.62 (1H), 7.82 (brs, 4H), 8.22 (d, J=7.1 Hz, 2H), 8.56 (s, 1H), 13.89 (brs, 1H).

Example 48

Synthesis of 4-(2-Amidino-1,2,3,4-tetrahydroisoquinolin-7-ylsulfonylamino)-1-(pyridin-4-yl)piperidine-4-carboxylic Acid Dihydrochloride

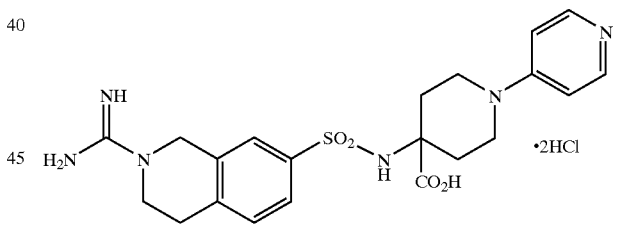

To 4-(2-amidino-1,2,3,4-tetrahydroisoquinolin-7-ylsulfonylamino)-1-(pyridin-4-yl)piperidine-4-carboxylic acid methyl ester dihydrochloride (415 mg) was added 6N hydrochloric acid (2 ml), and the mixture was stirred under reflux for 4 hours. After completion of the reaction, insoluble material was removed and the solvent was evaporated. Diethyl ether was added and the resultant solid was collected by filtration and dried under reduced pressure to give the title compound (363 mg).

$^1$H-NMR ($\delta$ ppm, DMSO-d$_6$) 1.85–2.10 (m, 4H), 2.99 (m, 2H), 3.30 (m, 2H), 3.67 (m, 2H), 3.80–3.95 (m, 2H), 4.71 (s, 2H), 7.16 (d, J=7.3 Hz, 2H), 7.44 (1H), 7.56 (1H), 7.67 (1H), 7.80 (brs, 4H), 8.20 (d, J=7.3 Hz, 2H), 8.35 (s, 1H).

Example 49

Synthesis of 4-(2-Amidino-1,2,3,4-tetrahydroisoquinolin-7-ylsulfonylaminomethyl)-1-(pyridin-4-yl)piperidine-4-carboxylic Acid Ethyl Ester Dihydrochloride Step 1
4-Benzyloxycarbonylaminomethyl-4-ethoxycarbonylpiperidine-1-carboxylic Acid tert-Butyl Ester

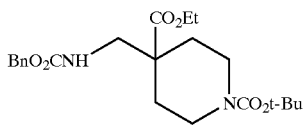

To a solution of 1-tert-butoxycarbonyl-4-ethoxycarbonylpiperidin-4-ylacetic acid (1.6 g) and triethylamine (0.71 ml) in dimethylformamide (20 ml) was added diphenylphosphoryl azide (1.1 ml) at room temperature, and the mixture was stirred at 70° C. for 30 min and then at 90° C. for 10 min. Benzyl alcohol (0.58 ml) was added at the same temperature, and the mixture was stirred for 20 hours. After completion of the reaction, water was added and the mixture was extracted with ethyl acetate and washed with 1N aqueous sodium hydroxide solution. The organic layer was dried over anhydrous magnesium sulfate and the solvent was evaporated. The obtained residue was purified by silica gel column chromatography and dried under reduced pressure to give the title compound (1.35 g).

$^1$H-NMR (δ ppm, CDCl$_3$) 1.26 (tr, J=7.0 Hz, 3H), 1.36–1.50 (m, 11H), 1.96–2.10 (m, 2H), 3.12 (m, 2H), 3.37 (m, 2H), 3.70 (m, 2H), 4.14 (q, J=7.0 Hz, 2H), 5.01 (brtr, 1H), 5.09 (s, 2H), 7.26–7.40 (m, 5H).

Step 2
4-Benzyloxycarbonylaminomethyl-1-(pyridin-4-yl)piperidine-4-carboxylic Acid Ethyl Ester

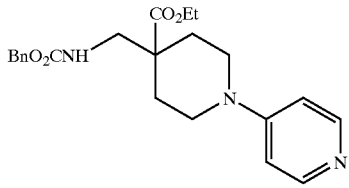

To a solution of 4-benzyloxycarbonylaminomethyl-4-ethoxycarbonylpiperidine-1-carboxylic acid tert-butyl ester (851 mg) in chloroform (5 ml) was added trifluoroacetic acid (5 ml), and the mixture was stirred at room temperature for 30 min. After completion of the reaction, the solvent was evaporated and to the obtained residue were added ethanol (5 ml), 4-chloropyridine hydrochloride (304 mg) and triethylamine (1.69 ml). The mixture was stirred at 150° C. for 2 days in a sealed tube. After completion of the reaction, the solvent was evaporated. To the obtained residue was added 2N aqeuous sodium hydroxide solution, and the mixture was extracted chloroform. The organic layer was dried over anhydrous sodium sulfate and the solvent was evaporated. The obtained residue was purified by silica gel column chromatography (chloroform:methanol=93:7) and dried under reduced pressure to give the title compound (738 mg).

$^1$H-NMR (δ ppm, CDCl$_3$) 1.27 (tr, J=7.0 Hz, 3H), 1.50–1.70 (m, 2H), 2.05–2.22 (m, 2H), 3.10–3.22 (m, 2H), 3.35–3.45 (m, 2H), 3.52–3.68 (m, 2H), 4.19 (q, J=7.0 Hz, 2H), 5.05 (brtr, 1H), 5.09 (s, 2H), 6.63 (d, J=6.4 Hz, 2H), 7.26–7.38 (m, 5H), 8.25 (d, J=6.4 Hz, 2H).

Step 3
4-Aminomethyl-1-(pyridin-4-yl)piperidine-4-carboxylic Acid Ethyl Ester Dihydrobromide

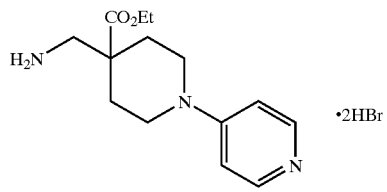

To a solution of 4-benzyloxycarbonylaminomethyl-1-(pyridin-4-yl)piperidine-4-carboxylic acid ethyl ester (331 mg) in chloroform (0.5 ml) was added 25% hydrogen bromide-acetic acid (2 ml), and the mixture was stirred at room temperature for 10 min. After completion of the reaction, hexane, diisopropyl ether and diethyl ether were added and the supernatant was removed. Then, dimethylformamide (1 ml) was added and the resultant solid was collected by filtration, and washed with diethyl ether and dried under reduced pressure to give the title compound (423 mg).

Step 4
1-(Pyridin-4-yl)-4-(2-trifluoroacetyl-1,2,3,4-tetrahydroisoquinolin-7-ylsulfonylaminomethyl)piperidine-4-carboxylic Acid Ethyl Ester

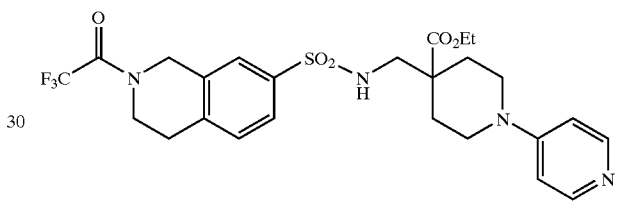

To 4-aminomethyl-1-(pyridin-4-yl)piperidine-4-carboxylic acid ethyl ester dihydrobromide (423 mg) were added pyridine (2 ml) and 7-chlorosulfonyl-2-trifluoroacetyl-1,2,3,4-tetrahydroisoquinoline (273 mg), and the mixture was stirred at room temperature for 2 hours. After completion of the reaction, the solvent was evaporated and water was added. The mixture was extracted with chloroform and the organic layer was dried over anhydrous sodium sulfate. The solvent was evaporated and the obtained residue was purified by silica gel column chromatography (chloroform:methanol=4:1) and dried under reduced pressure to give the title compound (222 mg).

$^1$H-NMR (δ ppm, CDCl$_3$) 1.20–1.35 (3H), 1.75–1.85 (2H), 2.15–2.30 (2H), 2.88–3.15 (4H), 3.30–3.45 (2H), 3.75–3.95 (4H), 4.15–4.25 (2H), 4.65–4.85 (2H), 6.80–6.88 (2H), 7.12–7.36 (1H), 7.65–7.80 (2H), 8.15–8.25 (2H).

Step 5
4-(2-Amidino-1,2,3,4-tetrahydroisoquinolin-7-ylsulfonylaminomethyl)-1-(pyridin-4-yl)piperidine-4-carboxylic Acid Ethyl Ester Dihydrochloride

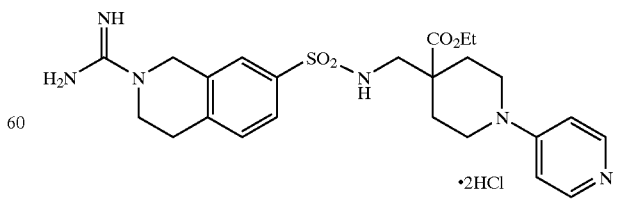

In the same manner as in Example 47, Step 4, the title compound (75 mg) was obtained from 1-(pyridin-4-yl)-4-(2-trifluoroacetyl-1,2,3,4-tetrahydroisoquinolin-7- ylsulfonylaminomethyl)piperidine-4-carboxylic acid ethyl ester (222 mg), diisopropylethylamine (0.28 ml) and 1H-pyrazole-1-carboxamidine hydrochloride (117 mg).

$^1$H-NMR (δ ppm, DMSO-$d_6$) 1.21 (tr, J=7.1 Hz, 3H), 1.50–1.65 (m, 2H), 2.00–2.15 (m, 2H), 2.89–3.15 (m, 4H), 3.28 (m, 2H), 3.64 (m, 2H), 3.95–4.18 (m, 4H), 4.67 (s, 2H), 7.18 (2H), 7.46 (1H), 7.57 (1H), 7.60–7.70 (m, 5H), 7.94 (brtr, 1H), 8.22 (2H).

Example 50

Synthesis of 4-(2-Amidino-1,2,3,4-tetrahydroisoquinolin-7-ylsulfonylaminomethyl)-1-(pyridin-4-yl)piperidine-4-carboxylic Acid Dihydrochloride

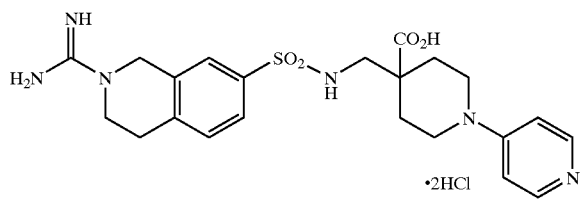

In the same manner as in Example 48, the title compound (52 mg) was obtained from 4-(2-amidino-1,2,3,4-tetrahydroisoquinolin-7-ylsulfonylaminomethyl)-1-(pyridin-4-yl)piperidine-4-carboxylic acid ethyl ester dihydrochloride (59 mg).

$^1$H-NMR (δ ppm, DMSO-$d_6$) 1.50–1.65 (m, 2H), 1.96–2.10 (m, 2H), 2.86–3.05 (m, 4H), 3.28 (m, 2H), 3.64 (m, 2H), 4.04 (m, 2H), 4.67 (s, 2H), 7.19 (d, J=7.3 Hz, 2H), 7.45 (1H), 7.58 (1H), 7.60–7.70 (m, 5H), 7.90 (brtr, 1H), 8.21 (d, J=7.3 Hz, 2H), 12.88 (brs, 1H), 13.57 (brs, 1H).

Example 52

Synthesis of 1-[2-(Benzothiazol-2-yl)-2-oxoethyl]-2-phenoxymethylbenzimidazole-5-carboxamidine Hydrochloride Step 1
N-(4-Cyano-2-phenoxyacetamidophenyl)glycine tert-Butyl Ester

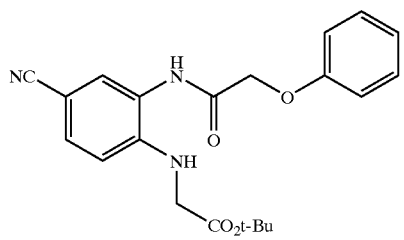

In the same manner as in Example 17, Step 8, the title compound (6.66 g) was obtained from N-(2-amino-4-cyanophenyl)glycine tert-butyl ester (5.97 g), phenyloxyacetic acid (3.44 g) and 1-ethoxycarbonyl-2-ethoxy-1,2-dihydroxyquinoline (6.15 g).

$^1$H-NMR (δ ppm, CDCl$_3$) 1.49 (s, 9H), 3.81 (d, J=4.8 Hz, 2H), 4.72 (s, 2H), 4.95 (brtr, 1H), 6.58 (d, J=8.7 Hz, 1H), 7.02 (d, J=7.5 Hz, 2H), 7.08 (tr, J=7.5 Hz, 1H), 7.36 (d, J=7.5 Hz, 1H), 7.39 (d, J=7.5 Hz, 1H), 7.44 (dd, J=1.5, 8.7 Hz, 1H), 7.57 (d, J=1.5 Hz, 1H), 8.06 (brs, 1H).

Step 2
5-Cyano-2-phenoxymethylbenzimidazole-1-acetic Acid

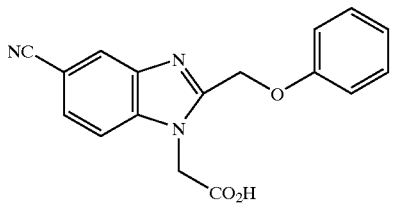

A solution of N-(4-cyano-2-phenoxyacetamidophenyl) glycine tert-butyl ester (6.61 g) in acetic acid (250 ml) was stirred at 80° C. for 12 hours. After completion of the reaction, the solvent was evaporated and to the obtained residue was added trifluoroacetic acid (60 ml), and the mixture was stirred at 50° C. for 30 min. After completion of the reaction, the solvent was evaporated. To the obtained residue were added chloroform and acetone and the resultant solid was collected by filtration and dried under reduced pressure to give the title compound (5.0 g).

$^1$H-NMR (δ ppm, CDCl$_3$) 5.25 (s, 2H), 5.43 (s, 2H), 6.97 (1H), 7.05 (2H), 7.27–7.33 (2H), 7.68 (dd, J=1.3, 8.4 Hz, 1H), 7.82 (d, J=8.4 Hz, 1H), 8.23 (d, J=1.3 Hz, 1H).

Step 3
N-Methoxy-N-methyl-(5-cyano-2-phenoxymethylbenzimidazole)-1-acetamide

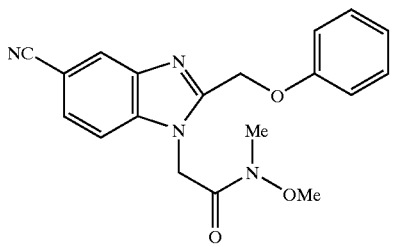

In the same manner as in Example 17, Step 10, the title compound (1.83 g) was obtained as a white solid from 5-cyano-2-phenoxymethylbenzimidazole-1-acetic acid (2.14 g), N,O-dimethylhydroxylamine hydrochloride (815 mg), N-methylmorpholine (0.919 ml), 1-hydroxybenzotriazole hydrate (1.13 g) and 1-(3-dimethylaminopropyl)-3-ethylcarbodiimide hydrochloride (1.6 g).

$^1$H-NMR (δ ppm, CDCl$_3$) 3.22 (s, 3H), 3.77 (s, 3H), 5.27 (s, 2H), 5.41 (s, 2H), 6.98–7.03 (3H), 7.26–7.36 (3H), 7.54 (1H), 8.11 (1H).

Step 4
N-Methoxy-N-methyl-[5-(N',N''-di-tert-butoxycarbonylamidino)-2-phenoxymethylbenzimidazole]-1-acetamide

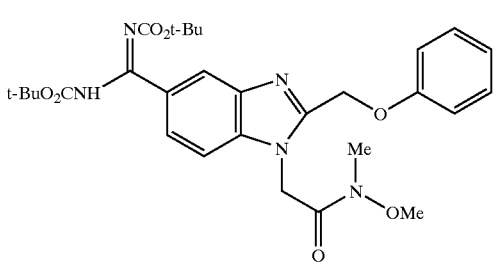

In the same manner as in Example 17, Step 12, N-methoxy-N-methyl-(5-amidino-2- phenoxymethylbenzimidazole)-1-acetamide was obtained from N-methoxy-N-methyl-(5-cyano-2-phenoxymethylbenzimidazole)-1-acetamido (893 mg), methyl iodide (1.6 ml) and ammonium acetate (295 mg). In the same manner as in Example 1, Step 1, the title compound (144 mg) was obtained from this compound and di-tert-butyl dicarbonate (1.11 g). The solvent used was tetrahydrofuran (10 ml) and saturated aqueous sodium hydrogencarbonate solution (10 ml) was used instead of 1N aqueous sodium hydroxide solution.

$^1$H-NMR (δ ppm, CDCl$_3$) 1.57 (s, 9H), 3.22 (s, 3H), 3.70–3.80 (m, 3H), 5.25 (s, 2H), 5.40 (s, 2H), 6.90–7.05 (m, 3H), 7.25–7.35 (m, 3H), 7.94–8.19 (m, 2H).

Step 5
N,N'-Di-tert-Butoxycarbonyl-1–12-(benzothiazol-2-yl)-2-oxoethyl]-2-phenoxymethylbenzimidazole-5-carboxamidine

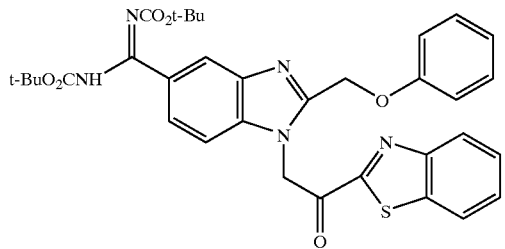

To a solution of benzothiazole (42 mg) in tetrahydrofuran (5 ml) was dropwise added a 1.66M n-butyl lithium -hexane solution (0.204 ml) at −78° C., and the mixture was stirred at the same temperature for 10 min. Then, a solution of N-methoxy-N-methyl-5-[(N'-N"-di-tert-butoxycarbonylamidino)-2-phenoxymethylbenzimidazole]-1-acetamide (144 mg) in tetrahydrofuran (1 ml) was added dropwise, and the mixture was stirred at the same temperature for 3 hours. After completion of the reaction, aqueous ammonium chloride solution and water were added, and the mixture was extracted with ethyl acetate and washed successively with water and saturated brine. The organic layer was dried over anhydrous sodium sulfate, and the solvent was evaporated. The obtained residue was purified by silica gel column chromatography (hexane:ethyl acetate=2:3) and dried under reduced pressure to give the title compound (25 mg).

$^1$H-NMR (δ ppm, CDCl$_3$) 1.57 (s, 9H), 5.45 (s, 2H), 6.07 (s, 2H), 6.898–6.95 (3H), 7.17–7.22 (2H), 7.34 (1H), 7.63 (2H), 7.97 (1H), 8.03 (1H), 8.22–8.25 (2H).

Step 6
1-[2-(Benzothiazol-2-yl)-2-oxoethyl]-2-phenoxymethylbenzimidazole-5-carboxamidine Hydrochloride

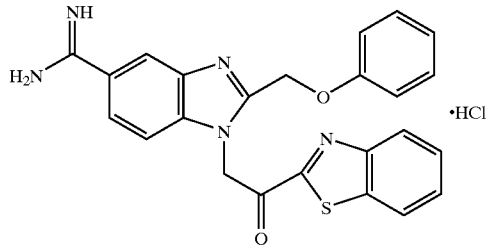

In the same manner as in Example 19, Step 11, the title compound (18 mg) was obtained from N,N'-di-tert-butoxycarbonyl-1-[2-(benzothiazol-2-yl)-2-oxoethyl]-2-phenoxymethylbenzimidazole-5-carboxamidine (25 mg) and trifluoroacetic acid (1 ml).

$^1$H-NMR (δ ppm, DMSO-d$_6$) 5.52 (s, 2H), 6.32 (s, 2H), 6.84–6.88 (m, 3H), 7.13–7.18 (m, 2H), 7.69–7.76 (m, 3H), 7.93 (d, 1H), 8.28–8.34 (m, 3H), 9.01 (brs, 2H), 9.32 (brs, 2H).

Example 53

Synthesis of trans-4-[2-[4-(1-Acetimidoylpiperidin-4-yloxy)phenoxymethyl]-5-amidinobenzimidazol-1-ylacetylaminomethyl]cyclohexanecarboxylic Acid Dihydrochloride Step 1
Ethyl 4-Benzyloxyphenoxyacetate

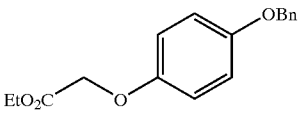

To a solution of 4-benzyloxyphenol (18.34 g) in tetrahydrofuran (150 ml) was added 60% sodium hydride (4.76 g) with ice-cooling, and the mixture was stirred at the same temperature for 15 min. Ethyl bromoacetate (14.2 ml) was added dropwise, and the mixture was stirred at room temperature for 16 hours. After completion of the reaction, 5% hydrochloric acid was added and the mixture was extracted with hexane. The extract was dried over anhydrous magnesium sulfate. The solvent was evaporated and the obtained solid was filtrated with hexane and dried under reduced pressure to give the title compound (21.78 g) as a white solid.

$^1$H-NMR (δ ppm, CDCl$_3$) 1.29 (tr, J=7.2 Hz, 3H), 4.26 (q, J=7.2 Hz, 2H), 4.56 (s, 2H), 5.01 (s, 2H), 6.84–6.92 (m, 4H), 7.26–7.43 (m, 5H).

Step 2
Ethyl 4-hydroxyphenoxyacetate

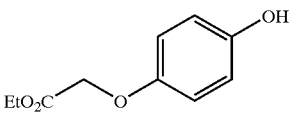

Ethy 4-benzyloxyphenoxyacetate (21.78 g) was hydrogenated using 7.5% palladium carbon (3.2 g) in tetrahydrofuran (220 ml) at 3 atm over 7 hours. After completion of the reaction, the reaction mixture was filtered through celite, and the solvent was evaporated. The obtained solid was filtrated with diisopropyl ether and dried under reduced pressure to give the title compound (13.88 g) as a white solid.

$^1$H-NMR (δ ppm, DMSO-d$_6$) 1.19 (tr, J=7.2 Hz, 3H), 4.14 (q, J=7.2 Hz, 2H), 4.61 (s, 2H), 6.63–6.76 (m, 4H), 8.95 (s, 1H).

Step 3
Ethy 4-(1-tert-Butoxycarbonylpiperidin-4-yloxy)phenoxyacetate

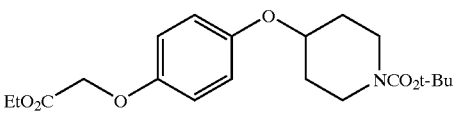

In the same manner as in Example 37, Step 7, the title compound (23.71 g) was obtained from 4-hydroxypiperidinecarboxylic acid tert-butyl ester (35.59 g), ethyl 4-hydroxyphenoxyacetate (5 g), triphenylphosphine (46.4 g) and diethyl azodicarboxylate (27.8 ml).

$^1$H-NMR (δ ppm, CDCl$_3$) 1.30 (tr, J=7.2 Hz, 3H), 1.47 (s, 9H), 1.73 (m, 2H), 1.88 (m, 2H), 3.30 (m, 2H), 3.70 (m, 2H), 4.27 (q, J=7.2 Hz, 2H), 4.33 (m, 1H), 4.56 (s, 2H), 6.85 (s, 4H).

Step 4

4-(1-tert-Butoxycarbonylpiperidin-4-yloxy)phenoxyacetic Acid

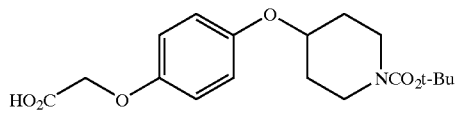

To a solution of ethyl 4-(1-tert-butoxycarbonylpiperidin4-yloxy)-phenoxyacetate (23.71 g) in a mire of tetrahydrofuran (34 ml) and ethanol (34 ml) was dropwise added 1N aqueous lithium hydroxide solution (68.7 ml) with ice-cooling, and the mixture was stirred at room temperature for 20 min. After completion of the reaction, the solvent was evaporated and to the obtained residue was added 10% aqueous citric acid solution. The mixture was extracted with ethyl acetate and washed successively with water and saturated brine. The organic layer was dried over anhydrous magnesium sulfate, and the solvent was evaporated. The obtained solid was filtrated with hexane and dried under reduced pressure to give the title compound (19.09 g).

$^1$H-NMR (δ ppm, DMSO-d$_6$) 1.40 (s, 9H), 1.49 (m, 2H), 1.83 (m, 2H), 3.15 (m, 2H), 3.63 (m, 2H), 4.40 (m, 1H), 4.58 (s, 2H), 6.83 (d, J=9.2 Hz, 2H), 6.91 (d, J=9.2 Hz, 2H).

Step 5

N-[4-Cyano-2-[4-(1-tert-butoxycarbonylpiperidin-4-yloxy) phenoxyacetamido]-phenyl]glycine tert-Butyl Ester

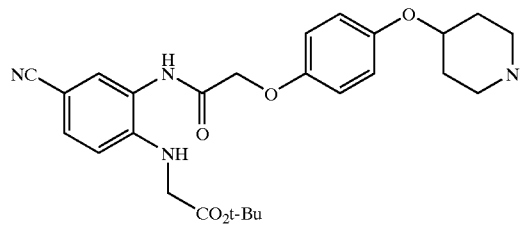

In the same manner as in Example 17, Step 8, the title compound (17.11 g) was obtained as a white solid from N-(2-amino-4-cyanophenyl)glycine tert-butyl ester (9.11 g) and 4-(1-tert-butoxycarbonylpiperidin-4-yloxy) phenoxyacetic acid (12.94 g).

$^1$H-NMR (δ ppm, CDCl$_3$) 1.47 (s, 9H), 1.50 (s, 9H), 1.71 (m, 2H), 1.88 (m, 2H), 3.31 (m, 2H), 3.71 (m, 2H), 3.82 (brd, 2H), 4.37 (m, 1H), 4.66 (s, 2H), 4.99 (brtr, 1H), 6.58 (d, J=8.7 Hz, 1H), 6.89–6.97 (m, 4H), 7.45 (d, J=8.7 Hz, 1H), 7.57 (s, 1H), 8.07 (brs, 1H).

Step 6

5-Cyano-2-[4-(1-tert-butoxycarbonylpiperidin-4-yloxy) phenoxymethyl]-benzimidazole-1-acetic Acid

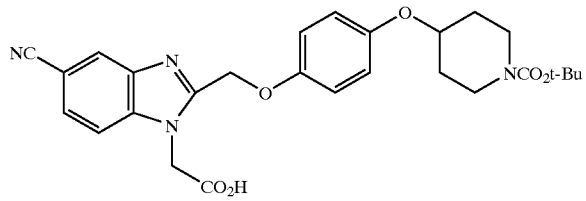

A solution of N-[4-cyano-2-[4-(1-tert-butoxycarbonylpiperidin-4-yloxy)phenoxyacetamido] phenyl]glycine tert-butyl ester (16.91 g) in acetic acid (500 ml) was stirred at 75° C. for 12 hours. The solvent was evaporated and to the obtained residue was added trifluoroacetic acid (100 ml), and the mixture was stirred at room temperature for 30 min. After completion of the reaction, the solvent was evaporated. To the obtained residue was added ice and then aqueous sodium hydroxide solution and the resultant solid was collected by filtration and washed successively with water and ethyl acetate to give N-[4-cyano-2-[4-(piperidin-4-yloxy)phenoxyacetamido]phenyl]glycine (8.642 g). In the same manner as in Example 1, Step 1, the title compound (9.506 g) was obtained from this compound, di-tert-butyl dicarbonate (6.96 g) and 1N aqueous sodium hydroxide solution (23.4 ml).

$^1$H-NMR (δ ppm, CDCl$_3$) 1.46 (s, 9H), 1.64 (m, 2H), 1.79 (m, 2H), 3.25 (m, 2H), 3.63 (m, 2H), 4.28 (m, 1H), 5.12 (s, 2H), 5.33 (s, 2H), 6.77 (d, J=9.1 Hz, 2H), 6.88 (d, J=9.1 Hz, 2H), 7.43 (d, J=8.4 Hz, 1H), 7.59 (dd, J=1.2, 8.4 Hz, 1H), 8.10 (d, J=1.2 Hz, 1H)

Step 7 trans-4-Aminomethylcyclohexanecarboxylic Acid Methyl Ester Hydrochloride

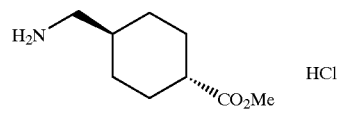

The title compound (8.8 g) was obtained from trans-4-aminomethylcyclohexanecarboxylic acid (7 g) and thionyl chloride (11.6 ml) by a conventional method.

$^1$H-NMR (δ ppm, DMSO-d$_6$) 0.98 (m, 2H), 1.29 (m, 2H), 1.55 (m, 1H), 1.82 (m, 2H), 1.91 (m, 2H), 2.25 (m, 1H), 2.26 (m, 2H), 3.59 (s, 3H), 8.07 (brs, 3H).

Step 8

2-[4-(1-tert-Butoxycarbonylpiperidin-4-yloxy) phenoxymethyl]-5-cyano-1-(trans-4-methoxycarbonylcyclohexylmethylcarbamoylmethyl) benzimidazole

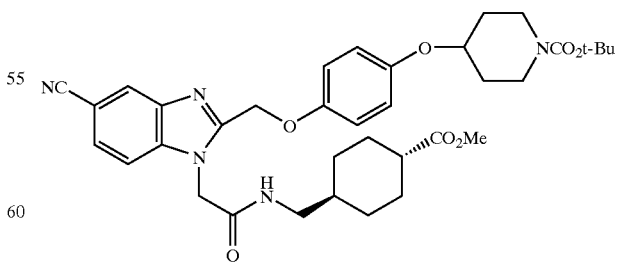

In the same manner as in Example 17, Step 10, the title compound (1.37 g) was obtained from 5-cyano-2-[4-(1-tert-butoxycarbonylpiperidin-4-yloxy)phenoxymethyl] benzimidazole-1-acetic acid (1.1 g), trans-4- aminomethylcyclohexanecarboxylic acid methyl ester hydrochloride (452 mg), N-methylmorpholine (0.263 ml), 1-hydroxybenzotriazole hydrate (293 mg) and 1-(3-dimethylaminopropyl)-3-ethylcarbodiimide hydrochloride (437 mg).

$^1$H-NMR (δ ppm, CDCl$_3$) 0.79 (m, 2H), 1.27 (m, 3H), 1.46 (s, 9H), 1.55 (m, 2H), 1.72 (m, 2H), 1.85 (m, 4H), 2.09 (m, 1H), 3.02 (tr, 2H), 3.30 (m, 2H), 3.64 (s, 3H), 3.67 (m, 2H), 4.35 (m, 1H), 4.97 (s, 2H), 5.37 (s, 2H), 5.66 (brtr, 1H), 6.87 (d, J=9.0 Hz, 2H), 6.95 (d, J=9.0 Hz, 2H), 7.48 (1H), 7.61 (1H), 8.14 (1H).

Step 9

2-[4-(1-tert-Butoxycarbonylpiperidin-4-yloxy) phenoxymethyl]-1-(trans-4-methoxycarbonylcyclohexylmethylcarbamoylmethyl) benzimidazole-5-carboxamidine

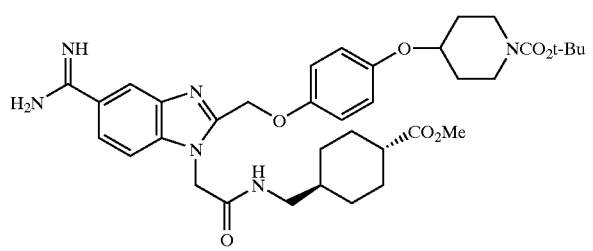

Hydrogen sulfide was blown into a solution of 2-[4-(1-tert-butoxycarbonylpiperidin-4-yloxy)phenoxymethyl]-5-cyano-1-(trans-4-methoxycarbonylcyclohexylmethylcarbamoylmethyl) benzimidazole (1.1 g) in a mixture (30 ml) of pyridine-triethylamine (5:1) with ice-cooling, and the mixture was stirred at room temperature for 12 hours. After completion of the reaction, the solvent was evaporated and the obtained residue was collected by filtration with toluene. To the obtained solid were added acetone (30 ml) and methyl iodide (1.3 ml), and the mixture was stirred under reflux for 1 hour. After completion of the reaction, the solvent was evaporated, and the residue was dried under reduced pressure to give 2-[4-(1-tert-butoxycarbonylpiperidin-4-yloxy) phenoxymethyl]-1-(trans4-methoxycarbonylcyclohexylmethyl-carbamoylmethyl) benzimidazole-5-carbothioimidic acid methyl ester (1.819 g). A part (606 mg) thereof was dissolved in ethanol (10 ml) and thereto was added ammonium acetate (80 mg) at room temperature. The mixture was stirred at 75° C. for 3 hours. After completion of the reaction, the solvent was evaporated and the obtained residue was purified by silica gel column chromatography (chloroform:methanol=95:5–93:7) and dried under reduced pressure to give the title compound (341 mg).

$^1$H-NMR (δ ppm, DMSO-d$_6$) 0.91 (m, 2H), 1.20–1.55 (m, 14H), 1.70 (m, 2H), 1.86 (m, 4H), 2.18 (m, 1H), 2.94 (brtr, 2H), 3.15 (m, 2H), 3.58 (s, 3H), 3.62 (m, 2H), 4.40 (m, 1H), 5.10 (s, 2H), 5.30 (s, 2H), 6.91 (d, J=9.0 Hz, 2H), 6.99 (d, J=9.0 Hz, 2H), 7.70 (1H), 7.78 (1H), 8.21 (1H), 8.35 (brtr, 1H), 8.79 (brtr, 1H), 9.26 (brtr, 1H).

Step 10 trans-4-[2-[4-(1-Acetimidoylpiperidin-4-yloxy) phenoxymethyl]-5-amidinobenzimidazol-1-ylacetylaminomethyl]cyclohexanecarboxylic Acid Dihydrochloride

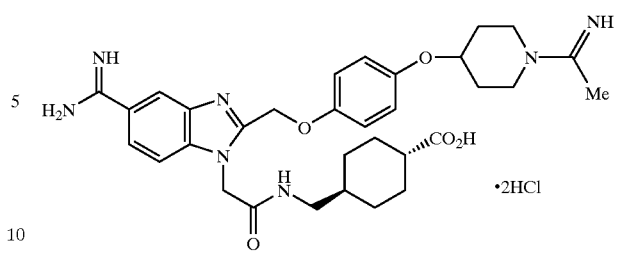

In the same manner as in Example 19, Step 11, 2-[4-(piperidin-4-yloxy)phenoxymethyl]-1-(trans-4-methoxycarbonylcyclohexylmethyl-carbamoylmethyl) benzimidazole-5-carboxamidine (299 mg) was obtained from 2-[4-(1-tert-butoxycarbonylpiperidin-4-yloxy) phenoxymethyl]-1-(trans-4-methoxycarbonylcyclohexylmethylcarbamoylmethyl) benzimidazole-5-carboxamidine (341 mg) and trifluoroacetic acid (5 ml). To a solution of this compound (205 mg) in methanol (1 ml) was added in aqueous sodium hydroxide solution (1.57 ml) at room temperature, and the mixture was stirred for 15 hours. After completion of the reaction, 1N-hydrochloric acid (0.944 ml) was added and the solvent was evaporated and the residue was dried under reduced pressure. To the obtained residue were added methanol (5 ml), triethylamine (0.439 ml) and ethyl acetimidate hydrochloride (195 mg), and the mixture was stirred at room temperature for 15 hours. After completion of the reaction, the solvent was evaporated and the obtained residue was separated by HPLC (40% methanol-water, 0.05% trifluoroacetic acid). Thereto was added dil. hydrochloric acid and the solvent was evaporated. The residue was dried under reduced pressure to give the title compound (78 mg).

Example 54

Synthesis of trans-4-[2-[4-(1-Acetimidoylpiperidin-4-yloxy)phenoxymethyl]-5-(N-methylamidino) benzimidazol-1-ylacetylaminomethyl] cyclohexanecarboxylic Acid Dihydrochloride Step 1

N-Methyl-2-[4-(1-tert-butoxycarbonylpiperidin-4-yloxy) phenoxymethyl]-1-(trans-4-methoxycarbonylcyclohexylmethylcarbamoylmethyl) benzimidazole-5-carboxamidine

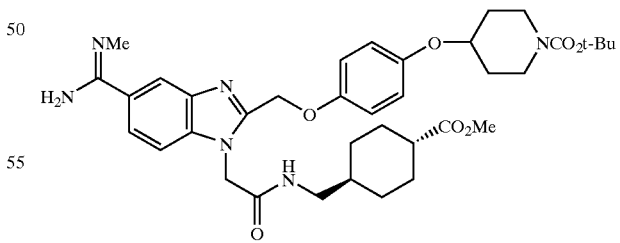

In the same manner as in Example 53, Step 9, the title compound (447 mg) was obtained from 2-[4-(1-tert-butoxycarbonylpiperidin-4-yloxy)-phenoxymethyl]-1-(trans-4-methoxycarbonylcyclohexylmethylcarbamoylmethyl)-benzimidazole-5-carbothioimidic acid methyl ester (606 mg), methylamine hydrochloride (70 mg) and sodium acetate (85 mg).

¹H-NMR (δ ppm, DMSO-d₆) 0.91 (m, 2H), 1.16–1.55 (m, 14H), 1.70 (m, 2H), 1.85 (m, 4H), 2.18 (m, 1H), 2.94 (brtr, 2H), 3.03 (s, 3H), 3.16 (m, 2H), 3.58 (s, 3H), 3.61 (m, 2H), 4.42 (m, 1H), 5.10 (s, 2H), 5.30 (s, 2H), 6.91 (d, J=9.0 Hz, 2H), 6.99 (d, J=9.0 Hz, 2H), 7.64 (dd, J=1.5, 8.5 Hz, 1H), 7.77 (d, J=7.77 Hz, 1H), 8.11 (d, J=1.5 Hz, 1H), 8.34 (brtr, 1H).

Step 2
trans-4-[2-[4-(1-Acetimidoylpiperidin-4-yloxy)phenoxymethyl]-5-(N-methylamidino)benzimidazol-1-ylacetylaminomethyl]cyclohexanecarboxylic Acid Dihydrochloride

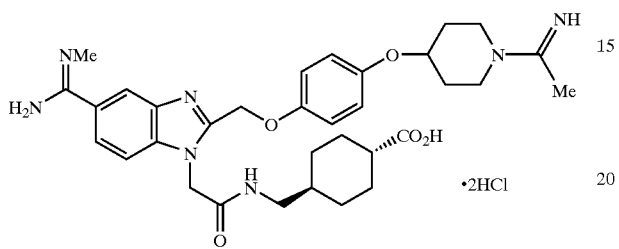

In the same manner as in Example 53, Step 10, the title compound (149 mg) was obtained from N-methyl-2-[4-(1-tert-butoxycarbonylpiperidin-4-yloxy)phenoxymethyl]-1-(trans-4-methoxycarbonylcyclohexylmethyl-carbamoylmethyl)benzimidazole-5-carboxamidine (447 mg), trifluoroacetic acid (5 ml), 1N aqueous sodium hydroxide solution (2.15 ml), triethylamine (0.599 ml) and ethyl acetimidate hydrochloride (265 mg).

¹H-NMR (δ ppm, DMSO-d₆) 0.8–1.0 (m, 2H), 1.12–1.42 (m, 3H), 1.71 (m, 4H), 1.86 (m, 2H), 1.92–2.18 (m, 3H), 2.30 (s, 3H), 2.95 (m, 2H), 3.05 (d, 3H), 3.42–3.88 (m, 4H), 4.58 (m, 1H), 5.19 (s, 2H), 5.37 (s, 2H), 6.96 (d, J=9.3 Hz, 2H), 7.04 (d, J=9.3 Hz, 2H), 7.74 (d, J=8.7 Hz, 1H), 7.85 (d, J=8.7 Hz, 1H), 8.18 (s, 1H), 8.63 (brtr, 1H), 8.87 (brs, 1H), 9.01 (brs, 1H), 9.43 (brs, 1H), 9.53 (brs, 1H), 9.94 (brs, 1H).

Example 55

Synthesis of trans-4-[2-[4-(1-Acetimidoylpiperidin-4-yloxy)phenoxymethyl]-5-[amino(hydroxyimino)methyl]benzimidazol-1-ylacetylaminomethyl]-cyclohexanecarboxylic Acid Dihydrochloride Step 1
2-[4-(1-tert-Butoxycarbonylpiperidin-4-yloxy)phenoxymethyl]-1-(trans-4-methoxycarbonylcyclohexylmethylcarbamoylmethyl)benzimidazole-5-carboxamide Oxime

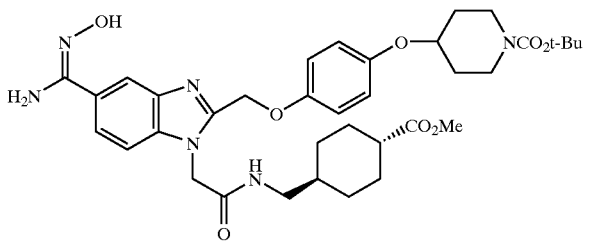

In the same manner as in Example 53, Step 9, the title compound (181 mg) was obtained from 2-[4-(1-tert-butoxycarbonylpiperidin-4-yloxy)-phenoxymethyl]-1-(trans-4-methoxycarbonylcyclohexylmethylcarbamoylmethyl)-benzimidazole-5-carbothioimidic acid methyl ester (606 mg), hydroxyamine hydrochloride (72 mg) and sodium acetate (85 mg).

¹H-NMR (δ ppm, DMSO-d₆) 0.90 (m, 2H), 1.15–1.55 (m, 14H), 1.70 (m, 2H), 1.86 (m, 4H), 2.19 (m, 1H), 2.94 (tr, 2H), 3.16 (m, 2H), 3.58 (s, 3H), 3.65 (m, 2H), 4.40 (m, 1H), 5.00 (s, 2H), 5.26 (s, 2H), 5.92 (brs, 1H), 6.91 (d, J=9.0 Hz, 2H), 7.00 (d, J=9.0 Hz, 2H), 7.49 (1H), 7.63 (1H), 7.95 (1H), 8.27 (brtr, 1H), 9.59 (brs, 1H).

Step 2
trans-4-[2-[4-(1-Acetimidoylpiperidin-4-yloxy)phenoxymethyl]-5-[amino (hydroxyimino)methyl]benzimidazol-1-ylacetylaminomethyl]-cyclohexanecarboxylic Acid Dihydrochloride

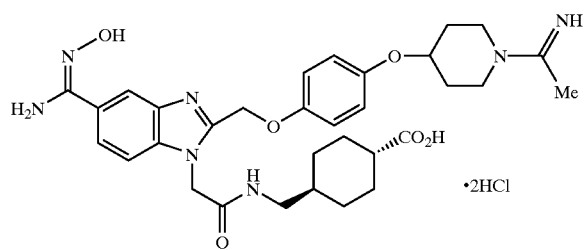

In the same manner as in Example 53, Step 10, the title compound (22 mg) was obtained from 2-[4-(1-tert-butoxycarbonylpiperidin-4-yloxy)-phenoxymethyl]-1-(trans-4-methoxycarbonylcyclohexylmethylcarbamoyl-methyl)benzimidazole-5-carboxamide oxime (181 mg), trifluoroacetic acid (5 ml), 1N aqueous hydroxide solution (0.669 ml), triethylamine (0.187 ml) and ethyl acetimidate hydrochloride (83 mg).

¹H-NMR (δ ppm, DMSO-d₆) 0.8–1.0 (m, 2H), 1.12–1.42 (m, 3H), 1.71 (m, 4H), 1.86 (m, 2H), 2.04 (m, 3H), 2.29 (s, 3H), 2.94 (m, 2H), 3.45–3.60 (m, 2H), 4.58 (m, 1H), 5.14 (s, 2H), 5.34 (s, 2H), 6.95 (d, J=9.0 Hz, 2H), 7.02 (d, J=9.0 Hz, 2H), 7.64 (d, J=8.7 Hz, 1H), 7.81 (d, J=8.7 Hz, 1H), 8.10 (s, 1H), 8.49 (brtr, 1H), 8.74 (brs, 1H), 8.98 (brs, 1H), 9.29 (brs, 2H), 11.20 (brs, 1H), 12.86 (brs, 1H).

Example 56

2-[4-(Piperidin-4-yloxy)phenoxymethyl]-1-phenacylbenzimidazole-5-carboxamidine Dihydrochloride Step 1
3,4-Diaminobenzonitrile

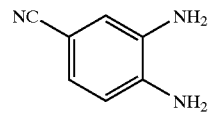

2-Nitro-4-cyanoaniline (2.21 g) was hydrogenated using 7.5% palladium carbon (320 mg) in ethanol (44 ml) at atmospheric pressure over 2 hours. After completion of the reaction, the reaction mixture was filtered through celite, and the solvent was evaporated. To the obtained residue was added chloroform and the resultant solid was collected by filtration and dried under reduced pressure to give the title compound (474 mg).

¹H-NMR (δ ppm, DMSO-d₆) 4.82–4.85 (2H), 5.41–5.43 (2H), 6.54 (d, J=8.1 Hz, 1H), 6.75 (d, J=2.1 Hz, 1H), 6.79 (dd, J=2.1, 8.1 Hz, 1H).

Step 2
4-[4-(2-Amino-5-cyanophenylcarbamoylmethoxy)phenyloxy]piperidine-1-carboxylic Acid tert-Butyl Ester

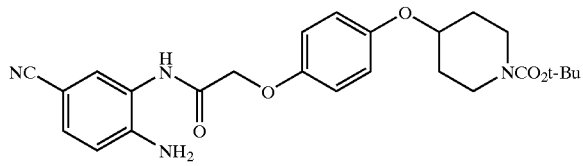

To a solution of 3,4-diaminobenzonitrile (474 mg), 4-(1-tert-butoxycarbonylpiperidin-4-yloxy)phenoxyacetic acid (1.25 g) in tetrahydrofuran (50 ml) was added 1-ethoxycarbonyl-2-ethoxy-1,2-dihydroxyquinoline (1.06 g) with ice-cooling, and the mixture was stirred at room temperature for 16 hours. After completion of the reaction, the solvent was evaporated and to the obtained residue were added chloroform and hexane. The resultant solid was collected by filtration and dried under reduced pressure to give the title compound (1.55 g).

$^1$H-NMR (δ ppm, CDCl$_3$) 1.47 (s, 9H), 1.74 (m, 2H), 1.90 (m, 2H), 3.32 (m, 2H), 3.70 (m, 2H), 4.28 (brs, 2H), 4.38 (m, 1H), 4.64 (s, 2H), 6.80 (d, J=8.4 Hz, 1H), 6.92 (s, 4H), 7.37 (dd, J=1.8, 8.4 Hz, 1H), 7.56 (d, J=1.8 Hz, 1H), 8.10 (brs, 1H).

Step 3
2-[4-(1-tert-Butoxycarbonylpiperidin-4-yloxy)phenoxymethyl]-5-cyanobenzimidazole

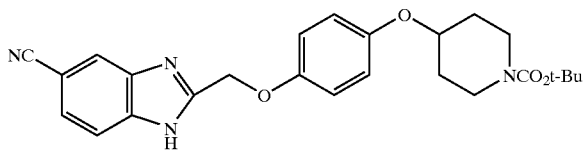

In the same manner as in Example 19, Step 8, the title compound (1.04 g) was obtained from 4-[4-(2-amino-5-cyanophenylcarbamoylmethoxy)phenyloxy]piperidine-1-carboxylic acid tert-butyl ester (1.52 g).

$^1$H-NMR (δ ppm, CDCl$_3$) 1.47 (s, 9H), 1.73 (m, 2H), 1.88 (m, 2H), 3.30 (m, 2H), 3.69 (m, 2H), 4.35 (m, 1H), 5.36 (s, 2H), 6.86–6.96 (m, 4H), 7.54 (s, 1H).

Step 4
2-[4-(1-tert-Butoxycarbonylpiperidin-4-yloxy)phenoxymethyl]-5-cyano-1-phenacylbenzimidazole

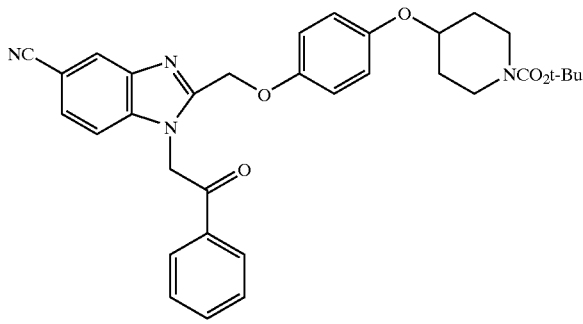

To a solution of 2-[4-(1-tert-butoxycarbonylpiperidin-4-yloxy)-phenoxymethyl]-5-cyanobenzimidazole (915 mg) in dimethylformamide (15 ml) was added 60% sodium hydride (90 mg) with ice-cooling, and the mixture was stirred at the same temperature for 20 min. Phenacyl bromide (426 mg) was added and the mixture was stirred at room temperature for 15 hours. After completion of the reaction, the reaction mixture was extracted with ethyl acetate and washed successively with water and saturated brine. The organic layer was dried over anhydrous sodium sulfate, and the solvent was evaporated. The obtained residue was purified by HPLC (hexane:ethyl acetate=2:3) to give the title compound (385 mg).

$^1$H-NMR (δ ppm, CDCl$_3$) 1.46 (s, 9H), 1.68 (m, 2H), 1.83 (m, 2H), 3.27 (m, 2H), 3.66 (m, 2H), 4.29 (m, 1H), 5.34 (s, 2H), 5.79 (s, 2H), 6.75–6.82 (m, 4H), 7.27 (1H), 7.54 (1H), 7.59 (2H), 7.72 (tr, 1H), 8.02 (2H), 8.15 (1H).

Step 5
2-[4-(Piperidin-4-yloxy)phenoxymethyl]-1-phenacylbenzimidazole-5-carboxamidine Dihydrochloride

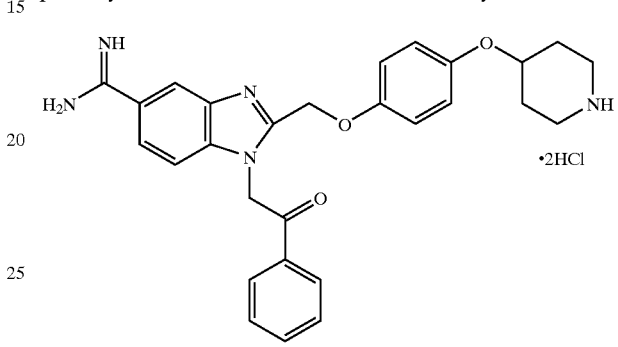

In the same manner as in Example 53, Step 9, 2-[4-(1-tert-butoxycarbonylpiperidin-4-yloxy)phenoxymethyl]-1-phenacylbenzimidazole-5-carbothioimidic acid methyl ester (127 mg) was obtained from 2-[4-(1-tert-butoxycarbonylpiperidin-4-yloxy)phenoxymethyl]-5-cyano-1-phenacylbenzimidazole (182 mg), hydrogen sulfide, methyl iodide (0.204 ml) and ammonium acetate (38 mg). To a solution of this compound in chloroform (1 ml) was added trifluoroacetic acid (1 ml), and the mixture was stirred for 5 min. The solvent was evaporated and the obtained residue was dissolved in methanol. Thereto was added 10% hydrogen chloride-methanol (0.5 ml) and the solvent was evaporated. The residue was dried under reduced pressure to give the title compound (109 mg).

$^1$H-NMR (δ ppm, DMSO-d$_6$) 1.77 (m, 2H), 2.00 (m, 2H), 3.01 (m, 2H), 3.15 (m, 2H), 4.45 (m, 1H), 5.37 (s, 2H), 6.18 (s, 2H), 6.78–6.86 (m, 4H), 7.59–7.84 (m, 5H), 8.09 (d, 2H), 8.26 (s, 1H), 8.80–9.10 (m, 4H), 9.33 (brs, 2H).

Example 57

Synthesis of 2-[4-(1-Acetimidoylpiperidin-4-yloxy)phenoxymethyl]-1-phenacylbenzimidazole-5-carboxamidine Dihydrochloride

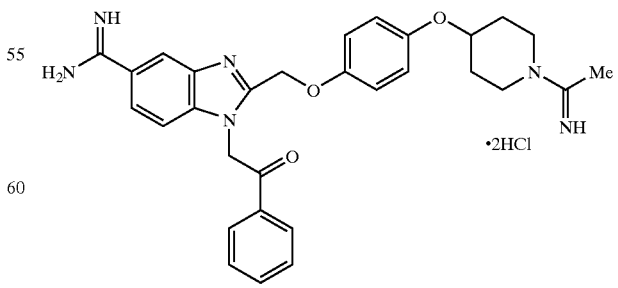

In the same manner as in Example 29, Step 1, 2-[4-(1-acetimidoylpiperidin-4-yloxy)phenoxymethyl]-1- phenacylbenzimidazole-5-carboxamidine was obtained from 2-[4-(piperidin-4-yloxy)phenoxymethyl]-1-phenacylbenzimidazole-5-carboxamidine dihydrochloride (85 mg), triethylamine (0.128 ml) and ethyl acetimidate hydrochloride (57 mg). Isopropanol was added to this compound and the resultant solid was collected by filtration and dried under reduced pressure to give the title compound (17 mg).

$^1$H-NMR (δ ppm, DMSO-$d_6$) 1.69 (m, 2H), 1.95 (m, 2H), 2.27 (s, 3H), 3.50 (m, 2H), 3.71 (m, 2H), 4.52 (m, 1H), 5.37 (s, 2H), 6.19 (s, 2H), 6.80 (d, J=9.0 Hz, 2H), 6.86 (d, J=9.0 Hz, 2H), 7.63 (tr, 2H), 7.71–7.79 (m, 2H), 7.83 (1H), 8.10 (2H), 8.26 (s, 1H), 8.60, 8.95, 9.20, 9.31 (6H).

Example 58

Synthesis of 2-[2-[4-Ethoxycarbonyl-1-(pyridin-4-yl)piperidin-4-yl]ethyl]-1-(cyclohexylcarbamoylmethyl)bennimidazole-5-carboxamidine Dihydrochloride Step 1
4-Ethoxycarbonyl-4-[2-(1,3-dioxolan-2-yl)ethyl]piperidine-1-carboxylic Acid tert-Butyl Ester

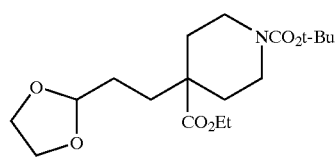

In the same manner as in Example 10, Step 5, the title compound (520 mg) was obtained from 1-tert-butoxycarbonylisonipecotinic acid ethyl ester (500 mg), a 1.5M lithium diisopropylamide-tetrahydrofuran solution (1.6 ml) and 2-(2-bromoethyl)-1,3-dioxolane (0.27 ml).

$^1$H-NMR (δ ppm, CDCl$_3$) 1.26 (tr, J=7.2 Hz, 2H), 1.35 (m, 2H), 1.44 (s, 9H), 1.62 (m, 4H), 2.07–2.11 (m, 2H), 2.88 (m, 2H), 3.81–3.97 (m, 6H), 4.17 (q, J=7.2 Hz, 2H), 4.81 (tr, 1H).

Step 2
4-Ethoxycarbonyl-4-[2-(1,3-dioxolan-2-yl)ethyl]piperidine-1-carboxylic Acid Benzyl Ester

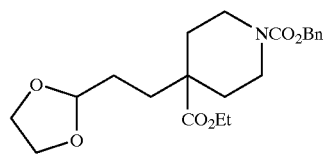

To a solution of 4-ethoxycarbonyl-4-[2-(1,3-dioxolan-2-yl)ethyl]piperidine-1-carboxylic acid tert-butyl ester (450 mg) in chloroform (2 ml) was added trifluoroacetic acid (2 ml), and the mixture was stirred for several minutes. After completion of the reaction, the solvent was evaporated and to the obtained residue was added aqueous sodium hydrogencarbonate solution. The mixture was extracted with ethyl acetate and washed with saturated brine. The organic layer was dried over anhydrous sodium sulfate and the solvent was evaporated to give 4-[2-(1,3-dioxolan-2-yl)ethyl]piperidine-4-carboxylic acid ethyl ester. Then, in the same manner as in Example 10, Step 1, the title compound (460 mg) was obtained from sodium hydrogencarbonate (127 mg) and benzyloxycarbonyl chloride (0.22 ml).

Step 3
4-Ethoxycarbonyl-4-(2-formylethyl)piperidine-1-carboxylic Acid Benzyl Ester

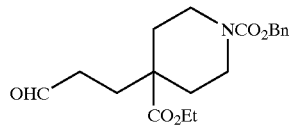

4-Ethoxycarbonyl-4-[2-(1,3-dioxolan-2-yl)ethyl]piperidine-1-carboxylic acid benzyl ester (460 mg) was dissolved in tetrahydrofuran (5 ml) and thereto was dropwise added conc. hydrochloric acid (5 ml) with ice-cooling, and the mixture was stirred at room temperature for 1 hour. After completion of the reaction, the reaction mixture was poured into aqueous sodium hydrogencarbonate solution and the mixture was extracted with ethyl acetate. The organic layer was washed successively with water and saturated brine and dried over anhydrous sodium sulfate. The solvent was evaporated and the obtained residue was purified by silica gel column chromatography (hexane:acetone=5:1) to give the title compound (300 mg).

$^1$H-NMR (δ ppm, CDCl$_3$) 1.27 (tr, J=7.2 Hz, 3H), 1.36 (m, 2H), 1.85 (tr, J=8.0 Hz, 2H), 2.10 (m, 2H), 2.43 (tr, J=8.0 Hz, 2H), 2.94(m, 2H), 3.98 (m, 2H), 4.18 (q, J=7.2 Hz, 2H), 5.12 (s, 2H), 7.28–7.38 (m, 5H), 9.74 (s, 1H).

Step 4
Cyclohexylcarbamoylmethylcarbamic Acid Benzyl Ester

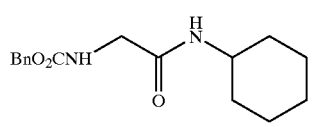

To a solution of N-(benzyloxycarbonyl)glycine (13.21 g), 1-hydroxybenzotriazole hydrate (9.39 g) in dimethylformamide (92 ml) were added cyclohexylamine (7.95 ml) and 1-(3-dimethylaminopropyl)-3-ethylcarbodiimide hydrochloride (13.32 g), and the mixture was stirred at room temperature for 7 hours. After completion of the reaction, the reaction mixture was extracted with ethyl acetate and washed successively with water, aqueous sodium hydrogencarbonate solution, 10% hydrochloric acid and saturated brine. The organic layer was dried over anhydrous magnesium sulfate and the solvent was evaporated. The obtained residue was recrystallized from ethyl acetate and hexane to give the title compound (16.799 g).

$^1$H-NMR (δ ppm, CDCl$_3$) 1.13 (m, 3H), 1.35 (m, 2H), 1.67 (m, 3H), 1.86 (m, 2H), 3.76 (m, 1H), 3.82 (d, J=5.7 Hz, 2H), 5.13 (s, 2H), 5.41 (brs, 1H), 5.81 (brs, 1H), 7.32–7.37 (m, 5H).

Step 5
4-(Cyclohexylcarbamoylmethylamino)-3-nitrobenzonitrile

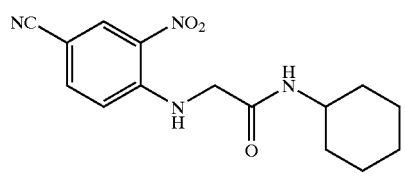

Cyclohexylcarbamoylmethylcarbamic acid benzyl ester (16.359 g) was hydrogenated using 7.5% palladium carbon (3.24 g) in ethanol (164 ml) solution at atmospheric pressure over 8 hours. After completion of the reaction, the reaction mixture was filtered through celite, and the solvent was evaporated. The obtained residue was dissolved in a mixture of ethanol (50 ml) and isopropanol (50 ml). Thereto were added 4-chloro-3-nitrobenzonitrile (8.23 g) and triethylamine (7.1 ml), and the stirred under reflux for 6 hours. After completion of the reaction, water was added under reflux and the mixture was ice-cooled. The resultant solid was collected by filtration and washed successively with water and diisopropyl ether to give the title compound (10.211 g).

$^{1}$H-NMR (δ ppm, CDCl$_{3}$) 1.13 (m, 3H), 1.38 (m, 2H), 1.70 (m, 3H), 1.91 (m, 2H), 3.84 (m, 1H), 4.01 (d, J=5.4 Hz, 2H), 5.76 (brd, 1H), 6.81 (d, J=8.7 Hz, 1H), 7.65 (dd, J=2.1, 8.7 Hz, 1H), 8.54 (d, J=2.1 Hz, 1H), 8.81 (brtr, 1H).

Step 6
3-Amino-4-(cyclohexylcarbamoylmethylamino) benzonitrile

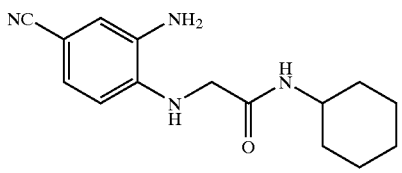

4-(Cyclohexylcarbamoylmethylamino)-3-nitrobenzonitrile (3.64 g) was hydrogenated using 7.5% palladium carbon (1.1 g) in tetrahydrofuran (100 ml) at atmospheric pressure over 40 min. After completion of the reaction, the reaction mixture was filtered through celite, and the solvent was evaporated and the residue was dried under reduced pressure to give the title compound (3.274 g).

$^{1}$H-NMR (δ ppm, DMSO-d$_{6}$) 1.21 (m, 5H), 1.52–1.72 (m, 5H), 3.57 (m, 1H), 3.70 (d, J=5.7 Hz, 2H), 4.97 (brs, 2H), 5.74 (d, J=5.7 Hz, 1H), 6.30 (d, J=8.4 Hz, 1H), 6.82 (d, J=1.8 Hz, 1H), 6.92 (dd, J=1.8, 8.4 Hz, 1H), 7.80 (brd, 1H).

Step 7
4-[2-[5-Cyano-2-(cyclohexylcarbamoylmethylamino) phenylcarbamoyl]ethyl]-4-ethoxycarbonylpiperidine-1-carboxylic Acid Benzyl Ester

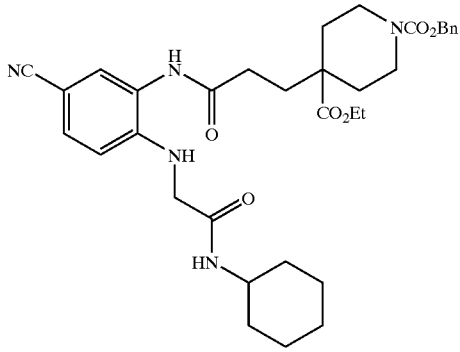

To a solution of 4-ethoxycarbonyl-4-(2-formylethyl) piperidine-1-carboxylic acid benzyl ester (50 mg) in tert-butanol (1 ml) were added aqueous sodium dihydrogenphosphate solution (25 mg/0.5 ml), amylene (0.06 ml) and aqueous sodium chlorite solution (40 mg/0.5 ml), and the mixture was stirred at room temperature for 1 hour. After completion of the reaction, hydrochloric acid and 5% aqueous sodium thiosulfate solution were added and the reaction mixture was extracted with ethyl acetate. The organic layer was washed with saturated brine and dried over anhydrous sodium sulfate. The solvent was evaporated and the obtained residue was dissolved in dimethylformamide (1 ml). Thereto were added 3-amino4-(cyclohexylcarbamoylmethylamino) benzonitrile (39 mg), 1-hydroxybenzotriazole hydrate (21 mg) and 1-(3-dimethylaminopropyl)-3-ethylcarbodiimide hydrochloride (30 mg), and the mixture was stirred at room temperature for 12 hours. After completion of the reaction, aqueous sodium hydrogencarbonate solution was added and the reaction mixture was extracted with ethyl acetate and washed successively with water and saturated brine. The organic layer was dried over anhydrous sodium sulfate and the solvent was evaporated. The obtained residue was recrystallized from ethyl acetate and dried under reduced pressure to give the title compound (51 mg).

$^{1}$H-NMR (δ ppm, CDCl$_{3}$) 1.29 (tr, J=7.2 Hz, 3H), 0.95–1.76 (m, 12H), 1.99 (m, 2H), 2.18 (m, 2H), 2.44 (tr, 2H), 2.96 (m, 2H), 3.74 (m, 1H), 3.90 (d, J=6.3 Hz, 2H), 4.00 (m, 2H), 4.17 (q, J=7.2 Hz, 2H), 5.12 (s, 2H), 5.22 (tr, J=6.3 Hz, 1H), 6.59 (1H), 6.82 (1H), 7.31–7.44 (m, 8H).

Step 8
2-[2-(1-Benzyloxycarbonyl-4-ethoxycarbonylpiperidin-4-yl)ethyl]-5-cyano-1-(cyclohexylcarbamoylmethyl) benzimidazole

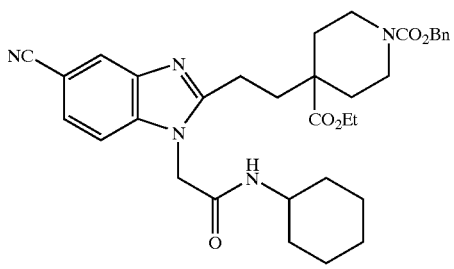

A solution of 4-[2-[5-cyano-2-(cyclohexylcarbamoylmethylamino)-phenylcarbamoyl] ethyl]-4-ethoxycarbonylpiperidine-1-carboxylic acid benzyl ester (300 mg) in acetic acid (10 ml) was stirred at 100° C. for 24 hours. After completion of the reaction, the reaction mixture was extracted with ethyl acetate and washed with aqueous sodium hydrogencarbonate solution. The organic layer was dried over anhydrous sodium sulfate and the solvent was evaporated. The obtained residue was purified by silica gel column chromatography (hexane:ethyl acetate= 2:3) and dried under reduced pressure to give the title compound (200 mg).

$^{1}$H-NMR (δ ppm, CDCl$_{3}$) 0.8–1.75 (m, 13H), 1.80 (m, 2H), 2.22 (m, 4H), 2.84 (tr, 2H), 3.01 (m, 2H), 3.77 (m, 1H), 3.85–4.05 (m, 4H), 4.72 (s, 2H), 5.13 (s, 2H), 5.91 (d, 1H), 7.26–7.45 (m, 6H), 7.54 (1H), 8.01 (1H).

Step 9
2-[2-(4-Ethoxycarbonylpiperidin-4-yl)ethyl]-5-cyano-1-(cyclohexylcarbamoylmethyl)benzimidazole

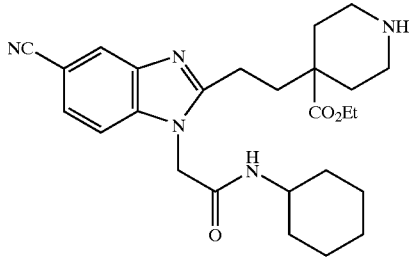

In the same manner as in Example 14, Step 2, the title compound (150 mg) was obtained from 2-[2-(1-benzyloxycarbonyl-4-ethoxycarbonylpiperidin-4-yl)ethyl]-

5-cyano-1-(cyclohexylcarbamoylmethyl)bennimidazole (200 mg), 7.5% palladium carbon (100 mg) and ammonium formate (105 mg).

¹H-NMR (δ ppm, CDCl₃) 0.9–1.85 (m, 12H), 1.26 (tr, J=7.2 Hz, 3H), 2.15–2.25 (m, 4H), 2.68 (m, 2H), 2.85 (tr, 2H), 2.90–3.00 (m, 2H), 3.79 (m, 1H), 3.98 (q, J=7.2 Hz, 2H), 4.73 (s, 2H), 6.04 (d, 1H), 7.37 (1H), 7.53 (1H), 8.01 (1H).

Step 10

2-[2-[4-Ethoxycarbonyl-1-(pyridin-4-yl)piperidin-4-yl]ethyl]-5-cyano-1-(cyclohexylcarbamoylmethyl)benzimidazole

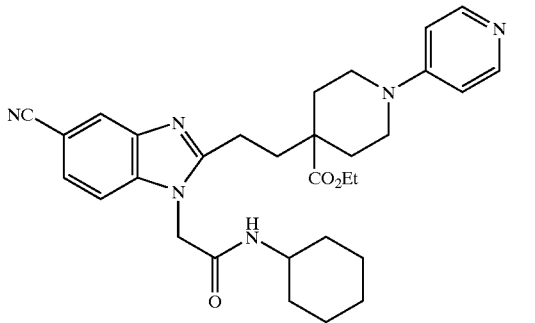

In the same manner as in Example 10, Step 7, the title compound (110 mg) was obtained from 2-[2-(4-ethoxycarbonylpiperidin-4-yl)ethyl]-5-cyano-1-(cyclohexylcarbamoylmethyl)benzimidazole (150 mg), 4-chloropyridine hydrochloride (48 mg) and triethylamine (0.14 ml).

¹H-NMR (δ ppm, CDCl₃) 0.95–1.40 (m, 6H), 1.28 (tr, J=7.2 Hz, 3H), 1.82 (m, 2H), 2.25 (tr, J=7.6 Hz, 2H), 2.32 (m, 2H), 2.87 (tr, J=7.6 Hz, 2H), 3.02 (m, 2H), 3.69 (m, 2H), 3.80 (m, 1H), 4.03 (q, J=7.2 Hz, 2H), 4.73 (s, 2H), 5.97 (d, 1), 6.65 (d, J=6.6 Hz, 2H), 7.35 (1H), 7.54 (1H), 8.01 (1H), 8.26 (d, J=6.6 Hz, 2H).

Step 11

2-[2-[4-Ethoxycarbonyl-1-(pyridin-4-yl)piperidin-4-yl]ethyl]-1-(cyclohexylcarbamoylmethyl)benzimidazole-5-carboxamidine Dihydrochloride

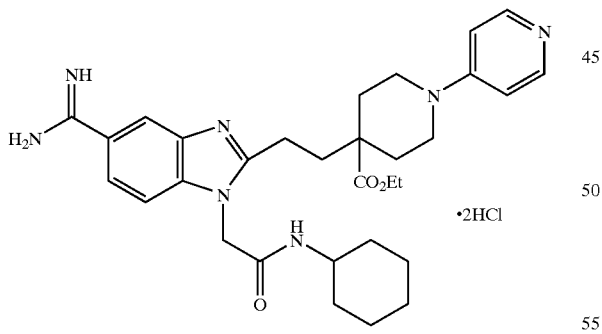

In the same manner as in Example 38, Step 8, the title compound (60 mg) was obtained from 2-[2-[4-ethoxycarbonyl-1-(pyridin-4-yl)piperidin-4-yl]ethyl]-5-cyano-1-(cyclohexylcarbamoylmethyl)benzimidazole (100 mg), methyl iodide (1 ml), ammonium acetate (22 mg) and sodium acetate (23 mg).

¹H-NMR (δ ppm, DMSO-d₆) 1.10–1.38 (m, 8H), 1.50–1.70 (m, 7H), 2.10 (m, 2H), 2.22 (m, 2H), 2.77 (m, 2H), 3.26 (m, 2H), 3.51 (m, 1H), 4.92 (s, 2H), 7.20 (d, J=7.0 Hz, 2H), 7.66 (s, 2H), 8.08 (s, 1H), 8.22 (d, J=7.0 Hz, 2H), 8.37 (d, 1H), 8.94 (s, 2H), 9.20 (s, 2H), 13.34 (brs, 1H).

Example 59

Synthesis of 4-[2-[5-Amidino-1-(cyclohexylcarbamoylmethyl)benzimidazole-2-yl]ethyl]-1-(pyridin-4-yl)piperidine-4-carboxylic Acid Dihydrochloride

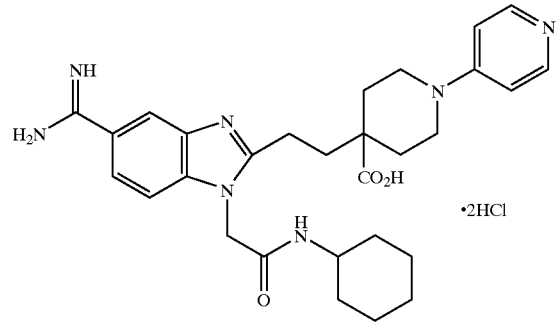

In the same manner as in Example 7, the title compound (20 mg) was obtained from 2-[2-[4-ethoxycarbonyl-1-(pyridin-4-yl)piperidin-4-yl]ethyl]-1-(cyclohexylcarbamoylmethyl)benzimidazole-5-carboxamidine dihydrochloride (50 mg) and conc. hydrochloric acid (1.5 ml). The compound was purified by preparative HPLC (30–50% methanol-water).

¹H-NMR (δ ppm, DMSO-d₆) 1.19 (m, 5H), 1.65 (m, 7H), 2.17 (m, 4H), 2.87 (m, 2H), 3.29 (m, 2H), 4.08 (m, 2H), 5.01 (s, 2H), 7.19 (2H), 7.72 (d, J=8.7 Hz, 1H), 7.77 (d, J=8.7 Hz, 1H), 8.14 (s, 1H), 8.21 (2H), 8.56 (d, 1H), 9.07 (brs, 2H), 9.34 (brs, 2H), 13.56 (brs, 1H).

Example 60

Synthesis of 1-(Cyclohexylcarbamoylmethyl)-2-[N-[1-(pyridin-4-yl)piperidin-4-yl]-N-ethoxalylaminomethyl]]benzimidazole-5-carboxamidine Dihydrochloride Step 1

1-(Pyridin-4-yl)piperidine-4-carbamic Acid Benzyl Ester

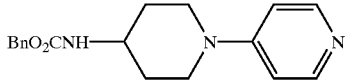

To a suspension of 1-(pyridin-4-yl)piperidine-4-carboxylic acid (11.18 g) and triethylamine (11.3 ml) in dimethylformamide (110 ml) was added diphenylphosphoryl azide (12.9 ml) at room temperature, and the mixture was stirred at 80° C. for 30 min. Benzyl alcohol (6.17 ml) was added at the same temperature, and the mixture was stirred for 12 hours. After completion of the reaction, the solvent was evaporated and the obtained residue was purified by silica gel column chromatography (chloroform:methanol=99:1–95:5) and dried under reduced pressure to give the title compound (9.46 g).

¹H-NMR (δ ppm, CDCl₃) 1.45 (m, 2H), 2.05 (m, 2H), 2.98 (m, 2H), 3.79 (m, 3H), 4.82 (brd, 1H), 5.10 (s, 2H), 6.64 (dd, J=1.2, 5.1 Hz, 2H), 7.29–7.41 (m, 5H), 8.25 (dd, J=1.2, 5.1 Hz, 2H).

Step 2
4-Amino-1-(pyridin-4-yl)piperidine

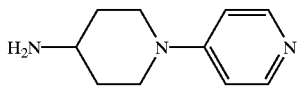

1-(Pyridin-4-yl)piperidine-4-carbamic acid benzyl ester (9.46 g) was hydrogenated using 7.5% palladium carbon (3.57 g) in ethanol (95 ml) solution at 3 atm over 3 hours. After completion of the reaction, the reaction mixture was filtered through celite, and the solvent was evaporated and the residue was dried under reduced pressure to give the title compound (5.38 g).

$^1$H-NMR (δ ppm, DMSO-$d_6$) 1.22 (m, 2H), 1.73 (m, 2H), 2.87 (m, 3H), 3.82 (m, 2H), 6.78 (d, J=6.5 Hz, 2H), 8.11 (d, J=6.5 Hz, 2H).

Step 3
2-Chloromethyl-1-(cyclohexylcarbamoylmethyl)-5-cyanobenzimidazole

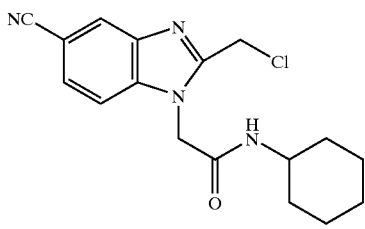

To a solution of chloroacetonitrile (3.9 ml) in methanol (166 ml) was added sodium methoxide (3.29 g), and the mixture was stirred at room temperature for 40 min under a nitrogen atmosphere. Methanesulfonic acid (7.91 ml) and 3-amino4-(cyclohexylcarbamoylmethylamino)benzonitrile (8.3 g) were added, and the mixture was stirred for 3 hours. After completion of the reaction, water (166 ml) was added and the precipitated solid was collected by filtration, and washed with a small amount of water. The obtained solid was stirred in a mixture of hexane and tetrahydrofuran, collected by filtration and dried under reduced pressure to give the title compound (9.30 g).

$^1$H-NMR (δ ppm, DMSO-$d_6$) 1.22 (m, 5H), 1.57 (m, 1H), 1.74 (m, 4H), 3.55 (m, 1H), 5.02–5.03 (m, 4H), 7.69 (s, 2H), 8.21 (s, 1H), 8.34 (brd, 1H).

Step 4
1-(Cyclohexylcarbamoylmethyl)-5-cyano-2-[1-(pyridin-4-yl)piperidin-4-ylamninomethyl]benzimidazole

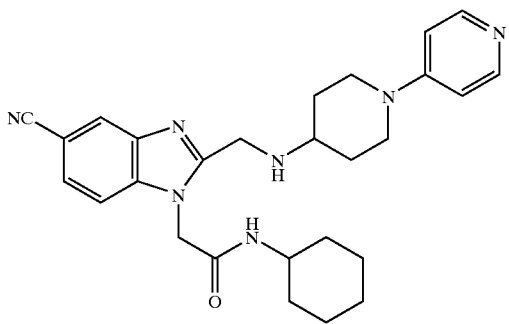

A solution of 4-amino-1-(pyridin-4-yl)piperidine (1.91 g), 2-chloromethyl-1-(cyclohexylcarbamoylmethyl)-5-cyanobenzimidazole (3.25 g) and tethylamine (2.74 ml) in dimethylforrramide (15 ml) was stirred at room temperature for 1 day. After completion of the reaction, the solvent was evaporated. The obtained residue was extracted with chloroform and washed with water. The organic layer was dried over anhydrous sodium sulfate and the solvent was evaporated. The obtained residue was purified by silica gel column chromatography (chloroform:methanol=9:1,1% aqueous ammonia) and dried under reduced pressure to give the title compound (1.464 g).

$^1$H-NMR (δ ppm, CDCl$_3$) 0.84–1.08 (m, 3H), 1.26 (m, 2H), 1.43 (m, 2H), 1.50 (m, 3H), 2.06 (m, 2H), 2.84–3.00 (m, 3H), 3.68 (m, 1H), 3.89 (m, 2H), 4.17 (s, 2H), 4.87 (s, 2H), 6.62–6.67 (m, 3H), 7.49 (1H), 7.56 (1H), 8.04 (1H), 8.24 (2H).

Step 5

1-(Cyclohexylcarbamoylmethyl)-5-cyano-2-[N-[1-(pyridin-4-yl)-piperidin-4-yl]-N-ethoxalylaminomethyl]benzimidazole

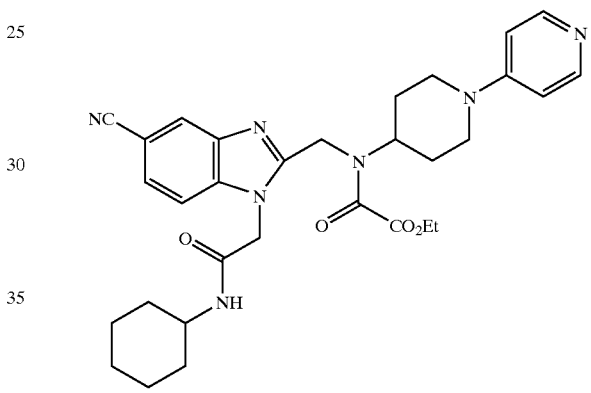

To a solution of 1-(cyclohexylcarbamoylmethyl)-5-cyano-2-[1-(pyridin-4-yl)piperidin-4-ylaminomethyl]benzimidazole (203 mg) and triethylamine (0.18 ml) in chloroform (5 ml) was added ethyl chlorooxalate (0.119 ml), and the mixture was stirred at room temperature for 2 hours. After completion of the reaction, water was added, and the mixture was extracted with chloroform and washed with aqueous sodium hydrogencarbonate solution. The organic layer was dried over anhydrous sodium sulfate. The solvent was evaporated and the obtained residue was purified by silica gel column chromatography (chloroform:methanol= 95:5, 1% aqueous ammonia) and dried under reduced pressure to give the title compound (205 mg).

$^1$H-NMR (δ ppm, CDCl$_3$) 1.04–1.36 (m, 6H), 1.39 (tr, J=7.2 Hz, 3H), 1.83 (m, 3H), 1.94–2.15 (m, 4H), 2.86 (m, 2H), 3.65–3.90 (m, 2H), 4.01 (m, 2H), 4.40 (q, J=7.2 Hz, 2H), 4.73 (s, 2H), 4.90 (s, 2H), 6.27 (1H), 6.65 (d, J=6.3 Hz, 2H), 7.43 (1H), 7.54 (1H), 8.00 (1H), 8.27 (d, J=6.3 Hz, 2H).

Step 6

1-(Cyclohexylcarbamoylmethyl)-2-[N-[1-(pyridin-4-yl)piperidin-4-yl]-N-ethoxalylaminomethyl]benzinmidazole-5-carboxamidine Dihydrochloride

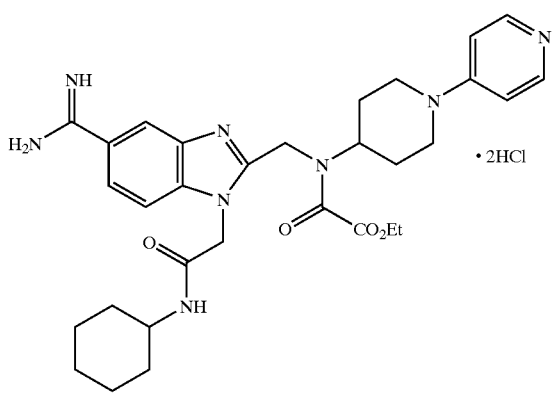

In the same manner as in Example 38, Step 8, the title compound (87 mg) was obtained from 1-(cyclohexylcarbamoylmethyl)-5-cyano-2-[N-[1-(pyridin-4-yl)piperidin-4-yl]-N-ethoxalylaminomethyl]benzimidazole (205 mg), hydrogen sulfide, methyl iodide (5 ml), ammonium acetate (138 mg) and sodium acetate (59 mg).

$^1$H-NMR (δ ppm, DMSO-d$_6$) 1.10–1.28 (m, 5H), 1.32 (tr, J=7.2 Hz, 3H), 1.45–2.03 (m, 9H), 3.15–3.30 (m, 2H), 3.56 (m, 1H), 4.25–4.42 (m, 2H), 4.38 (q, J=7.2 Hz, 2H), 4.76 (s, 1H), 4.90–5.10 (m, 3H), 7.15–7.19 (m, 2H), 7.76–7.75 (m, 2H), 8.15–8.25 (m, 3H), 8.40–8.52 (m, 1H), 8.90–9.00 (brs, 2H), 9.20–9.30 (m, 2H), 13.42 (brs, 1H).

Example 61

Synthesis of N-[5-Amidino-1-(cyclohexylcarbamoylmethyl)benzimidazole-2-ylmethyl]-N-[1-(pyridin-4-yl)piperidin-4-yl] aminooxalic Acid Dihydrochloride

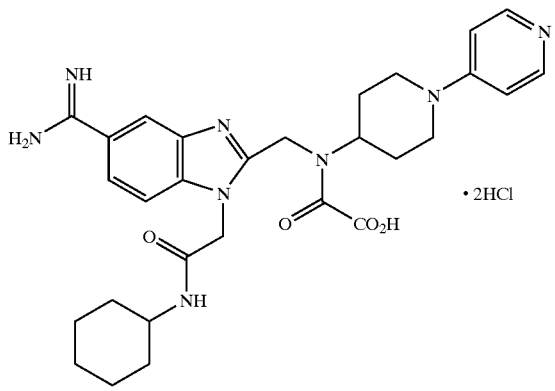

To a solution of 1-(cyclohexylcarbamoylmethyl)-2-[N-[1-(pyridin-4-yl)piperidin-4-yl]-N-ethoxalylaminomethyl] benzimidazole-5-carboxamidine dihydrochloride (50 mg) in methanol (1 ml) was added 2N aqueous sodium hydroxide solution (0.107 ml), and the mixture was stirred for 10 min. After completion of the reaction, dil. hydrochloric acid was added. The solvent was evaporated and the obtained residue was separated by HPLC (50% methanol-water, 0.05% trifluoroacetic acid). The obtained residue is treated with hydrogen chloride-ethanol and dried under reduced pressure to give the title compound (20 mg).

$^1$H-NMR (δ ppm, DMSO-d$_6$) 1.10–1.28 (m, 5H), 1.45–2.03 (m, 9H), 3.10–3.30 (m, 2H), 4.01 (m, 1H), 4.20–4.40 (m, 2H), 4.74 (s, 1H), 4.95–5.10 (m, 3H), 7.16–7.19 (m, 2H), 7.70–7.80 (m, 2H), 8.13–8.30 (m, 3H), 8.47–8.65 (m, 1H), 8.95–9.10 (brs, 2H), 9.23–9.30 (m, 2H), 13.57 (brs, 1H).

Example 62

Synthesis of 2-[N-[4-(1-Acetimidoylpiperidin-4-yloxy)phenyl]-N-ethoxycarbonyl-methylaminomethyl]-1-(cyclohexylcarbamoylmethyl)benzimidazole-5-carboxamidine Dihydrochloride Step 1

2-[4-(1-tert-Butoxycarbonylpiperidin-4-yloxy)phenylaminomethyl]-1-(cyclohexylcarbamoylmethyl)-5-cyanobenzimdazole

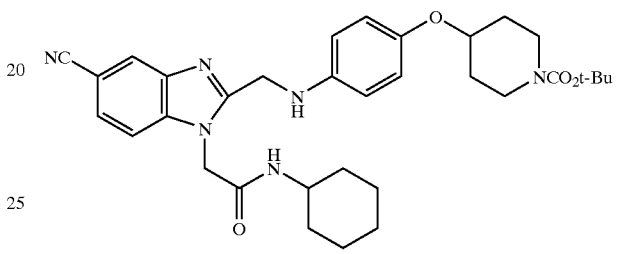

A solution of 4-(4-aminophenoxy)piperidine-1-carboxylic acid tert-butyl ester (8.21 g), 2-chloromethyl-1-(cyclohexylcarbamoylmethyl)-5-cyanobenzimidazole (9.29 g) and diisopropylethylamine (9.8 ml) in dimethylformamide (93 ml) was stirred at 60° C. for 14 hours. After completion of the reaction, the solvent was evaporated and the obtained residue was extracted with ethyl acetate and washed with water. The organic layer was dried over anhydrous magnesium sulfate and the solvent was evaporated. To the obtained residue were added ethyl acetate and hexane and the precipitated solid was collected by filtration, washed with diisopropyl ether and dried under reduced pressure to give the title compound (15.726 g).

$^1$H-NMR (δ ppm, CDCl$_3$) 0.75 (m, 2H), 0.97 (m, 1H), 1.23 (m, 2H), 1.46–1.73 (m, 16H), 1.85 (m, 2H), 3.27 (m, 2H), 3.65 (m, 3H), 4.28 (m, 1H), 4.61 (s, 2H), 4.90 (s, 2H), 5.63 (d, 1H), 6.74 (d, J=8.7 Hz, 2H), 6.82 (d, J=8.7 Hz, 2H), 7.44 (d, J=8.4 Hz, 1H), 7.57 (dd, J=1.2, 8.4 Hz, 1H), 8.10 (d, J=1.2 Hz, 1H).

Step 2

2-[N-[4-(1-tert-Butoxycarbonylpiperidin-4-yloxy)phenyl]-N-ethoxycarbonylmethyl-aminomethyl]-1-(cyclohexylcarbamoylmethyl)-5-cyanobenzimidazole

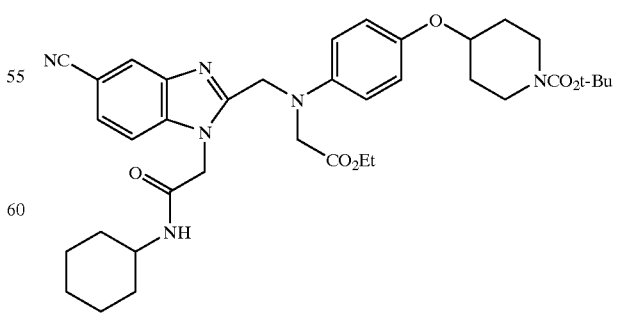

To a solution of 2-[4-(1-tert-butoxycarbonylpiperidin-4-yloxy)-phenylaminomethyl]-1-

(cyclohexylcarbamoylmethyl)-5-cyanobenzimidazole (247 mg) in dimethylformamide (2.5 ml) were added potassium carbonate (175 mg) and ethyl bromoacetate (0.07 ml), and the mire was stirred at room temperature for 24 hours. Thereto were added potassium carbonate (175 mg) and ethyl bromoacetate (0.07 ml), and the mixture was stirred at room temperature for 24 hours. Further, ethyl bromoacetate (0.07 ml) was added, and the mixture was stirred at room temperature for 24 hours. After completion of the reaction, water was added and the mixture was extracted with ethyl acetate and washed with water. The organic layer was dried over anhydrous magnesium sulfate and the solvent was evaporated. The obtained residue was purified by silica gel column chromatography (hexane:ethyl acetate=1:1) to give the title compound (124 mg).

$^1$H-NMR (δ ppm, CDCl$_3$) 0.88–1.35 (m, 10H), 1.46 (s, 9H), 1.67 (m, 5H), 1.86 (m, 2H), 3.29 (m, 2H), 3.67 (m, 3H), 4.01–4.07 (m, 4H), 4.32 (m, 1H), 4.69 (s, 2H), 4.93 (s, 2H), 6.50 (d, 1H), 6.81 (d, J=9.1 Hz, 2H), 6.88 (d, J=9.1 Hz, 2H), 7.44 (1H), 7.54 (1H), 8.03 (1H).

Step 3
2-[N-[4-(1-Acetimidoylpiperidin-4-yloxy)phenyl]-N-ethoxycarbonylmethyl-aminomethyl]-1-(cyclohexylcarbamoylmethyl)benzimidazole-5-carboxamidine Dihydrochloride

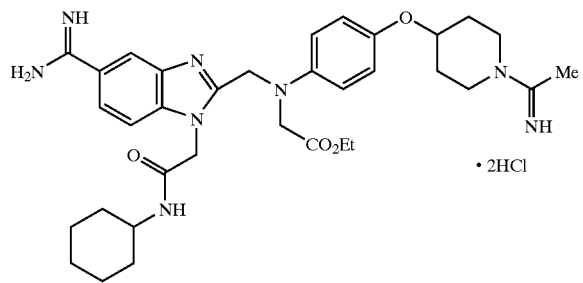

In the same manner as in Example 38, Step 8, 2-[N-[4-(1-tert-butoxycarbonylpiperidin-4-yloxy)phenyl]-N-ethoxycarbonylmethylaminomethyl]-1-(cyclohexylcarbamoylmethyl)benzidazole-5-carboxamidine (47 mg) was obtained from 2-[N-[4-(1-tert-butoxycarbonylpiperidin-4-yloxy)phenyl]-N-ethoxycarbonylmethylaninomethyl]-1-(cyclohexylcarbamoylmethyl)-5cyanobenzimidazole (247 mg), hydrogen sulfide, methyl iodide (1 ml) and ammonium acetate (21 mg). Then, in the same manner as in Example 53, Step 10, the title compound (28 mg) was obtained.

$^1$H-NMR (δ ppm, DMSO-d$_6$) 1.17 (tr, J=7.2 Hz, 3H), 1.10–1.35 (m, 5H), 1.50–1.80 (m, 7H), 1.99 (m, 2H), 2.28 (s, 3H), 3.40–3.60 (m, 3H), 4.10 (q, J=7.2 Hz, 2H), 4.18 (m, 2H), 4.46 (m, 1H), 4.86 (s, 2H), 5.07 (s, 2H), 6.74 (d, J=9.0 Hz, 2H), 6.85 (d, J=9.0 Hz, 2H), 7.73 (1H), 7.80 (1H), 8.15 (1H), 8.47 (1H), 8.70 (1H), 9.04 (2H), 9.25 (1H), 9.31 (2H).

Example 63

Synthesis of N-[5-Amidino-1-(cyclohexylcarbamoylmethyl)benzimidazol-2-ylmethyl]-N-[4-(1-acetimidoylpiperidin-4-yloxy)phenyl]carbamoylbenzoic Acid Step 1
2-[N-[4-(1-tert-Butoxycarbonylpiperidin-4-yloxy)phenyl]-N-(4-methoxycarbonyl-benzoyl)aminomethyl]-1-(cyclohexylcarbamoylmethyl)-5-cyanobenzimidazole

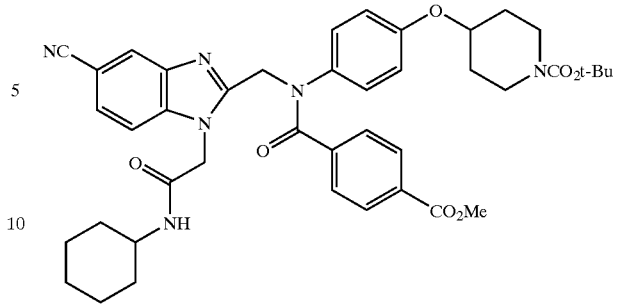

To a solution of 2-[4-(1-tert-butoxycarbonylpiperidin-4-yloxy)-phenylaminomethyl]-1-(cyclohexylcarbamoylmethyl)-5-cyanobenzimidazole (331 mg) and triethylamine (0.118 ml) in chloroform (10 ml) were added methyl 4-chloroformyl benzoate (112 mg) and 4-dimethylaminopyridine (15 mg), and the mixture was stirred at room temperature for 13 hours. After completion of the reaction, the solvent was evaporated and the obtained residue was extracted with ethyl acetate and washed successively with 10% aqueous citric acid solution and saturated brine. The organic layer was dried over anhydrous magnesium sulfate and the solvent was evaporated. The obtained residue was washed with chloroform-diisopropyl ether, collected by filtration and dried under reduced pressure to give the title compound (333 mg).

$^1$H-NMR (δ ppm, CDCl$_3$) 1.09–1.23 (m, 7H), 1.46 (s, 9H), 1.50–1.94 (m, 7H), 3.29 (m, 2H), 3.69 (m, 3H), 3.87 (s, 3H), 4.36 (m, 1H), 5.07 (s, 2H), 5.25 (s, 1H), 6.38 (d, 1H), 6.72 (d, J=8.9 Hz, 2H), 7.08 (d, J=8.9 Hz, 2H), 7.34 (d, J=8.4 Hz, 2H), 7.48 (d, J=8.6 Hz, 1H), 7.57 (dd, J=1.2, 8.6 Hz, 1H), 7.84 (d, J=8.4 Hz, 2H), 8.06 (d, J=1.2 Hz, 1H).

Step 2
2-[N-[4-(1-tert-Butoxycarbonylpiperidin-4-yloxy)phenyl]-N-(4-methoxycarbonylbenzoyl)aminomethyl]-1-(cyclohexylcarbamoylmethyl)-benzimidazole-5-carboxamidine

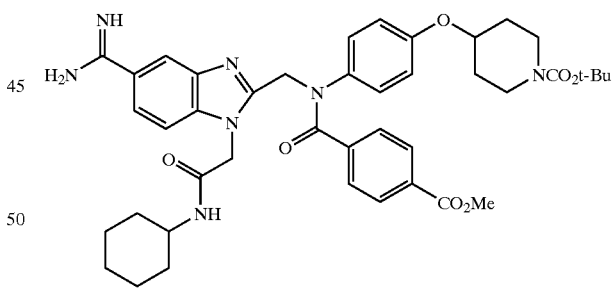

In the same manner as in Example 17, Step 12, the title compound (201 mg) was obtained from 2-[N-[4-(1-tert-butoxycarbonylpiperidin-4-yloxy)phenyl]-N-(4-methoxycarbonylbenzoyl)aminomethyl]-1-(cyclohexylcarbamoylmethyl)-5-cyanobenzimidazole (333 mg), hydrogen sulfide, methyl iodide (0.277 ml) and ammonium acetate (51 mg).

$^1$H-NMR (δ ppm, CDCl3) 1.08 (m, 3H), 1.23 (m, 2H), 1.46 (s, 9H), 1.52–1.80 (m, 7H), 1.86 (m, 2H), 3.29 (m, 2H), 3.67 (m, 3H), 3.87 (s, 3H), 4.36 (m, 1H), 5.07 (s, 2H), 5.25 (s, 2H), 6.41 (d, 1H), 6.72 (d, J=8.9 Hz, 2H), 7.08 (d, J=8.9 Hz, 2H), 7.34 (d, J=8.3 Hz, 2H), 7.47 (1H), 7.56 (1H), 7.84 (d, J=8.3 Hz, 2H), 8.05 (1H).

145

Step 3
2-[N-[4-(Piperidin-4-yloxy)phenyl]-N-(4-methoxycarbonylbenzoyl)aminomethyl]-1-(cyclohexylcarbamoylmethyl)benzimidazole-5-carboxamidine Dihydrochloride

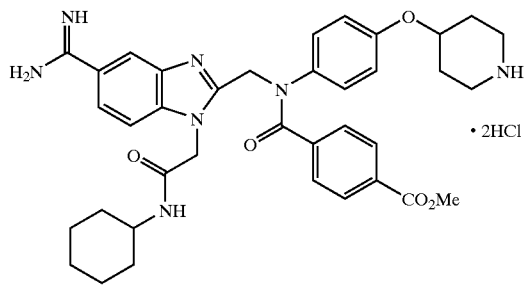

To a solution of 2-[N-[4-(1-tert-butoxycarbonylpiperidin-4-yloxy)phenyl]-N-(4-methoxycarbonylbenzoyl)aminomethyl]-1-(cyclohexylcarbamoylmethyl)-benzimidazole-5-carboxamidine (201 mg) in chloroform (1 ml) was added trifluoroacetic acid (1 ml), and the mixture was stirred for 5 min. After completion of the reaction, the solvent was evaporated and to the obtained residue was added a 1N hydrogen chloride-diethyl ether solution. The obtained solid was collected by filtration and dried under reduced pressure to give the title compound (175 mg).

$^1$H-NMR (δ ppm, DMSO-$d_6$) 1.21 (m, 5H), 1.50–1.84 (m, 7H), 2.00 (m, 2H), 2.99 (m, 2H), 3.14 (m, 2H), 3.53 (m, 1H), 3.81 (s, 3H), 4.52 (m, 1H), 5.18 (s, 2H), 5.35 (s, 2H), 6.82 (d, J=9.0 Hz, 2H), 7.21 (d, J=9.0 Hz, 2H), 7.40 (d, J=8.4 Hz, 2q), 7.75 (s, 2H), 7.79 (d, J=8.4 Hz, 2H), 8.19 (s, 1H), 8.57 (d, 1H), 9.05 (brs, 2H), 9.10 (brs, 2H), 9.33 (brs, 2H).

Step 4
N-[5-Amidino-1-(cyclohexylcarbamoylmethyl)benzimidazol-2-ylmethyl]-N-[4-(1-acetiridoylpiperidin-4-yloxy)phenyl]carbamoylbenzoic Acid

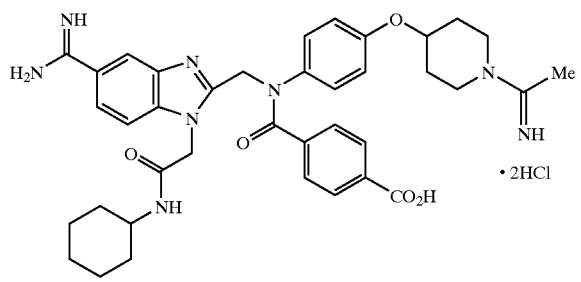

To a solution of 2-[N-[4-(piperidin-4-yloxy)phenyl]-N-(4-methoxycarbonylbenzoyl)aminomethyl]-1-(cyclohexylcarbamoylmethyl)-benzimidazole-5-carboxamidine dihydrochloride (93 mg) in methanol (1 ml) was added a 1N aqueous sodium hydroxide solution (0.629 ml), and the mixture was stirred at room temperature for 15 hours. After completion of the reaction, 1 N hydrochloric acid (0.377 ml) was added and the solvent was evaporated and dried under reduced pressure. The obtained residue was dissolved in methanol (2 ml) and treated in the same manner as in Example 29, Step 1 using triethylamine (0.175 ml) and ethyl acetimidate hydrochloride (78 mg) to give the title compound (28 mg) as a white solid.

$^1$H-NMR (δ ppm, DMSO-$d_6$) 1.20 (m, 5H), 1.46–1.60 (m, 7H), 1.96 (m, 2H), 2.27 (s, 3H), 3.35–3.60 (m, 3H), 4.57 (m, 1H), 5.17 (s, 2H), 5.34 (s, 2H), 6.82 (d, J=5.6 Hz, 2H), 7.20 (d, J=5.6 Hz, 2H), 7.37 (2H), 7.70–7.80 (m, 4H), 8.19 (s, 1H), 8.56 (1H), 8.75 (brs, 1H), 9.11 (brs, 2H), 9.33 (brs, 3H).

146

Example 64

Synthesis of 2-[N-[4-(1-Amidinopiperidin-4-yloxy)phenyl]-N-(4-methoxycarbonyl-benzoyl)aminomethyl]-1-(cyclohexylcarbamoylmethyl)benzimidazole-5-carboxamidine Dihydrochloride

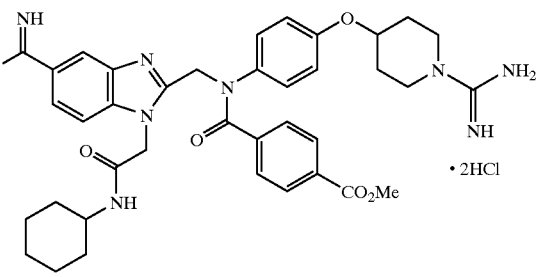

2-[N-[4-(Piperidin-4-yloxy)phenyl]-N-(4-methoxycarbonylbenzoyl)-aminomethyl]-1-(cyclohexylcarbamoylmethyl)benzimidazole-5-carboxamidine dihydrochloride (220 mg) was dissolved in 10% methanol (2 ml) and neutralized with ion-exchange resin (IRA-410). The mixture was filtrated, and the filtrate was concentrated. To a solution of the obtained residue in dimethylformamide (2 ml) were added diisopropylethylamine (0.053 ml) and 1H-pyrazole-1-carboxamidine hydrochloride (44 mg) at room temperature, and the mixture was stirred for 20 hours. After completion of the reaction, the solvent was evaporated and the obtained residue was separated with HPLC (50% methanol-water, 0.05% trifluoroacetic acid) and thereto was added dil. hydrochloric acid. The solvent was evaporated and dried under reduced pressure to give the title compound (155 mg).

$^1$H-NMR (δ ppm, DMSO-$d_6$) 1.20 (m, 5H), 1.45–1.75 (m, 7H), 1.87 (m, 2H), 3.27 (m, 2H), 3.45–3.65 (m, 3H), 3.80 (s, 3H), 5.16 (s, 2H), 5.33 (s, 2H), 6.80 (d, J=9.0 Hz, 2H), 7.19 (d, J=9.0 Hz, 2H), 7.39 (d, J=8.1 Hz, 2H), 7.52 (brs, 4H), 7.74 (s, 2H), 7.78 (d, J=8.1 Hz, 2H), 8.18 (s, 1H), 8.56 (d, 1H), 9.11 (brs, 2H), 9.32 (brs, 2H).

Example 65

Synthesis of N-[5-Amidino-1-(cyclohexylcarbamoylmethyl)benzimidazol-2-ylmethyl]-N-[4-(1-amidinopiperidin-4-yloxy)phenyl]carbamoylbenzoic Acid Dihydrochloride

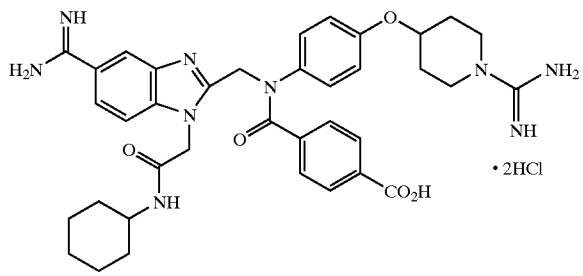

To a solution of 2-[N-[4-(1-amidinopiperidin-4-yloxy)phenyl]-N-(4-methoxycarbonylbenzoyl)aminomethyl]-1-(cyclohexylcarbamoylmethyl)-benzimidazole-5-carboxamidine dihydrochloride (130 mg) in methanol (2 ml) was added 1N aqueous sodium hydroxide solution (0.7 ml), and the mixture was stirred at room temperature for 6 hours.

After completion of the reaction, the solvent was evaporated and the obtained residue was separated by HPLC (50% methanol-water, 0.05% trifluoroacetic acid) and thereto was added dil. hydrochloric acid. The solvent was evaporated and dried under reduced pressure to give the title compound (100 mg).

$^1$H-NMR (δ ppm, DMSO-d$_6$) 1.19 (m, 5H), 1.45–1.75 (m, 7H), 1.90 (m, 2H), 3.27 (m, 2H), 4.51 (m, 1H), 5.17 (s, 2H), 5.33 (s, 2H), 6.80 (d, J=5.7 Hz, 2H), 7.18 (d, J=5.7 Hz, 2H), 7.36 (2H), 7.52 (s, 4H), 7.74–7.77 (m, 4H), 8.18 (s, 1H), 8.55 (1H), 9.10 (brs, 2H), 9.32 (brs, 2H).

Example 66

Synthesis of N-[5-amidino-1-(cyclohexylcarbamoylmethyl)benzimidazol-2-ylmethyl]-N-[4-(1-acetimidoylpiperidin-4-yloxy)phenyl]sulfamoylacetic Acid Dihydrochloride Step 1

2-[4-[N-(1-tert-Butoxycarbonylpiperidin-4-yloxy)phenyl]-N-ethoxycarbonylmethyl-sulfonylaminomethyl]-1-(cyclohexylcarbamoylmethyl)-5-cyanobenzimidazole

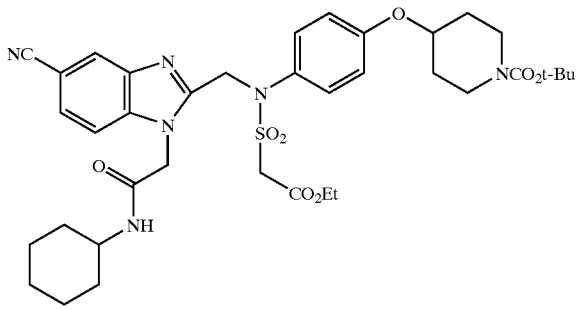

To a solution of chlorosulfonylacetyl chloride (2 g) in chloroform (40 ml) was added ethanol (0.696 ml) at −78° C. and the mixture was stirred at room temperature for 30 min. After completion of the reaction, the solvent was evaporated. A solution of obtained residue in chloroform (10 ml) was dropwise added to a solution of 2-[4-(1-tert-butoxycarbonylpiperidin-4-yloxy)-phenylaminomethyl]-1-(cyclohexylcarbamoylmethyl)-5-cyanobenzimidazole (5.1 g) and pyridine (2.1 ml) in chloroform (88 ml) with ice-cooling. The mixture was stirred at the same temperature for 1 hour. After completion of the reaction, water was added and the mixture was extracted with chloroform and washed successively with water and saturated brine. The organic layer was dried over anhydrous magnesium sulfate and the solvent was evaporated. The obtained residue was purified by silica gel column chromatography (hexane:ethyl acetate= 3:7→2:8) and dried under reduced pressure to give the title compound (4.25 g).

$^1$H-NMR (δ ppm, CDCl$_3$) 1.14–1.44 (m, 5H), 1.37 (tr, J=7.2 Hz, 3H), 1.46 (s, 9H), 1.55–1.78 (m, 5H), 1.80–2.00 (m, 4H), 3.32 (m, 2H), 3.65 (m, 2H), 3.77 (m, 1H), 4.10 (s, 2H), 4.34 (q, J=7.2 Hz, 2H), 4.39 (m, 1H), 4.99 (s, 2H), 5.21 (s, 2H), 6.04 (d, 1H), 6.84 (d, J=8.9 Hz, 2H), 7.32 (d, J=8.9 Hz, 2H), 7.53 (s, 2H), 7.94 (s, 1H).

Step 2

N-[5-Amidino-1-(cyclohexylcarbamoylmethyl)benzimidazol-2-ylmethyl]-N-[4-(1-acetimidoylpiperidin-4-yloxy)phenyl]sulfamoylacetic Acid Dihydrochloride

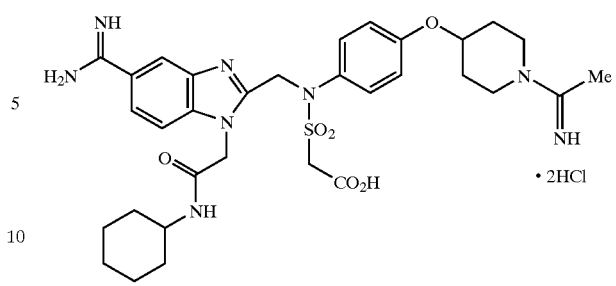

Hydrogen chloride was blown into a solution of 2-[4-[N-(1-tert-butoxycarbonylpiperidin-4-yloxy)phenyl]-N-ethoxycarbonylmethylsulfonyl-aminomethyl]-1-(cyclohexylcarbamoylmethyl)-5-cyanobenzimidazole (3.34 g) in ethanol (33 ml) with ice-cooling, and the mixture was stirred at room temperature for 15 hours. The solvent was evaporated and the obtained residue was dissolved in methanol (30 ml) and ethanol (33 ml). Ammonium acetate (3.49 g) was added, and the mixture was stirred at room temperature for 15 hours. After completion of the reaction, 4N hydrogen chloride-dioxane solution (7.9 ml) was added and the resultant insoluble material was removed. The solvent was evaporated, and the residue was dried under reduced pressure. The obtained residue was dissolved in methanol (33 ml) and reacted in the same manner as in Example 29, Step 1 with triethylamine (8.1 ml) and ethyl acetimidate hydrochloride (4.48 g). After completion of the reaction, insoluble material was removed and the solvent was evaporated. To the obtained residue was added 2N hydrochloric acid (50 ml), and the mixture was stirred under reflux for 2 hours. After completion of the reaction, the solvent was evaporated and the obtained residue was separated by HPLC (37–45% methanol-water, 0.05% trifluoroacetic acid) and dil. hydrochloric acid was added. The solvent was evaporated and dried under reduced pressure to give the title compound (1.76 g).

$^1$H-NMR (δ ppm, DMSO-d$_6$) 1.23 (m, 5H), 1.50–1.85 (m, 7H), 2.00 (m, 2H), 2.29 (s, 3H), 3.52 (m, 3H), 3.75 (m, 2H), 4.37 (s, 2H), 4.66 (m, 1H), 5.10 (s, 2H), 5.22 (s, 2H), 6.97 (d, J=8.9 Hz, 2H), 7.42 (d, J=8.9 Hz, 2H), 7.72 (s, 2H), 8.13 (s, 1H), 8.57 (d, 1H), 8.82 (brs, 1H), 9.15–9.50 (5H).

Example 67

Synthesis of 4-(2-Amidino-1,2,3,4-tetrahydroisoquinolin-7-yloxymethyl)-1-(pyridin-4-yl)piperidine-4-carboxylic Acid Methanesulfonate

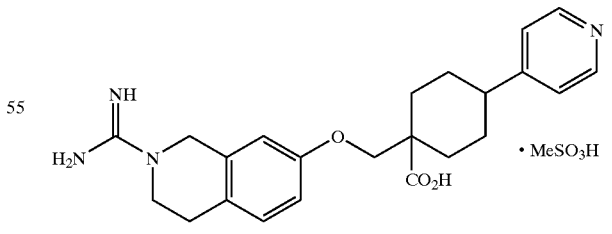

4-(2-Amidino-1,2,3,4-tetrahydroisoquinolin-7-yloxymethyl)-1-(pyridin-4-yl)piperidine-4-carboxylic acid (10 g) was suspended in water (50 ml) and methanesulfonic acid (1.6 ml) was added. The mixture was heated to 50° C. for dissolution. Then, acetone (150 ml) was added dropwise, and the mixture was stirred at the same temperature for 1 hour. The mixture was allowed to cool to room temperature. The precipitated crystals were collected by filtration to give the title compound (11.56 g).

$^1$H-NMR (δ ppm, D$_2$O) 1.60 (m, 2H), 2.19 (m, 2H), 2.72 (s, 3H), 2.77 (tr, J=5.8 Hz, 2H), 3.34 (m, 2H), 3.45 (tr, J=5.8 Hz, 2H), 3.84–3.92 (m, 4H), 4.38 (s, 2H), 6.72 (s, 1H), 6.79 (d, J=8.4 Hz, 1H), 6.92 (d, J=7.8 Hz, 2H), 7.09 (d, J=8.4 Hz, 1H), 7.89 (d, J=7.8 Hz, 2H).

In the same manner as in Example 1 to Example 67, the compounds of Example 68 to Example 115 were obtained. The obtained compounds are shown in Table 1 to Table 8.

Example 68

7-[1-(Pyridin-4-ylacetyl)piperidin-4-ylmethoxy]-1,2,3,4-tetrahydroisoquinoline-2-carboxamidine Dihydrochloride $^1$H-NMR (δ ppm, DMSO-d$_6$) 1.20 (m, 2H), 1.80 (m, 2H), 2.02 (m, 1H), 2.65 (m, 1H), 2.81 (m, 2H), 3.11 (m, 1H), 3.82 (d, 2H), 3.95 (m, 1H), 4.13 (s, 2H), 4.40 (m, 1H), 4.54 (s, 2H), 6.71 (s, 1H), 6.82 (d, J=8.4 Hz, 1H), 7.14 (d, J=8.4 Hz1H), 7.61 (brs, 4H), 7.90 (d, J=6.6 Hz, 2H), 8.83 (d, J=6.6 Hz, 2H).

Example 69

7-[1-(3-Aminobenzyl)piperidin-4-ylmethoxy]-1,2,3,4-tetrahydroisoquinoline-2-carboxamidine Dihydrochloride $^1$H-NMR (δ ppm, DMSO-d$_6$) 1.67 (m, 2H), 1.95 (m, 3H), 2.81 (m, 2H), 2.96 (m, 2H), 3.34 (m, 2H), 3.56 (m, 2H), 3.86 (m, 2H), 6.70 (1H), 6.81 (1H), 7.07–7.37 (m, 5H), 7.56 (brs, 4H), 10.52 (brs, 1H).

Example 70

7-[1-(2-Hydroxybenzyl)piperidin-4-ylmethoxy]-1,2,3,4-tetrahydroisoquinoline-2-carboxamidine Dihydrochloride $^1$H-NMR (δ ppm, DMSO-d$_6$) 1.64 (m, 2H), 1.94 (m, 3H), 2.81 (m, 2H), 3.00 (m, 2H), 3.38 (m, 2H), 3.79 (m, 2H), 4.17 (m, 2H), 4.53 (m, 2H), 6.69 (1H), 6.79–6.88 (m, 2H), 6.97 (1H), 7.13 (1H), 7.26 (t,1H), 7.46 (1H), 7.56 (brs, 4H), 9.94 (brs, 1H), 10.25 (brs, 1H).

Example 71

7-[1-(Pyridin-2-ylmethyl)piperidin-4-ylmethoxy]-1,2,3,4-tetrahydroisoquinoline-2-carboxamidine Trihydrochloride $^1$H-NMR (δ ppm, DMSO-d$_6$) 1.75 (m, 2H), 2.00 (m, 2H), 2.10 (m, 1H), 2.88 (m, 2H), 3.16 (m, 2H), 3.49 (m, 2H), 3.63 (m, 2H), 3.91 (m, 2H), 4.51 (s, 2H), 4.60 (s, 2H), 6.77 (d, J=2.3 Hz, 1H), 6.89 (dd, J=2.3, 8.4 Hz, 1H), 7.21 (d, J=8.4 Hz, 1H), 7.55 (1H), 7.63 (brs, 4H), 7.69 (1H), 7.99 (1H), 8.74 (1H), 10.35 (brs, 1H).

Example 72

2-[4-(2-Amidino-1,2,3,4-tetrahydroisoquinolin-7-yloxymethyl)piperidin-1-ylmethyl]indole-1-carboxylic Acid Aethy Aster Dihydrochloride $^1$H-NMR (δ ppm, DMSO-d$_6$) 1.54 (m, 2H), 1.86 (m, 3H), 2.68 (m, 2H), 3.03 (m, 2H), 3.43 (m, 2H), 3.94 (s, 3H), 4.40 (s, 2H), 4.54 (m, 2H), 6.57 (1H), 6.68 (1H), 6.99–7.02 (m, 2H), 7.18 (tr, J=7.8 Hz, 1H), 7.30 (tr, J=7.8 Hz, 1H), 7.44 (brs, 4H), 7.56 (d, J=7.8 Hz, 1H), 8.00 (d, J=7.8 Hz, 1H). 9.20 (brs, 1H).

Example 73

4-(2-Amidino-1,2,3,4-tetrahydroisoquinolin-7-yloxymethyl)piperidine-1-acetic Acid Benzyl Ester Dihydrochloride $^1$H-NMR (δ ppm, DMSO-d$_6$) 1.67 (m, 2H), 1.97 (m, 3H), 2.83 (m, 2H), 3.09 (m, 2H), 3.58 (m, 4H), 3.83 (m, 2H), 4.36 (s, 2H), 4.55 (s, 2H), 5.27 (s, 2H), 6.72 (1H), 6.84 (1H), 7.16 (1H), 7.36–7.44 (m, 5H), 7.58 (brs, 4H), 10.36 (brs, 1H).

Example 74

N-Benzyl-4-(2-amidino-1,2,3,4-tetrahydroisoquinolin-7-yloxymethyl)piperidine-1-carboxamide Hydrochloride $^1$H-NMR (δ ppm, DMSO-d$_6$) 1.17 (m, 2H), 1.70 (m, 2H), 1.94 (m, 1H), 2.70 (m, 2H), 2.82 (m, 2H), 3.60 (m, 2H), 3.81 (m, 2H), 4.04 (m, 2H), 4.23 (s, 2H), 4.54 (s, 2H), 6.70 (d, J=1.4 Hz, 1H), 6.82 (dd, J=1.4, 6.4 Hz, 1H), 7.13 (d, J=6.4 Hz, 1H), 7.00–7.31 (m, 6H), 7.61 (brs, 4H).

Example 75

7-[1-(Indol-2-ylmethyl)piperidin-4-ylmethoxy]-1,2,3,4-tetrahydroisoquinoline-2-carboxamidine Dihydrochloride $^1$H-NMR (δ ppm, DMSO-d$_6$) 1.67 (m, 2H), 1.97 (m, 3H), 2.81 (m, 2H), 2.98 (m, 2H), 3.58 (m, 2H), 3.81 (d, 2H), 4.44 (d, 2H), 4.56 (2H), 6.69 (2H), 6.82 (1H), 7.03 (1H), 7.13 (2H), 7.41 (1H), 7.56–7.65 (m, 5H), 11.05 (brs, 1H), 11.50 (s, 1H).

Example 76

4-(2-Amidino-1,2,3,4-tetrahydroisoquinolin-7-yloxymethyl)piperidine-1-acetic Acid Dihydrochloride $^1$H-NMR (δ ppm, DMSO-d$_6$) 1.70 (m, 2H), 1.97 (m, 3H), 2.83 (m, 2H), 3.12 (m, 2H), 3.84 (m, 2H), 4.11 (brs, 2H), 4.57 (s, 2H), 6.72 (s, 1H), 6.83 (d, J=8.3 Hz, 1H), 7.15 (d, J=8.3 Hz, 1H), 7.69 (brs, 4H), 10.18 (brs, 1H).

Example 77

N-Benzyl-4-(2-amidino-1,2,3,4-tetrahydroisoquinolin-7-yloxymethyl)piperidine-1-acetamide Dihydrochloride $^1$H-NMR (δ ppm, DMSO-d$_6$) 1.68 (m, 2H), 1.97 (m, 3H), 2.82 (m, 2H), 3.12 (m, 2H), 3.45–3.60 (m, 4H), 3.83 (m, 2H), 3.99 (m, 2H), 4.36 (d, J=5.8 Hz, 2H), 4.56 (s, 2H), 6.72 (1H), 6.83 (H), 7.15 (1H), 7.24–7.34 (m, 5H), 7.67 (brs, 4H), 9.26 (tr, J=5.8 Hz, 1H), 9.97 (brs, 1H).

Example 78

4-(2-Amidino-1,2,3,4-tetrahydroisoquinolin-7-yloxymethyl)piperidin-1-ylacetylaminoacetic Acid Dihydrochloride $^1$H-NMR (δ ppm, DMSO-d$_6$) 1.67 (m, 2H), 1.96 (m, 3H), 2.83 (tr, J=4.3 Hz, 2H), 3.11 (m, 2H), 3.51 (m, 2H), 3.59 (tr, J=4.3 Hz, 2H), 3.83 (m, 2H), 3.87 (2H), 3.96 (s, 1H), 4.56

(s, 1H), 6.72 (1H), 6.83 (1H), 7.15 (1H), 7.66 (brs, 4H), 9.06 (m, 1H), 10.00 (brs, 1H).

Example 79

7-[1-(5-Nitropyridin-2-yl)piperidin-4-ylmethoxy]-1,2,3,4-tetrahydroisoquinoline-2-carboxamidine Dihydrochloride $^1$H-NMR (δ ppm, DMSO-d$_6$) 1.26 (m, 2H), 1.88 (m, 2H), 2.12 (m, 1H), 2.81 (tr, J=6.0 Hz, 2H), 3.08 (m, 2H), 3.57 (tr, J=6.0 Hz, 2H), 3.83 (d, 2H), 4.53–4.59 (m, 4H), 6.70 (d, J=2.4 Hz, 1H), 6.82 (dd, J=2.4, 8.1 Hz, 1H), 6.95 (d, J=9.6 Hz, 1H), 7.12 (d, J=8.4 Hz, 1H), 7.60 (brs, 4H), 8.18 (dd, J=3.0, 9.6 Hz, 1H), 8.94 (d, J=3.0 Hz, 1H).

Example 80

7-[1-(2-Nitrobenzyl)piperidin-4-ylmethoxy]-1,2,3,4-tetrahydroisoquinoline-2-carboxamidine Dihydrochloride $^1$H-NMR (δ ppm, DMSO-d$_6$) 1.60–2.15 (m, 5H), 2.81 (m, 2H), 3.61 (m, 2H), 3.57 (m, 2H), 4.54–4.60 (m, 4H), 6.71 (1H), 6.82 (1H), 7.13 (1H), 7.62 (brs, 4H), 7.76 (tr, J=7.9 Hz, 1H), 7.87 (tr, J=7.9 Hz, 1H), 8.06 (d, J=7.9 Hz, 1H), 8.22 (d, J=7.9 Hz, 1H), 10.27 (brs, 1H).

Example 81

7-[1-(2-Aminobenzyl)piperidin-4-ylmethoxy]-1,2,3,4-tetrahydroisoquinoline-2-carboxamidine Trihydrochloride $^1$H-NMR (δ ppm, DMSO-d$_6$) 1.71 (m, 2H), 1.97 (m, 3H), 2.81 (m, 2H), 3.12 (m, 2H), 3.57 (m, 2H), 3.83 (m, 2H), 4.38 (s, 2H), 4.54 (s, 2H), 6.71 (1H), 6.83 (1H), 7.02 (1H), 7.13 (2H), 7.34 (1H), 7.51 (1H), 7.61 (4H).

Example 82

7-(1-Hexanimidoylpiperidin-4-ylmethoxy)-1,2,3,4-tetrahydroisoquinoline-2-carboxamidine Dihydrochloride $^1$H-NMR (δ ppm, DMSO-d$_6$) 0.87 (tr, 3H), 1.31 (m, 6H), 1.52 (m, 2H), 1.90 (m, 2H), 2.12 (m, 1H), 2.56 (m, 2H), 2.81 (m, 2H), 3.12 (m, 1H), 3.26 (m, 1H), 3.57 (m, 2H), 3.84 (m, 2H), 3.97 (m, 1H), 4.16 (m, 1H), 4.55 (s, 2H), 6.70 (d, J=2.4 Hz, 1H), 6.82 (dd, J=2,4, 8.4 Hz, 1H), 7.14 (d, J=8.4 Hz, 1H), 7.64 (brs, 4H), 8.79 (1H), 9.25 (1H).

Example 83

N-Benzyl-4-(2-amidino-1,2,3,4-tetrahydroisoquinolin-7-yloxymethyl)piperidine-1-sulfonamide hydrochloride $^1$H-NMR (δ ppm, DMSO-d$_6$) 1.19 (m, 2H), 1.76 (m, 3H), 2.61 (m, 2H), 2.81 (m, 2H), 3.55 (m, 4H), 3.77 (d, 2H), 4.08 (d, J=6 Hz, 2H), 4.53 (s, 2H), 6.69 (d, J=2.7 Hz), 6.81 (dd, J=2.7, 8.4 Hz, 1H), 7.13 (d, J=8.4 Hz, 1H), 7.22–7.34 (m, 5H), 7.53 (brs, 4H), 7.72 (tr, J=6 Hz, 1H).

Example 84

N-Butyl-4-(2-amidino-1,2,3,4-tetrahydroisoquinolin-7-yloxymethyl)piperidine-1-sulfonamide Hydrochloride $^1$H-NMR (δ ppm, DMSO-d$_6$) 0.85 (tr, 3H), 1.06–1.46 (m, 6H), 1.84 (m, 2H), 2.64 (m, 2H), 2.84 (m, 4H), 3.56 (m, 4H), 3.81 (m, 2H), 4.53 (s, 2H), 6.69 (1H), 6.81 (m, 2H), 7.10–7.14 (m, 2H), 7.55 (brs, 4H).

Example 85

N-Cyclohexyl-4-(2-amidino-1,2,3,4-tetrahydroisoquinolin-7-yloxymethyl)-piperidine-1-sulfonamide Hydrochloride $^1$H-NMR (δ ppm, DMSO-d$_6$) 1.05–1.83 (m, 15H), 2.59 (m, 2H), 2.81 (m, 2H), 2.95 (m, 1H), 3.56 (m, 4H), 3.81 (m, 2H), 4.53 (s, 2H), 6.70 (1H), 6.81 (1H), 7.13 (m, 2H), 7.54 (brs, 4H).

Example 86

N-(2-Nitrophenyl)-4-(2-amidino-1,2,3,4-tetrahydroisoquinolin-7-yloxymethyl)-piperidine-1-carbothioamide Hydrochloride $^1$H-NMR (δ ppm, DMSO-d$_6$) 1.35 (m, 2H), 1.85 (m, 2H), 2.11 (m, 1H), 2.82 (m, 2H), 3.18 (m, 2H), 3.57 (m, 2H), 4.54 (s, 2H), 4.73 (m, 2H), 6.73 (1H), 6.84 (1H), 7.14 (1H), 7.34–7.42 (m, 2H), 7.55 (brs, 4H), 7.66 (1H), 7.94 (1H), 9.62 (s, 1H).

Example 87

7-[1-(Benzimidazol-2-yl)piperidin-4-ylmethoxy)-1,2,3,4-tetrahydroisoquinoline-2-carboxamidine Dihydrochloride $^1$H-NMR (δ ppm, DMSO-d$_6$) 1.45 (m, 2H), 1.93 (m, 2H), 2.12 (m, 1H), 2.82 (m, 2H), 3.57 (m, 2H), 3.87 (m, 2H), 4.23 (m, 2H), 4.54 (s, 2H), 6.72 (s, 1H), 6.83 (d, J=8.4 Hz, 1H), 7.14 (d, J=8.4 Hz, 1H), 7.22–7.25 (m, 2H), 7.39–7.42 (m, 2H), 7.59 (brs, 4H), 13.46 (s, 2H).

Example 88

3-[4-[4-(2-Amidino-1,2,3,4-tetrahydroisoquinolin-7-yloxymethyl)piperidin-1-yl]pyridin-3-]propionic Acid Ethyl Ester Dihydrochloride $^1$H-NMR (δ ppm, DMSO-d$_6$) 1.14 (tr, J=7.2 Hz, 3H), 1.44 (m, 2H), 1.91 (m, 2H), 2.09 (m, 1H), 2.72–2.84 (m, 4H), 2.95 (m, 2H), 3.15 (m, 2H), 3.57 (m, 2H), 3.76 (m, 2H), 3.88 (m, 2H), 4.04 (q, J=7.2 Hz, 2H), 4.54 (s, 2H), 6.72 (1H), 6.83 (1H), 7.14 (1H), 7.26 (1H), 7.60 (brs, 4H), 8.33 (m, 2H).

Example 89

3-[4-[4-(2-Amidino-1,2,3,4-tetrahydroisoquinolin-7-yloxymethyl)piperidin-1-yl]pyridin-3-yl]propionic Acid Dihydrochloride $^1$H-NMR (δ ppm, DMSO-d$_6$) 1.46 (m, 2H), 1.90 (m, 3H), 2.59–2.87 (m, 8H), 3.57 (m, 2H), 3.88 (m, 2H), 4.53 (s, 2H), 6.72 (1H), 6.84 (1H), 6.97 (1H), 7.14 (1H), 7.51 (brs, 4H), 8.25 (m, 2H).

Example 90

4-(2-Amidino-1,2,3,4-tetrahydroisoquinolin-7-yloxymethyl)-1-(2-aminopyridin-5-ylcarbonyl)piperidine-4-carboxylic Acid Dihydrochloride $^1$H-NMR (δ ppm, DMSO-d$_6$) 1.59 (m, 2H), 2.07 (m, 2H), 2.82 (m, 2H), 3.20 (m, 2H), 3.59 (m, 2H), 4.01 (s, 2H), 4.51 (s, 2H), 6.69 (s, 1H), 6.82 (d, J=8.6 Hz, 1H), 6.91 (d, J=9.2 Hz, 1H), 7.13 (d, J=8.6 Hz, 1H), 7.48 (brs, 4H), 7.84 (dd, J=2.1, 9.2 Hz, 1H), 8.07 (d, J=2.1 Hz, 1H).

Example 91

4-(2-Amidino-1,2,3,4-tetrahydroisoquinolin-7-yloxymethyl)-1-(3-aminopropionyl)-piperidine-4-carboxylic Acid Dihydrochloride $^1$H-NMR (δ ppm, DMSO-$d_6$) 1.49 (m, 1H), 1.59 (m, 1H), 2.05 (m, 2H), 2.71 (m, 2H), 2.71 (m, 2H), 2.81 (m, 2H), 2.97 (m, 3H), 3.57 (m, 2H), 3.65 (m, 1H), 4.00 (m, 3H), 4.54 (s, 2H), 6.68 (s, 1H), 6.81 (d, J=8.4 Hz, 1H), 7.13 (d, J=8.4 Hz, 1H), 7.66 (brs, 4H), 7.98 (brs, 3H).

Example 92

4-(2-Amidino-1,2,3,4-tetrahydroisoquinolin-7-yloxymethyl)-1-(imidazol4-ylacetyl)piperidine-4-carboxylic Acid Dihydrochloride $^1$H-NMR (δ ppm, DMSO-$d_6$) 1.51 (m, 1H), 1.64 (m, 1H), 2.06 (m, 2H), 2.81 (m, 2H), 3.01 (m, 1H), 3.20 (m, 1H), 3.57 (m, 2H), 3.78 (m, 2H), 3.91 (s, 2H), 4.02 (s, 2H), 4.54 (s, 2H), 6.70 (s, 1H), 6.81 (d, J=8.6 Hz, 1H), 7.14 (d, J=8.6 Hz, 1H), 7.43 (s, 4H), 7.55 (s, 1H), 7.62 (brs, 4H), 9.01 (s, 1H), 14.36 (brs, 1H).

Example 93

4-(2-Amidino-1,2,3,4-tetrahydroisoquinolin-7-yloxymethyl)-1-(piperidin-4-ylsulfamoyl)piperidine-4-carboxylic Acid Hydrochloride $^1$H-NMR (δ ppm, DMSO-$d_6$) 1.62 (m, 4H), 1.93 (m, 2H), 2.11 (m, 2H), 2.78–3.00 (m, 6H), 3.17 (m, 2H), 3.36 (m, 3H), 3.57 (m, 2H), 3.99 (s, 2H), 4.53 (s, 2H), 6.69 (1H), 6.80 (d, J=8.4 Hz, 1H), 7.14 (d, J=8.4 Hz, 1H), 7.52 (d, 1H), 7.60 (brs, 4H), 8.85 (brs, 1H), 9.02 (brs, 1H).

Example 94

4-(2-Amidino-1,2,3,4-tetrahydroisoquinolin-7-yloxymethyl)-1-dimethylamninoacetylpiperidine-4-carboxylic Acid Dihydrochloride $^1$H-NMR (δ ppm, DMSO-$d_6$) 1.53–1.64 (m, 2H), 2.06 (m, 2H), 2.80 (m, 8H), 3.06 (m, 1H), 3.21 (m, 1H), 3.50–3.59 (m, 3H), 4.29 (m, 2H), 4.55 (s, 2H), 6.70 (1H), 6.81 (1H), 7.14 (1H), 7.65 (brs, 4H), 9.68 (brs, 1H).

Example 95

4-(2-Amidino-1,2,3,4-tetrahydroisoquinolin-7-yloxymethyl)-1-(pyridin-3-ylcarbamoyl)piperidine-4-carboxylic Acid Ethyl Ester Dihydrochloride $^1$H-NMR (δ ppm, DMSO-$d_6$) 1.16 (tr, J=6.9 Hz, 3H), 1.63 (m, 2H), 2. 10 (m, 8H), 2.81 (tr, J=5.7 Hz, 2H), 3.17 (m, 2H), 3.57 (tr, J=5.7 Hz, 2H), 3.99–4.05 (m, 4H), 4.14 (q, J=6.9 Hz, 2H), 4.53 (s, 2H), 6.69 (d, J=2.4 Hz, 1H), 6.80 (dd, J=2.4, 8.4 Hz, 1H), 7.13 (d, J=8.4 Hz, 1H), 7.58 (brs, 4H), 7.91 (dd, J=5.3, 9.1 Hz, 1H), 8.46 (d, J=5.3 Hz, 1H), 8.64 (d, J=9.1 Hz, 1H), 9.15 (s, 1H), 9.93 (s, 1H).

Example 96

4-(2-Amidino-1,2,3,4-tetrahydroisoquinolin-7-yloxymethyl)-1-(1-dimnethylaminoacetylpiperidin-2-ylcarbonyl)piperidine-4-carboxylic Acid Ethyl Ester Dihydrochloride $^1$H-NMR (δ ppm, DMSO-$d_6$) 1.39 (tr, 3H), 1.40–2.09 (m, 10H), 2.79 (m, 10H), 3.49 (m, 2H), 3.56 (m, 2H), 3.65–4.45 (m, 8H), 4.53 (s, 2H), 5.28 (m, 1H), 6.68 (1H), 6.79 (1H), 7.14 (1H), 7.58 (brs, 4H), 9.65 (brs, 1H).

Example 97

4-[4-(2-Amidino-1,2,3,4-tetrahydroisoquinolin-7-yloxymethyl)-4-carboxypiperidin-1-yl]-1-methylpyridinium Chloride Hydrochloride $^1$H-NMR (δ ppm, DMSO-$d_6$) 1.15 (tr, J=7.2 Hz, 3H), 1.72 (m, 2H), 2.17 (m, 2H), 2.81 (m, 2H), 3.40 (m, 2H), 3.57 (m, 2H), 3.89 (s, 3H), 4.004.07 (m, 4H), 4.14 (q, J=7.2 Hz, 2H), 4.53 (s, 1H), 6.68 (1H), 6.80 (1H), 7.13 (1H), 7.24 (d, J=7.8 Hz, 2H), 7.64 (brs, 4H), 8.25 (d, J=7.8 Hz, 2H).

Example 98

4-(2-Amidino-1,2,3,4-tetrahydroisoquinolin-7-yloxymethyl)-1-(4-amidinophenyl)-piperidine-4-carboxylic Acid Ethyl Ester Dihydrochloride $^1$H-NMR (δ ppm, DMSO-$d_6$) 1.14 (tr, J=6.9 Hz, 3H), 1.69 (m, 2H), 2.14 (m, 2H), 2.81 (m, 2H), 3.14 (m, 2H), 3.56 (m, 2H), 3.82 (m, 2H), 4.05 (s, 2H), 4.13 (q, J=6.9 Hz, 2H), 4.52 (s, 2H), 6.69 (1H), 6.81 (1H), 7.07 (d, J=9 Hz, 2H), 7.13 (1H), 7.56 (brs, 4H), 7.75 (d, J=9 Hz, 2H), 8.71 (brs, 2H), 8.97 (brs, 2H).

Example 99

4-(2-Amidino-1,2,3,4-tetrahydroisoquinolin-7-yloxymethyl)-1-(2,6-dimethylpyridin-4-yl) piperidine-4-carboxylic Acid Ethyl Ester Dihydrochloride $^1$H-NMR (δ ppm, DMSO-$d_6$) 1.16 (tr, J=7.0 Hz, 3H), 1.71 (m, 2H), 2.17 (m, 2H), 2.44 (m, 6H), 2.82 (m, 2H), 3.56 (m, 2H), 3.99 (m, 2H), 4.09 (s, 2H), 4.16 (q, J=7.0 Hz, 2H), 4.54 (s, 2H), 6.70 (1H), 6.82 (d, J=8.3 Hz, 1H), 6.98 (s, 2H), 7.15 (d, J=8.3 Hz, 1H), 7.59 (brs, 4H), 13.41 (brs, 1H).

Example 100

4-(2-Amidino-1,2,3,4-tetrahydroisoquinolin-7-yloxymethyl)-1-(2-methylpyridin-4-yl)piperidine-4-carboxylic Acid Ethyl Ester Dihydrochloride $^1$H-NMR (δ ppm, DMSO-$d_6$) 1.17 (tr, J=7.0 Hz, 3H), 1.73 (m, 2H), 2.18 (m, 2H), 2.47 (s, 3H), 2.83 (m, 2H), 3.37–3.57 (m, 4H), 4.00–4.08 (m, 4H), 4.16 (q, J=7.0 Hz, 2H), 4.54 (s, 2H), 6.70 (1H), 6.82 (1H), 7.07–7.16 (m, 3H), 7.58 (brs, 4H), 8.13 (1H), 13.64 (brs, 1H).

Example 101

4-(2-Amidino-1,2,3,4-tetrahydroisoquinolin-7-yloxymethyl)-1-(1-ethylpiperidin-4-yl)piperidine-4-carboxylic Acid Ethyl Ester Trihydrochloride $^1$H-NMR (δ ppm, DMSO-$d_6$) 1.26–1.42 (m, 6H), 2.07–2.40 (m, 8H), 2.82–3.07 (m, 7H), 3.50–3.70 (m, 5H), 3.96 (s, 2H), 4.16 (q,2H), 4.53 (s, 2H), 6.71 (1H), 6.82 (1H), 7.14 (1H), 7.57 (brs, 4H).

Example 102

4-(2-Amidino-1,2,3,4-tetrahydroisoquinolin-7-yloxymethyl)-1-(1-ethylpiperidin-4-yl)piperidine-4-carboxylic Acid Trihydrochloride $^1$H-NMR (δ ppm, DMSO-$d_6$) 1.25 (tr, 3H), 2.00–2.45 (m, 10H), 2.80–3.30 (m, 5H), 3.97 (s, 2H), 4.56 (s, 2H), 6.74

(1H), 6.84 (1H), 7.16 (1H), 7.64 (brs, 4H), 10.76 (brs, 1H), 11.34 (brs, 1H).

Example 103

7-[2-(4-Cyanopiperidin-4-yl)ethoxy]-1,2,3,4-tetrahydroisoquinoline-2-carboxamidine Dihydrochloride $^1$H-NMR (δ ppm, DMSO-$d_6$) 1.92 (m, 2H), 2.11 (m, 2H), 2.19 (m, 2H), 2.82 (m, 2H), 2.93 (m, 2H), 3.58 (m, 2H), 4.54 (m, 2H), 5.11 (s, 2H), 6.78 (s, 1H), 6.85 (d, J=6.3 Hz, 1H), 7.16 (d, J=6.3 Hz,1 H), 7.59 (brs, 4H), 9.26 (brs, 2H).

Example 104

4-[2-(2-Amidino-1,2,3,4-tetrahydroisoquinolin-7-yloxy)ethyl]-1-(pyridin-4-yl)piperidine-4-carboxylic Acid Ethyl Ester Dihydrochloride $^1$H-NMR (δ ppm, DMSO-$d_6$) 1.19 (tr, J=7.1 Hz, 3H), 1.62 (m, 2H), 2.05 (m, 2H), 2.20 (m, 2H), 2.82 (m, 2H), 3.27 (m, 2H), 3.58 (m, 2H), 3.97 (m, 2H), 4.06 (m, 2H), 4.15 (q, J=7.1 Hz, 2H), 4.55 (s, 2H), 6.65 (1H), 6.76 (1H), 7.14 (1H), 7.19 (d, J=7.6 Hz, 2H), 7.60 (brs, 4H), 8.22 (d, J=7.6 Hz, 2H).

Example 105

4-(2-Amidino-6-methoxy-1,2,3,4-tetrahydroisoquinolin-7-yloxymethyl)-1-(pyridin-4-yl)piperidine-4-carboxylic Acid Dihydrochloride $^1$H-NMR (δ ppm, DMSO-$d_6$) 1.74 (m, 2H), 2.18 (m, 2H), 2.82 (m, 2H), 3.44 (m, 2H), 3.59 (m, 2H), 3.72 (s, 3H), 4.04 (m, 2H), 4.49 (s, 2H), 6.69 (s, 1H), 6.99 (s, 1H), 7.21 (2H), 7.71 (brs, 4H), 8.23 (2H).

Example 106

4-(2-Amidino-6-methyl-1,2,3,4-tetrahydroisoquinolin-7-yloxymethyl)-1-(pyridin-4-yl)piperidine-4-carboxylic Acid Dihydrochloride $^1$H-NMR (δ ppm, DMSO-$d_6$) 1.73 (m, 2H), 2.08 (s, 3H), 2.22 (m, 2H), 2.78 (m, 2H), 3.42 (m, 2H), 3.58 (m, 2H), 4.05 (m, 2H), 4.53 (s, 2H), 6.69 (s, 1H), 6.99 (s, 1H), 7.21 (2H), 7.71 (brs, 4H), 8.23 (2H).

Example 107

2-[4-(1-Acetimidoylpiperidin-4-yloxy)phenoxymethyl]-1-benzylbenzimidazole-5-carboxamidine Dihydrochloride $^1$H-NMR (δ ppm, DMSO-$d_6$) 1.70 (m, 2H), 2.00 (m, 2H), 2.29 (s, 3H), 3.52 (m, 2H), 3.73 (m, 2H), 4.56 (m, 1H), 5.42 (s, 2H), 5.69 (s, 2H), 6.93 (s, 4H), 7.17 (d, 2H), 7.28–7.33 (m, 3H), 7.71 (s, 2H), 8.23 (s, 1H), 8.77 (brs, 1H), 9.12 (brs, 2H), 9.31–9.32 (m, 3H).

Example 108

2-[4-(1-Acetimidoylpiperidin-4-yloxy)phenoxymethyl]-1-(3-oxo-3-piperidinopropyl)benzimidazol-5-carboxamidine Dihydrochloride $^1$H-NMR (δ ppm, DMSO-$d_6$) 1.30 (m, 4H), 1.49 (m, 2H), 1.70 (m, 2H), 1.99 (m, 2H), 2.27 (s, 3H), 2.90 (brtr, 2H), 3.21 (brtr, 2H), 3.34 (m, 2H), 3.53 (m, 2H), 4.60 (m, 3H), 5.47 (s, 2H), 6.96 (d, J=9.0 Hz, 2H), 7.04 (d, J=9.0 Hz, 2H), 7.75 (d, J=8.4 Hz, 1H), 7.91 (d, J=8.4 Hz, 1H), 8.23 (s, 1H), 9.01 (brs, 2H), 9.25 (brs, 1H), 9.30 (brs, 2H).

Example 109

N-[5-Amidino-1-(3-phenyl-2-propenyl)benzimidazol-2-ylmethyl]-N-[4-(1-acetimidoylpiperidin-4-yloxy)phenyl]carbamoylbenzoic Acid Dihydrochloride $^1$H-NMR (δ ppm, DMSO-$d_6$) 1.61 (m, 2H), 1.92 (m, 2H), 2.25 (s, 3H), 3.35–3.50 (m, 2H), 3.60–3.83 (m, 2H), 5.24 (s, 2H), 5.41 (s, 2H), 6.40–6.60 (m, 2H), 6.82 (2H), 7.20–7.38 (m, 9H), 7.73–7.76 (m, 3H), 7.87 (1H), 8.24 (s, 1H), 8.74 (brs, 1H), 9.10 (brs, 2H), 9.29 (brs, 3H).

Example 110

N-[5-Amidino-1-(cyclohexylcarbamoylmethyl)benzimidazol-2-ylmethyl]-N-[4-[1-[amino(benzylinino)methyl]piperidin-4-yloxy]phenyl]carbamoylbenzoic Acid Dihydrochloride $^1$H-NMR (δ ppm, DMSO-$d_6$) 1.19 (m, 5H), 1.43–1.75 (m, 7H), 1.89 (m, 2H), 3.32 (m, 2H), 4.45 (d, 2H), 4.52 (m, 1H), 5.16 (s, 2H), 5.32 (s, 2H), 6.80 (d, J=5.7 Hz, 2H), 7.18 (d, J=5.7 Hz, 2H), 7.25–7.38 (m, 7H), 7.70–7.78 (m, 6H), 8.18 (s, 1), 8.41 (m, 1H), 8.56 (d, 1H), 9.11 (brs, 2H), 9.32 (brs, 2H).

Example 111

N-15-Amidino-1-(cyclohexylcarbamoylmethyl)benzimidazol-2-ylmethyl]-N-[4-(1-acetimidoylpiperidin-4-yloxy)phenyl]carbamoylbenzoic Acid Dihydrochloride $^1$H-NMR (δ ppm, DMSO-$d_6$) 1.21 (m, 5H), 1.45–1.80 (m, 5H), 5.18 (s, 2H), 5.40 (s, 2H), 6.98 (m, 4H), 7.35–7.42 (m, 4H), 7.75 (s, 2H), 7.82 (m, 4H), 8.20 (s, 1H), 8.61 (brd, 1H), 9.13 (m, 4H), 9.32 (brs, 4H).

Example 112

N-[5-Amidino-1-(cyclohexylcarbamoylmethyl)benzimidazol-2-ylmethyl]-N-[4-[1-(N-ethylamidino)piperidin-4-yloxy]phenyl]carbamoylbenzoic Acid Dihydrochloride $^1$H-NMR (δ ppm, DMSO-$d_6$) 1.07–1.20 (m, 8H), 1.42–1.75 (m, 7H), 1.87 (m, 2H), 3.15–3.35 (m, 4H), 4.50 (m, 1H), 5.20 (s, 2H), 5.36 (s, 2H), 6.80 (2H), 7.18 (2H), 7.39 (2H), 7.62–7.85 (m, 7H), 8.18, 8.20 (1H), 8.55, 8.65 (1H), 9.09, 9.19, 9.32, 9.38 (4H).

Example 113

1-(Cyclohexylcarbamoylmethyl)-2-[4-methoxycarbonyl-1-(pyridin-4-yl)piperidin-4-ylaminomethyl]benzimidazole-5-carboxamidine Dihydrochloride $^1$H-NMR (δ ppm, DMSO-$d_6$) 1.13–1.25 (m, 5H), (m, 1H), 1.64–1.72 (m, 4H), 1.82 (m, 2H), 2.01 (m, 2H), 3.49 (m, 1H), 3.59–3.65 (m, 5H), 3.75 (m, 2H), 3.99 (s, 2H), 5.06 (s, 2H), 7.18 (d, J=5.5 Hz, 2H), 7.66–7.72 (m, 2H), 8.15 (s, 1H), 8.21 (d, J=5.5 Hz, 2H), 8.30 (1H), 9.02 (brs, 2H), 9.23 (brs, 2H), 13.38 (brs, 1H).

Example 114

1-(Cyclohexylcarbamoylmethyl)-2-[4-methoxycarbonyl-1-(pyridin-4-yl)piperidin-4-ylcarbamoyl]benzimidazole-5-carboxamidine Dihydrochloride $^1$H-NMR (δ ppm, DMSO-d$_6$) 1.06–1.30 (m, 5H), 1.54 (m, 1H), 1.70 (m, 4H), 2.11 (m, 2H), 2.25–2.33 (m, 2H), 3.41–3.62 (m, 6H), 3.95 (m, 2H), 5.32 (s, 2H), 7.23 (2H), 7.80 (1H), 7.89 (1H), 8.20–8.26 (m, 4H), 9.18 (brs, 2H), 9.34 (brs, 2H), 9.55 (brs, 1H), 13.46 (brs, 1H).

Example 115

(S)-N-[5-Amidino-1-[(1-phenylethyl)carbamoylmethyl]benzimidazol-2-ylmethyl]-N-[4-(1-acetimidoylpiperidin-4-yloxy)phenyl] sulfamoylacetic Acid Dihydrochloride $^1$H-NMR (δ ppm, DMSO-d$_6$) 1.41 (d, 3H), 1.70 (m, 2H), 2.00 (m, 2H), 2.28 (s, 3H), 3.50 (m, 2H), 3.72 (m, 2H), 4.37 (s, 2H), 4.66 (m, 1H), 4.90 (m, 1H), 5.19 (brs, 4H), 6.95 (2H), 7.18–7.42 (m, 7H), 7.71 (s, 2H), 8.12 (s, 1H), 8.78 (brs, 1H), 9.09 (brs, 2H), 9.18 (brd, 1H), 9.30–9.33 (3H).

TABLE 1

| Ex. | R$^1$ | R$^2$ | R$^3$ | R |
|---|---|---|---|---|
| 68 | H | H | H | 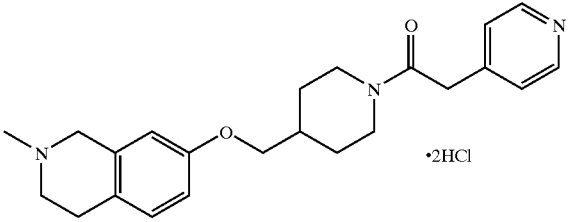 |
| 69 | H | H | H | 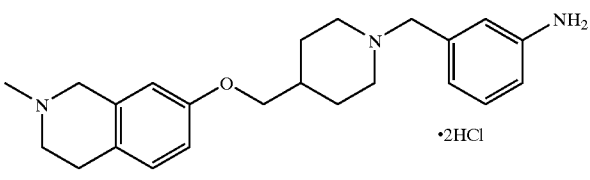 |
| 70 | H | H | H | 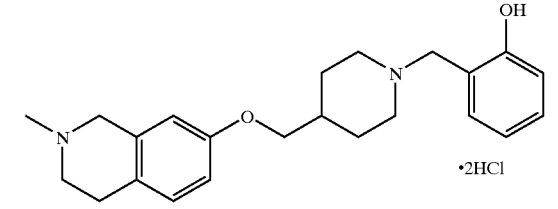 |
| 71 | H | H | H | 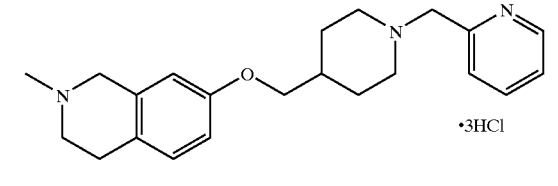 |
| 72 | H | H | H | 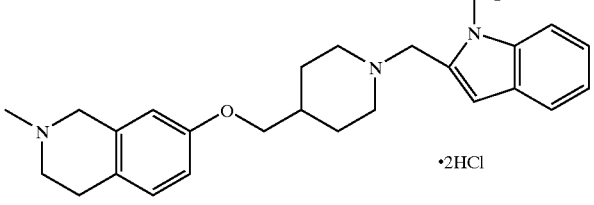 |
| 73 | H | H | H | 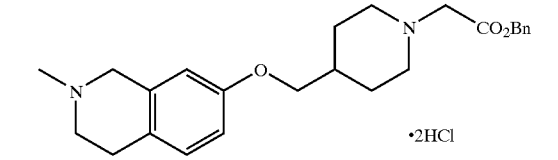 |

TABLE 1-continued
| Ex. | R¹ | R² | R³ | R |
|---|---|---|---|---|
| 74 | H | H | H | 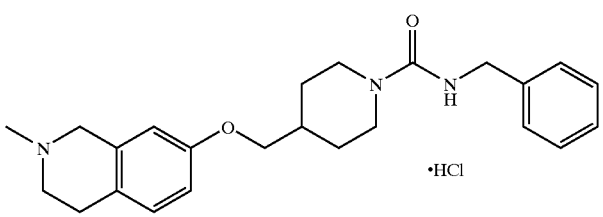 •HCl |
TABLE 2
| Ex. | R¹ | R² | R³ | R |
|---|---|---|---|---|
| 75 | H | H | H | 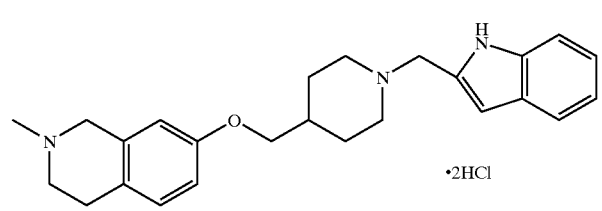 •2HCl |
| 76 | H | H | H | 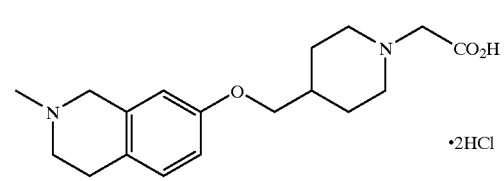 •2HCl |
| 77 | H | H | H | 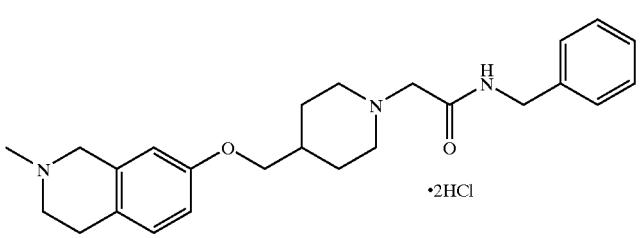 •2HCl |
| 78 | H | H | H | 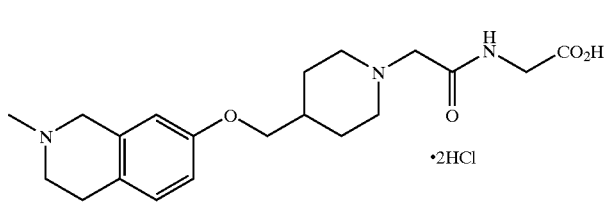 •2HCl |
| 79 | H | H | H | 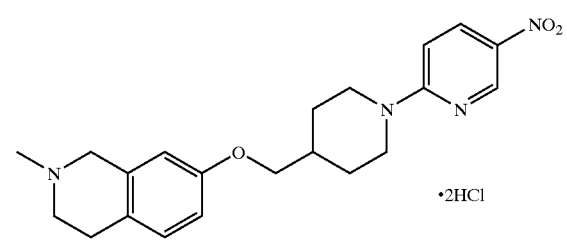 •2HCl |

TABLE 2-continued

| Ex. | R¹ | R² | R³ | R |
|---|---|---|---|---|
| 80 | H | H | H | (2-nitrobenzyl piperidinyl methoxy methyl-tetrahydroisoquinoline) ·2HCl |
| 81 | H | H | H | (2-aminobenzyl piperidinyl methoxy methyl-tetrahydroisoquinoline) ·3HCl |

TABLE 3

| Ex. | R¹ | R² | R³ | R |
|---|---|---|---|---|
| 82 | H | H | H | (hexanimidoyl piperidinyl methoxy methyl-tetrahydroisoquinoline) ·2HCl |
| 83 | H | H | H | (N-benzylsulfamoyl piperidinyl methoxy methyl-tetrahydroisoquinoline) ·HCl |
| 84 | H | H | H | (N-butylsulfamoyl piperidinyl methoxy methyl-tetrahydroisoquinoline) ·HCl |
| 85 | H | H | H | (N-cyclohexylsulfamoyl piperidinyl methoxy methyl-tetrahydroisoquinoline) ·HCl |

TABLE 3-continued
| Ex. | R¹ | R² | R³ | R |
|-----|----|----|----|---|
| 86 | H | H | H | 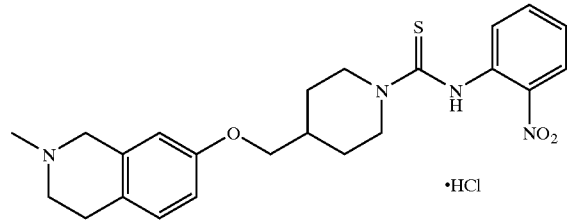 •HCl |
| 87 | H | H | H | 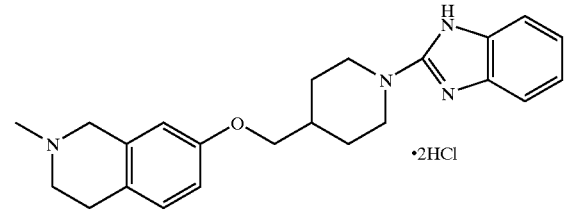 •2HCl |
| 88 | H | H | H | 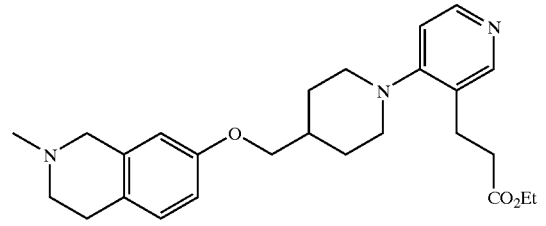 •2HCl |
TABLE 5
| Ex. | R¹ | R² | R³ | R |
|-----|----|----|----|---|
| 96 | H | H | H | 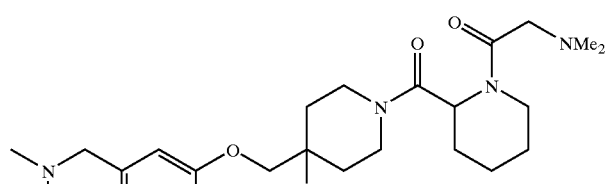 •2HCl |
| 97 | H | H | H | 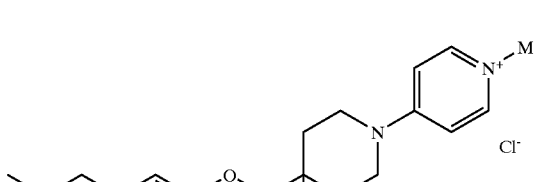 •HCl |

TABLE 5-continued
| Ex. | R¹ | R² | R³ | R |
|---|---|---|---|---|
| 98 | H | H | H | 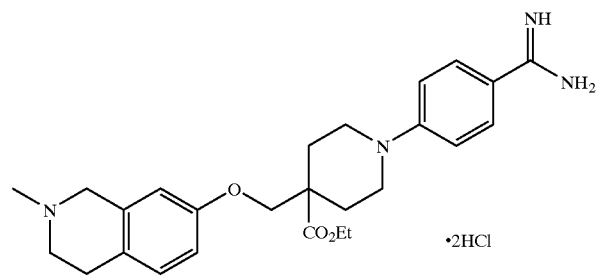 •2HCl |
| 99 | H | H | H | 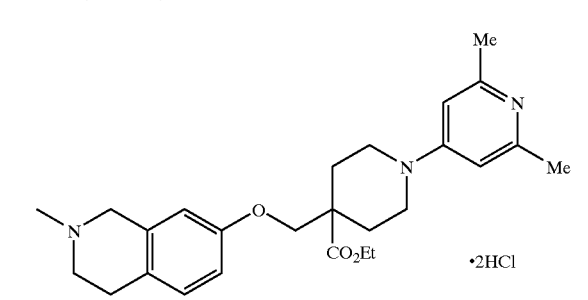 •2HCl |
| 100 | H | H | H | 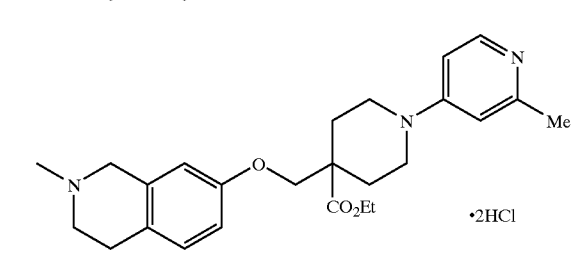 •2HCl |
| 101 | H | H | H | 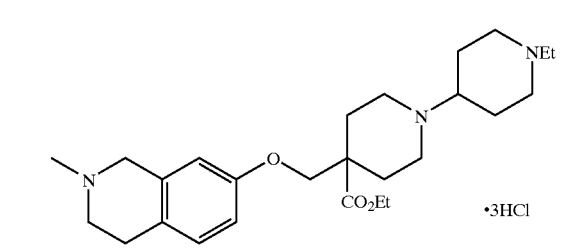 •3HCl |
| 102 | H | H | H | 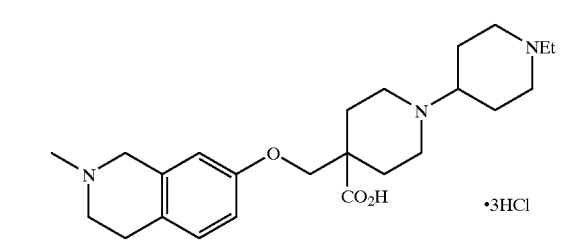 •3HCl |
TABLE 6
| Ex. | R¹ | R² | R³ | R |
|---|---|---|---|---|
| 103 | H | H | H | 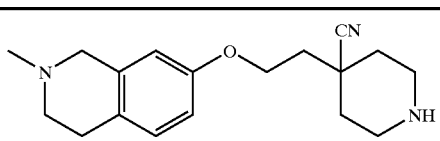 •2HCl |

TABLE 6-continued

| Ex. | R¹ | R² | R³ | R |
|---|---|---|---|---|
| 104 | H | H | H | (structure with 2-methyl-tetrahydroisoquinoline-O-CH2CH2-piperidine(CO2Et)-pyridyl) •2HCl |
| 105 | H | H | H | (structure with 2-methyl-6-methoxy-tetrahydroisoquinoline-O-CH2-piperidine(CO2H)-pyridyl) •2HCl |
| 106 | H | H | H | (structure with 2-methyl-6-methyl-tetrahydroisoquinoline-O-CH2-piperidine(CO2H)-pyridyl) •2HCl |
| 107 | H | H | H | (structure with 5-methyl-1-benzyl-benzimidazole-CH2-O-phenyl-O-piperidine-C(=NH)Me) •2HCl |

TABLE 7

| Ex. | R¹ | R² | R³ | R |
|---|---|---|---|---|
| 108 | H | H | H |  •2HCl |

TABLE 7-continued
| Ex. | R¹ | R² | R³ | R |
|-----|----|----|----|---|
| 109 | H | H | H | 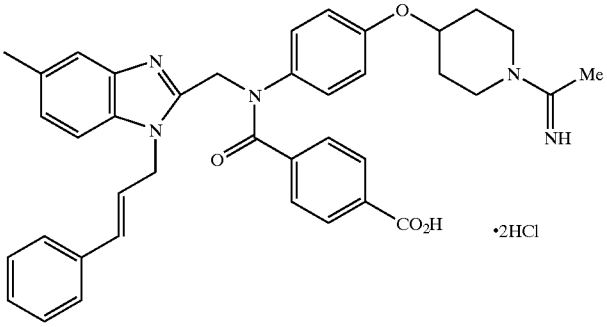 ·2HCl |
| 110 | H | H | H | 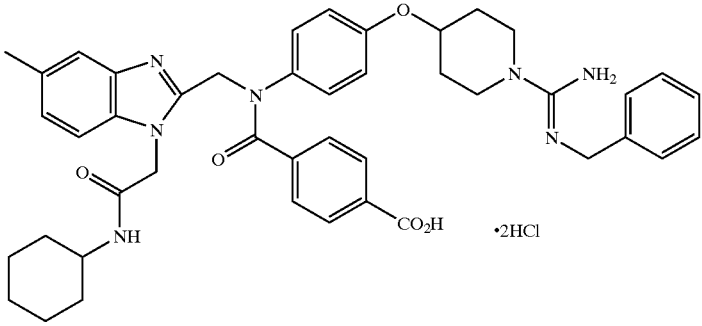 ·2HCl |
| 111 | H | H | H | 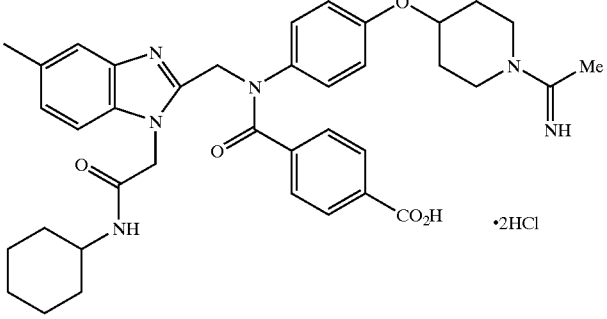 ·2HCl |
| 112 | H | H | H | 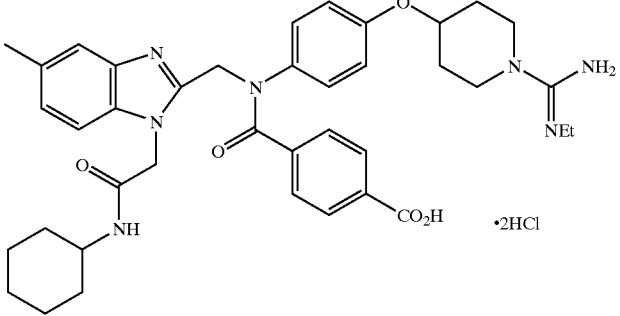 ·2HCl |

TABLE 8

| Ex. | R¹ | R² | R³ | R |
|---|---|---|---|---|
| 113 | H | H | H | 5-methylbenzimidazole with N-CH₂-NH-[4-(CO₂Me)-1-(pyridin-4-yl)piperidin-4-yl], N1 substituted with CH₂C(O)NH-cyclohexyl · 2HCl |
| 114 | H | H | H | 5-methylbenzimidazole-2-C(O)NH-[4-(CO₂Me)-1-(pyridin-4-yl)piperidin-4-yl], N1 substituted with CH₂C(O)NH-cyclohexyl · 2HCl |
| 115 | H | H | H | 5-methylbenzimidazole with 2-CH₂-N(SO₂CH₂CO₂H)-[4-({1-[C(Me)=NH]piperidin-4-yl}oxy)phenyl], N1 substituted with CH₂C(O)NH-(R)-CH(Me)(phenyl) · 2HCl |

Experimental Examples

The biological activity of the compound of the present invention was tested. The compound of the present invention was compared with a control compound, (2S)-2-[4-[(3S)-1-acetimidoylpyrrolidin-3-yloxy]phenyl]-3-[7-amidinonaphthalen-2-yl]propionic acid hydrochloride pentahydrate of the following formula:

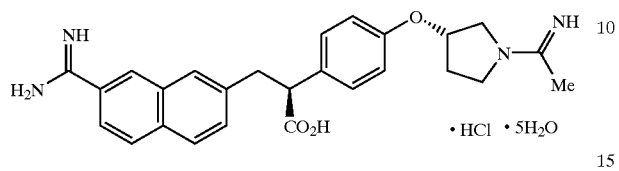

as Comparative

Example 1

Test of enzyme inhibition using synthetic substrate (Experimental Examples 1–2)

Experimental Example 1
Determination of Anti-factor Xa (FXa) Activity

Human FXa [Enzyme research Laboratories (USA)] enzyme (40 μl, 0.16U/ml) and test compounds (40 l) adjusted to various concentrations were incubated in 0.1M Tris (Tris-hydroxymethyl-aminomethane) buffer (pH 8.4) containing 0.2M sodium chloride (herein to be referred to as 0.1 M tris-0.2M NaCl buffer) (40 μl) at 37° C. for 10 min. A synthetic substrate S-2222 (Daiichi Pure Chemical (Tokyo, Japan), 40 μl) adjusted to 0.8 mM was added and the mixture was incubated at 37° C. for 10 min. The reaction was stopped by addition of 60% acetic acid (40 μl) and absorbance at 405 nm was measured by Model 3550 (BIO-RAD). For the control, the solvent was used instead of the test compound. The value of control was taken as 100% and the drug concentration showing 50% absorbance of control was taken as $IC_{50}$. The results are shown in Table 9.

Experimental Example 2
Determination of Anti-factor IIa (FIIa) Activity

Human FIIa (Sigma) enzyme (40 μl, 3.2 U/ml) and test compounds (40 μl adjusted to various concentrations were incubated in 0.1M tris-0.2M NaCl buffer (pH 8.4)(40 μl) at 37° C. for 10 min. A synthetic substrate S-2238 (Daiichi Pure Chemical (Tokyo, Japan), 40 μl) adjusted to 0.8 mM was added and the mixture was incubated at 37° C. for 20 min. The reaction was stopped by addition of 60% acetic acid (40 μl) and absorbance at 405 nm was measured by Model 3550 (BIO-RAD). For the control, the solvent was used instead of the test compound. The value of control was taken as 100% and the drug concentration showing 50% absorbance of control was taken as $IC_{50}$ (μM). The results are shown in Table 9.

TABLE 9

| test compound | Experimental Example 1 (μM) | Experimental Example 2 (μM) |
|---|---|---|
| Example 1 | 0.06 | >10 |
| Example 2 | 0.4 | >10 |
| Example 4 | 0.6 | >10 |
| Example 6 | 0.08 | >10 |
| Example 7 | 0.03 | >10 |
| Example 10 | 0.7 | >10 |
| Example 11 | 0.3 | >10 |
| Example 12 | 0.6 | >10 |
| Example 13 | 0.2 | >10 |
| Example 14 | 0.1 | >10 |
| Example 15 | 0.2 | >10 |
| Example 16 | 0.2 | >10 |
| Example 17 | 0.003 | >10 |
| Example 18 | 0.01 | >10 |
| Example 21 | 0.7 | >10 |
| Example 22 | 0.8 | >10 |
| Example 29 | 0.5 | >10 |
| Example 30 | 0.4 | >10 |
| Example 32 | 0.4 | >10 |
| Example 33 | 0.3 | >10 |
| Example 34 | 0.2 | >10 |
| Example 37 | 0.04 | >10 |
| Example 39 | 0.5 | >10 |
| Example 40 | 0.5 | >10 |
| Example 43 | 0.4 | >10 |
| Example 44 | 0.7 | >10 |
| Example 53 | 0.5 | >10 |
| Example 57 | 0.05 | >10 |
| Example 60 | 0.9 | >10 |
| Example 61 | 0.3 | >10 |
| Example 62 | 0.1 | >10 |
| Example 63 | 0.01 | >10 |
| Example 64 | 0.1 | >10 |
| Example 65 | 0.02 | >10 |
| Example 67 |  | >10 |
| Example 83 | 0.7 | >10 |
| Example 88 | 0.2 | >10 |
| Example 89 | 0.2 | >10 |
| Example 98 | 0.4 | >10 |
| Example 99 | 0.7 | >10 |
| Example 100 | 0.6 | >10 |
| Example 109 | 0.2 | >10 |
| Example 110 | 0.08 | >10 |
| Example 112 | 0.02 | >10 |

Experimental Example 3
Determination of prothrombin time (PT)

Blood was taken from mouse, rat, crab-eating monkey and healthy human volunteers, and citric acid was added. The blood was centrifuged at 4° C. and 2000 G for 15 min to obtain normal plasma of various animals.

Purified water (5 μl) containing various concentrations of test compound was added to plasma (45 μl) and the resultant mixtures were used as samples. Thrombin reagent (Baxter) was prepared and heated at 370° C. for 5 min, and a sample (50 μl) was admixed with the thrombin reagent (100 μl). The time (PT) until precipitation of fibrin was measured. The drug concentration that doubled the PT hours of the drug untreated group was calculated and taken as $CT_2$. The results are shown in Table 10.

TABLE 10

| test compound | $CT_2$ (μM) | | | |
|---|---|---|---|---|
| | mouse | rat | crab-eating monkey | human |
| Example 7 | 10 | 30 | | 0.5 |
| Example 17 | 2 | 2 | | 0.5 |
| Example 67 | | | 5 | |
| Comparative Example 1 | 10 | 10 | 4 | 2 |

Intravenous administration tests (Experimental Examples 4–5)

Experimental Example 4

Intravenous Administration Tests in Mouse

A test compound dissolved in physiological saline was intravenously administered to ICR mice (body weight 20–30 g, 4–6 weeks old) and the activity of the test compound was evaluated based on the human FXa inhibitory activity in serum as an indicator.

At 10, 30, 60, 120 min from the intravenous administration, blood was taken from the eye ground using a hematocrit tube. The blood was centrifuged at 9000 G for 5 min and the obtained serum was used for the determination.

Human FXa inhibitory activity was measured as follows. Human FXa [Enzyme research Laboratories (USA)] enzyme (40 µl, 0.5 U/ml) and a 4-fold diluted plasma sample (40 µl) were incubated in 0.1M Tris-0.2M NaCl buffer (pH 8.4) (40 µl) at 37° C. for 10 min. A synthetic substrate S-2222 (Daiichi Pure Chemical (Tokyo, Japan), 40 µl) adjusted to 0.8 mM was added and the mixture was incubated at 37° C. for 5 min. The reaction was stopped by addition of 60% acetic acid (40 µl) and absorbance at 405 nm was measured by Model 3550 (BIO-RAD). For the control, serum or plasma obtained prior to blood sampling was used for measurement. Human FXa inhibitory activity was calculated as inhibition percentage (%) against control. The results are shown in Table 11.

TABLE 11

| test compound | dose (mg/kg) | Inhibition (%) (mean ± S. D.; n = 3) | | | |
|---|---|---|---|---|---|
| | | 10 minutes | 30 minutes | 60 minutes | 120 minutes |
| Example 7 | 1 | 64 ± 2 | 54 ± 1 | 46 ± 4 | 30 ± 5 |
| | 3 | 82 ± 1 | 78 ± 1 | 72 ± 2 | 59 ± 5 |
| Example 17 | 0.1 | 31 ± 3 | 10 ± 3 | 0 ± 4 | 0 ± 7 |
| | 0.3 | 65 ± 1 | 38 ± 5 | 16 ± 3 | 8 ± 4 |
| | 1 | 70 ± 1 | 69 ± 2 | 41 ± 10 | 1 ± 3 |
| Example 18 | 1 | 73 ± 1 | 60 ± 4 | 40 ± 3 | 23 ± 5 |
| Example 63 | 0.3 | 32 ± 2 | 16 ± 3 | 4 ± 3 | 1 ± 3 |
| | 1 | 55 ± 3 | 46 ± 5 | 16 ± 7 | 3 ± 6 |
| Example 64 | 1 | 55 ± 2 | 43 ± 5 | 28 ± 6 | |
| Example 65 | 1 | 55 ± 1 | 34 ± 2 | 17 ± 2 | |
| Example 112 | 1 | 49 ± 1 | 41 ± 8 | 23 ± 11 | |
| Comparative Example 1 | 1 | 43 ± 3 | 14 ± 2 | 0 ± 1 | 1 ± 2 |

Experimental Example 5

Intravenous Administration Tests in Monkey

A test compound dissolved in physiological saline was intravenously administered to monkey (crab-eating monkey, body weight 3.5–4.5 kg) and the activity of the test compound was evaluated based on the human FXa inhibitory activity in plasma as an indicator.

At 10, 30, 60, 120, 180 min from the intravenous administration, blood was taken from the saphenous vein with the passage of time and the blood was centrifuged at 2000 G for 10 min. The obtained citric acid plasma was used for the determination. Human FXa inhibitory activity was determined in the same manner as in the test using mouse. The results are shown in Table 12.

TABLE 12

| test compound | dose (mg/kg) | Inhibition (%) (mean ± S. D.; n = 3) | | | | |
|---|---|---|---|---|---|---|
| | | 10 minutes | 30 minutes | 60 minutes | 120 minutes | 180 minutes |
| Example 9 | 1 | 82 ± 1 | 72 ± 2 | 58 ± 4 | 41 ± 3 | 29 ± 2 |
| Example 17 | 1 | 90 ± 6 | 90 ± 1 | 86 ± 2 | 77 ± 6 | 65 ± 12 |

Oral administration tests (Experimental Examples 6–7)

Experimental Example 6

Oral Administration Tests in Mouse

A test compound dissolved in distilled water was orally administered to ICR mice (body weight 20–30 g, 4–6 weeks old) and the activity of the test compound was evaluated based on the human FXa inhibitory activity in serum as an indicator.

At 30, 60, 120, 180 min from the oral administration, blood was taken from the eye ground using a hematocrit tube. The blood was centrifuged at 9000 G for 5 min and the obtained serum was used for the determination. Human FXa inhibitory activity was determined in the same manner as in the test by intravenous administration. The results are shown in Table 13.

TABLE 13

| test compound | dose (mg/kg) | Inhibition (%) (mean ± S. D.; n = 3) | | | |
|---|---|---|---|---|---|
| | | 30 minutes | 60 minutes | 120 minutes | 180 minutes |
| Example 7 | 10 | 48 ± 7 | 40 ± 9 | 26 ± 7 | 18 ± 9 |
| Example 17 | 10 | 46 ± 3 | 34 ± 7 | 20 ± 0 | 21 ± 5 |
| Example 63 | 10 | 22 ± 6 | 14 ± 9 | 12 ± 10 | 12 ± 4 |
| Comparative Example 1 | 10 | 11 ± 4 | 6 ± 4 | 6 ± 4 | 6 ± 4 |

Experimental Example 7

Oral Administration Tests in Monkey

A test compound dissolved in distilled water was orally administered to monkey (carb-eating monkey, body weight 3.5–4.5 kg) and the activity of the test compound was evaluated based on the human FXa inhibitory activity in plasma as an indicator.

At 30, 60, 120, 240, 480 min from the oral administration, blood was taken from the saphenous vein with the passage of time and the blood was centrifuged at 2000 G for 10 min. The obtained citric acid plasma was used for the determination. Human FXa inhibitory activity was determined in the same manner as in the test by intravenous administration. The results are shown in Table 14.

TABLE 14

| test compound | dose (mg/kg) | Inhibition (%) (mean ± S. D.; n = 3) | | | | |
|---|---|---|---|---|---|---|
| | | 30 minutes | 60 minutes | 120 minutes | 240 minutes | 480 minutes |
| Example 9 | 10 | 28 ± 33 | 37 ± 27 | 46 ± 20 | 49 ± 9 | 23 ± 11 |
| Example 17 | 10 | 62 ± 53 | 62 ± 51 | 83 ± 13 | 68 ± 16 | 27 ± 10 |

Experimental Example 8
Blood Coagulation Model in Rat

Intravenous administration of thromboplastin (Sigma) to rat promotes coagulation system, which in turn decreases platelets and increases fibrin degradation product (FDP). Thus, the test compound was intravenously administered 10 min before thromboplastin administration and the inhibitory effects of the test compound on the decrease of platelets and the formation of FDP by thromboplastin were studied. The thromboplastin administered had such concentration as to form clots within 20 seconds from the addition of one plasma dose to two thromboplastin doses and was administered in 1 ml/kg dose. Platelets were counted (PLT value) 10 min later on a blood cell counter sysmex F-800 [Dade International Inc. (USA)], and FDP was measured 30 min later using FDP latex reagent for serum [Teikoku Hormone Mfg. Co., Ltd. (Tokyo, Japan)]. The results are shown in Table 15. In every Example, the PLT value of the thromboplastin untreated group was $(106\pm13)\times10^4$ and the FDP value of this group was $0\pm0$ μg/ml.

TABLE 15

| | | (n = 3) | |
|---|---|---|---|
| test compound | dose (mg/kg) | PLT value (×10⁴ blood platelet/μl) | FDP value (μg/ml) |
| Example 7 | 1 | 96 ± 18 | 0 ± 0 |
| | 0.3 | 72 ± 10 | 4 ± 1 |
| | 0.1 | 66 ± 21 | 7 ± 3 |
| | Vehicle | 49 ± 11 | 8 ± 3 |
| Example 17 | 1 | 108 ± 6 | 0 ± 0 |
| | 0.03 | 92 ± 11 | 1 ± 1 |
| | 0.01 | 41 ± 13 | 6 ± 3 |
| | Vehicle | 49 ± 11 | 8 ± 3 |

TABLE 15-continued

| | | (n = 3) | |
|---|---|---|---|
| test compound | dose (mg/kg) | PLT value (×10⁴ blood platelet/μl) | FDP value (μg/ml) |
| Comparative Example 1 | 0.3 | 100 ± 5 | 1 ± 1 |
| | 0.1 | 67 ± 16 | 3 ± 2 |
| | 0.03 | 41 ± 9 | 9 ± 2 |
| | Vehicle | 42 ± 18 | 8 ± 3 |

(mean ± S.D)

INDUSTRIAL APPLICABILITY

The compound of the formula [I] of the present invention has superior blood coagulation factor Xa inhibitory activity, as is evident from the foregoing Experimental Examples. Therefore, the compound is useful as an agent for the prophylaxis and/or treatment of various diseases caused by blood coagulation or thrombus, namely, cerebrovascular diseases such as cerebral infarction, cerebral thrombosis, cerebral embolism, transient ischemia attack (TIA), subarachnoid hemorrhage and the like; ischemic heart diseases such as acute or chronic myocardial infarction, unstable angina, coronary thrombosis and the like; pulmonary vascular diseases such as pulmonary infarction, pulmonary embolism and the like; and diseases associated with various vascular disorders such as peripheral arterial embolism, deep vein thrombosis, disseminated intravascular coagulation, thrombosis after surgery of artificial blood vessels or replacement of artificial valve, reocclusion or restenosis after coronary bypass, reocclusion or restenosis after recanalization such as percutaneous transluminal coronary angioplasty (PICA), percutaneous transluminal coronary recanalization (PTCR) and the like, thrombosis due to extracorporeal circulation and the like, glomerulonephritis, nephrotic syndrome, diabetic retinopathy, arteriosclerotic obliteration, Buerger disease, tumor thrombosis, thrombus by atrial fibrillation, and the like. It is expected, therefore, that the compound of the present invention will make an extremely useful therapeutic agent of these diseases.

This application is based on application Nos. 116233/1998 and 237869/1998 filed in Japan, the contents of which are incorporated hereinto by reference.

TABLE 4

| Ex. | $R^1$ | $R^2$ | $R^3$ | R |
|---|---|---|---|---|
| 89 | H | H | H | 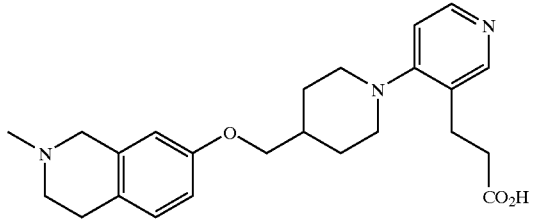 |

·2HCl

TABLE 4-continued

| Ex. | R¹ | R² | R³ | R |
|---|---|---|---|---|
| 90 | H | H | H | 2-amino-pyridine-5-carbonyl-piperidine derivative, ·2HCl |
| 91 | H | H | H | β-alanyl-piperidine derivative, ·2HCl |
| 92 | H | H | H | (1H-imidazol-4-yl)acetyl-piperidine derivative, ·2HCl |
| 93 | H | H | H | 4-piperidinyl-sulfamoyl-piperidine derivative, ·HCl |
| 94 | H | H | H | N,N-dimethylcarbamoyl-piperidine derivative, ·2HCl |
| 95 | H | H | H | N-(pyridin-3-yl)carbamoyl-piperidine ethyl ester derivative, ·2HCl |

What is claimed is:

1. An amidine compound of the formula I

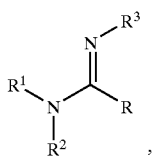

[I]

wherein
R is a group of the formula

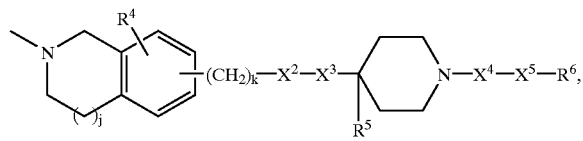

wherein
R$^4$ is hydrogen atom, hydroxy group, lower alkyl group, lower alkoxy group or halogen atom,
R$^5$ is hydrogen atom, cyano group, carboxy group or lower alkoxycarbonyl group,
R$^6$ is hydrogen atom, cycloalkyl group, hydroxy group, carboxy group, lower alkoxycarbonyl group, aralkyloxycarbonyl group,
wherein the aryl moiety of said aralkyloxycarbonyl group is optionally substituted by halogen atom, nitro group, alkyl group, alkoxy group or trifluoromethyl group, nitro group, amino group, lower alkylamino group, di(lower)alkylamino group, aryl group, heteroaryl selected from the group consisting of an imidazolyl group, a pyridyl group, a pyridine-1-oxide group, a pyrimidyl group, a thienyl group, a thiazolyl group, an isoxazolyl group, an oxadiazolyl group, a triazolyl group, an indolyl group, a quinolyl group, a furyl group, a benzofuryl group, a 1H-benzimidazolyl group and a 2-benzothiazolyl group,
wherein said aryl group or heteroaryl group is optionally substituted by 1 to 3 substituents selected from lower alkyl group, hydroxy group, lower alkoxy group, carboxy group, lower alkoxycarbonyl group, aralkyloxycarbonyl group, nitro group,
amino group, acylamino group, amidino group and hydroxyamidino group, 5- to 7-membered saturated heterocycle having one or two heteroatoms selected from O, S or N and three to six carbon atoms provided that at least one nitrogen atom is present,
wherein said saturated heterocycle is optionally substituted by lower alkyl group, acyl group, di(lower)alkylamino(lower)alkanoyl group or imidoyl group, or R$^6$ is

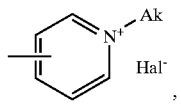

wherein Ak is lower alkyl group and Hal is halogen atom,
X$^2$ is oxygen atom, sulfur atom, —SO$_2$—, —SO$_2$NH— or a single bond, X$^3$ is —(CH$_2$)$_m$— wherein m is 0 or an integer of 1 to 3,
X$^4$ is

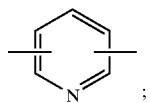

or a single bond,
X$^5$ is alkylene group having 1 to 6 carbon atoms, alkenylene group having 2 to 6 carbon atoms, or a single bond,
j is 1,
k is 0 or 1, and
m and n are the same or different and each is 0 or an integer of 1 to 3; and
R$^1$, R$^2$ and R$^3$ are the same or different and each is hydrogen atom, hydroxy group, lower alkyl group or aryl group,
provided that when X$^4$ is a single bond, R$^6$ is hydrogen atom, carboxy group, lower alkoxycarbonyl group, aryl group or heteroaryl group (the aryl or heteroaryl group is optionally substituted by 1 to 3 substituents selected from the group consisting of lower alkyl group, hydroxy group, lower alkoxy group, carboxy group, lower alkoxycarbonyl group, aralkyloxycarbonyl group, nitro group, amino group, acylamino group, amidino group and hydroxyamidino group), or a pharmaceutically acceptable salt thereof.

2. The amidine compound of the formula according to claim 1, wherein R is a group of the formula

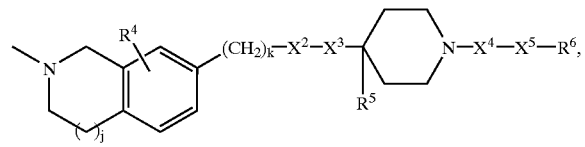

wherein R$^4$, R$^5$ R$^6$, X$^2$, X$^3$, X$^4$, X$^5$, j and k are as defined above,
or a pharmaceutically acceptable salt thereof.

3. The amidine compound of the formula according to claim 2, wherein X$^3$ —(CH$_2$)$_m$— wherein m is as defined above and X$^4$ is a group of the formula

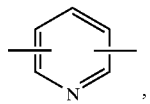

and j is 1,
or a pharmaceutically acceptable salt thereof.

4. The amidine compound of the formula according to claim 3, wherein R$^6$ is hydrogen atom, X$^2$ is oxygen atom, and X$^5$ is a single bond, or a pharmaceutically acceptable salt thereof.

5. An amidine compound, which is selected from the group consisting of
7-[1-(pyridin-4-yl)piperidin-4-ylmethoxy]-1,2,3,4-tetrahydroisoquinoline-2-carboxamidine,
7-[1-(quinolin-4-yl)piperidin-4-ylmethoxy]-1,2,3,4-tetrahydroisoquinoline-2-carboxamidine,
N-methyl-7-[1-(pyridin-4-yl)piperidin-4-ylmethoxy]-1,2,3,4-tetrahydroisoquinoline-2-carboxamidine, 7-[1-(pyridin-4-yl)piperidin-4-ylmethoxy]-1,2,3,4-tetrahydroisoquinoline-2-carboxamide oxime, N-phenyl-7-[1-(pyridin-4-yl)piperidin-4-ylmethoxy]-1,2,3,4-tetrahydroisoquinoline-2-carboxamidine, 4-(2-amidino-1,2,3,4-tetrahydroisoquinolin-7-yloxymethyl)-1-(pyridin-4-yl)piperidine-4-carboxylic acid ethyl ester, 4-(2-amidino-1,2,3,4-tetrahydroisoquinolin-7-yloxymethyl)-1-(pyridin-4-yl)piperidine-4-carboxylic acid, 4-(2-amidino-1,2,3,4-tetrahydroisoquinolin-7-yloxymethyl)-1-(2,6-dimethylpyridin-4-yl)piperidine-4-carboxylic acid ethyl ester, 4-(2-amidino-1,2,3,4-tetrahydroisoquinolin-7-yloxymethyl)-1-(2,6-dimethylpyridin-4-yl)piperidine-4-carboxylic acid, 4-(2-amidino-1,2,3,4-tetrahydroisoquinolin-7-yloxymethyl)-1-(2-methylpyridin-4-yl)piperidine-4-carboxylic acid methyl ester, 4-(2-amidino-1,2,3,4-tetrahydroisoquinolin-7-yloxymethyl)-1-(2-methylpyridin-4-yl)piperidine-4-carboxylic acid, 4-(2-amidino-1,2,3,4-tetrahydroisoquinolin-7-yloxymethyl)-1-(pyrimidin-4-yl)piperidine-4-carboxylic acid, 4-[2-(2-amidino-1,2,3,4-tetrahydroisoquinolin-7-yloxy)ethyl]-1-(pyridin-4-yl)piperidine-4-carboxylic acid ethyl ester, 4-[2-(2-amidino-1,2,3,4-tetrahydroisoquinolin-7-yloxy)ethyl]-1-(pyridin-4-yl)piperidine-4-carboxylic acid, 7-[1-(2-hydroxyethyl)piperidin-4-ylmethoxy]-1,2,3,4-tetrahydroisoquinoline-2-carboxamidine, 7-[1-(pyridin-4-ylmethyl)piperidin-4-ylmethoxy]-1,2,3,4-tetrahydroisoquinoline-2-carboxamidine, 7-[1-(2-hydroxy-2-phenylethyl)piperidin-4-ylmethoxy]-1,2,3,4-tetrahydroisoquinoline-2-carboxamidine, 4-(2-amidino-1,2,3,4-tetrahydroisoquinolin-7-yloxymethyl)piperidin-1-ylacetylglycine ethyl ester, 4-(2-amidino-1,2,3,4-tetrahydroisoquinolin-7-yloxymethyl)piperidine-1-acetic acid N-methylamide, 7-(1-acetylpiperidin-4-ylmethoxy)-1,2,3,4-tetrahydroisoquinoline-2-carboxamidine, 7-(1-benzylsulfonylpiperidin-4-ylmethoxy)-1,2,3,4-tetrahydroisoquinoline-2-carboxamidine, 7-[1-(2-naphthylsulfonyl)piperidin-4-ylmethoxy]-1,2,3,4-tetrahydroisoquinoline-2-carboxamidine, 7-(1-acetimidoylpiperidin-4-ylmethoxy)-1,2,3,4-tetrahydroisoquinoline-2-carboxamidine, 7-(1-phenylacetimidoylpiperidin-4-ylmethoxy)-1,2,3,4-tetrahydroisoquinoline-2-carboxamidine, N-[2-[4-(2-amidino-1,2,3,4-tetrahydroisoquinolin-7-yloxymethyl)piperidin-1-yl]pyridin-5-yl]acetamide, N-[2-[4-(2-amidino-1,2,3,4-tetrahydroisoquinolin-7-yloxymethyl)piperidin-1-yl]pyridin-5-yl]benzamide, 3-[4-[4-(2-amidino-1,2,3,4-tetrahydroisoquinolin-7-yloxymethyl)piperidin-1-yl]pyridin-3-yl]-2-propenoic acid ethyl ester, 4-[4-(2-amidino-1,2,3,4-tetrahydroisoquinolin-7-yloxymethyl)piperidin-1-yl]pyridine-3-carboxylic acid methyl ester, 4-[4-(2-amidino-1,2,3,4-tetrahydroisoquinolin-7-yloxymethyl)piperidin-1-yl]pyridine-3-carboxylic acid, 6-[1-(pyridin-4-yl)piperidin-4-ylmethoxy]-1,2,3,4-tetrahydroisoquinoline-2-carboxamidine, 7-[2-[4-cyano-1-(pyridin-4-yl)piperidin-4-yl]ethoxy]-1,2,3,4-tetrahydroisoquinoline-2-carboxamidine, 4-(2-amidino-1,2,3,4-tetrahydroisoquinolin-7-ylthiomethyl)-1-(pyridin-4-yl)piperidine-4-carboxylic acid, 4-[2-(2-amidino-1,2,3,4-tetrahydroisoquinolin-7-ylthio)ethyl]-1-(pyridin-4-yl)piperidine-4-carboxylic acid, 4-(2-amidino-1,2,3,4-tetrahydroisoquinolin-7-ylsulfonylmethyl)-1-(pyridin-4-yl)piperidine-4-carboxylic acid, 4-[2-(2-amidino-1,2,3,4-tetrahydroisoquinolin-7-ylsulfonyl)ethyl]-1-(pyridin-4-yl)piperidine-carboxylic acid, 4-(2-amidino-1,2,3,4-tetrahydroisoquinolin-7-ylsulfonylamino)-1-(pyridin-4-yl)piperidine-4-carboxylic acid methyl ester, 4-(2-amidino-1,2,3,4-tetrahydroisoquinolin-7-ylsulfonylamino)-1-(pyridin-4-yl)piperidine-4-carboxylic acid, 4-(2-amidino-1,2,3,4-tetrahydroisoquinolin-7-ylsulfonylaminomethyl)-1-(pyridin-4-yl)piperidine-4-carboxylic acid ethyl ester, 4-(2-amidino-1,2,3,4-tetrahydroisoquinolin-7-ylsulfonylaminomethyl)-1-(pyridin-4-yl)piperidine-4-carboxylic acid, 7-[1-(pyridin-4-ylacetyl)piperidin-4-ylmethoxy]-1,2,3,4-tetrahydroisoquinoline-2-carboxamidine, 7-[1-(3-aminobenzyl)piperidin-4-ylmethoxy]-1,2,3,4-tetrahydroisoquinoline-2-carboxamidine, 7-[1-(2-hydroxybenzyl)piperidin-4-ylmethoxy]-1,2,3,4-tetrahydroisoquinoline-2-carboxamidine, 7-[1-(pyridin-2-ylmethyl)piperidin-4-ylmethoxy]-1,2,3,4-tetrahydroisoquinoline-2-carboxamidine, 2-[4 (2-amidino-1,2,3,4-tetrahydroisoquinolin-7-yloxymethyl)piperidin-1-ylmethyl]indole-1-carboxylic acid methy ester, 4-(2-amidino-1,2,3,4-tetrahydroisoquinolin-7-yloxymethyl)piperidine-1-acetic acid benzyl ester, N-benzyl-4-(2-amidino-1,2,3,4-tetrahydroisoquinolin-7-yloxymethyl)piperidine-1-carboxamide, 7-[1-(indol-2-ylmethyl)piperidin-4-ylmethoxy]-1,2,3,4-tetrahydroisoquinoline-2-carboxamidine, 4-(2-amidino-1,2,3,4-tetrahydroisoquinolin-7-yloxymethyl)piperidine-1-acetic acid, N-benzyl-4-(2-amidino-1,2,3,4-tetrahydroisoquinolin-7-yloxymethyl)piperidine-1-acetamide, 4-(2-amidino-1,2,3,4-tetrahydroisoquinolin-7-yloxymethyl)piperidin-1-ylacetylaminoacetic acid, 7-[1-(5-nitropyridin-2-yl)piperidin-4-ylmethoxy]-1,2,3,4-tetrahydroisoquinoline-2-carboxamidine, 7-[1-(2-nitrobenzyl)piperidin-4-ylmethoxy]-1,2,3,4-tetrahydroisoquinoline-2-carboxamidine, 7-[1-(2-aminobenzyl)piperidin-4-ylmethoxy]-1,2,3,4-tetrahydroisoquinoline-2-carboxamidine, 7-(1-hexaneimidoylpiperidin-4-ylmethoxy)-1,2,3,4-tetrahydroisoquinoline-2-carboxamidine, N-benzyl-4-(2-amidino-1,2,3,4-tetrahydroisoquinolin-7-yloxymethyl)piperidine-1-sulfonamide, N-butyl-4-(2-amidino-1,2,3,4-tetrahydroisoquinolin-7-yloxymethyl)piperidine-1-sulfonamide, N-cyclohexyl-4-(2-amidino-1,2,3,4-tetrahydroisoquinolin-7-yloxymethyl)piperidine-1-sulfonamide, N-(2-nitrophenyl)-4-(2-amidino-1,2,3,4-tetrahydroisoquinolin-7-yloxymethyl)piperidine-1-carbothioamide, 7-[1-(benzimidazol-2-yl)piperidin-4-ylmethoxy)-1,2,3,4-tetrahydroisoquinoline-2-carboxamidine, 3-[4-[4-(2-amidino-1,2,3,4-tetrahydroisoquinolin-7-yloxymethyl)piperidin-1-yl]pyridin-3-yl]propionic acid ethyl ester, 3-[4-[4-(2-amidino-1,2,3,4-tetrahydroisoquinolin-7-yloxymethyl)piperidin-1-yl]pyridin-3-yl]propionic acid, 4-(2-amidino-1,2,3,4-tetrahydroisoquinolin-7-yloxymethyl)-1-(2-aminopyridin-5-ylcarbonyl)piperidine-4-carboxylic acid, 4-(2-aimidino-1,2,3,4-tetrahydroisoquinolin-7-yloxymethyl)-1-(3-aminopropionyl)piperidine-4-carboxylic acid, 4-(2-amidino-1,2,3,4-tetrahydroisoquinolin-7-yloxymethyl)-1-(imidazol-4-ylacetyl)piperidine-4-carboxylic acid, 4-(2-amidino-1,2,3,4-tetrahydroisoquinolin-7-yloxymethyl)-1-(piperidin-4-ylsulfamoyl)piperidine-4-carboxylic acid, 4-(2-amidino-1,2,3,4-tetrahydroisoquinolin-7-yloxymethyl)-1-dimethylaminoacetylpiperidine-4-carboxylic acid, 4-(2-amidino-1,2,3,4-tetrahydroisoquinolin-7-yloxymethyl)-1-(pyridin-3-ylcarbamoyl)piperidine-4-carboxylic acid ethyl ester, 4-(2-amidino-1,2,3,4-tetrahydroisoquinolin-7-yloxymethyl)-1-(1-dimethylaminoacetylpiperidin-2-ylcarbonyl)piperidine-4-carboxylic acid ethyl ester, 4-[4-(2-amidino-1,2,3,4-tetrahydroisoquinolin-7-yloxymethyl)-4-carboxypiperidin-1-yl]-1-methylpyridinium chloride, 4-(2-amidino-1,2,3,4-tetrahydroisoquinolin-7-yloxymethyl)-1-(4-amidinophenyl)piperidine-4-carboxylic acid ethyl ester, 4-(2-amidino-1,2,3,4-tetrahydroisoquinolin-7-yloxymethyl)-1-(2,6-dimethylpyridin-4-yl)piperidine-4-carboxylic acid ethyl ester, 4-(2-amidino-1,2,3,4-tetrahydroisoquinolin-7-yloxymethyl)-1-(2-methylpyridin-4-yl)piperidine-4-carboxylic acid ethyl ester, 4-(2-amidino-1,2,3,4-tetrahydroisoquinolin-7-yloxymethyl)-1-(1-ethylpiperidin-4-yl)piperidine-4-carboxylic acid ethyl ester, 4-(2-amidino-1,2,3,4-tetrahydroisoquinolin-7-yloxymethyl)-1-(1-ethylpiperidin-4-yl)piperidine-4-carboxylic acid, 7-[2-(4-cyanopiperidin-4-yl)ethoxy]-1,2,3,4-tetrahydroisoquinoline-2-carboxamidine, 4-[2-(2-amidino-1,2,3,4-tetrahydroisoquinolin-7-yloxy)ethyl]-1-(pyridin-4-yl)piperidine-4-carboxylic acid ethyl ester, 4-(2-amidino-6-methoxy-1,2,3,4-tetrahydroisoquinolin-7-yloxymethyl)-1-(pyridin-4-yl)piperidine-4-carboxylic acid, and 4-(2-amidino-6-methyl-1,2,3,4-tetrahydroisoquinolin-7-yloxymethyl)-1-(pyridin-4-yl)piperidine-4-carboxylic acid, or a pharmaceutically acceptable salt thereof.

6. The amidine compound according to claim 5, 4-(2-amidino-1,2,3,4-tetrahydroisoquinolin-7-yloxymethyl)-1-(pyridin-4-yl)piperidine-4-carboxylic acid or a pharmaceutically acceptable salt thereof.

7. The amidine compound according to claim 6, wherein the pharmaceutically acceptable salt is an inorganic acid addition salt.

8. The amidine compound according to claim 7, wherein the inorganic acid addition salt is a mono-hydrochloride or di-hydrochloride acid addition salt.

9. The amidine compound according to claim 6, wherein the pharmaceutically acceptable salt is an organic acid addition salt.

10. The amidine compound according to claim 9, wherein the organic acid addition salt is a mono-methanesulfonic acid addition salt.

11. 4-(2-amidino-1,2,3,4-tetrahydroisoquinolin-7-yloxymethyl)-1-(pyridin-4-yl)piperidine-4-carboxylic acid mono-methanesulfonate or a hydrate thereof.

12. The compound of claim 11 in hydrate form.

13. A pharmaceutical composition comprising an effective amount of said amidine compound of claim 1 or a pharmaceutically acceptable salt thereof, and a pharmaceutically acceptable additive.

14. A method for inhibiting coagulation of blood, which comprises administering the amidine compound of claim 1 or a pharmaceutically acceptable salt thereof.

15. A method for the prophylaxis or treatment of diseases caused by blood coagulation or thrombus, which comprises administering the amidine compound of claim 1 or a pharmaceutically acceptable salt thereof.

* * * * *